(12) United States Patent
Yabunouchi

(10) Patent No.: US 8,703,304 B2
(45) Date of Patent: Apr. 22, 2014

(54) AROMATIC AMINE DERIVATIVE AND ORGANIC ELECTROLUMINESCENCE DEVICE

(75) Inventor: Nobuhiro Yabunouchi, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 13/413,963

(22) Filed: Mar. 7, 2012

(65) Prior Publication Data

US 2012/0161119 A1    Jun. 28, 2012

Related U.S. Application Data

(63) Continuation of application No. 12/428,554, filed on Apr. 23, 2009, now abandoned.

(30) Foreign Application Priority Data

May 29, 2008 (JP) .................................. 2008-140650

(51) Int. Cl.
   *H01L 51/54* (2006.01)

(52) U.S. Cl.
   USPC ........... 428/690; 428/917; 313/504; 313/505; 313/506; 257/40; 257/E51.05; 257/E51.026; 257/E51.032; 564/26; 564/426; 564/431; 564/433

(58) Field of Classification Search
   USPC ............ 428/90, 690, 917; 313/504, 505, 506; 257/40, E51.05, E51.026, E51.032; 564/431, 433, 26, 426
   See application file for complete search history.

(56) References Cited

U.S. PATENT DOCUMENTS

| 2007/0075635 A1 | 4/2007 | Yabunouchi et al. |
| 2007/0278938 A1 | 12/2007 | Yabunouchi et al. |
| 2009/0066235 A1 | 3/2009 | Yabunouchi et al. |

FOREIGN PATENT DOCUMENTS

| EP | 1 885 008 A1 | 2/2008 |
| JP | 9-151182 | 6/1997 |
| JP | 2005-112765 | 4/2005 |
| JP | 2006-352088 | 12/2006 |
| JP | 2007-108216 | 4/2007 |
| JP | 2008-7424 | 1/2008 |
| JP | 2008-21687 | 1/2008 |
| WO | 2007/039952 A1 | 4/2007 |
| WO | 2007/125714 A1 | 8/2007 |

OTHER PUBLICATIONS

U.S. Appl. No. 13/360,513, filed Jan. 27, 2012, Yabunouchi, et al.

*Primary Examiner* — Gregory Clark
(74) *Attorney, Agent, or Firm* — Oblon, Spivak, McClelland, Maier & Neustadt, L.L.P.

(57) ABSTRACT

An aromatic amine derivative having a specific structure. An organic electroluminescence device which is composed of one or more organic thin film layers sandwiched between a cathode and an anode, wherein at least one of the organic thin film layers, especially a hole transporting layer, contains the aromatic amine derivative. The aromatic amine derivative has at least one substituted or unsubstituted dibenzofuran skeleton and at least one substituted or unsubstituted terphenylene skeleton. Because the molecules in the aromatic amine derivate hardly crystallize, organic electroluminescence devices improving their production yield and having prolonged lifetime are provided.

14 Claims, No Drawings

AROMATIC AMINE DERIVATIVE AND ORGANIC ELECTROLUMINESCENCE DEVICE

This is a continuation application of U.S. application Ser. No. 12/428,554, filed Apr. 23, 2009.

TECHNICAL FIELD

The present invention relates to an aromatic amine derivative, a material for an organic electroluminescence (EL) device, and an organic EL device using the same; and more particularly, to an aromatic amine derivative actualizing the organic EL device capable of lengthening a lifetime of the organic EL device by using an aromatic amine derivative having a specific structure as a hole injecting material or a hole transporting material.

BACKGROUND ART

An organic EL device is a spontaneous light emitting device which utilizes a phenomenon that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company [C. W. Tang and S. A. Vanslyke, Applied Physics Letters, Volume 51, Page 913, 1987], many studies have been conducted on organic EL devices using organic materials as the constituting materials. Tang et al. used tris(8-quinolinolato)aluminum for the light emitting layer and a triphenyldiamine derivative for the hole transporting layer. Advantages of the laminate structure are that the efficiency of hole injection into the light emitting layer can be increased, that the efficiency of forming excitons which are formed by blocking and recombining electrons injected from the cathode can be increased, and that the excitons formed in the light emitting layer can be confined. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. In order to increase the efficiency of recombination of injected holes and electrons in the devices of the laminate type, the structure of the device and the process for forming the device have been studied.

Usually, driving or storing the organic EL devices under an environment of elevated temperatures causes adverse influences such as changes of luminescent colors, degradation of current efficiency of light emission, increase of their driving voltage, reduction of lifetime in their light emission, etc. In order for preventing the adverse influences, it was necessary to elevate a glass transition temperature (Tg) of a hole transporting material. Accordingly, it is necessary for the hole transporting materials to have many aromatic groups in molecules thereof (for example, aromatic diamine derivatives disclosed in Patent Document 1, aromatic fused ring diamine derivatives disclosed in Patent Document 2), and usually, structures having 8 to 12 benzene rings are preferably employed.

However, in a compound having a symmetrical structure in a molecule, crystallization is liable to occur upon production of the organic EL device through the formation of a thin film by using those hole transporting materials. As a result, there arises a problem such as clogging of an outlet of a crucible to be used in vapor deposition or a reduction in yields of the organic EL device due to generation of defects of the thin film resulting from the crystallization. In addition, a compound having a large number of aromatic groups in any one of molecules thereof generally has a high glass transition temperature (Tg), but has a high sublimation temperature. Accordingly, there arises a problem in that the lifetime is short, because a phenomenon such as decomposition at the time of the vapor deposition or the formation of a nonuniform deposition film is expected to occur.

Further, although Patent Documents 3 to 5 report about compounds having dibenzofuran structures, they disclose structures having dibenzofuran as a central skeleton of a diamine compound. Patent Documents 6 to 8 disclose about compounds having dibenzofuran structures through an aryl group in monoamines thereof, however, the compounds do not sufficiently improve the performance as the organic EL device.

Also, Patent Documents 9 to 11 report about monoamine compounds having a terphenyl group, however, the compounds are only used for electrophotographic photoreceptors. Although Patent Documents 12 to 14 disclose about usages as materials for the organic EL device, the materials do not sufficiently improve the performance as the organic EL device.

As mentioned above, there are many reports about the organic EL devices with prolonged lifetime. However, the lifetime is still insufficient. Accordingly, development of an organic EL device having a more superior performance has been eagerly desired.

Patent Document 1: U.S. Pat. No. 4,720,432
Patent Document 2: U.S. Pat. No. 5,061,569
Patent Document 3: JP 2005-112765A
Patent Document 4: JP 11-111460A
Patent Document 5: WO 2006/122630
Patent Document 6: WO 2006/128800
Patent Document 7: JP 2006-151844A
Patent Document 8: JP 2008-021687A
Patent Document 9: JP 2-134643A
Patent Document 10: JP 2-190862A
Patent Document 11: JP 3-118548A
Patent Document 12: JP 6-228062A
Patent Document 13: JP 2001-196183A
Patent Document 14: JP 2006-352088A

DISCLOSURE OF THE INVENTION

Problems to be Solved by the Invention

The present invention has been made to overcome the above problems and has an object of providing an organic EL device with a prolonged lifetime, and an object of providing an aromatic amine derivative actualizing the organic EL device.

Means for Solving the Problem

The inventors of the present invention have made extensive studies with a view toward achieving the above-mentioned object. As a result, the inventors have found that the above-mentioned problems can be solved by using a novel aromatic amine derivative having a specific substituent as a material for an organic EL device, and particularly, as a hole injecting material or a hole transporting material. It was also found that there is preferred an amino group substituted with an aryl group having a dibenzofuran structure and an aryl group having a terphenyl structure as an amine unit having specific substituent.

Further, it has been found that the amine unit shows a small intermolecular interaction because of the steric hindrance thereof, thereby preventing the crystallization, improving the yield in producing organic EL devices. It has been also found that presence of terphenyl group being superior in reduction stability improves the reduction stability of the molecules thereby prolonging the lifetime in the organic EL devices obtained. Especially, it has been found that remarkable effects of prolonging the lifetime is obtainable by combining the derivative with an EL device emitting blue light. The present invention has been accomplished on the basis of the above findings.

Namely, the present invention provides:

(I) An aromatic amine derivative represented by the following general formula (1).

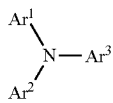
(1)

wherein at least one group among $Ar^1$ to $Ar^3$ is represented by the following general formula (2):

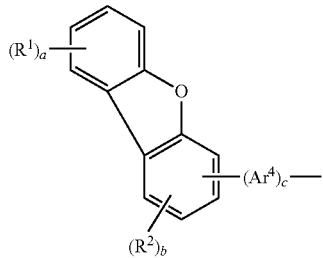
(2)

wherein $R^1$ and $R^2$ each independently represents a substituted or unsubstituted aryl group having the number of carbon atoms of 6 to 50 forming the aromatic ring, or a substituted or unsubstituted alkyl group having carbon atoms of 1 to 50; "a" represents an integer of 0 to 4, "b" represents an integer of 0 to 3, and "c" represents an integer of 1 to 3; plural $R^1$'s or $R^2$'s together may be bonded to each other to form a saturated or unsaturated, five- or six-membered ring structure which may be substituted; $Ar^4$ represents a substituted or unsubstituted arylene group having the number of carbon atoms of 6 to 50 forming the aromatic ring, or a substituted or unsubstituted fluonylene group.

In the general formula (1), at least one of $Ar^1$ to $Ar^3$ is represented by the following general formula (3):

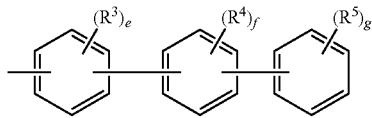
(3)

wherein $R^3$ to $R^5$ are each independently selected from the same groups as the above $R^1$; "e" and "f" each independently represents an integer of 0 to 4, and "g" represents an integer of 0 to 5; plural $R^3$'s, $R^4$'s, or $R^5$'s together may be bonded to each other to form a saturated or unsaturated, five- or six-membered ring structure which may be substituted.

In the general formula (1), one of $Ar^1$ to $Ar^3$ which is represented by neither the general formula (2) nor the general formula (3) is independently represented by a substituted or unsubstituted aryl group having the number of carbon atoms of 6 to 50 forming the aromatic ring with the proviso that it does not include the structure of the general formula (3);

(II) The aromatic amine derivative as described in the above (I), wherein $Ar^4$ is represented by any one of the following general formula (4) or (5):

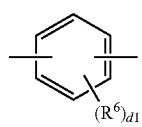
(4)

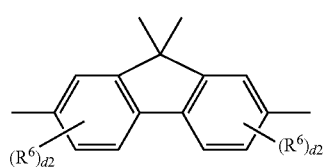
(5)

wherein $R^6$'s each independently represents a substituted or unsubstituted aryl group having the number of carbon atoms of 6 to 50 forming the aromatic ring, or a substituted or unsubstituted alkyl group having 1 to 50 carbon atoms respectively, "d1" represents an integer of 0 to 4, "d2" represents an integer of 0 to 3; and plural $R^6$'s on the same benzene rings or $R^6$'s on 2 neighboring benzene rings together may be bonded to each other to form a saturated or unsaturated, five- or six-membered ring structure which may be substituted;

(III) The aromatic amine derivative as described in the above (I), wherein $Ar^4$ is represented by the following general formula (6):

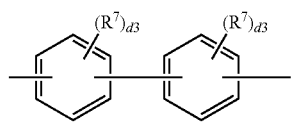
(6)

wherein $R^7$'s each independently represents a substituted or unsubstituted aryl group having the number of carbon atoms of 6 to 50 forming the aromatic ring, or a substituted or unsubstituted alkyl group having 1 to 50 carbon atoms respectively, and "d3" represents an integer of 0 to 4;

(IV) The aromatic amine derivative as described in the above (I), wherein the above general formula (3) is represented by any one of the following general formula (7), (8) or (9):

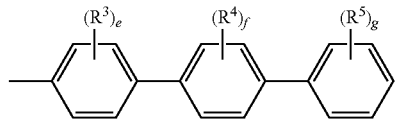
(7)

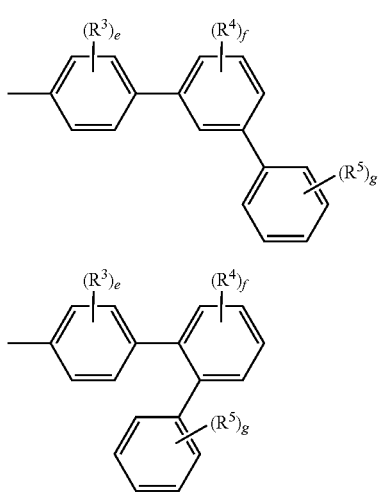

wherein $R^3$ to $R^5$ and "e" to "g" are the same as those in the above general formula (3);

(V) The aromatic amine derivative as described in the above (I), wherein one group among the above $Ar^1$ to $Ar^3$ is represented by the above general formula (2); and two groups among the above $Ar^1$ to $Ar^3$ are represented by the above general formula (3);

(VI) The aromatic amine derivative as described in the above (I), wherein two groups among the above $Ar^1$ to $Ar^3$ are represented by the above general formula (2); and one group among the above $Ar^1$ to $Ar^3$ is represented by the above general formula (3);

(VII) The aromatic amine derivative as described in the above (I), wherein one group among the above $Ar^1$ to $Ar^3$ is represented by the general formula (2); at the same time, $Ar^4$ in the general formula (2) is represented by the above general formula (4), (5) or (6), and two groups among the above $Ar^1$ to $Ar^3$ are each represented by any one of the general formula (7) or (8) respectively;

(VIII) The aromatic amine derivative as described in the above (I), wherein two groups among the above $Ar^1$ to $Ar^3$ are represented by the general formula (2); at the same time, $Ar^4$ in the general formula (2) is represented by the above general formula (4), (5) or (6), and one group among the above $Ar^1$ to $Ar^3$ is represented by the general formula (7) or (8);

(IX) The aromatic amine derivative as described in the above (I), wherein the above general formula (2) has a structure represented by the following general formula (10):

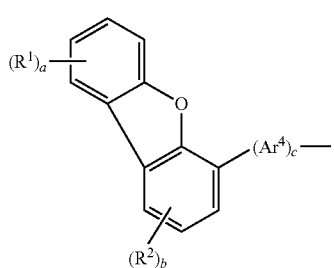

wherein $R^1$, $R^2$, $Ar^4$, "a", "b" and "c" are the same as the above definition;

(X) The aromatic amine derivative as described in the above (I), wherein one group among the above $Ar^1$ to $Ar^3$ is represented by the general formula (2); and two groups among the above $Ar^1$ to $Ar^3$ are each represented by any one of the general formula (7) or (8) respectively;

(XI) The aromatic amine derivative as described in the above (1), wherein two groups among the above $Ar^1$ to $Ar^3$ are represented by the general formula (2); and one group among the above $Ar^1$ to $Ar^3$ is represented by any one of the general formula (7) or (8);

(XII) The aromatic amine derivative as described in the above (I), wherein the aromatic amine derivative is used as a material for organic electroluminescence devices;

(XIII) The aromatic amine derivative as described in the above (I), wherein the aromatic amine derivative is used as a hole injecting material or a hole transporting material;

(XIV) An organic electroluminescence device which is composed of one or more organic thin film layers including at least one light emitting layer sandwiched between a cathode and an anode, wherein at least one of the organic thin film layers contains the aromatic amine derivative described in the above (I) singly or as mixture component thereof;

(XV) The organic electroluminescence device as described in the above (XIV), wherein the organic thin film layer has a hole injecting layer or a hole transporting layer, and the hole injecting layer or the hole transporting layer contains the aromatic amine derivative described in the above (I);

(XVI) The organic electroluminescence device as described in the above (XIV), wherein the light emitting layer contains at least one of styrylamine and arylamine; and (XVII) The organic electroluminescence device as described in the above (XIV), which emits blue light.

Effect by the Invention

The aromatic amine derivative of the present invention hardly causes the crystallization of a molecule and further, it improves yields upon production of the organic EL device, and contributes to prolong the lifetime of the organic EL devices.

BEST MODE TO CARRY OUT THE INVENTION

In the general formula (1), at least one of $Ar^1$ to $Ar^3$ is represented by the above general formula (2).

$R^1$ and $R^2$ in the general formula (2) each independently represents a substituted or unsubstituted aryl group having the number of carbon atoms of 6 to 50 forming the aromatic ring, preferably 6 to 20, or a substituted or unsubstituted alkyl group having 1 to 50, preferably 1 to 20 carbon atoms; "a" represents an integer of 0 to 4, preferably 0 or 1, and further preferably 0; "b" represents an integer of 0 to 3, preferably 0 or 1, and further preferably 0; and "c" represents an integer of 1 to 3.

Specific examples of the aryl group include a phenyl group, a naphthyl group, a phenanthryl group, a crycenyl group, a benzphenanthryl group, a terphenyl group, a benzanthranyl group, a benzo crycenyl group, a biphenyl group, a naphthacenyl group, an anthranyl group, a pentacenyl group, a picenyl group, a pentaphenyl group, etc.

Specific examples of the alkyl group include a methyl group, an ethyl group, an isopropyl group, an n-propyl group, a sec-butyl group, a tert-butyl group, a pentyl group, a hexyl group, etc.

Examples of the substituent in the aryl group and the alkyl group include an aryl group having the number of carbon atoms of 6 to 50 (preferably 6 to 20) forming the aromatic ring (specifically a phenyl group, a naphthyl group, a phenanthryl group, a crycenyl group, benzphenanthryl group, a terphenyl group, a benz anthranyl group, a benzo crycenyl group, a biphenyl group, a naphthacenyl group, an anthranyl group, a pentacenyl group, a pycenyl group) a substituted or unsubstituted alkyl group having 1 to 50 (preferably 1 to 20) carbon atoms (specifically a methyl group, an ethyl group, an isopropyl group, an n-propyl group, a sec-butyl group, a tert-butyl group, a pentyl group, a hexyl group), a fluorine atom, a silyl group whose alkyl group or aryl group is substituted (a trimethylsilyl group, a triethylsilyl group, a triphenylsilyl group, a tert-butyldimethylsilyl group), etc.

In the general formula (2), plural $R^1$'s or $R^2$'s together may be bonded to each other to form a saturated or unsaturated, five- or six-membered ring structure which may be substituted. Specific examples of the ring structure formed by the substituent $R^1$'s or $R^2$'s in the dibenzofuran structure being bonded each other [a constitutional section made by removing $(Ar^4)c$ unit from the general formula (2)] are as follows:

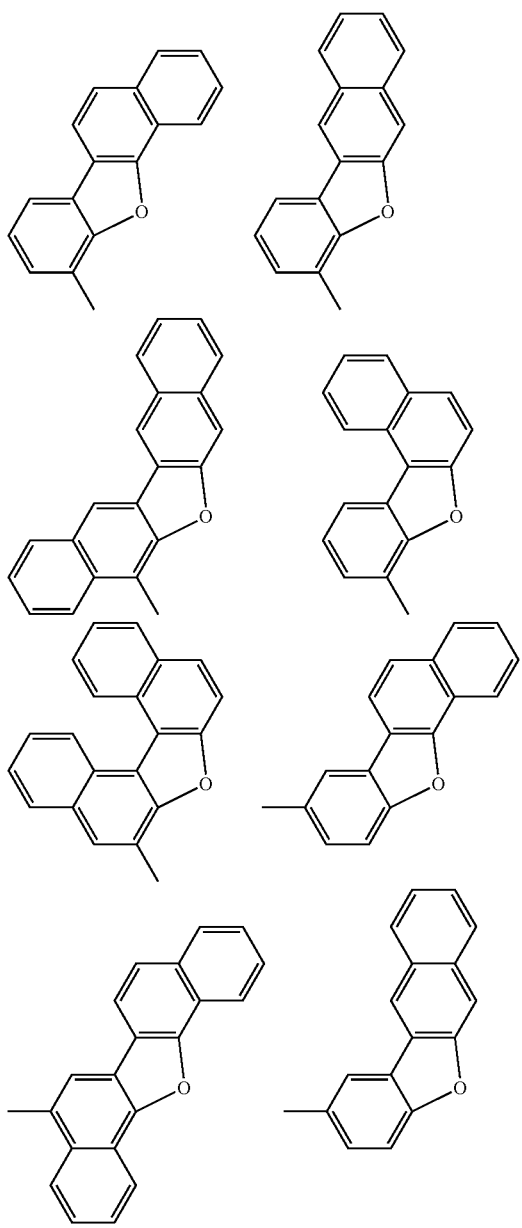

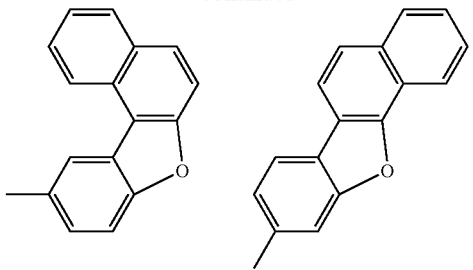
-continued

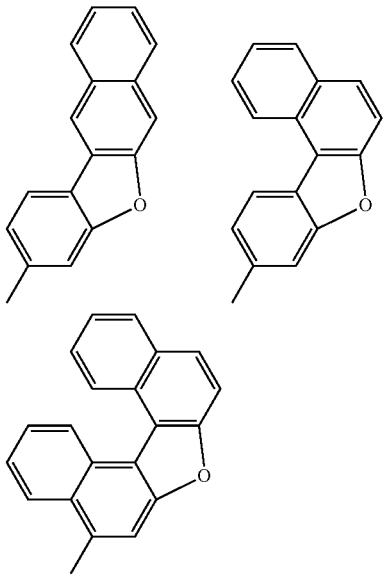

$Ar^4$ represents a substituted or unsubstituted arylene group having the number of carbon atoms of 6 to 50 forming the aromatic ring, preferably 6 to 20, or a substituted or unsubstituted fluonylene group.

Specific examples of the arylene group include a phenylene group, a naphthylene group, a biphenylene group, a terphenylene group, a phenanthrene group, a triphenylene group, an anthranylene group, a pentacenylene group, a perilenylene group, a picenylene group, a pyrenylene group, a pentaphenylene group, 9,9-dimethylfluonylene group, 9,9-diphenyl fluonylene group and the following compounds, etc.

Examples of the substituent in the arylene group or the fluonylene group include the same examples as the substituent in the aryl group or the alkyl group.

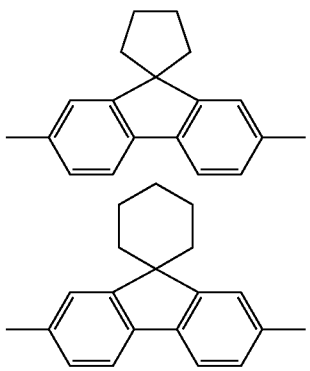

-continued

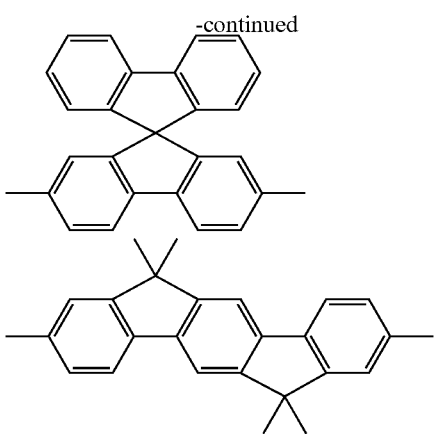

Especially, it is preferable to be any one of the phenylene group or the 9,9-dimethylfluonylene group represented by the above general formula (4), (5) or (6).

$R^6$ and $R^7$ in the above general formula (4), (5) or (6) each independently represents a substituted or unsubstituted aryl group having the number of carbon atoms of 6 to 50 forming the aromatic ring, preferably 6 to 20, or a substituted or unsubstituted alkyl group having carbon atoms of 1 to 50, preferably 1 to 20; "d1" represents an integer of 0 to 4, preferably 0 to 2; "d2" independently represents an integer of 0 to 3; and "d3" independently represents an integer of 0 to 4, preferably 0 to 2. Plural $R^6$'s and plural $R^7$'s on the same benzene rings or R6's and R7's on the neighboring benzene rings together may be bonded to each other to form a saturated or unsaturated, five- or six-membered ring structure which may be substituted; and c representing the number of $Ar^4$ is preferably 1 or 2.

Specific examples of the aryl group and the alkyl group in $R^6$ and $R^7$, and examples of the substituent that can be bonded with the aryl group or the alkyl group are the same as those mentioned about the foregoing $R^1$ and $R^2$.

In the general formula (1), at least one of $Ar^1$ to $Ar^3$ is represented by the above general formula (3).

In the general formula (3), $R^3$ to $R^5$ are each independently selected from the same groups as the above $R^1$. The substituent which can be bonded to the aryl group or alkyl group is selected from the same groups as the above $R^1$; "e" and "f" each independently represents an integer of 0 to 4, preferably 0 or 1, and further preferably 0; "g" represents an integer of 0 to 5, preferably 0 or 1, and further preferably 0. Plural $R^3$'s, $R^4$'s or $R^5$'s together may be bonded to each other to form a saturated or unsaturated, five- or six-membered ring structure which may be substituted. $R^3$, $R^4$ and $R^5$ may be bonded to each other to form a saturated or unsaturated, five- or six-membered ring structure which may be substituted. Preferred specific examples of the general formula (3) is the case where $R^3$, $R^4$ and $R^5$ do not form a ring, or the case where $R^3$ and $R^4$ become a bonding group forming five-membered ring; in other words, those with a structure in which a phenyl group or a naphthyl group is bonded to the para position of 9,9-dimethylfluonylene group. Another example is the case where $R^4$ and $R^5$ become a bonding group forming five-membered ring, in other words, those with a structure in which 9,9-dimethylfluonylene group is bonded to the para position of a phenyl group or a naphthyl group.

When $Ar^4$ is represented by the general formula (4), (5) or (6), it is preferable that the general formula (3) is represented by any one of the general formulae (7) to (9).

In the general formulae (7) to (9), $R^3$ to $R^5$ are each independently selected from the same groups as the above $R^1$ and $R^2$ respectively. The substituent which can be bonded to the aryl group or alkyl group is selected from the same groups as the above $R^1$; "e" and "f" each independently represents an integer of 0 to 4, preferably 0 or 1, and further preferably 0; "g" represents an integer of 0 to 5, preferably 0 or 1, and further preferably 0. $R^3$, $R^4$ and $R^5$ may be bonded to each other to form a saturated or unsaturated, five- or six-membered ring structure which may be substituted.

In the general formula (1), any one of $Ar^1$ to $Ar^3$ which is represented by neither the general formula (2) nor the general formula (3) is each independently represented by a substituted or unsubstituted aryl group having the number of carbon atoms of 6 to 50 forming the aromatic ring, preferably 6 to 20. Specific examples of the aryl group are the same as those particularized about the above $R^1$ and $R^2$. Preferred specific examples include a biphenyl group, a naphthyl group and a phenanthryl group.

The aromatic amine derivatives wherein at least one group among the above $Ar^1$ to $Ar^3$ is represented by the general formula (2), and those which are not represented by the general formula (2) are represented by the general formula (3) are preferable.

Further, there are preferred the aromatic amine derivatives wherein at least one group among the above $Ar^1$ to $Ar^3$ is represented by the general formula (2), $Ar^4$ in the general formula (2) is represented by the general formula (4), (5) or (6), and those remained among the above $Ar^1$ to $Ar^3$ are represented by any one of the general formulae (7) to (9).

Also, there are preferred the aromatic amine derivatives wherein the one group among the above $Ar^1$ to $Ar^3$ is represented by the general formula (2), $Ar^4$ in the general formula (2) is represented by any one of the general formulae (4), (5) or (6); and the two groups among the above $Ar^1$ to $Ar^3$ are represented by any one of the general formulae (7) to (9).

Still further, there are preferred the aromatic amine derivative wherein the two groups among the above $Ar^1$ to $Ar^3$ are represented by the general formula (2), Ar4 in the general formula (2) is represented by any one of the general formulae (4), (5) and (6); and the one group among the above $Ar^1$ to $Ar^3$ is represented by any one of the general formulae (7) to (9).

Furthermore, among the aromatic amine derivative represented by the above general formula (1), the following embodiments are also preferable:
(a) The aromatic amine derivative wherein the above general formula (2) is represented by the foregoing general formula (10). [$R^1$, $R^2$, $Ar^4$, "a", "b", and "c" in the general formula (10) are the same as those in the general formula (2)]
(b) The aromatic amine derivative wherein one group among the above $Ar^1$ to $Ar^3$ is represented by the above general formula (2); and two groups among the above $Ar^1$ to $Ar^3$ are each represented by any one of the above general formula (7) or (8) respectively.
(c) The aromatic amine derivative wherein two groups among the above $Ar^1$ to $Ar^3$ are represented by the above general formula (2); and one group among the above $Ar^1$ to $Ar^3$ is represented by any one of the above general formula (7) or (8).

The aromatic amine derivative of the present invention represented by the general formula (1) can be synthesized, for example, by the following reaction.

At first, by allowing the compound [e.g., dibenzofuran-4-boronic acid and 4-iodobromobenzene] which generates the structure represented by the general formula (2) to react among the aqueous solution of a solvent [e.g., toluene] and alkaline compound [e.g., sodium carbonate] under the presence of a catalyst [e.g., tetrakis(triphenylphosphine) palladium(0)] at the temperature of 50 to 150° C., Intermediate X is synthesized. It is preferable that the reaction is performed under the atmosphere of an inert gas such as argon.

On the other hand, after allowing the halide [e.g., 4-bromo-p-terphenyl] which generates the structure represented by the general formula (3), and a compound which generates an amino group (a compound which generates a substituted or unsubstituted aryl group having 6 to 50 ring forming carbon atoms may be included) [e.g., benzamide] to react each other in a solvent [e.g., xylene] at the temperature of 50 to 250° C. and under the presence of a catalyst (metal halide such as copper iodide and amine such as N,N'-dimethylethylenediamine) and an alkaline material [e.g., potassium carbonate], Intermediate Y is synthesized by allowing the resultant solution to react among the solvent [e.g., xylene] at the temperature of 50 to 250° C. and under the presence of an alkaline material [e.g., potassium hydroxide] and water. It is preferable that the reaction is performed under the atmosphere of an inert gas such as argon.

Then, by allowing Intermediate X and Intermediate Y to react each other among a solvent (e.g. dehydrated toluene) at the temperature of 0 to 150° C. under the presence of a catalyst (e.g. t-butoxy sodium and tris(dibenzylideneacetone) dipalladium (0), the aromatic amine derivative of the present invention can be synthesized. It is preferable that the reaction is performed under the atmosphere of an inert gas such as argon.

After completing the reaction, cooling the reaction product down to the room temperature, adding water to the reaction product and filtering it, extracting the filtrate with solvent such as toluene or so, drying it using a desiccant such as sulfuric anhydride magnesium or so, removing the solvent and condensing under reduced pressure, column refining the crude product, re-crystallizing with solvent such as toluene or so, and separating with filtration, followed by drying provides a purified aromatic amine derivative of the present invention.

For the purpose of introducing a substituted or unsubstituted aryl group having 6 to 50 ring forming carbon atoms of neither the general formula (2) nor the general formula (3) into the aromatic amine derivative represented by the general formula (1), it is suitable that when Intermediate X and Intermediate Y are allowed to react each other, or when Intermediate Y is synthesized, a reacting content ratio is controlled and a halide (e.g., 1-bromonaphthalene) of the substituted or unsubstituted aryl group having 6 to 50 to 20 ring forming carbon atoms of neither the general formula (2) nor the general formula (3) is allowed to react and to be introduced similarly and sequentially. (For example, after allowing benzamide and 4-bromo-p-terphenyl to react in mass ratio of 1:1 each other, throwing 1 equivalent of 1-bromonaphthalene into the resultant solution and hydrolyzing it provides Intermediate Y into which the aryl group of the general formula (3) and "the aryl group of neither the general formula (2) nor the general formula (3)" were introduced.)

A halide of the general formula (2), a halide of the general formula (3), and the halide of the substituted or unsubstituted aryl group having 6 to 50 to 20 ring forming carbon atoms of neither the general formula (2) nor the general formula (3) can be arbitrarily introduced into Intermediate Y. Also, the aryl group can be introduced singly or in pair, and further, it can be introduced in arbitrary combination. Allowing the resultant amine compound (Intermediate Y) and arbitrary halide (Intermediate X) to react each other can provide the aimed product. These reaction order or combination can be settled considering the reactivity, easiness of purification, and so on.

Examples of the general formula wherein $Ar^1$ to $Ar^3$ in the general formula (1) are partially or entirely specified further are as follows:

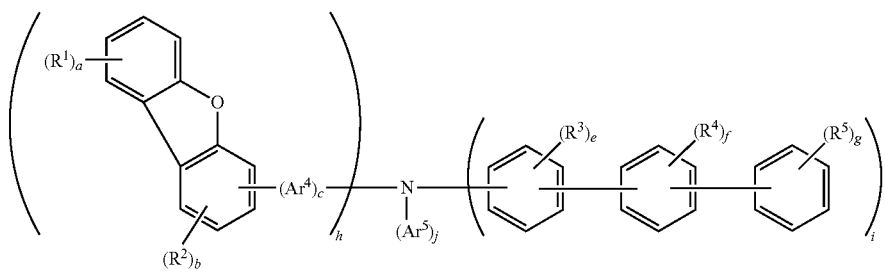

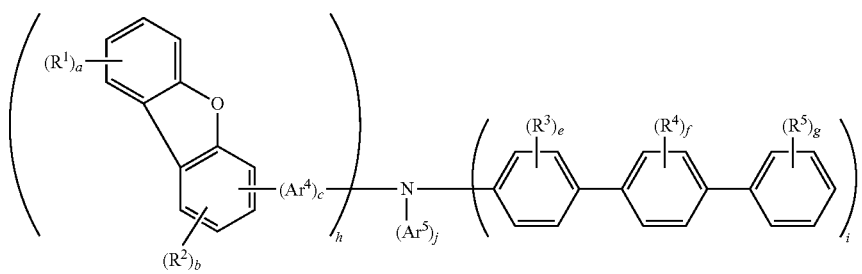

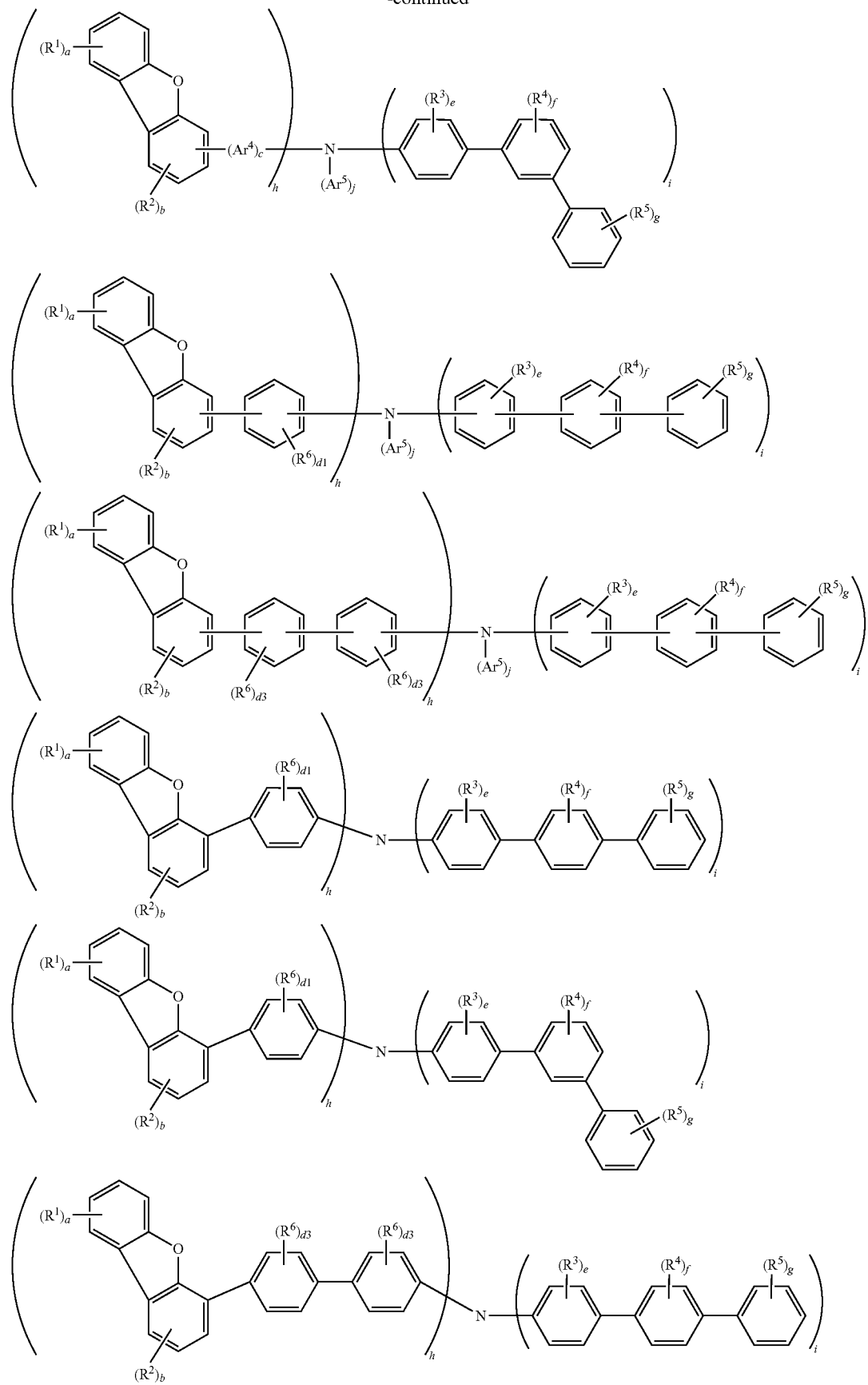

-continued

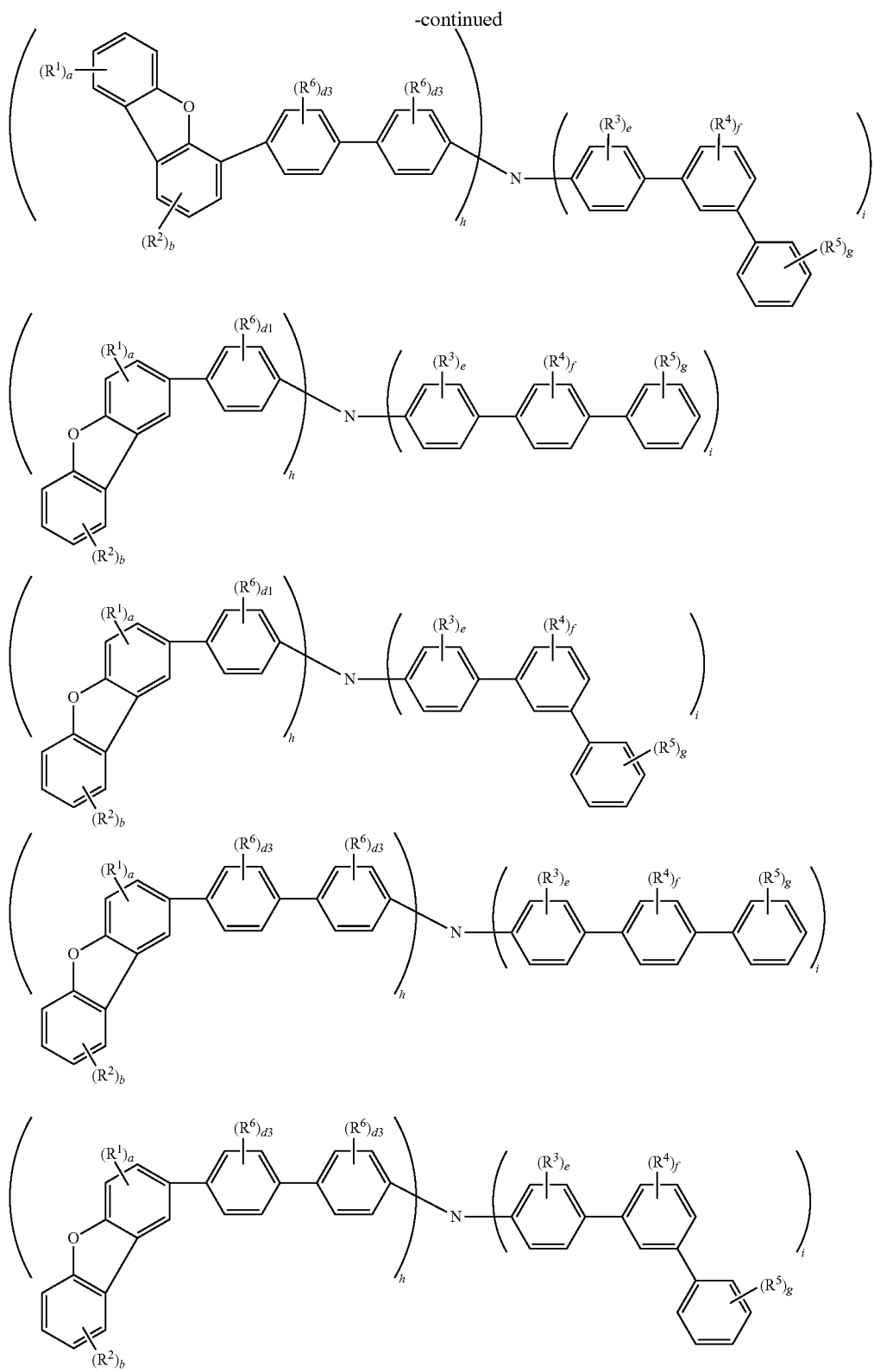

In the above constitutional formula, "h" represents an integer of 1 to 3, "i" and "j" each independently represents an integer of 0 to 2, and "h+i+j"=3. $R^1$ to $R^6$, "a" to "c", "d1" to "d3", and "e" to "h" are the same as those described above. $Ar^5$ corresponds to any one group among the above $Ar^1$ to $Ar^3$.

Specific examples of the aromatic amine derivatives represented by the general formula (1) include the following compounds enumerated below, though not particularly limited thereto.

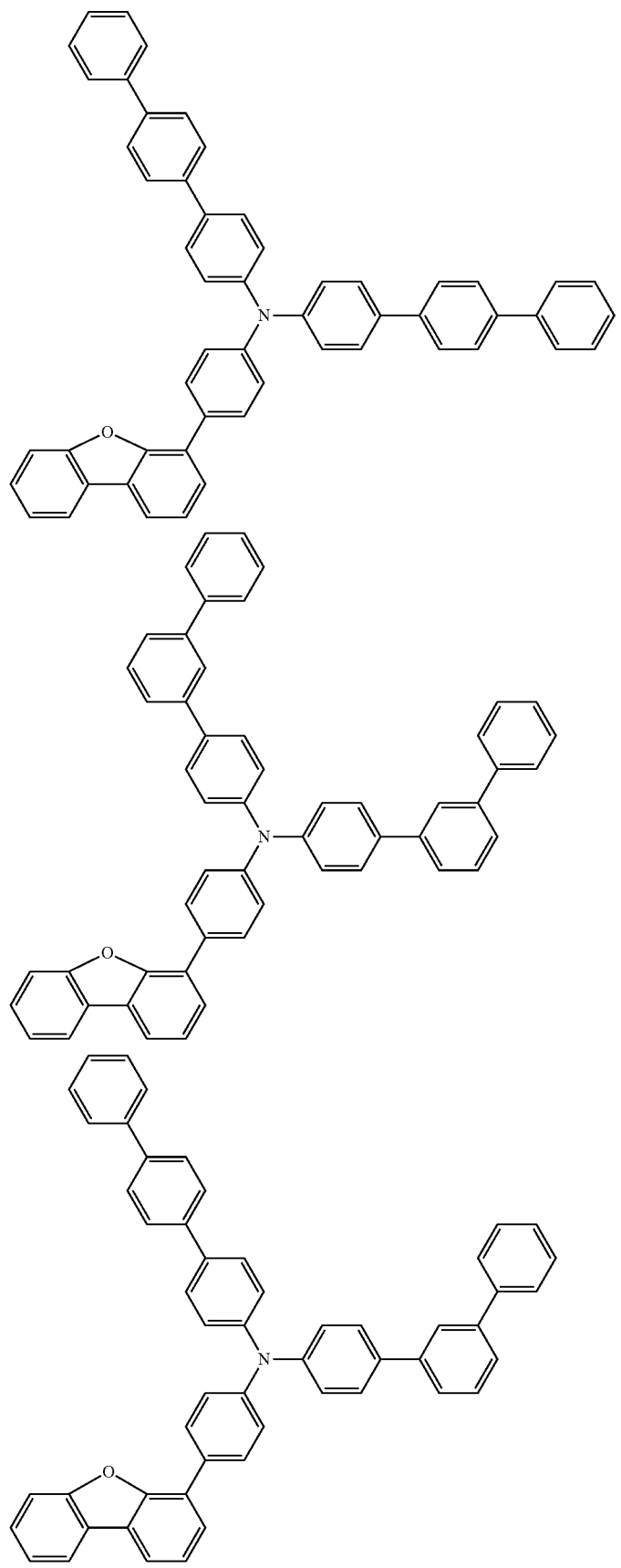

-continued
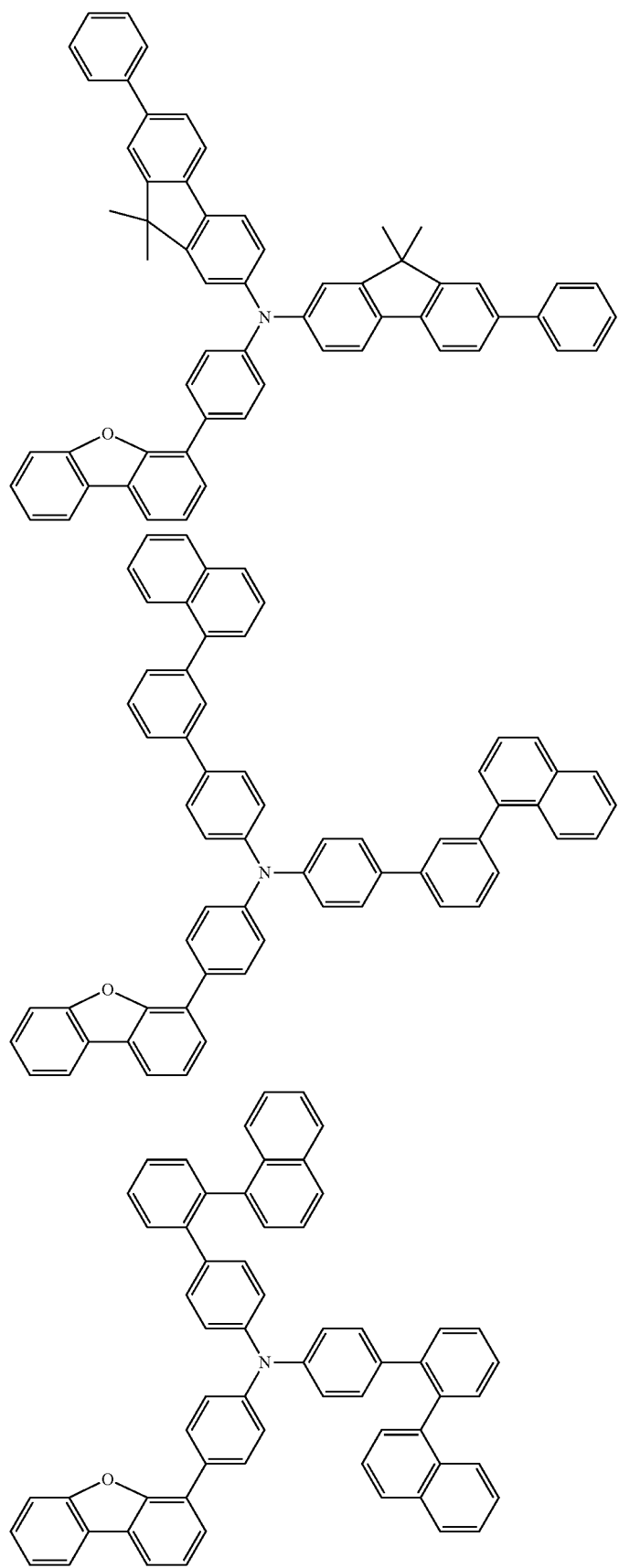

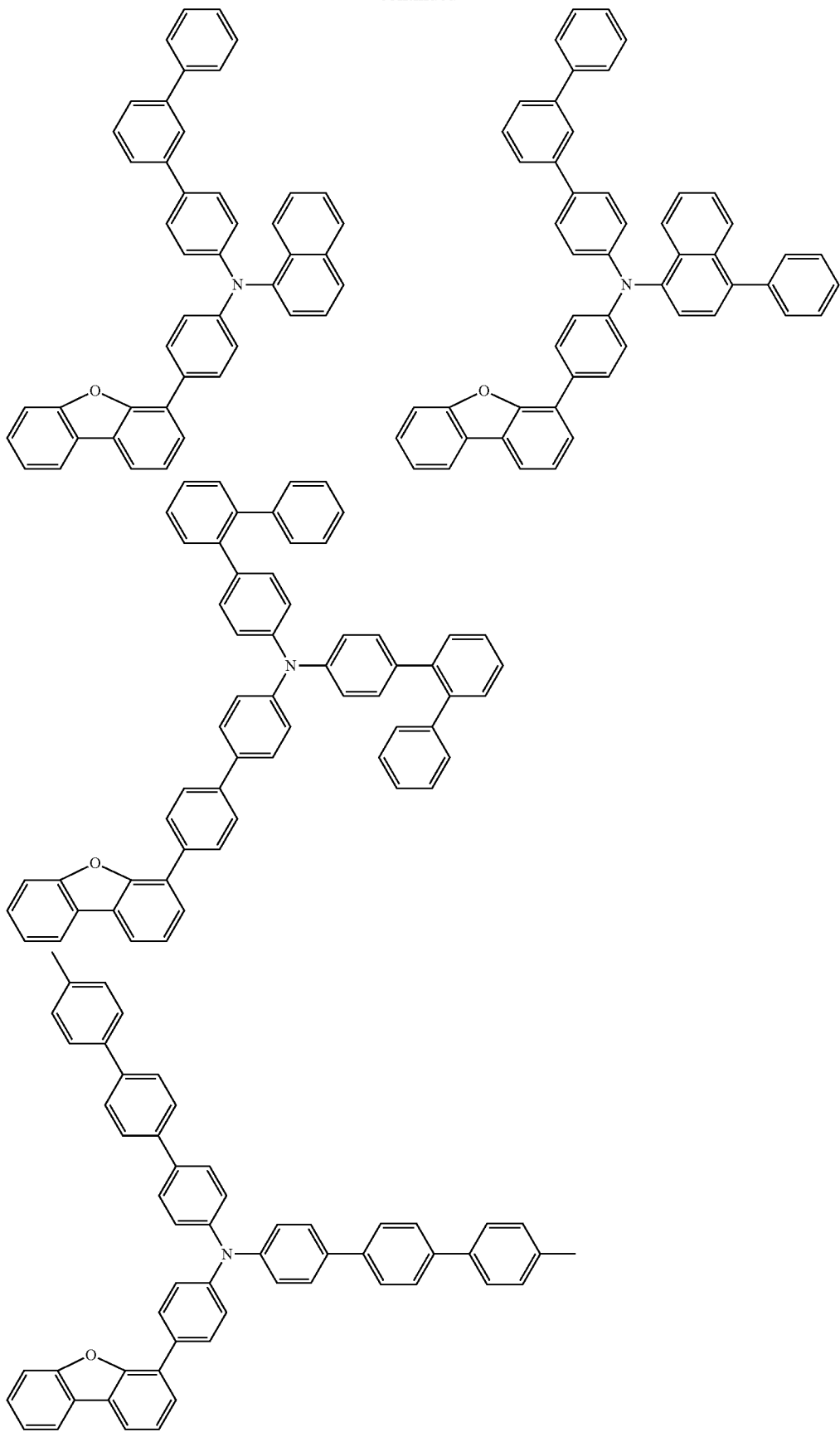

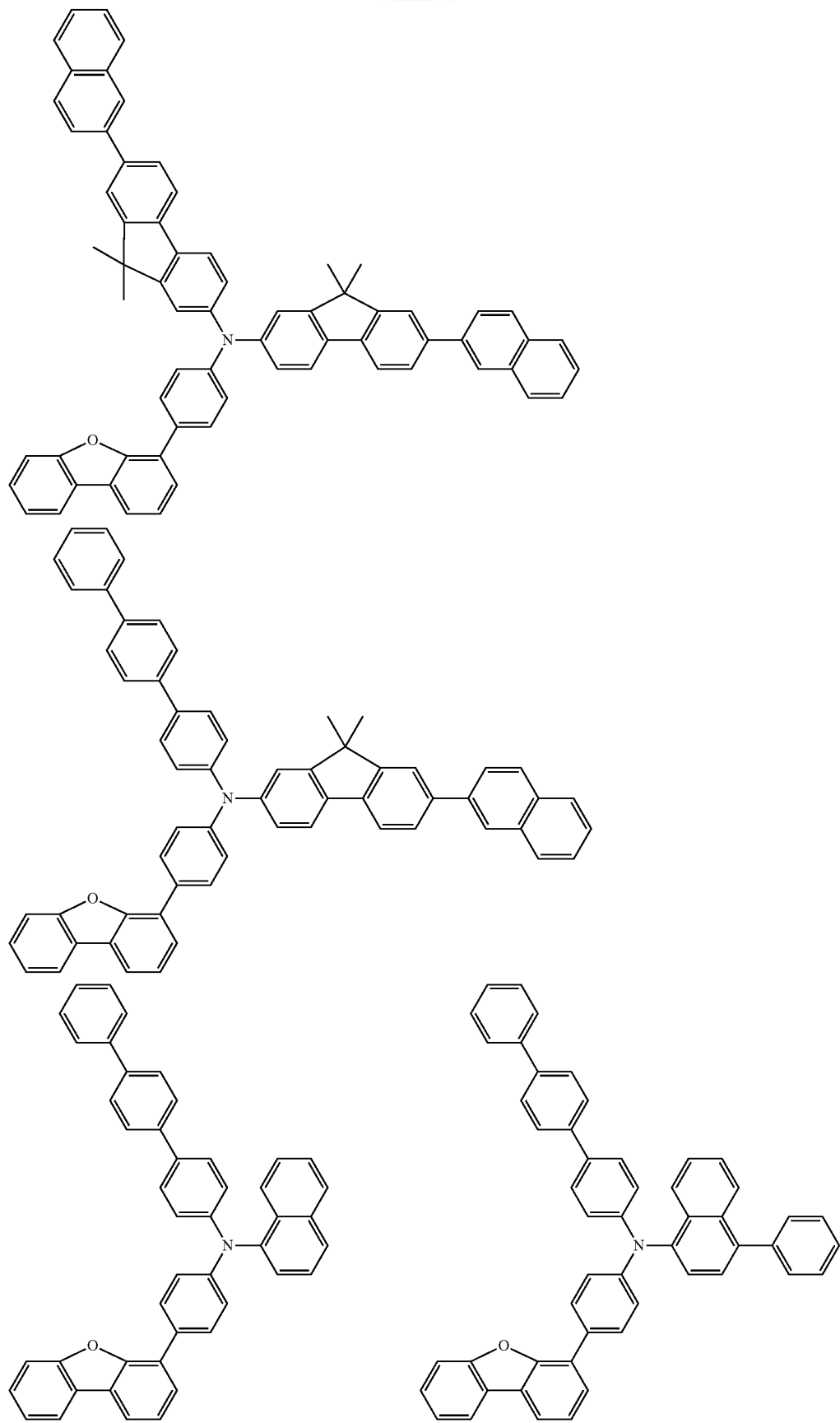

-continued
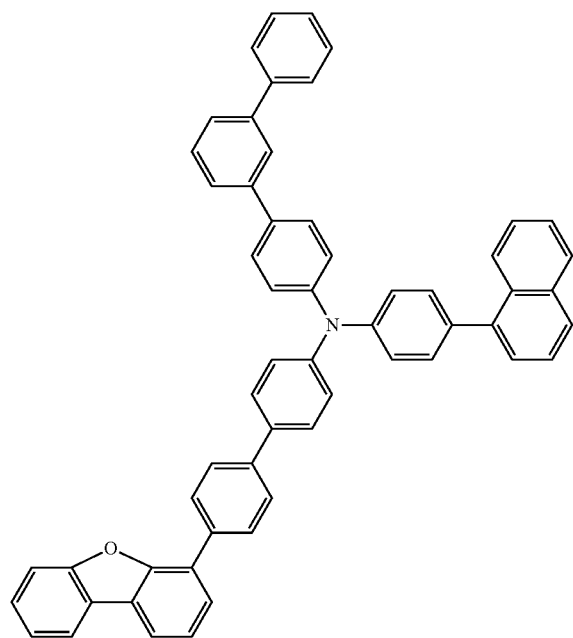
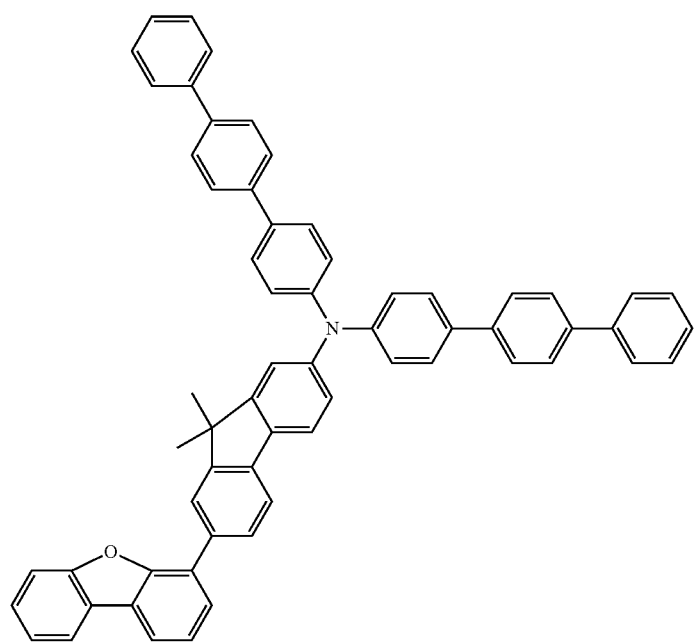

-continued
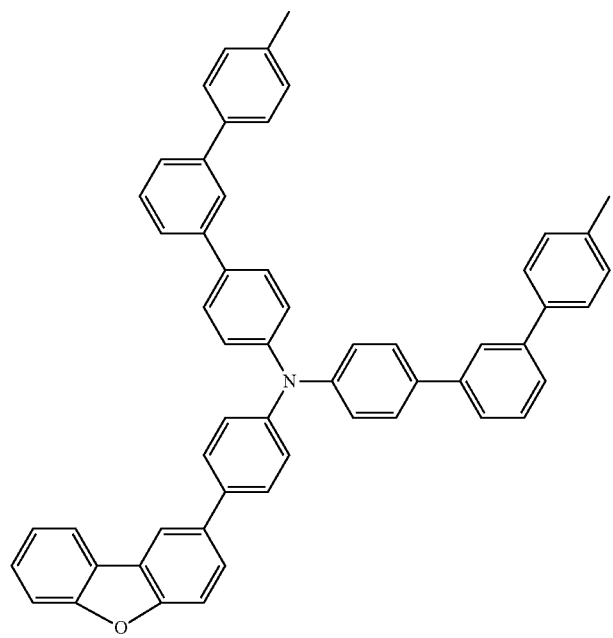 [SMILES: Cc1ccc(-c2cccc(-c3ccc(N(c4ccc(-c5cccc(-c6ccc(C)cc6)c5)cc4)c4ccc(-c5ccc6oc7ccccc7c6c5)cc4)cc3)c2)cc1]
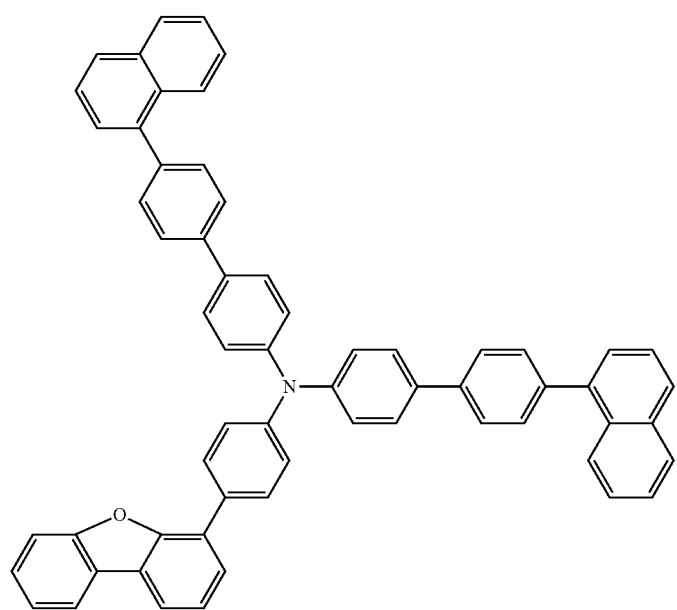 [SMILES: c1ccc2c(-c3ccc(-c4ccc(N(c5ccc(-c6ccc(-c7cccc8ccccc78)cc6)cc5)c5ccc(-c6cccc7c6oc6ccccc67)cc5)cc4)cc3)cccc2c1]

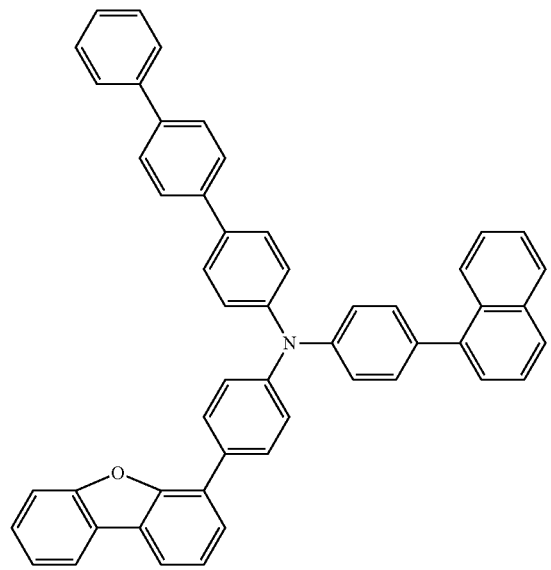 [SMILES: c1ccc(-c2ccc(-c3ccc(N(c4ccc(-c5cccc6ccccc56)cc4)c4ccc(-c5cccc6c5oc5ccccc56)cc4)cc3)cc2)cc1]
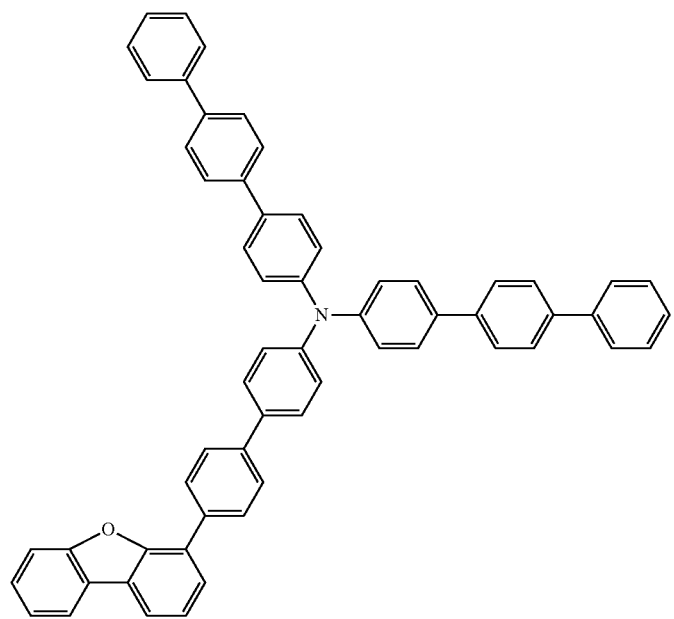

-continued
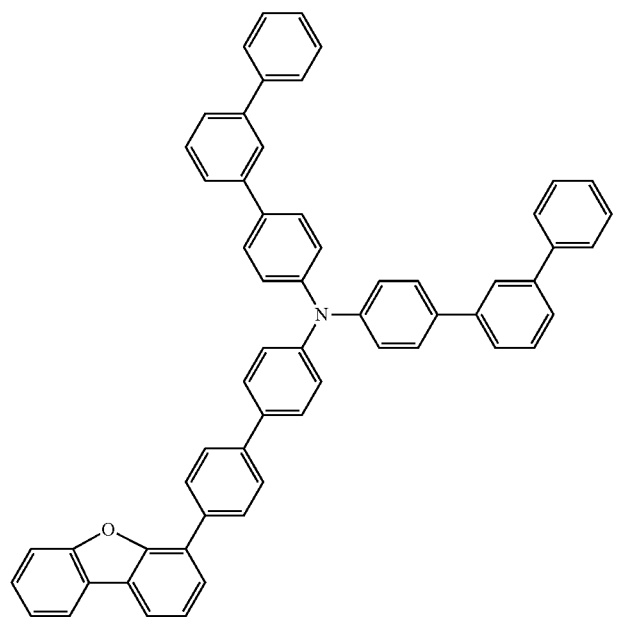
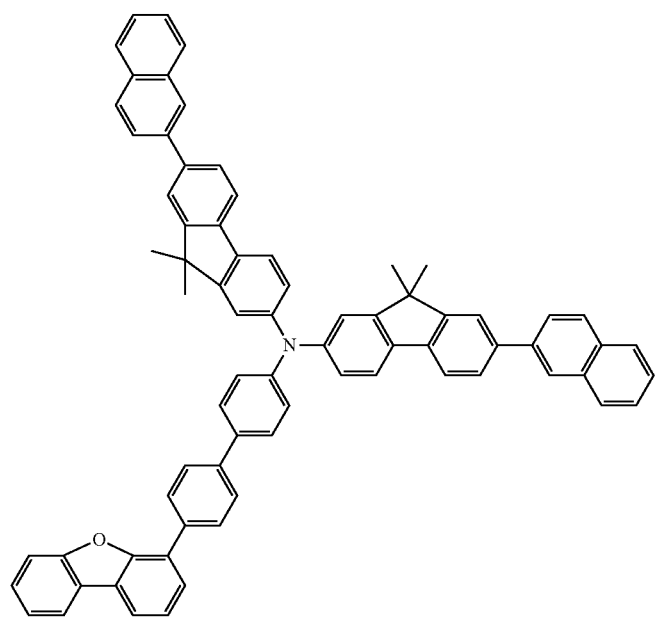 [SMILES: CC1(C)c2cc(-c3ccc4ccccc4c3)ccc2-c2ccc(N(c3ccc(-c4ccc(-c5cccc6c5oc5ccccc56)cc4)cc3)c3ccc4c(c3)C(C)(C)c3cc(-c5ccc6ccccc6c5)ccc3-4)cc21]

-continued
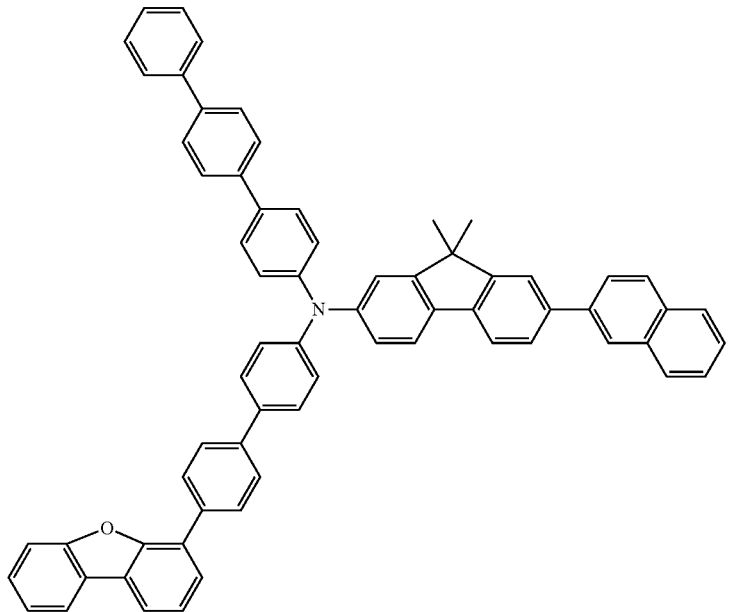 [SMILES: CC1(C)c2cc(-c3ccc4ccccc4c3)ccc2-c2ccc(N(c3ccc(-c4ccc(-c5ccccc5)cc4)cc3)c3ccc(-c4ccc(-c5cccc6c5oc5ccccc56)cc4)cc3)cc21]
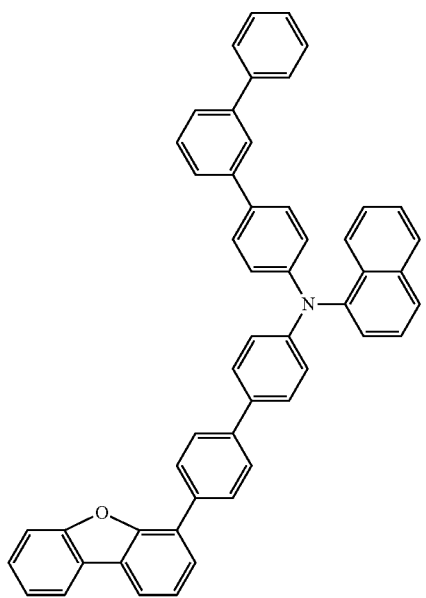 [SMILES: c1ccc(-c2cccc(-c3ccc(N(c4ccc(-c5ccc(-c6cccc7c6oc6ccccc67)cc5)cc4)c4cccc5ccccc45)cc3)c2)cc1]

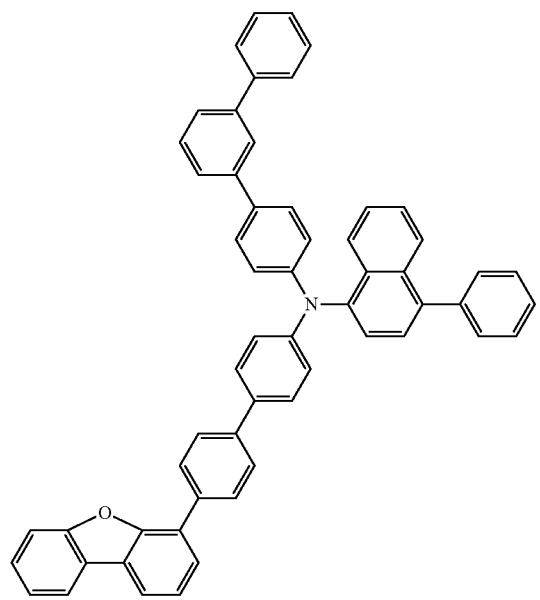 [SMILES: c1ccc(-c2cccc(-c3ccc(N(c4ccc(-c5ccc(-c6cccc7c6oc6ccccc67)cc5)cc4)c4ccc(-c5ccccc5)c5ccccc45)cc3)c2)cc1]
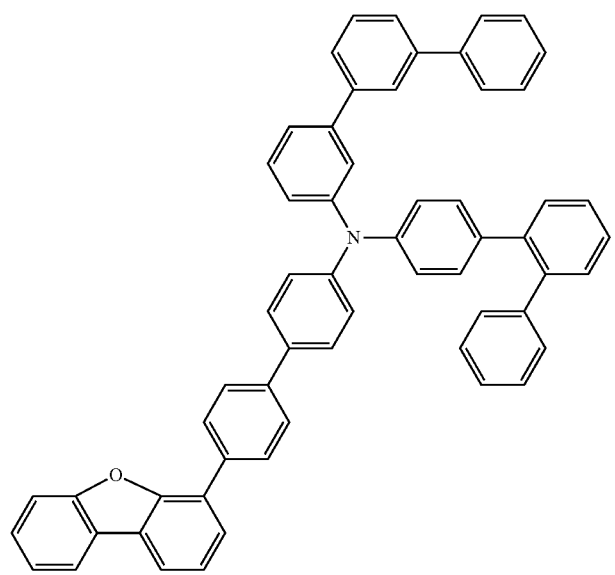 [SMILES: c1ccc(-c2cccc(-c3cccc(N(c4ccc(-c5ccc(-c6cccc7c6oc6ccccc67)cc5)cc4)c4ccc(-c5ccccc5-c5ccccc5)cc4)c3)c2)cc1]

37 38
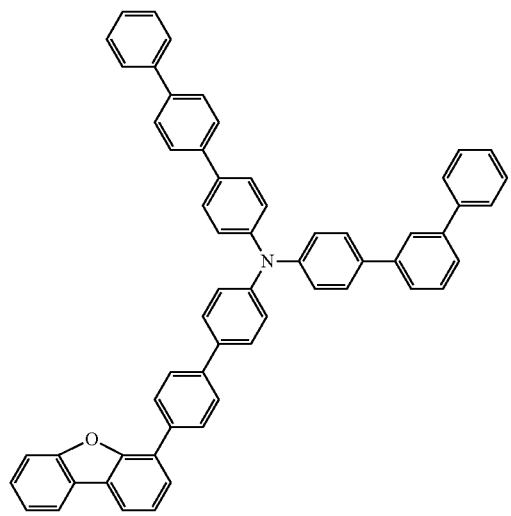
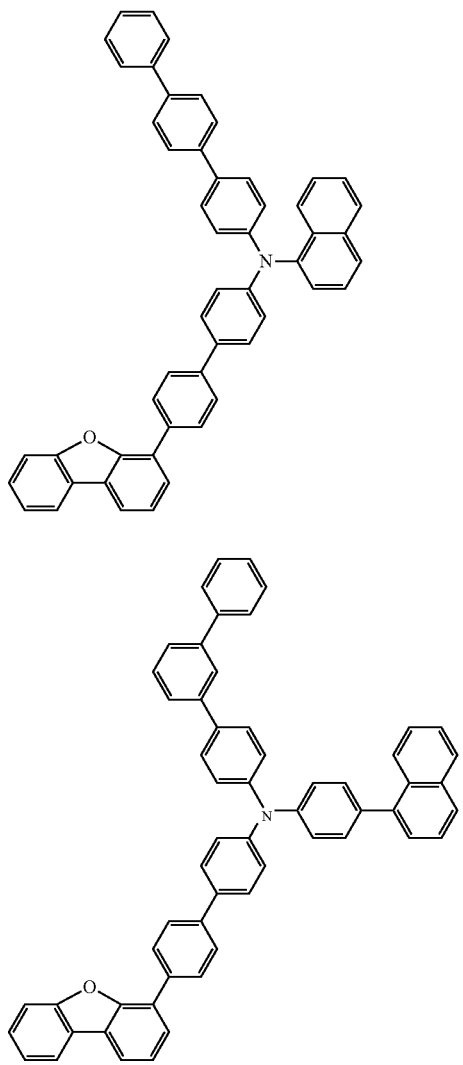
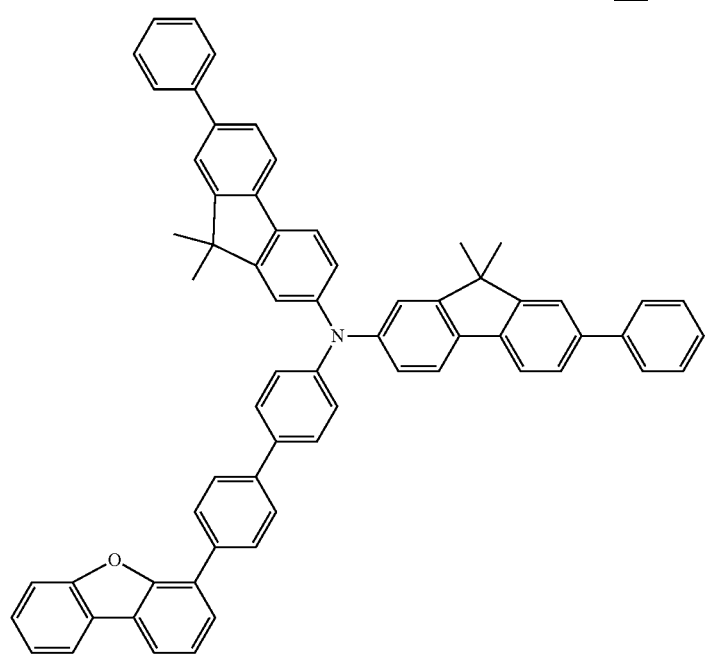

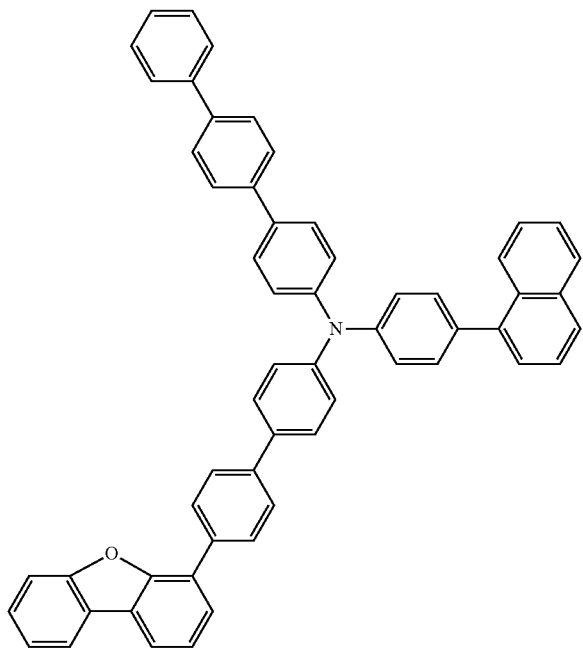
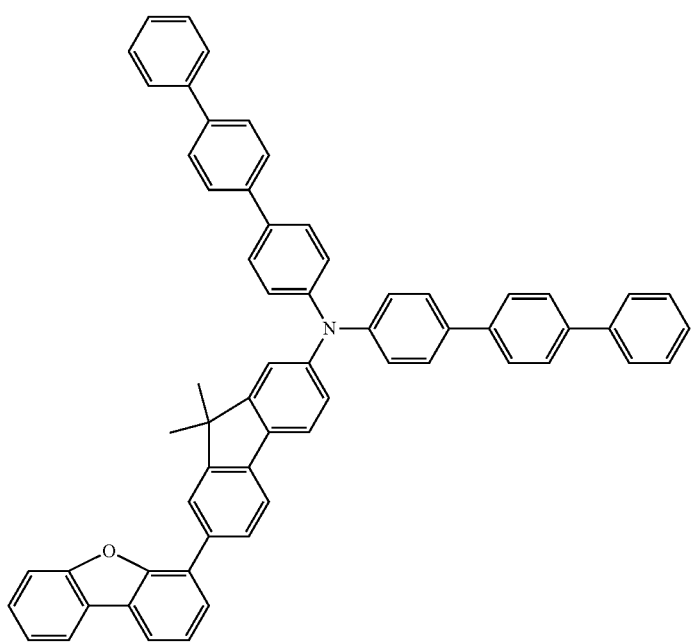

-continued
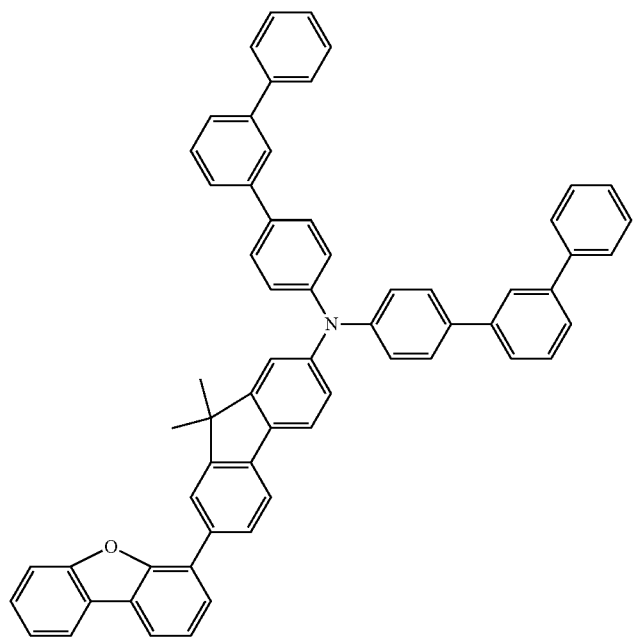
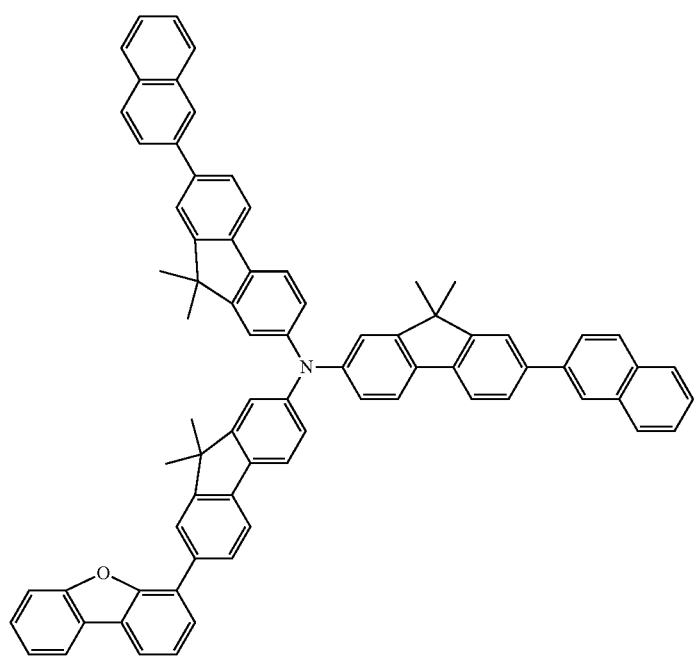

-continued
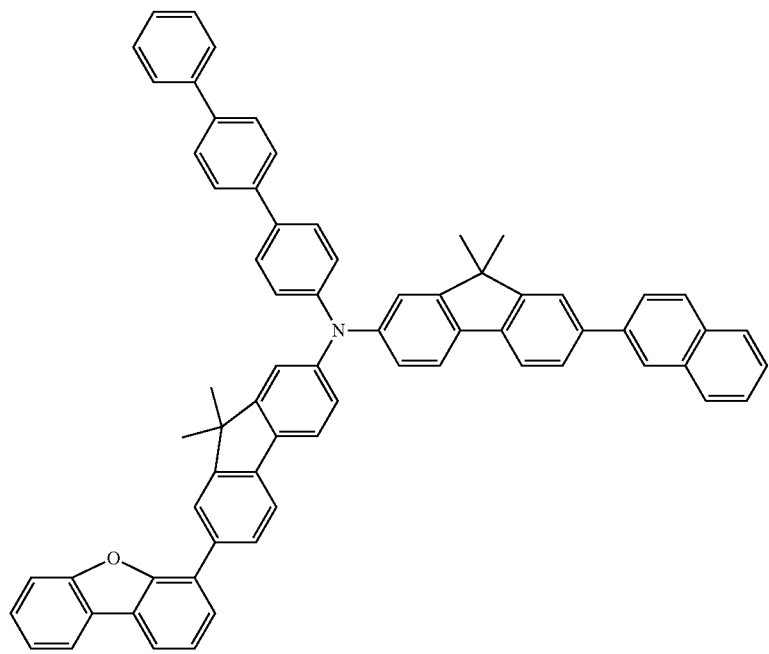
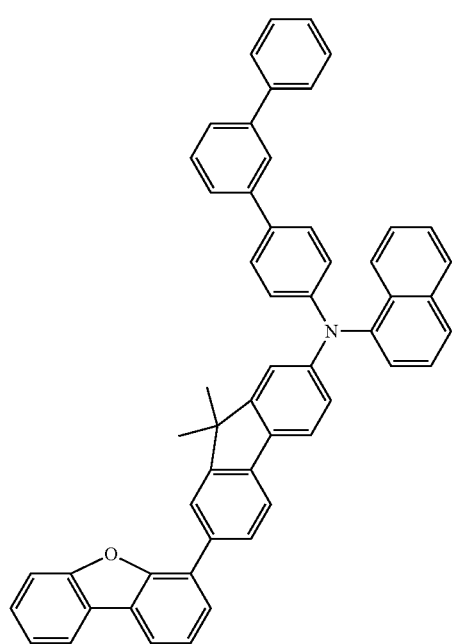
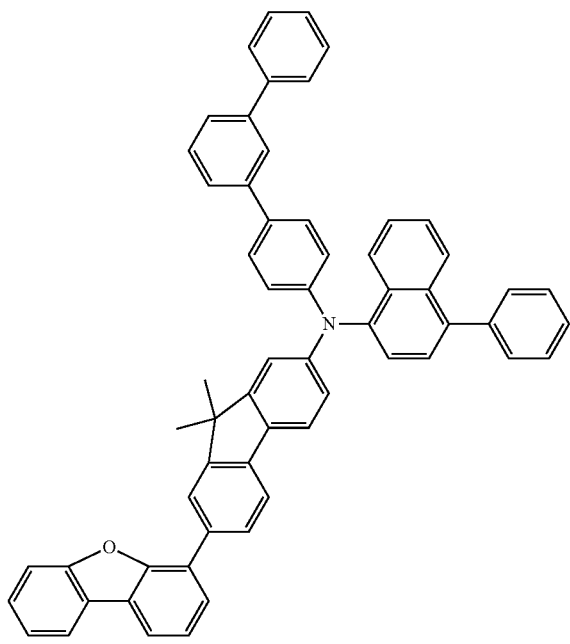

-continued
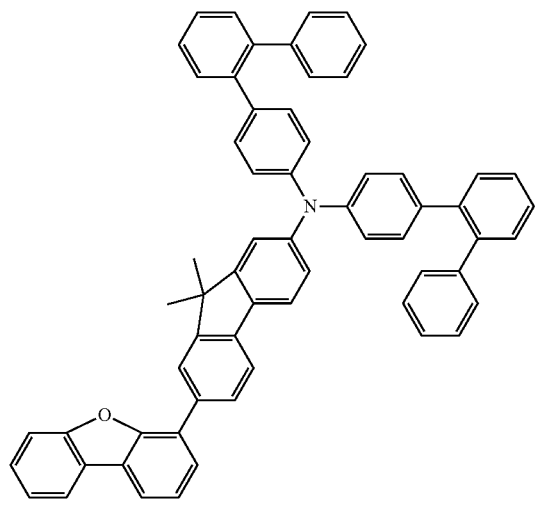
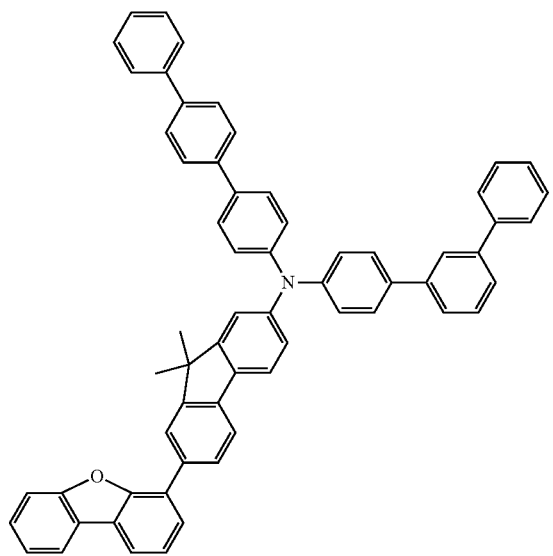
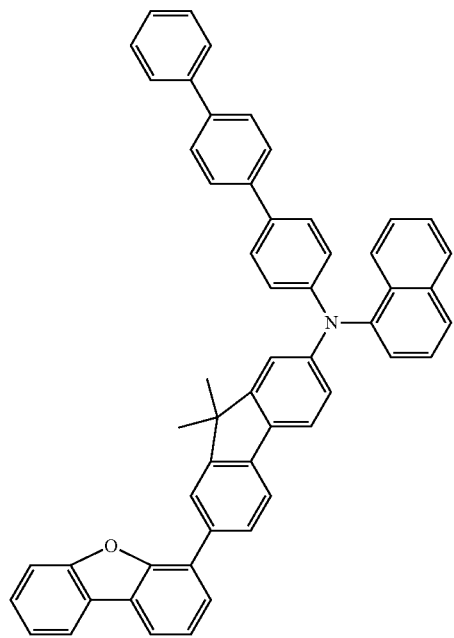
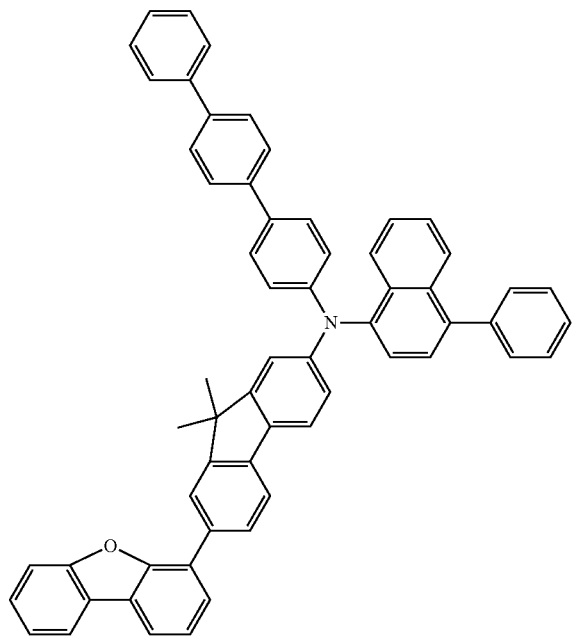

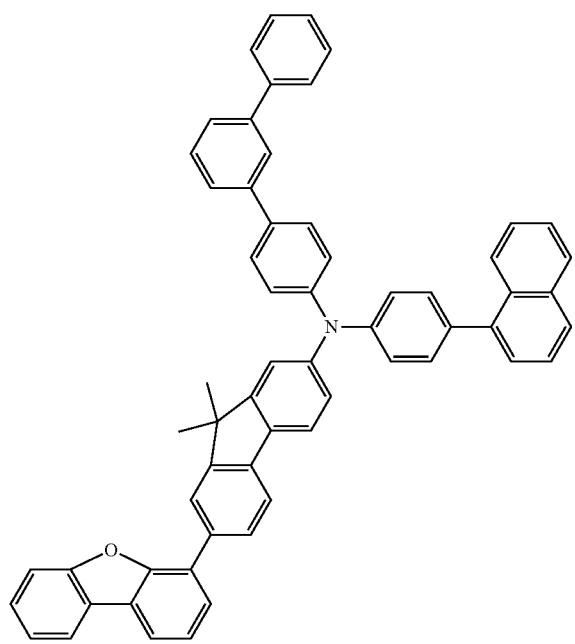
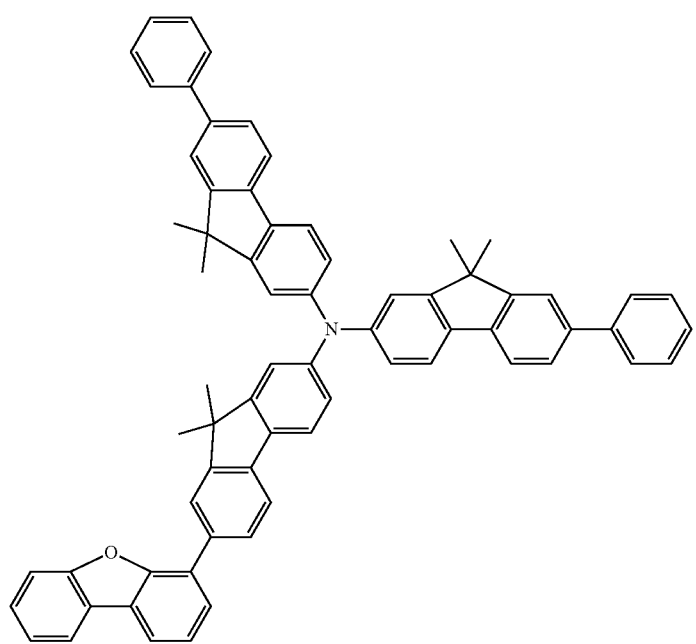

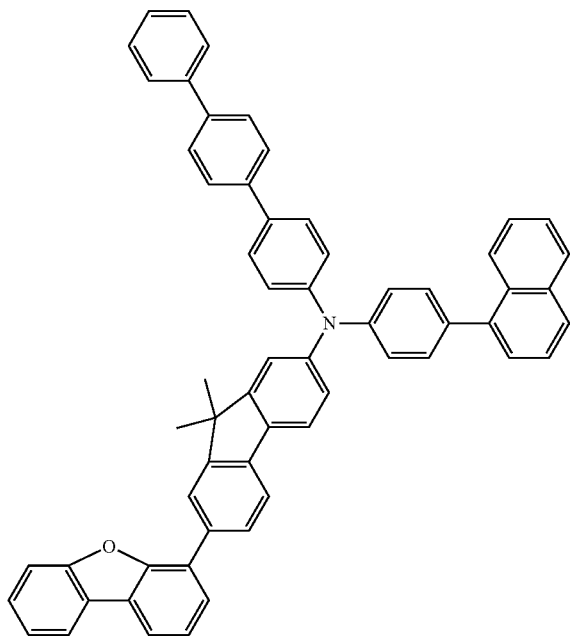
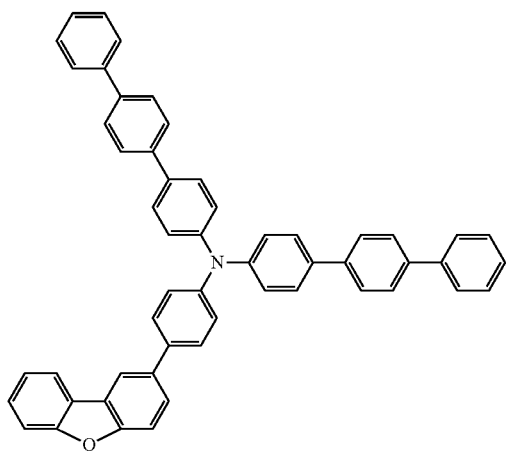
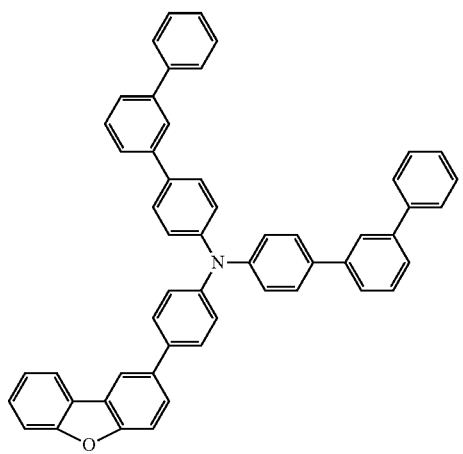
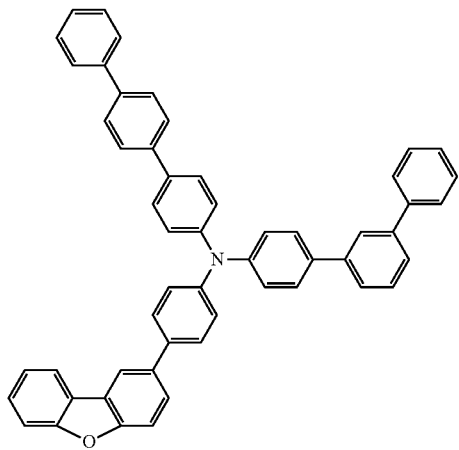
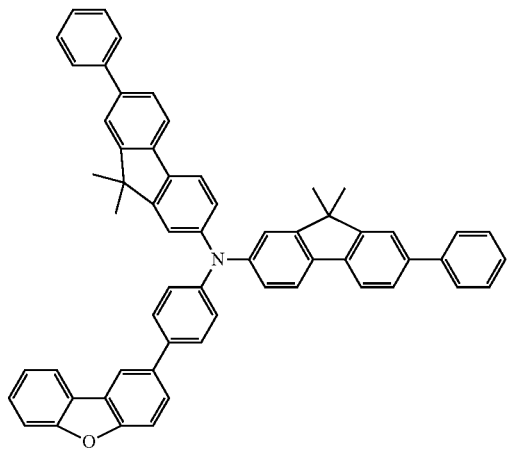

-continued
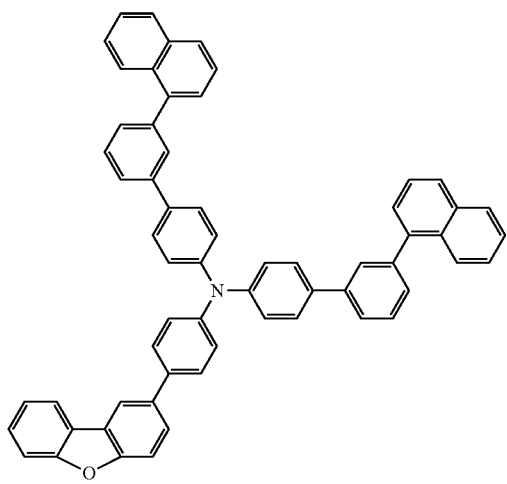
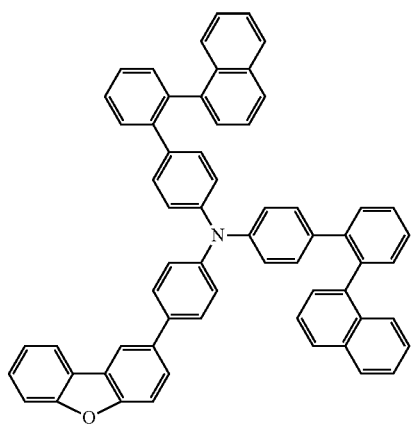
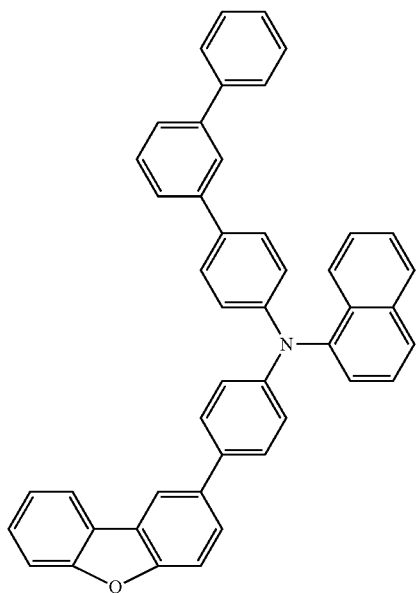
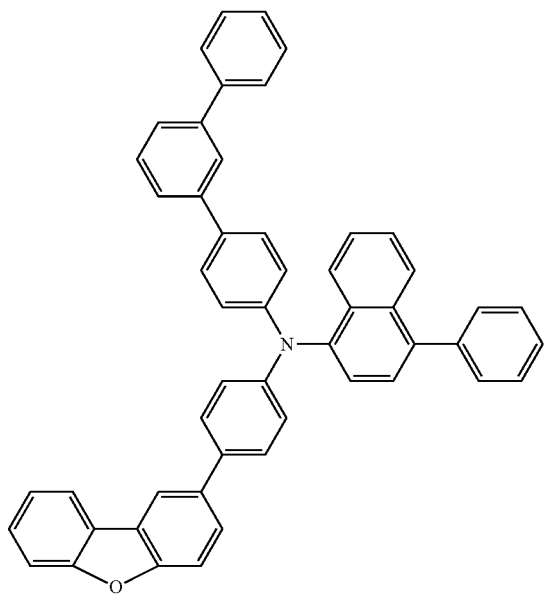
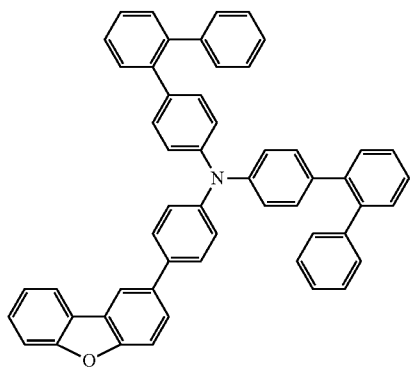
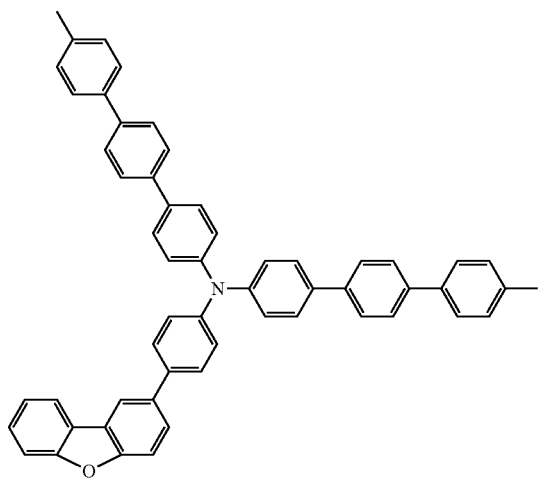

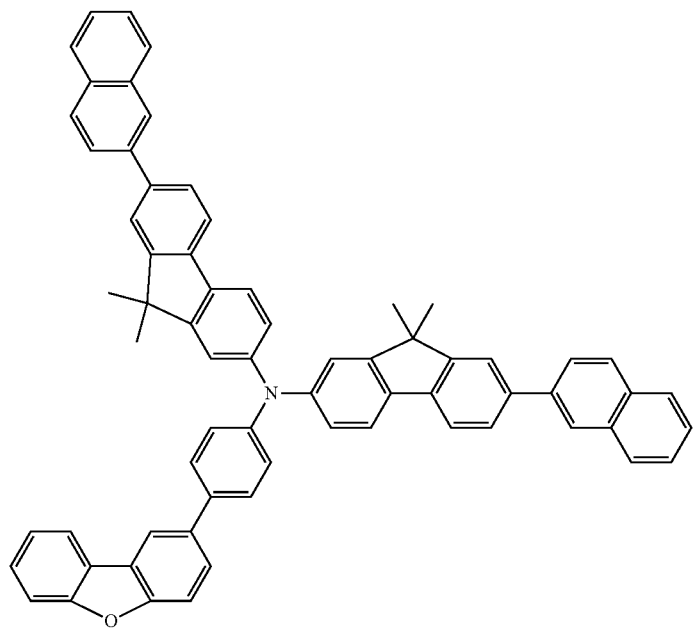
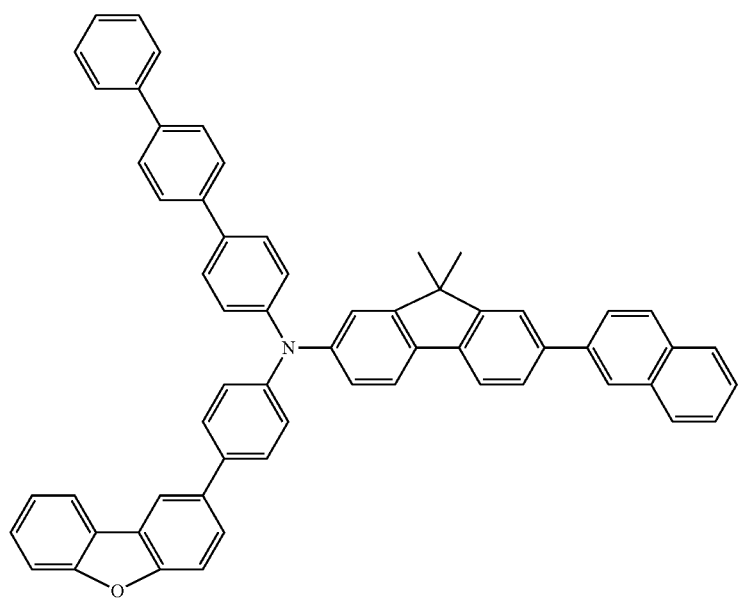

-continued
55
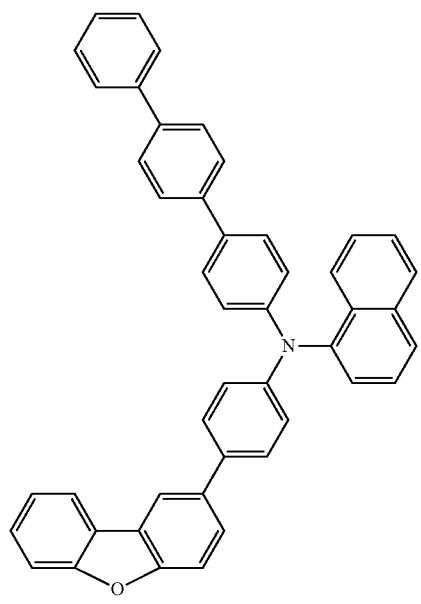
56
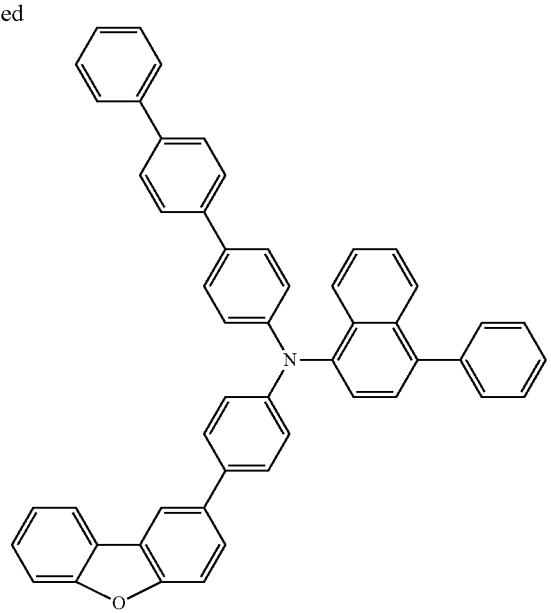
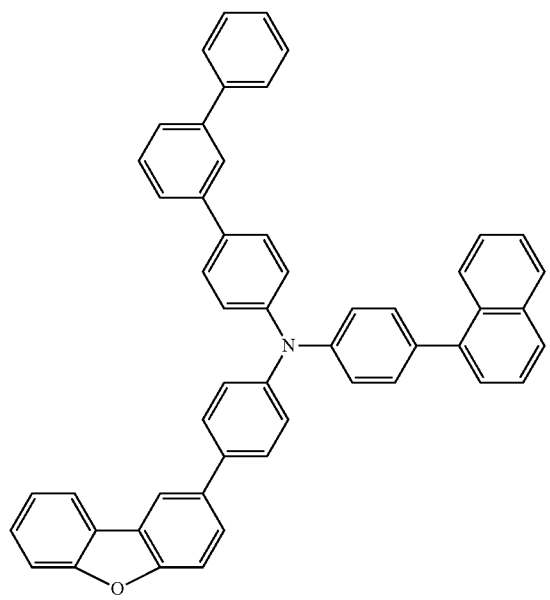
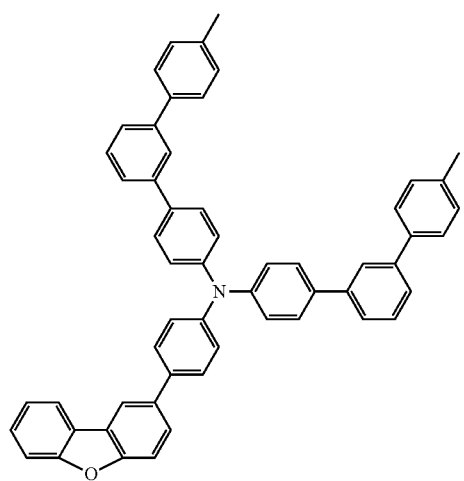
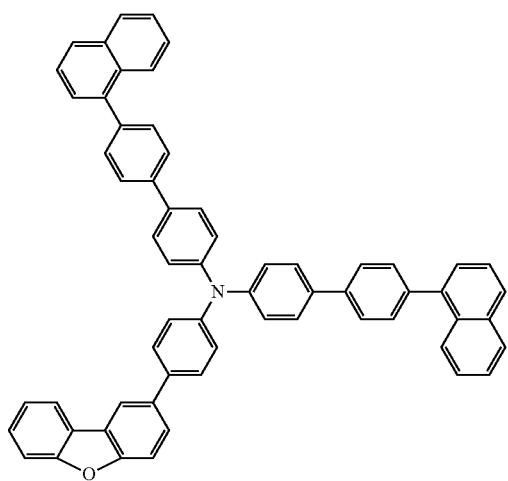

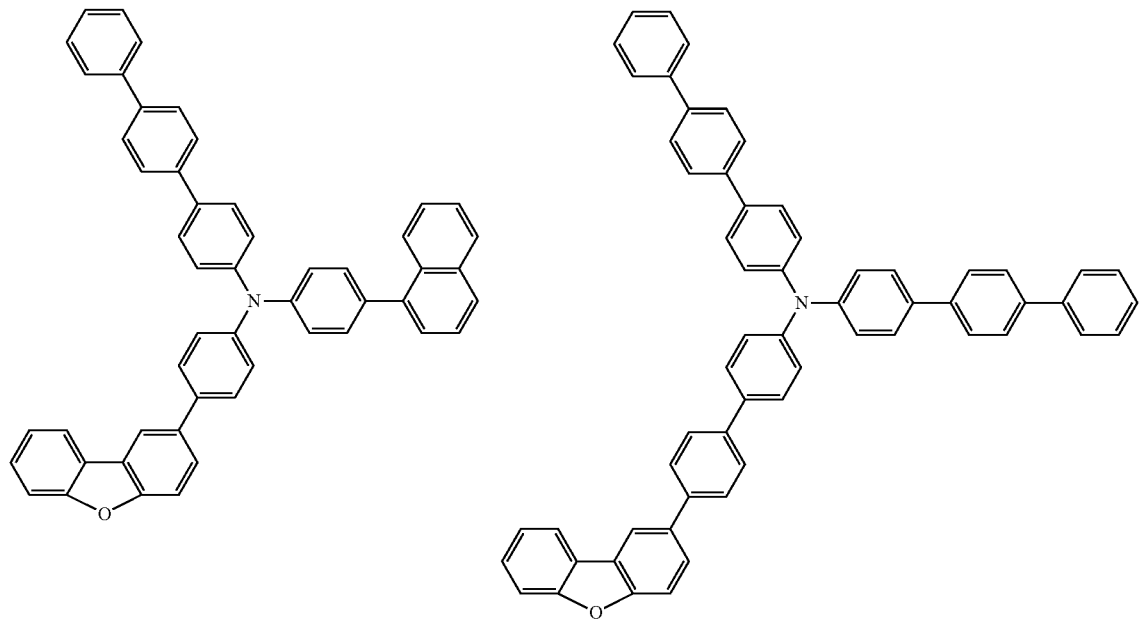
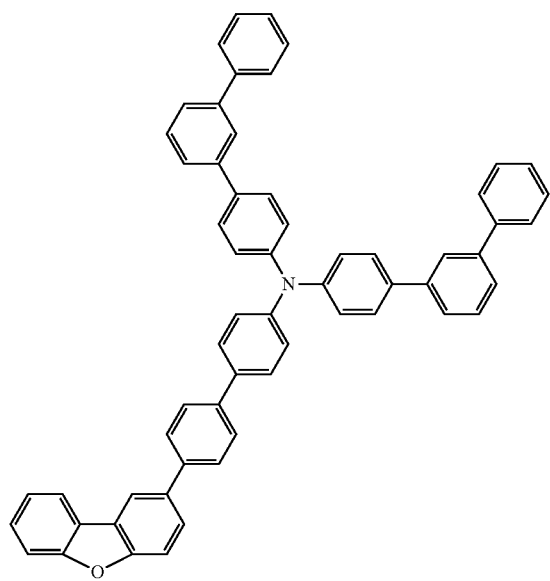

-continued
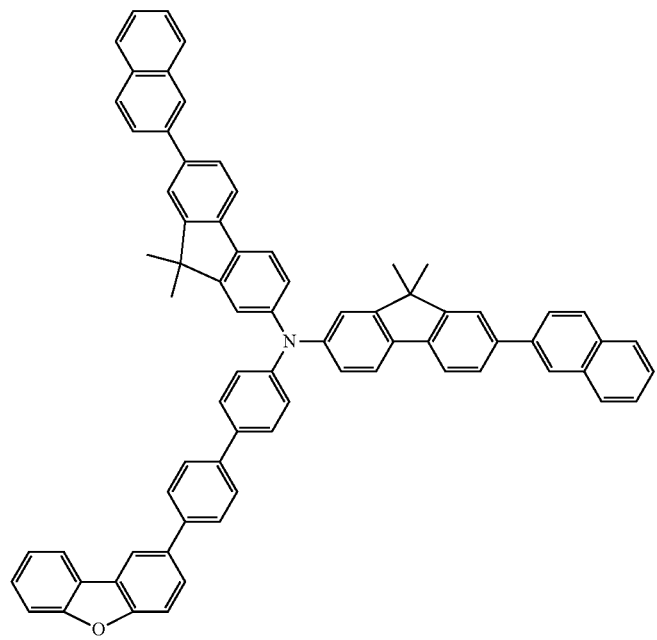
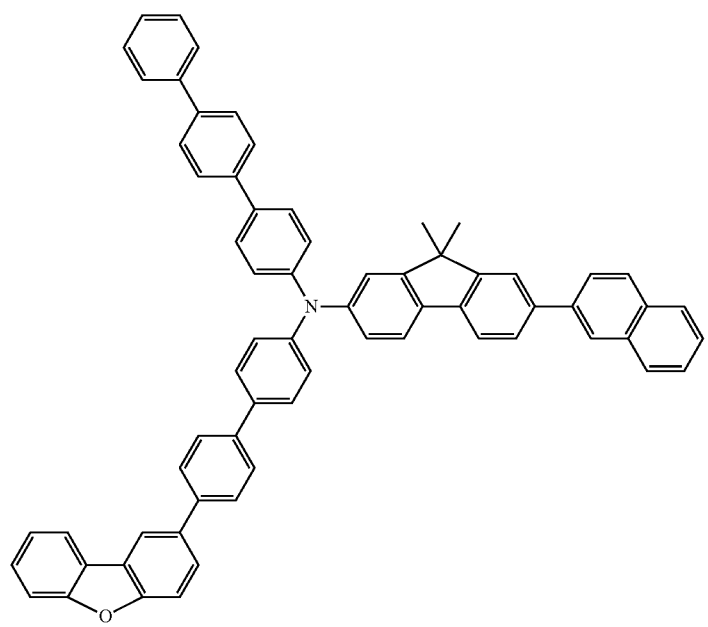

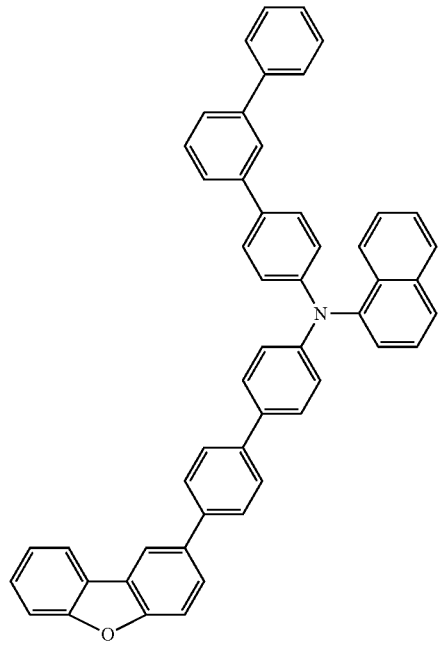
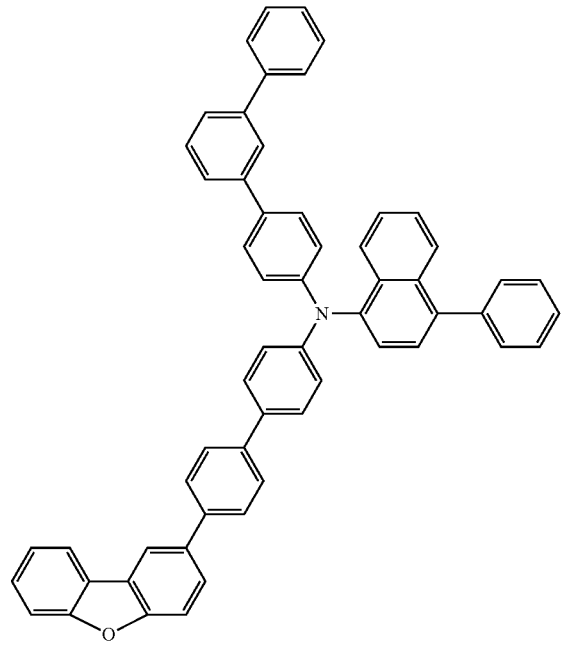
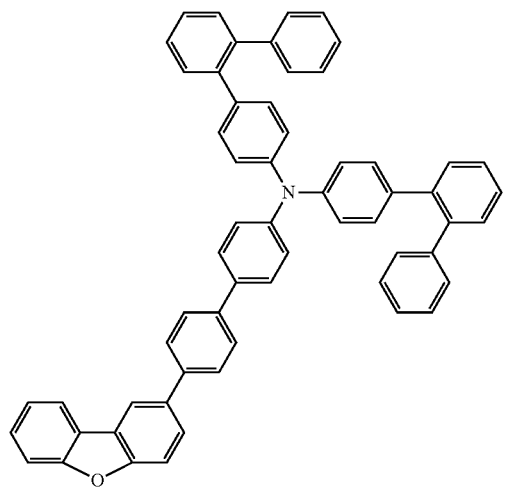
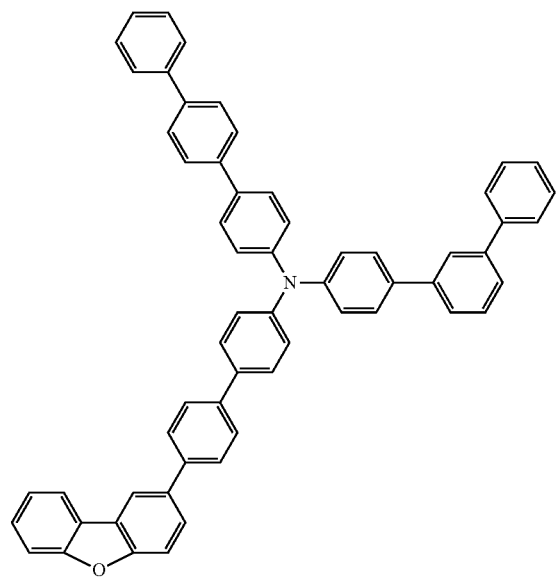

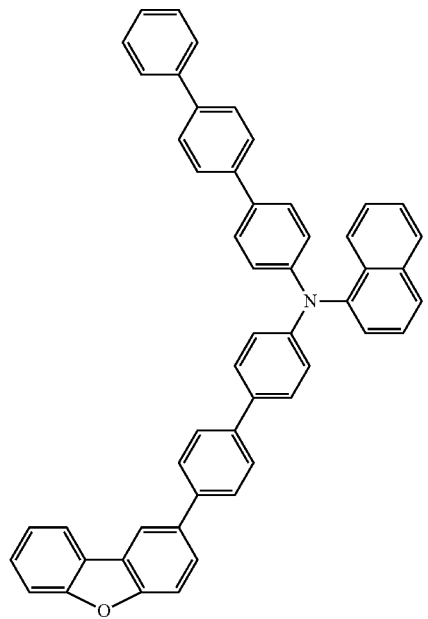
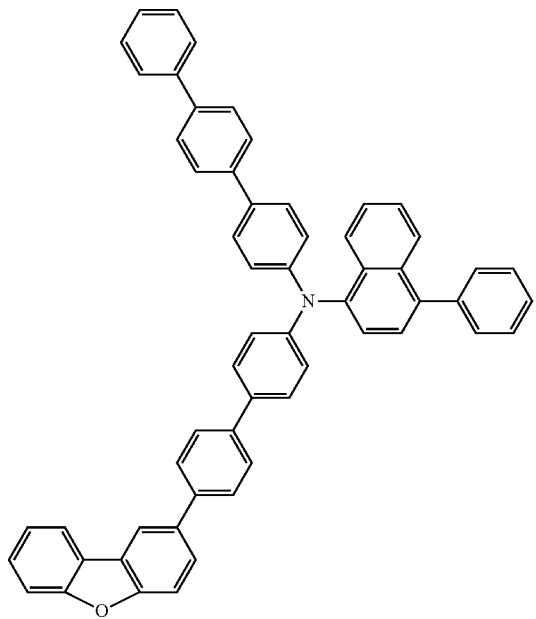
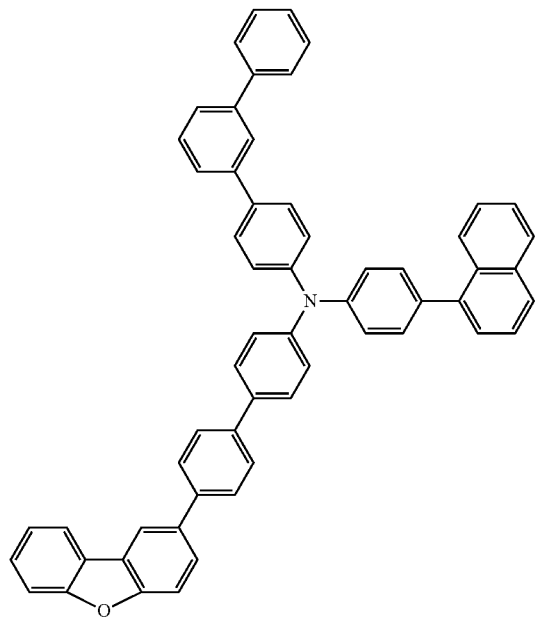

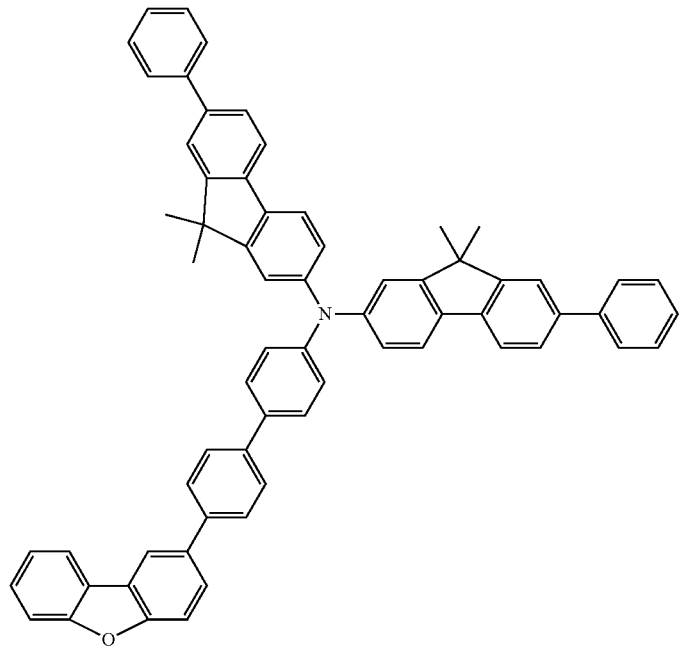
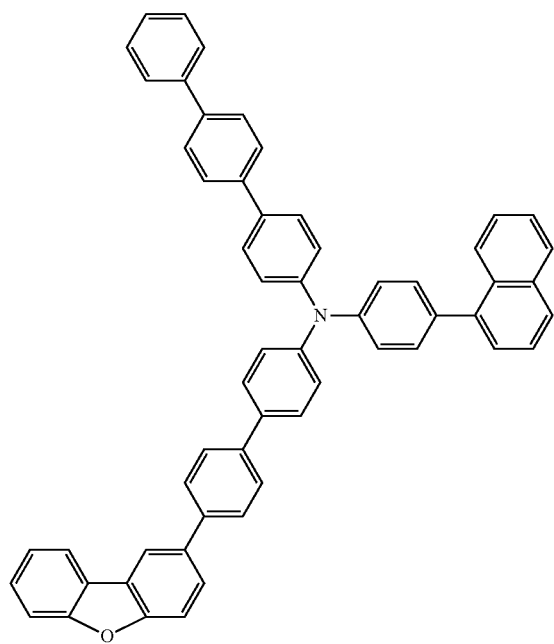

-continued
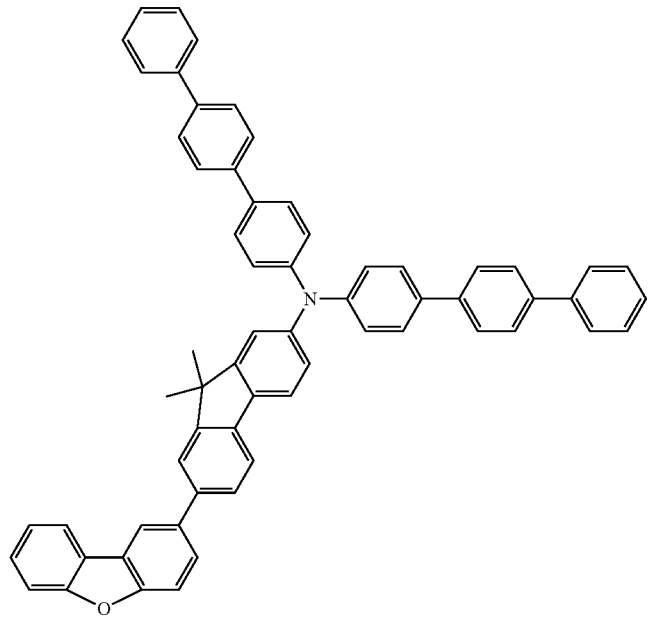
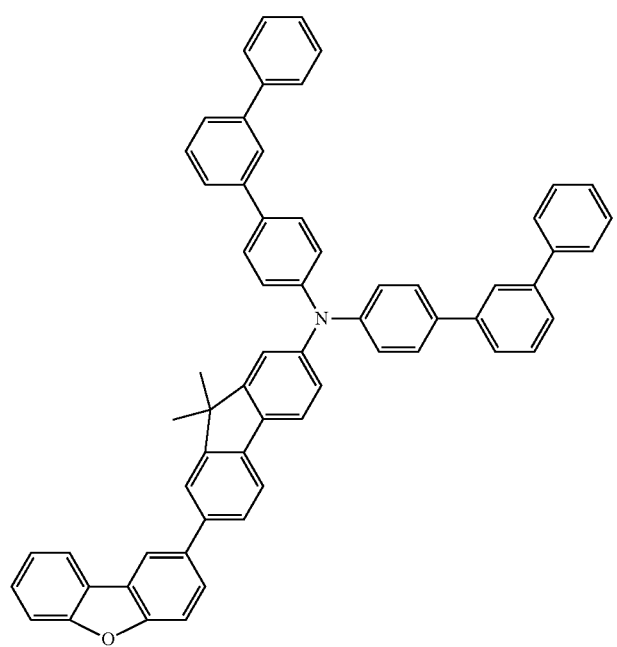

-continued
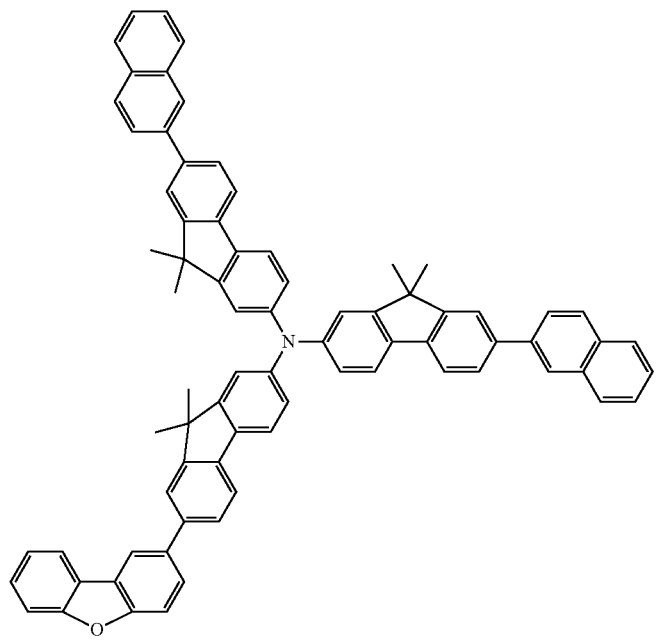
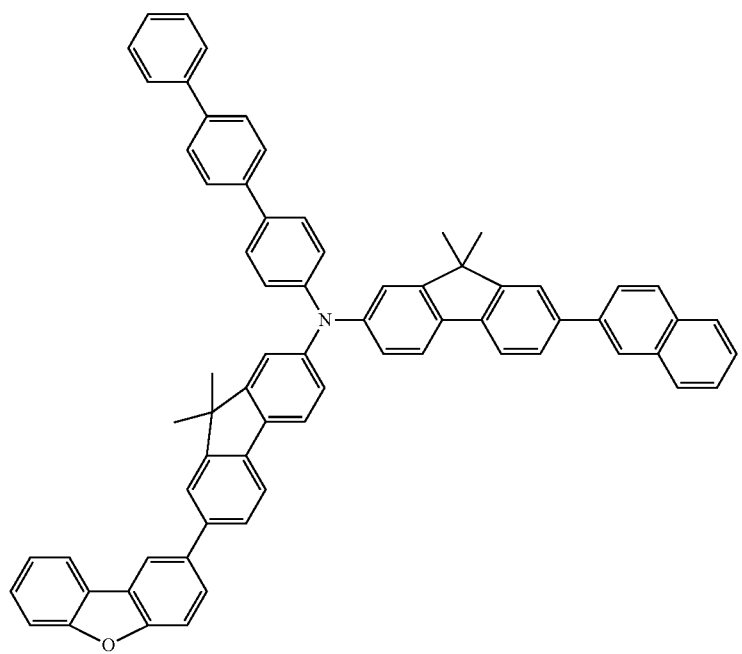

-continued
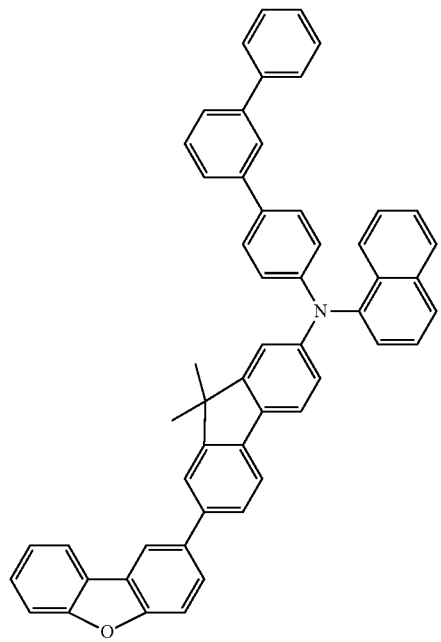
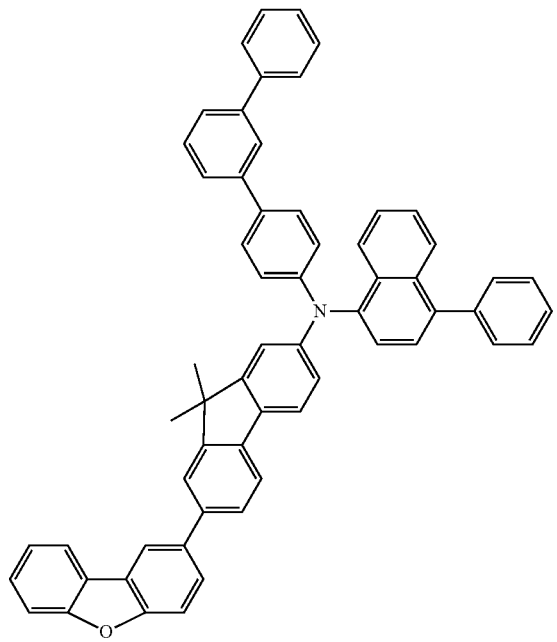
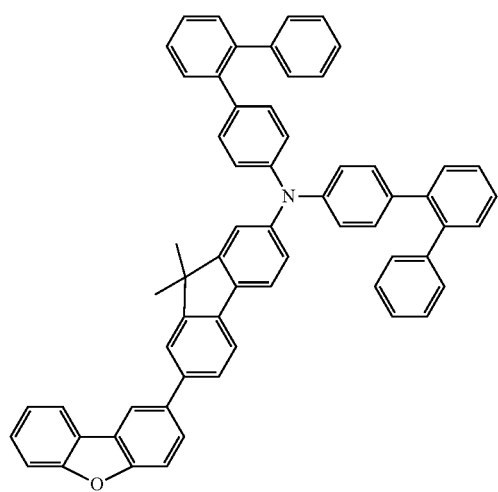
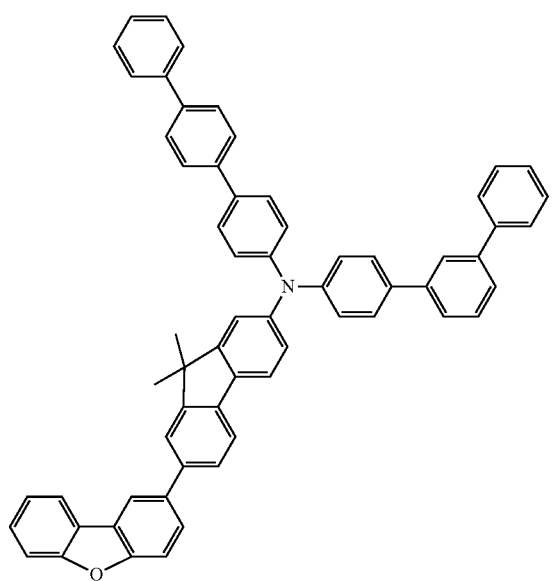

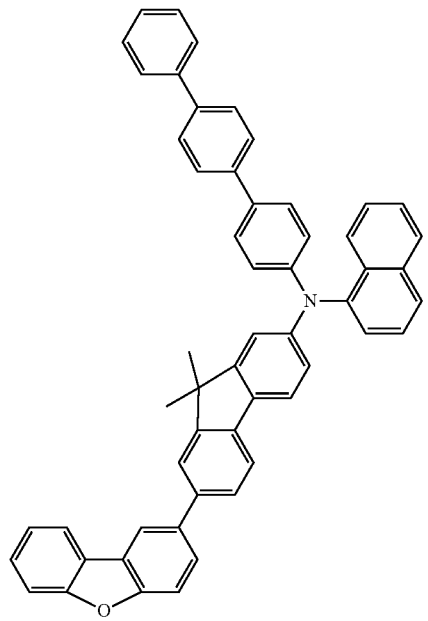
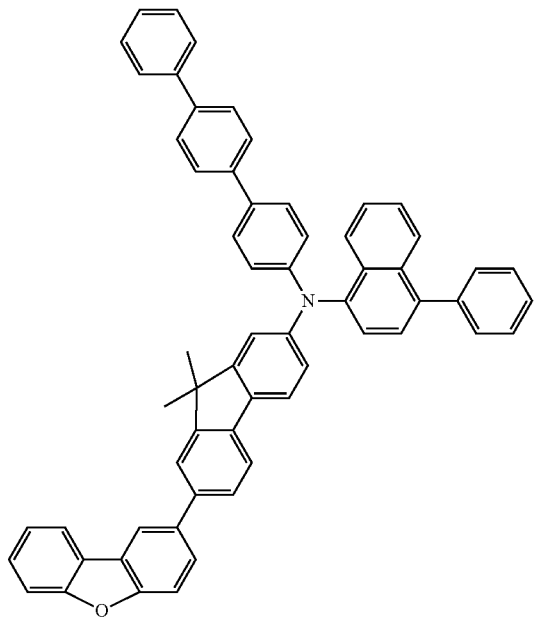
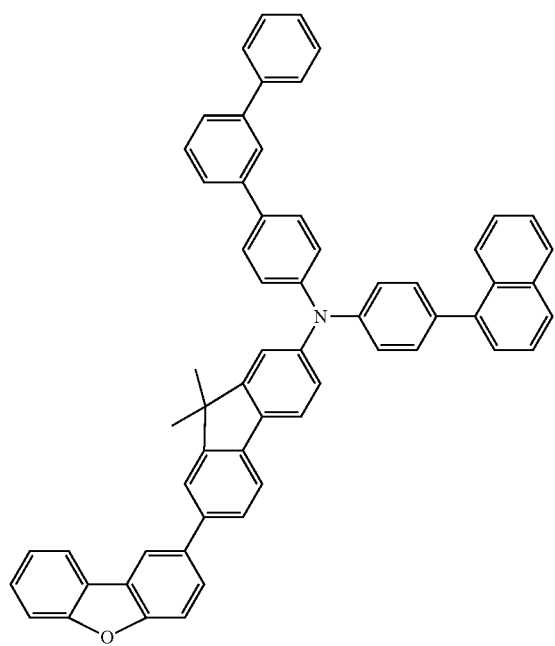

-continued
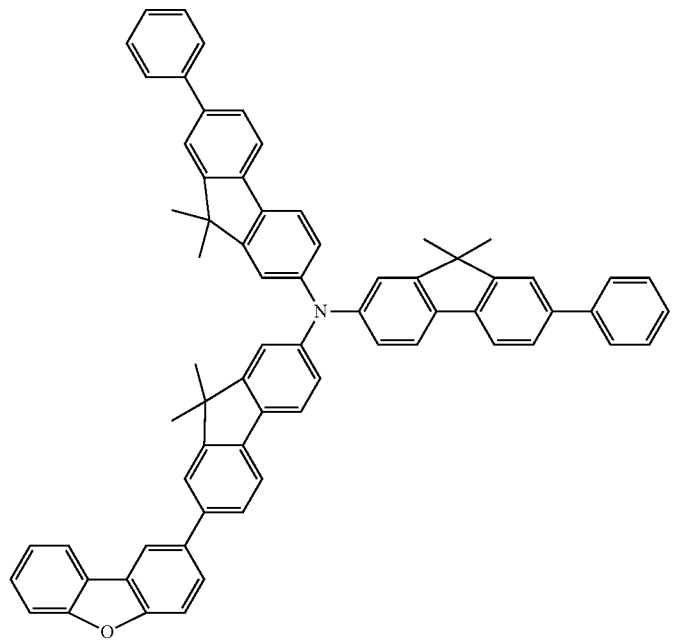
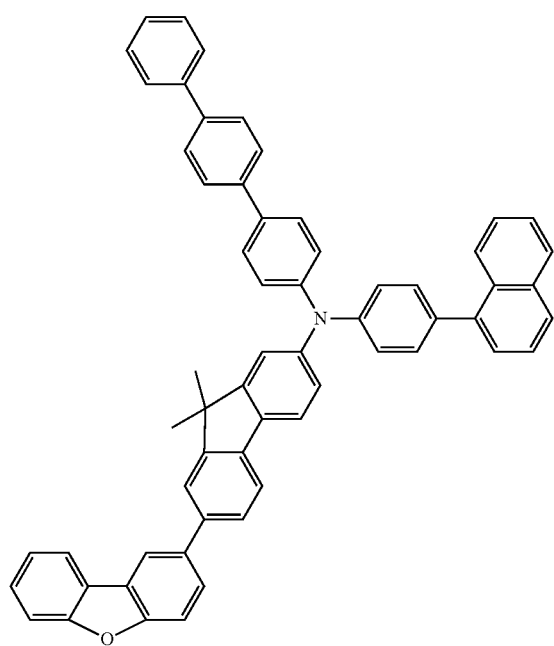

-continued
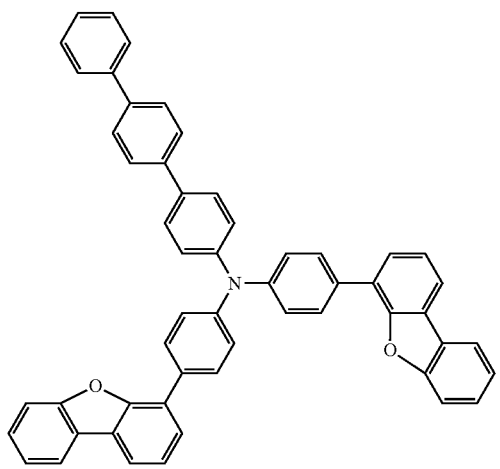
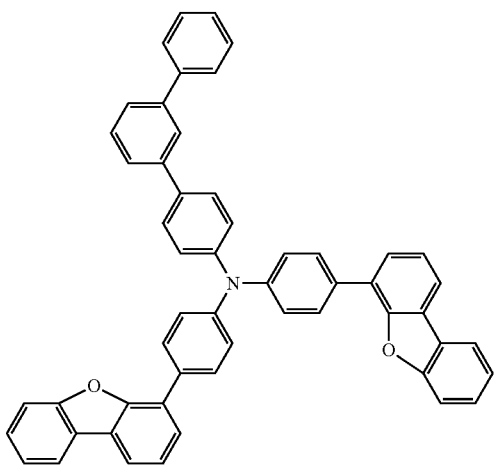
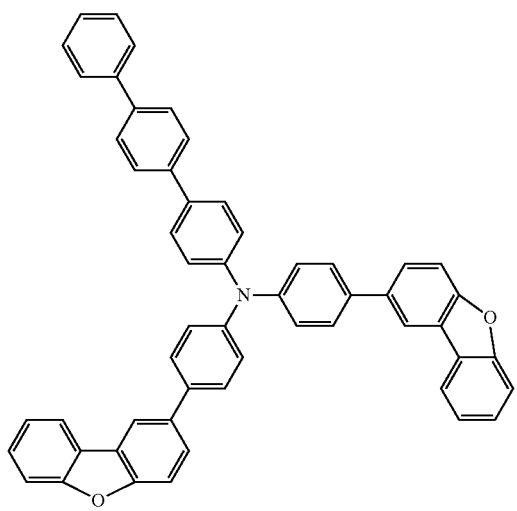
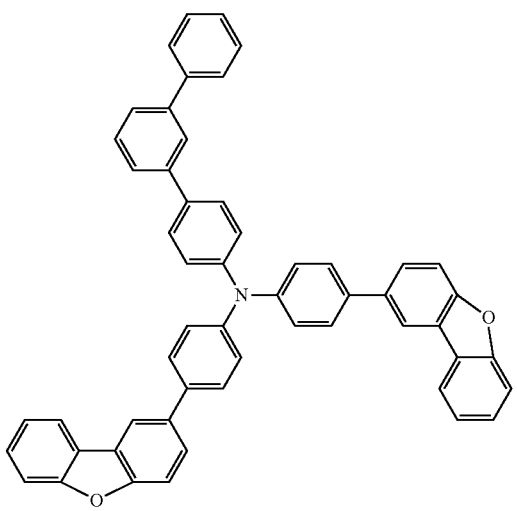
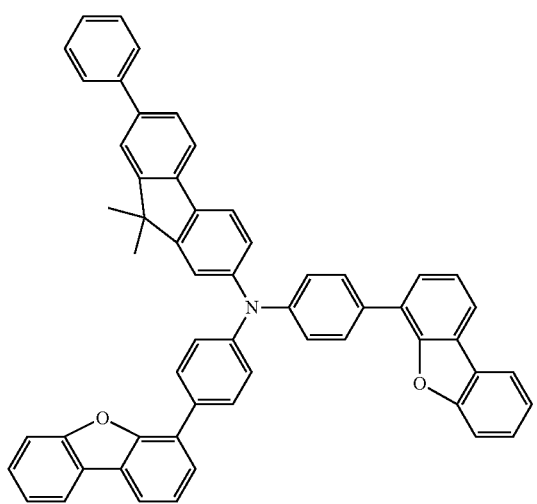

-continued
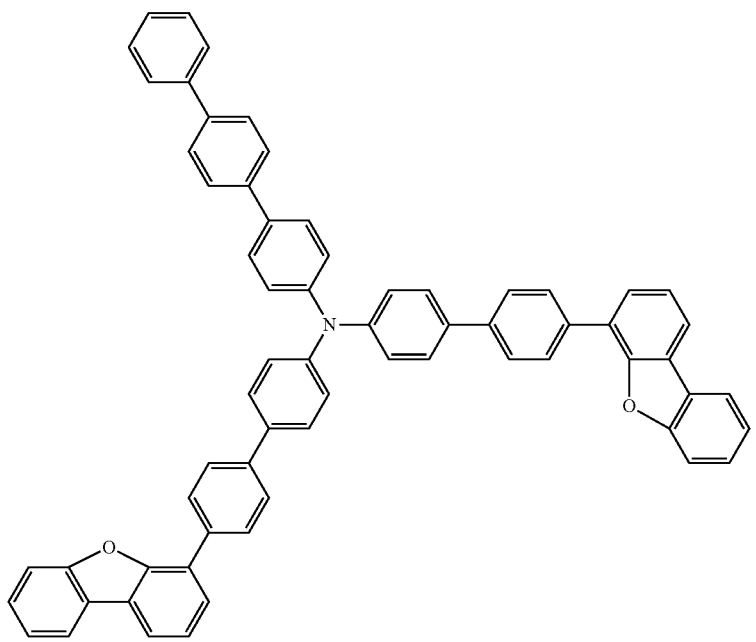
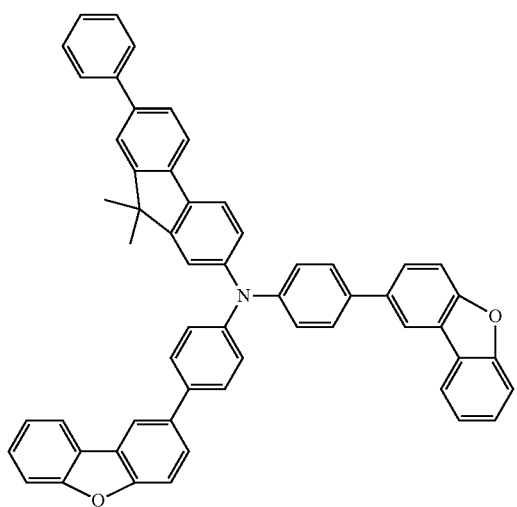

-continued
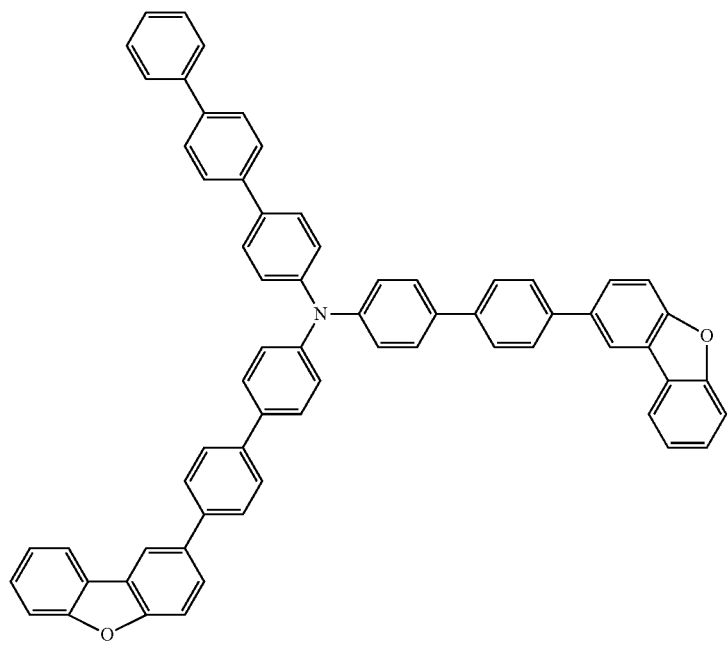
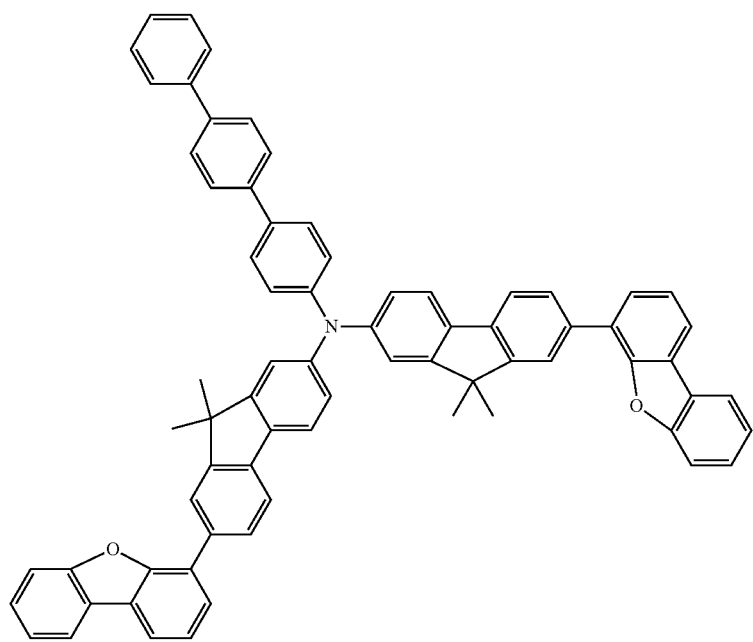

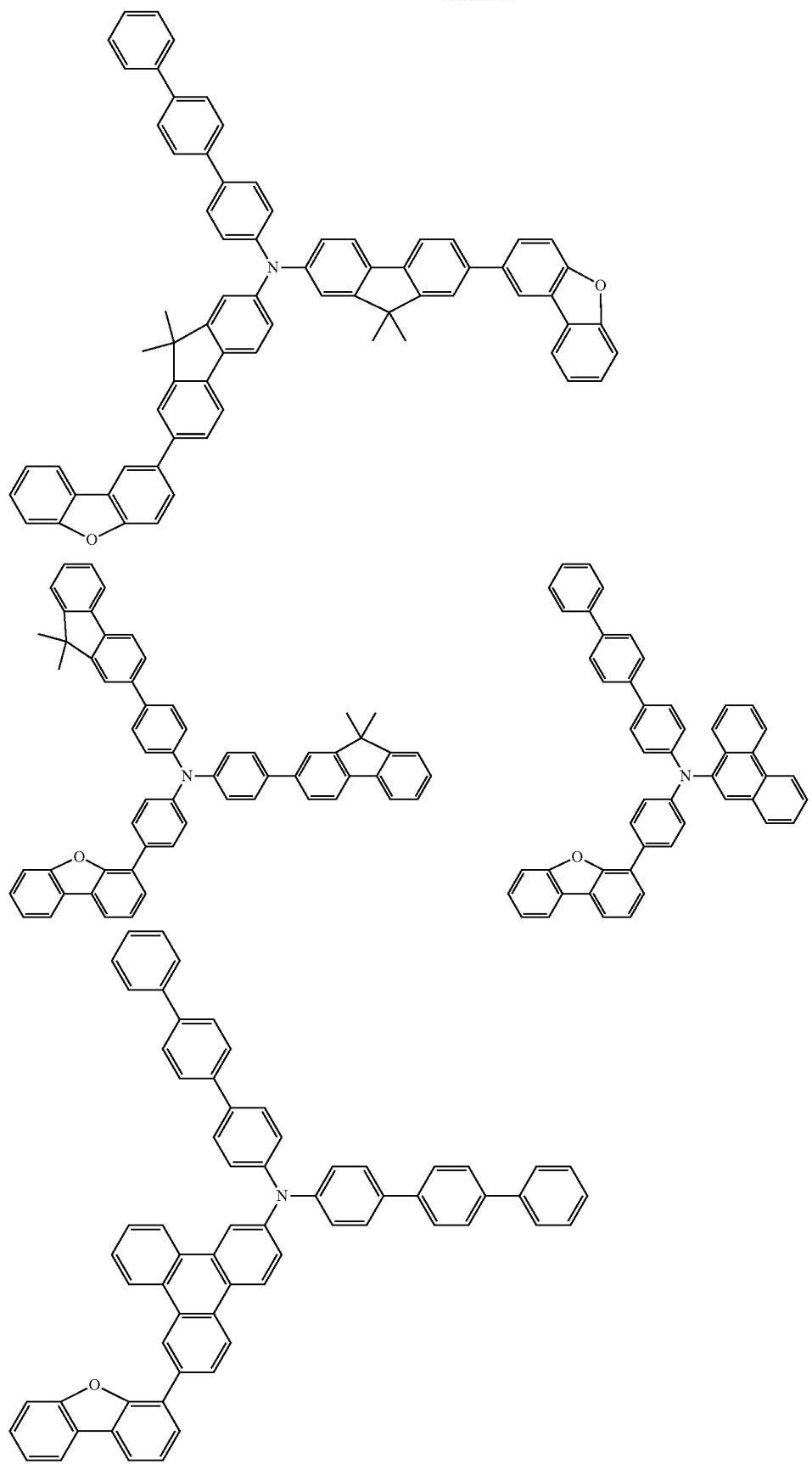

-continued
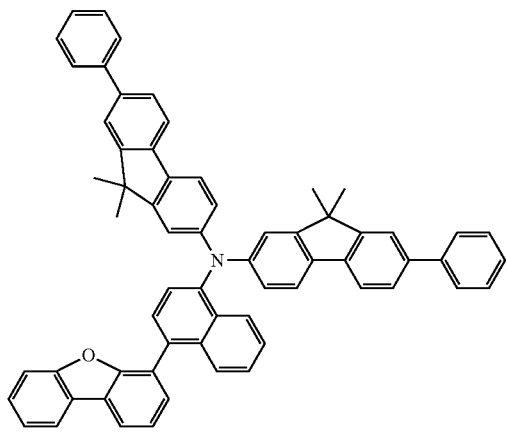
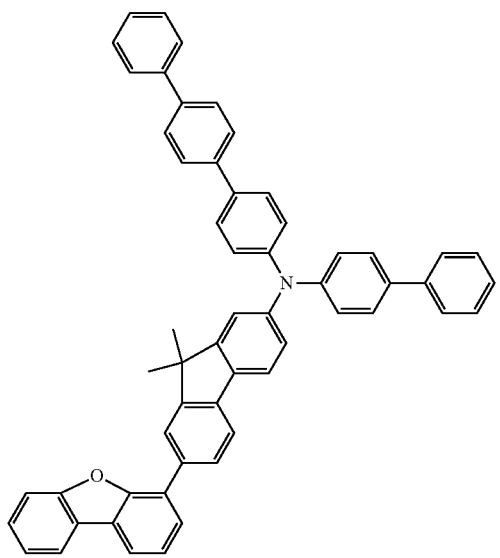
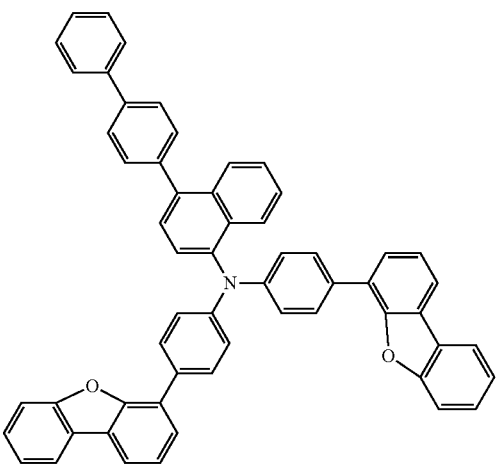
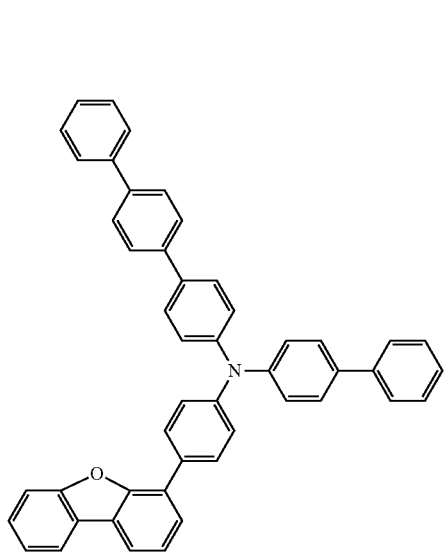
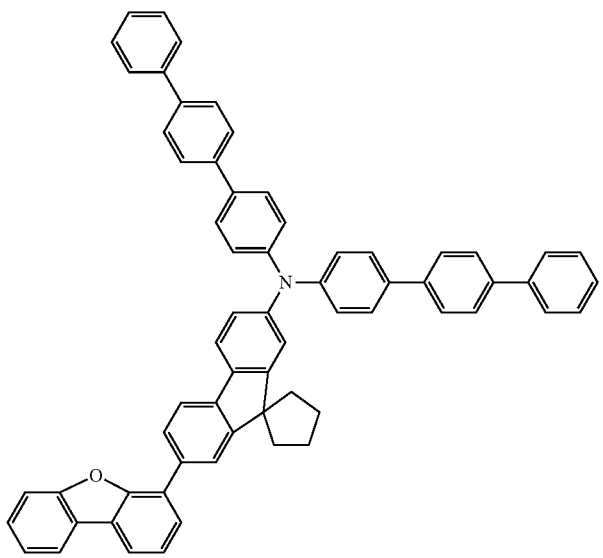

-continued
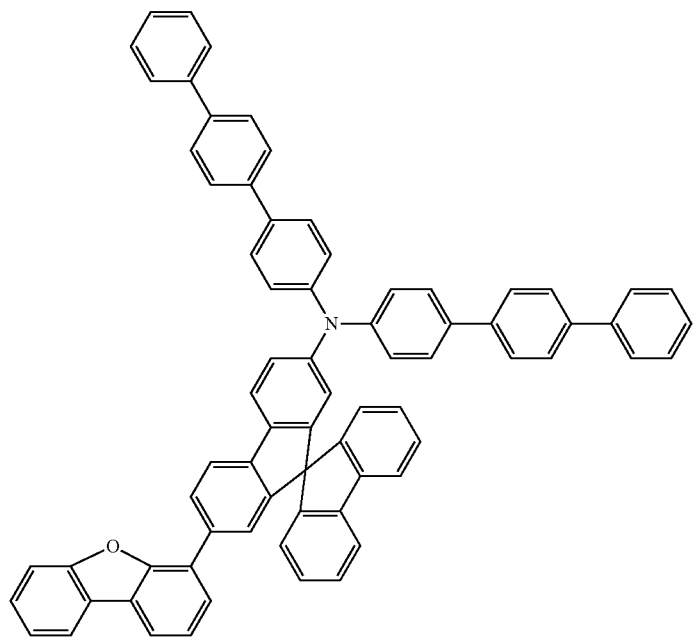
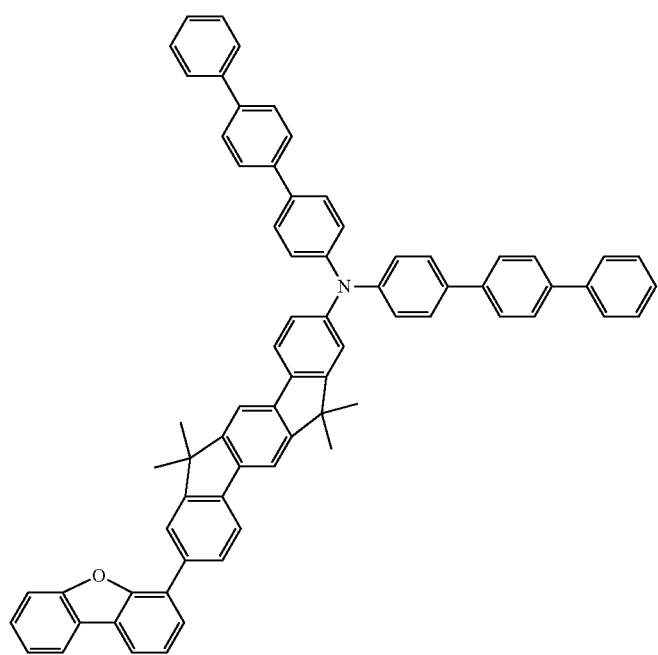

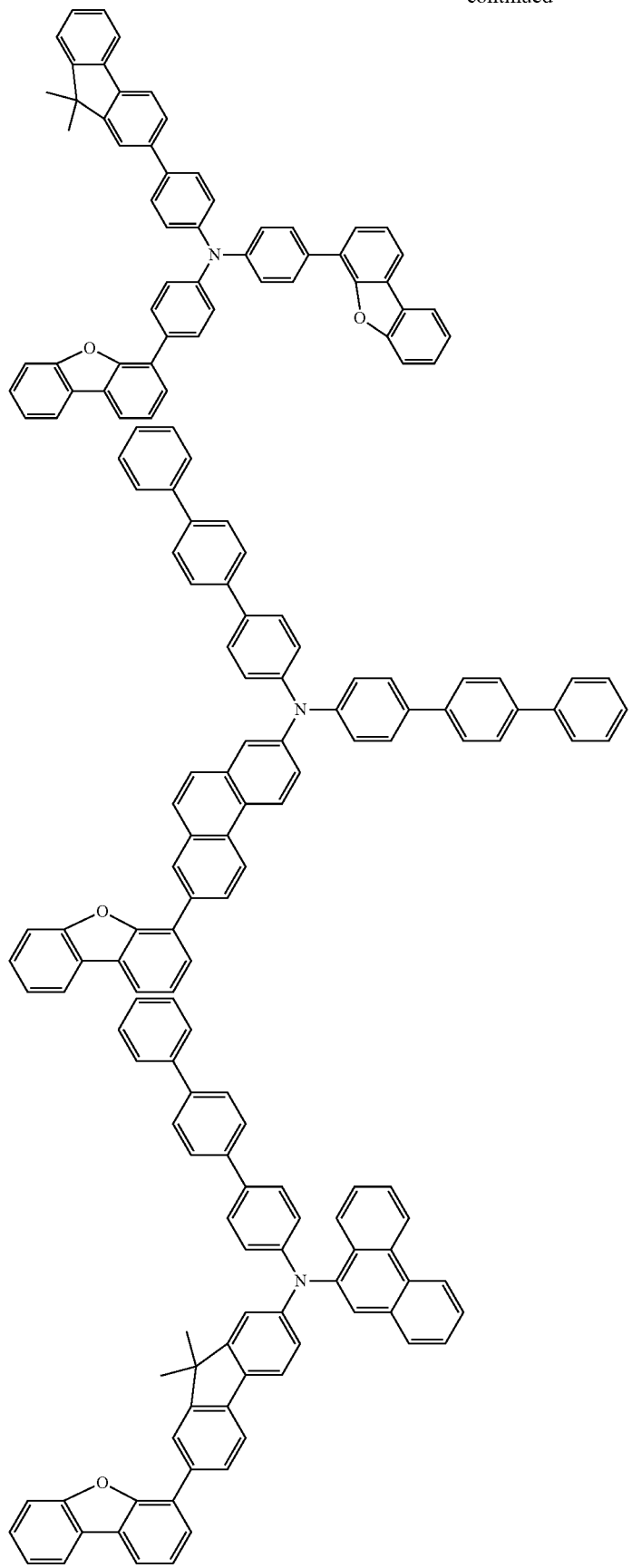

91 92
-continued
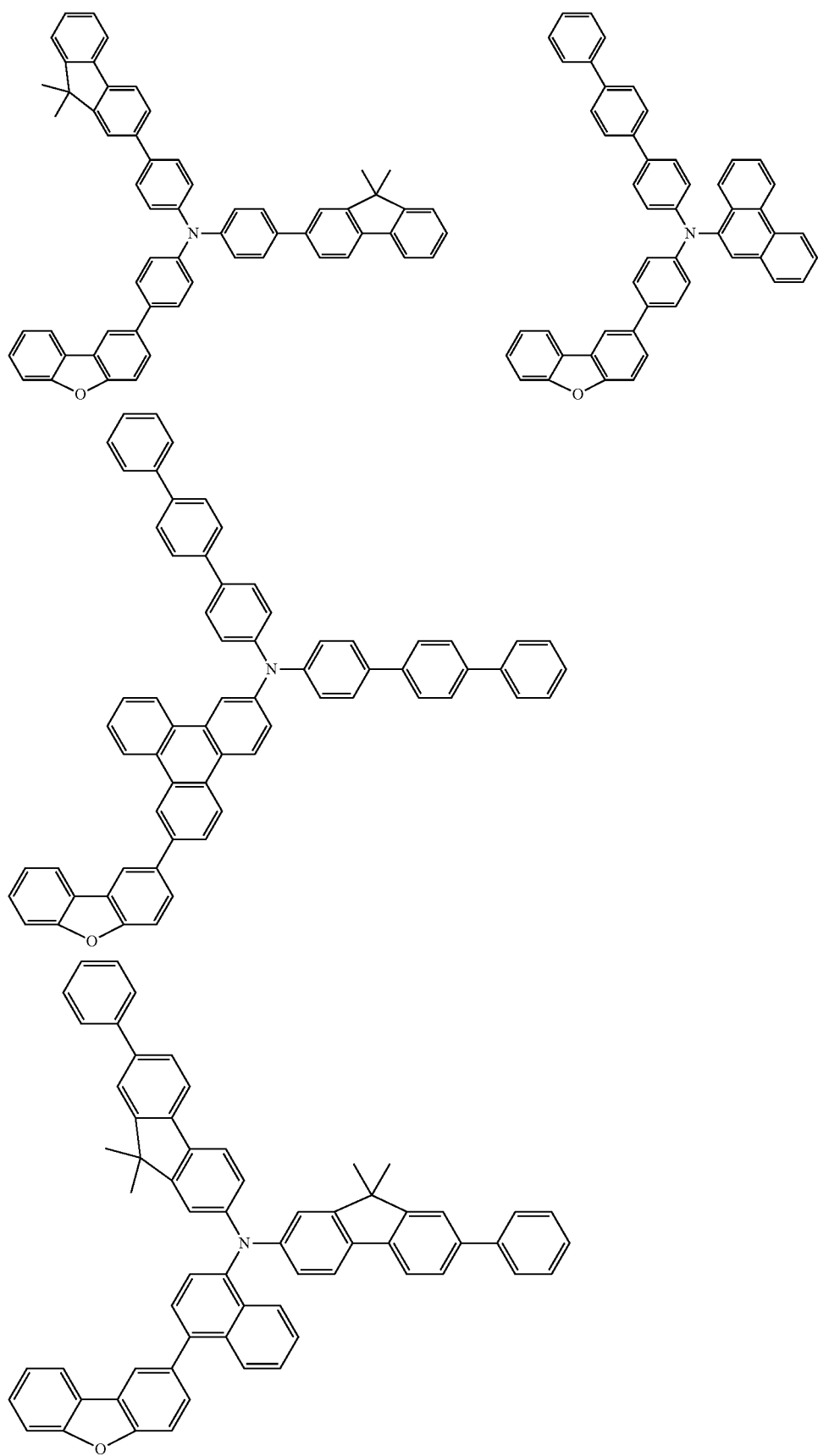

-continued
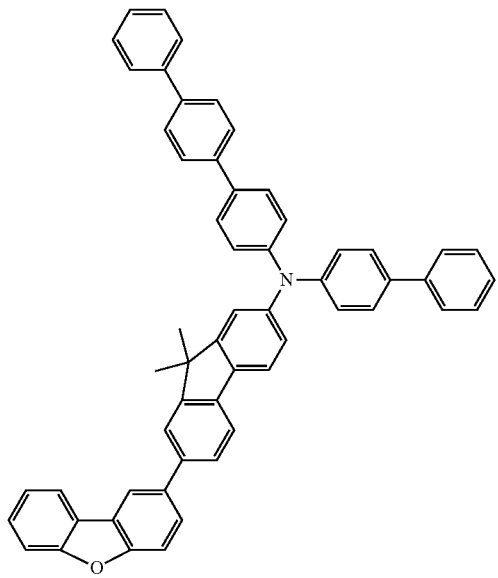
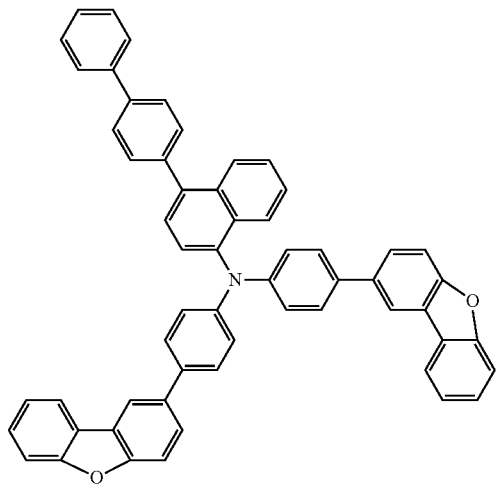
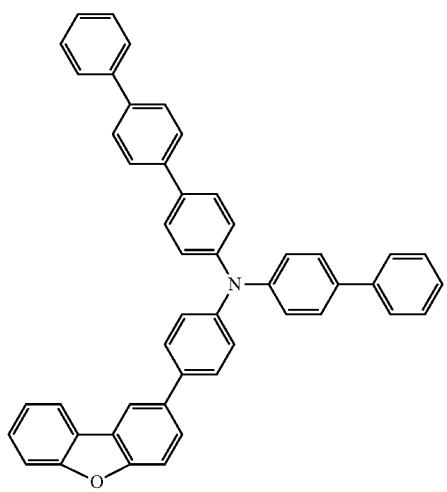
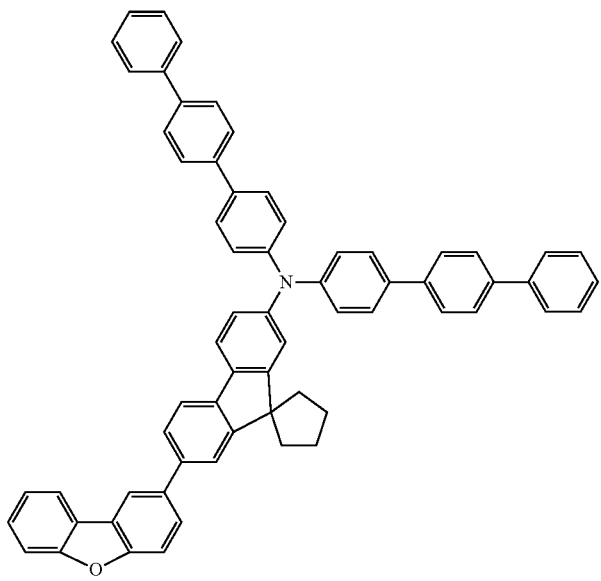

95 96
-continued
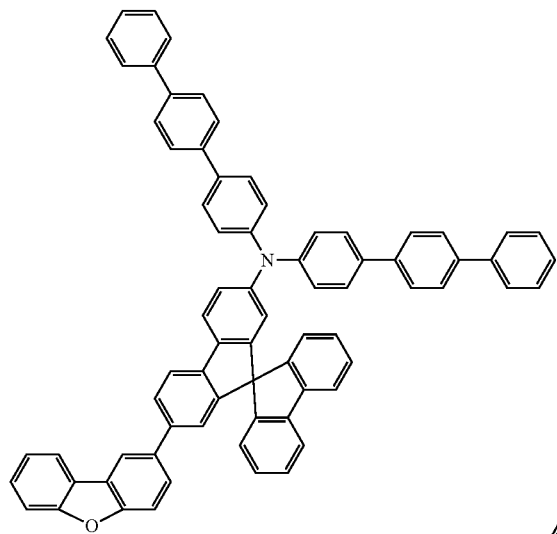
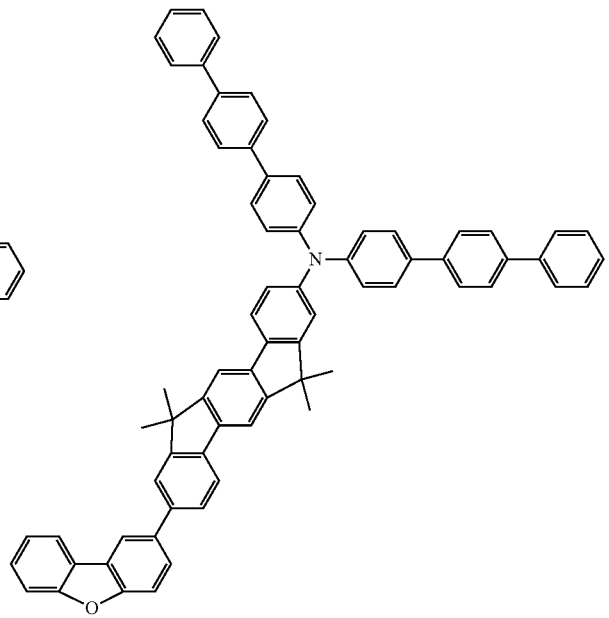
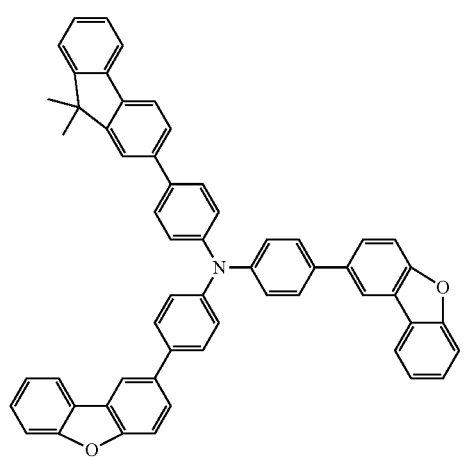
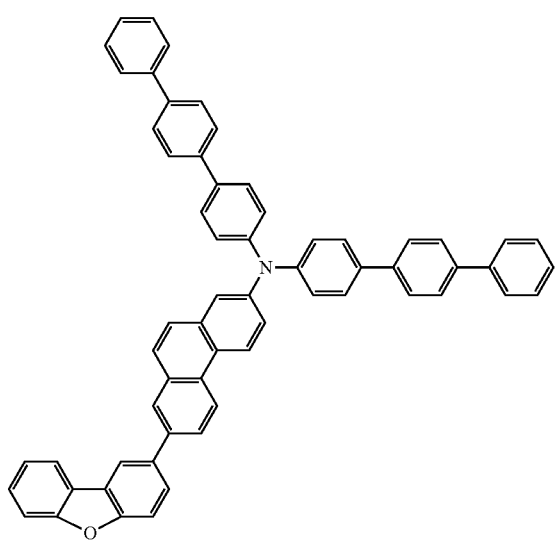
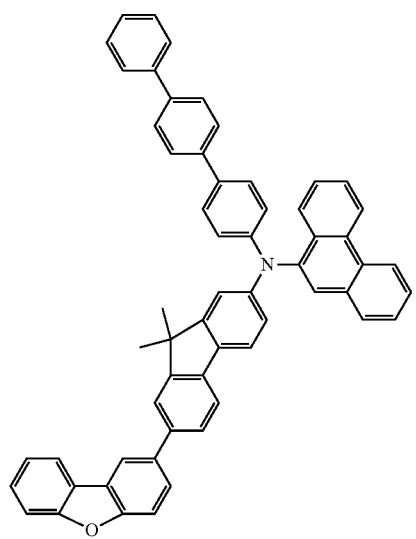
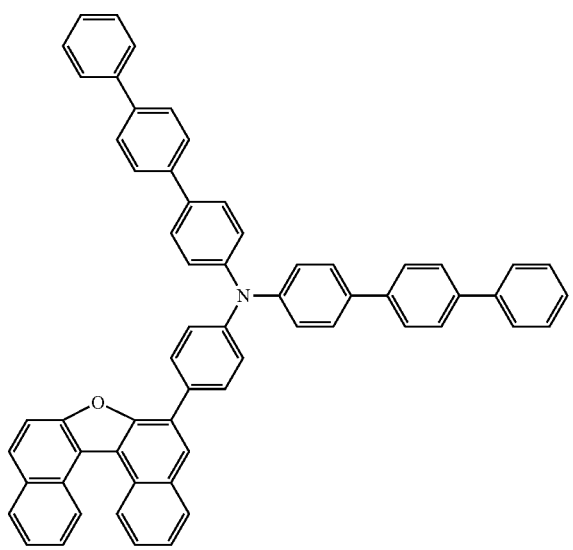

-continued
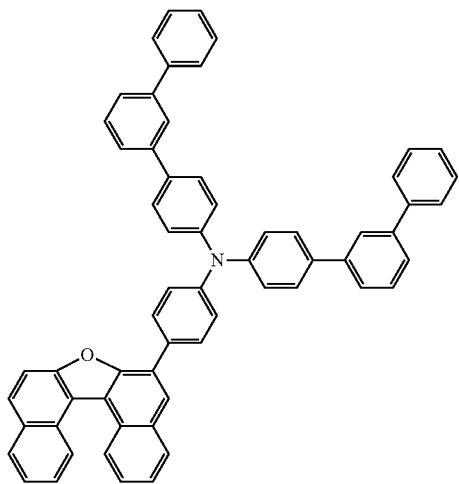
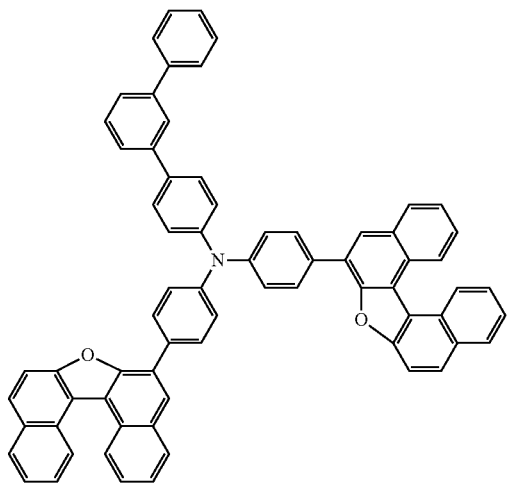
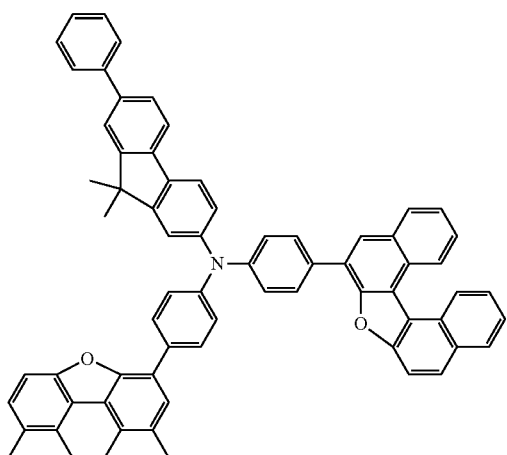
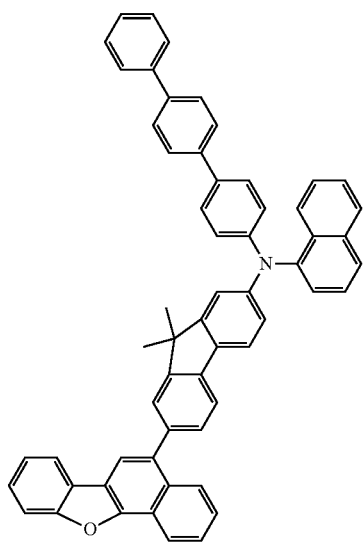
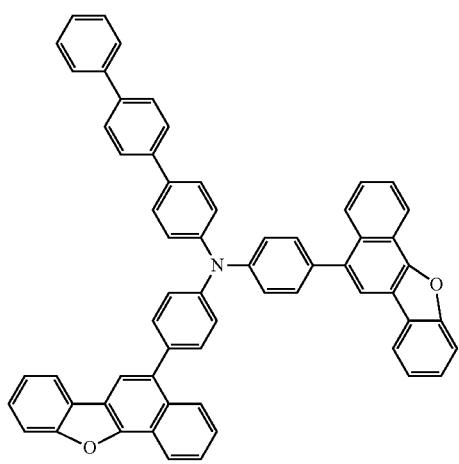
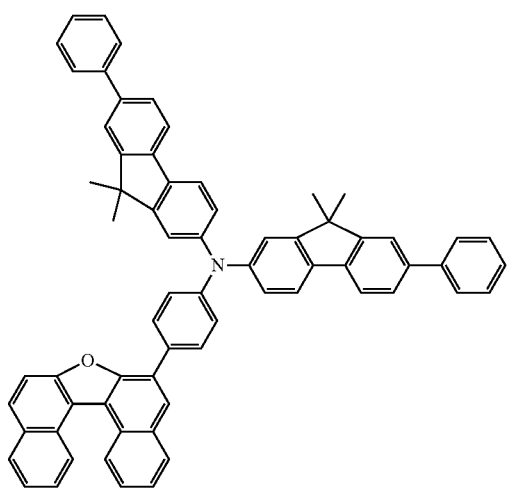

-continued
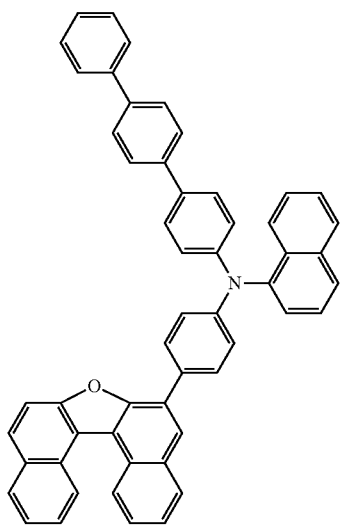
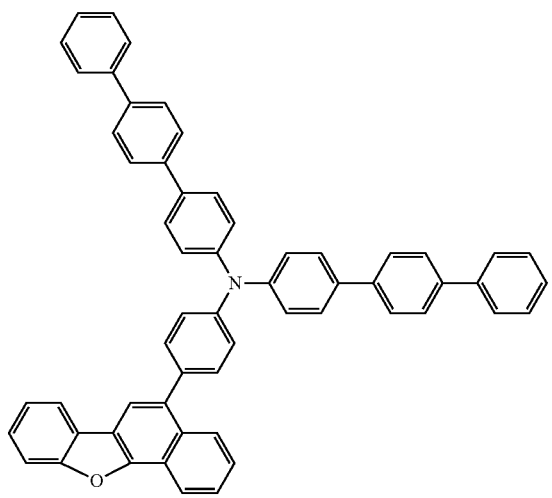
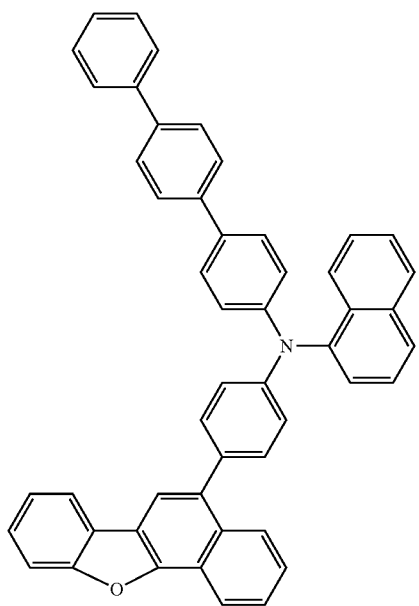
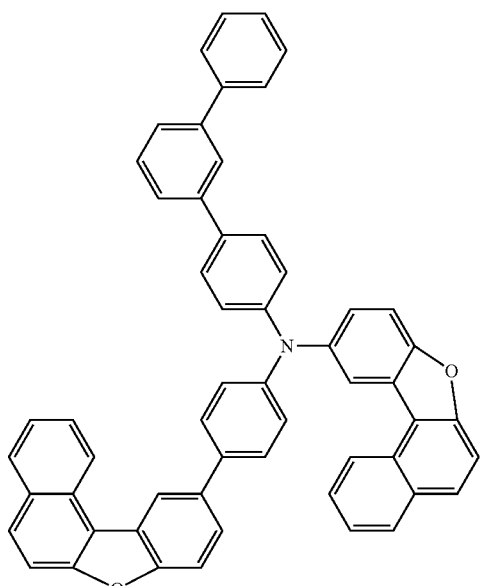
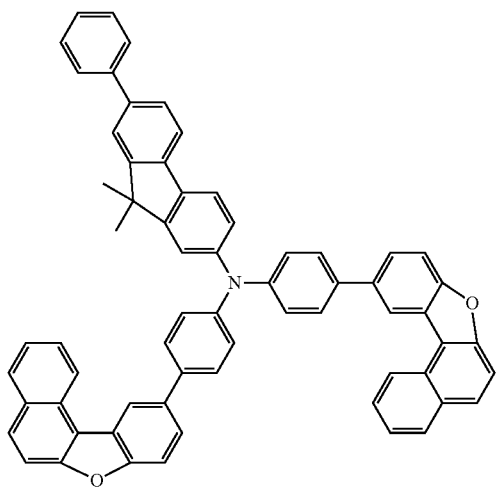
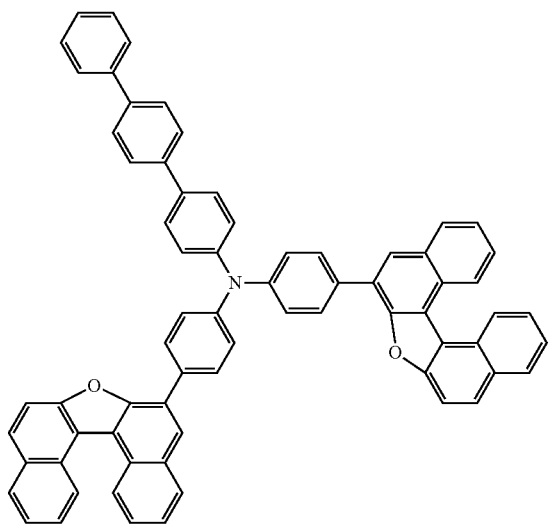

101 102
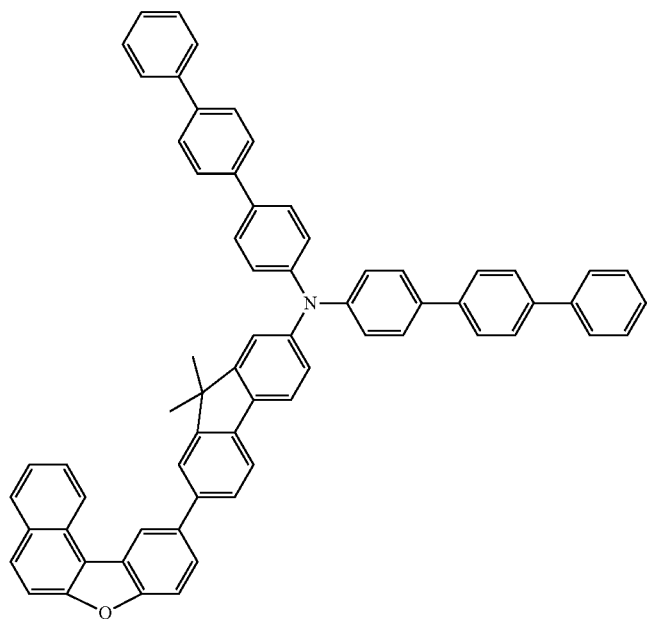
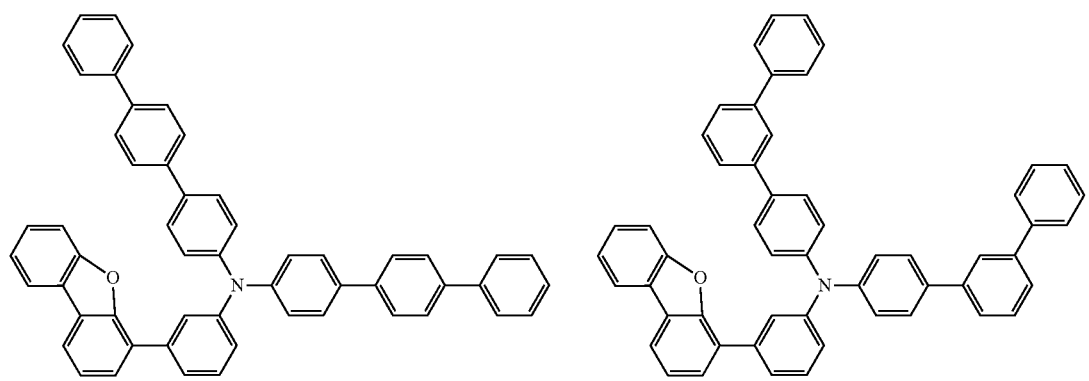
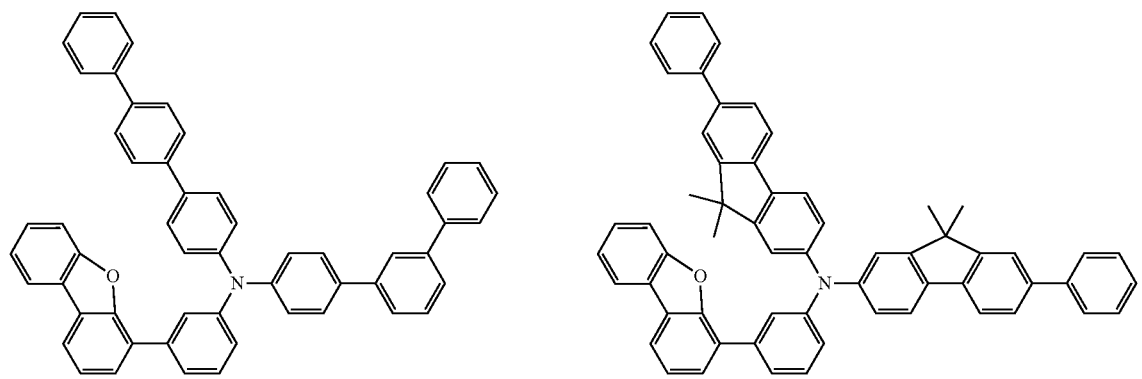

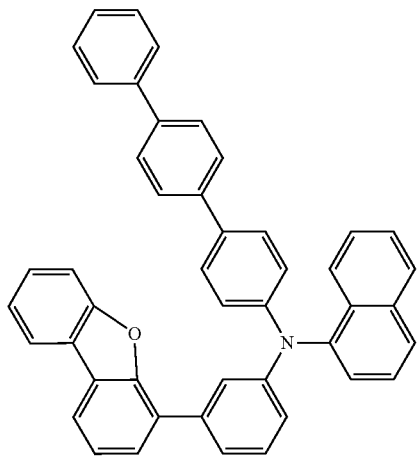
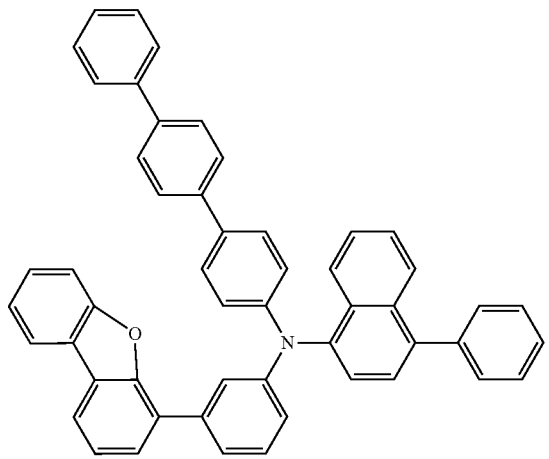
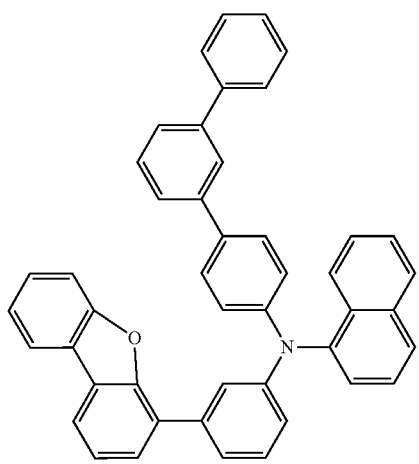
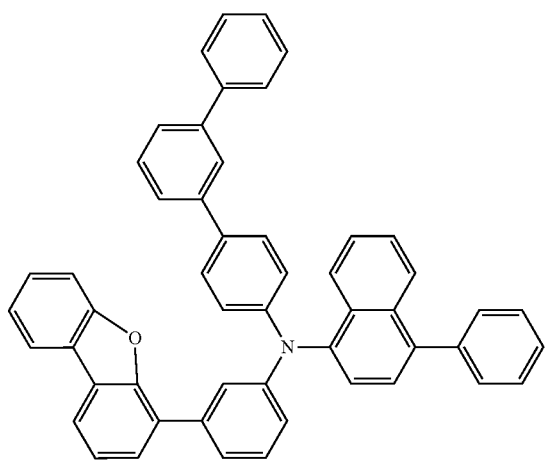
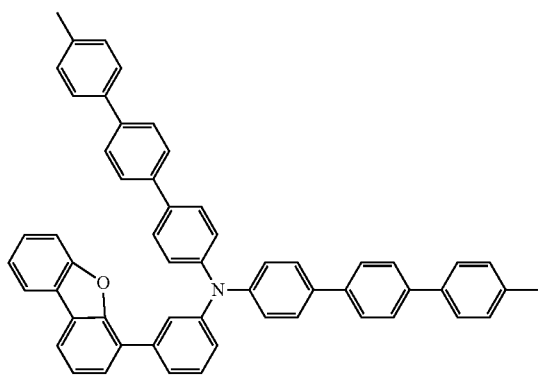
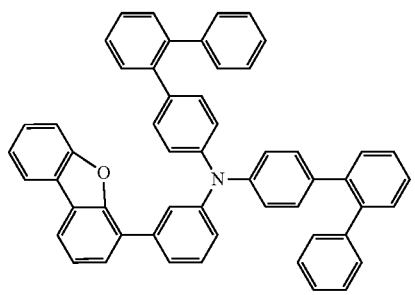

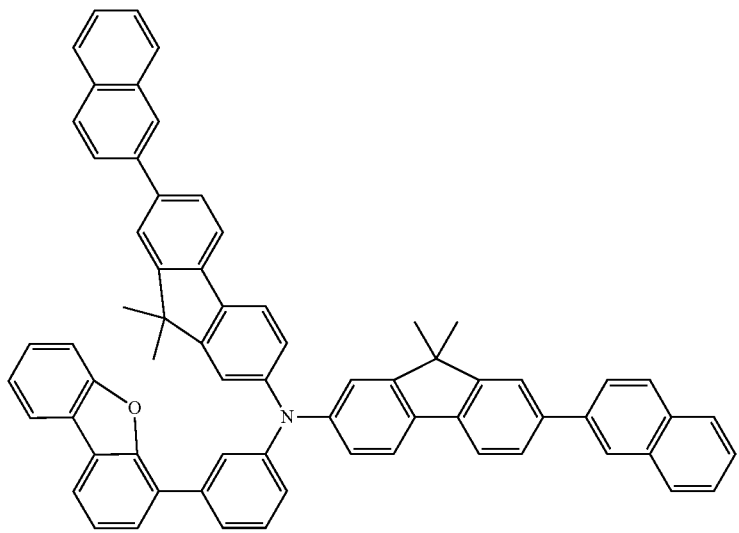
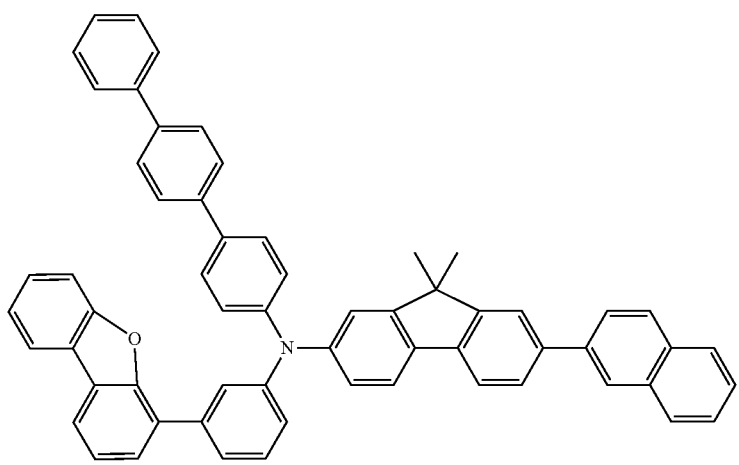
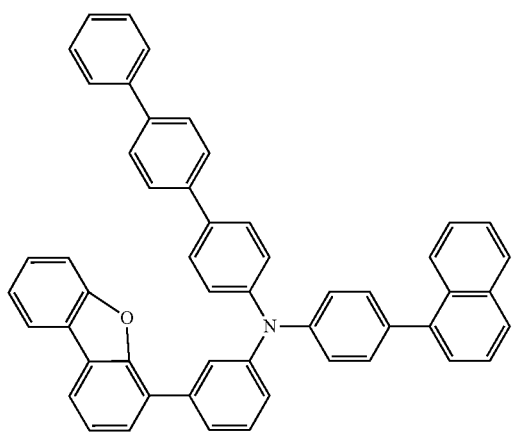
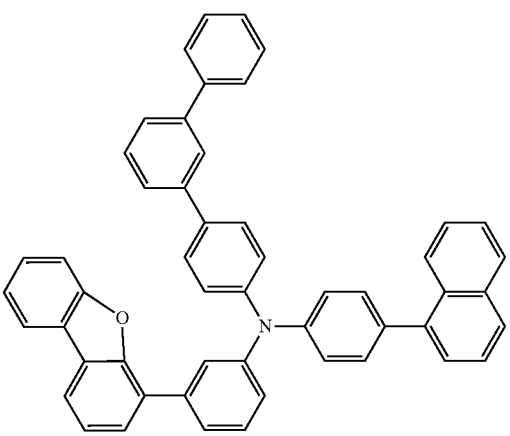

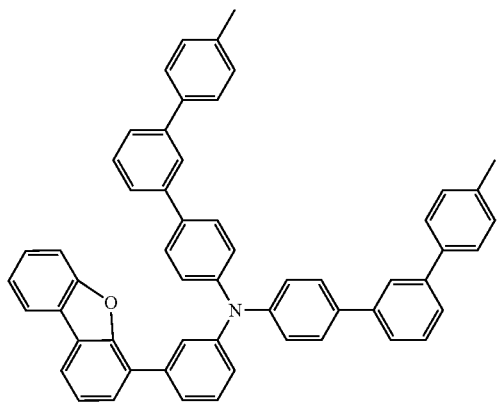
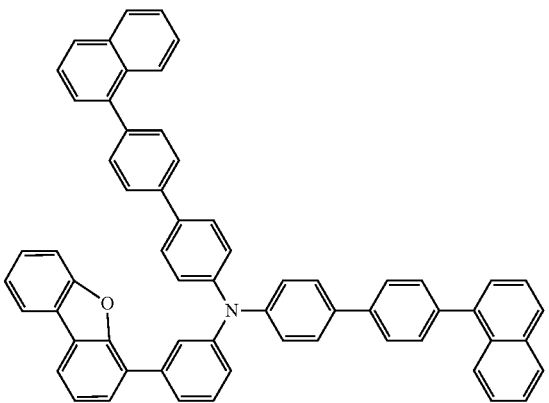
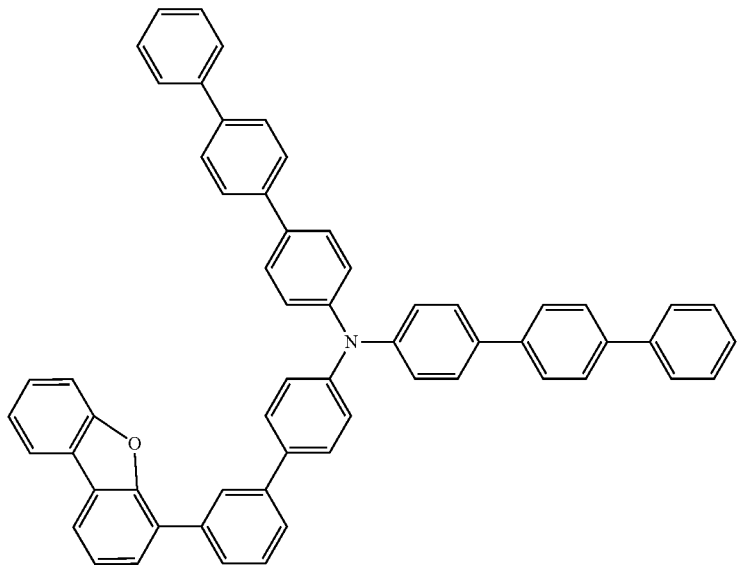
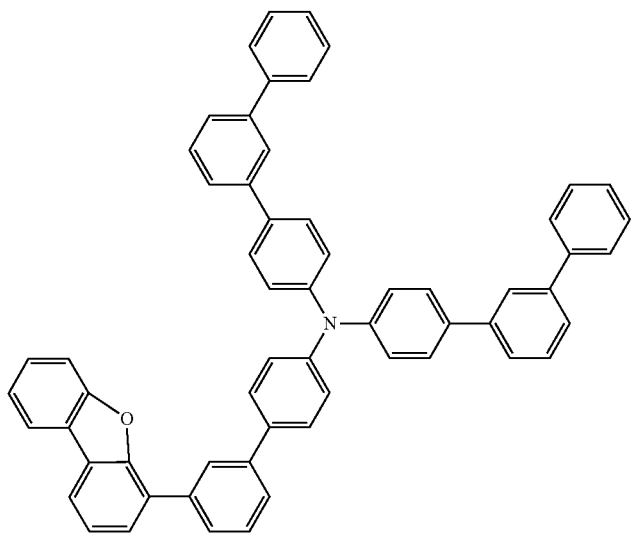

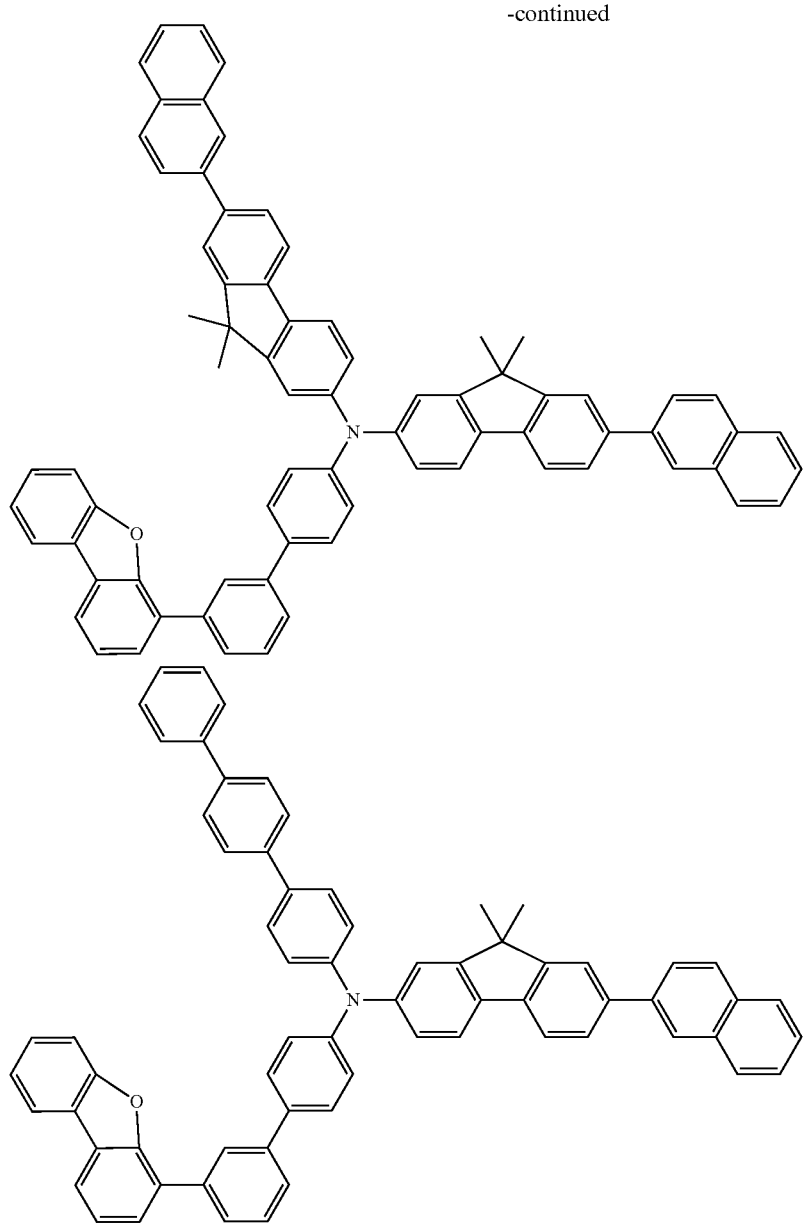
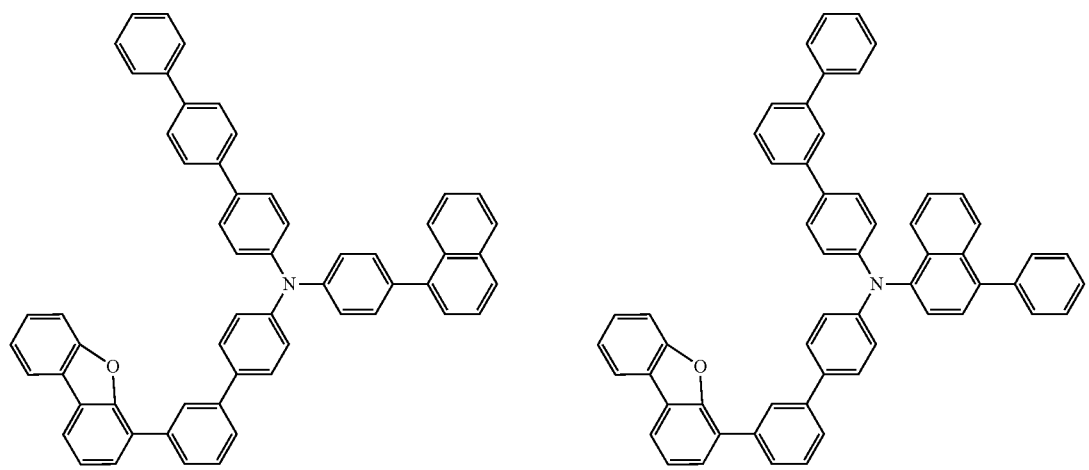

-continued
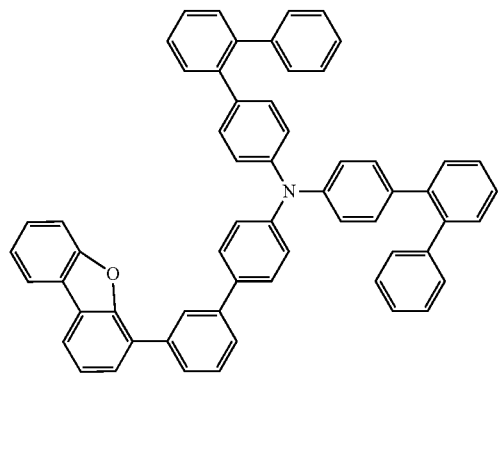
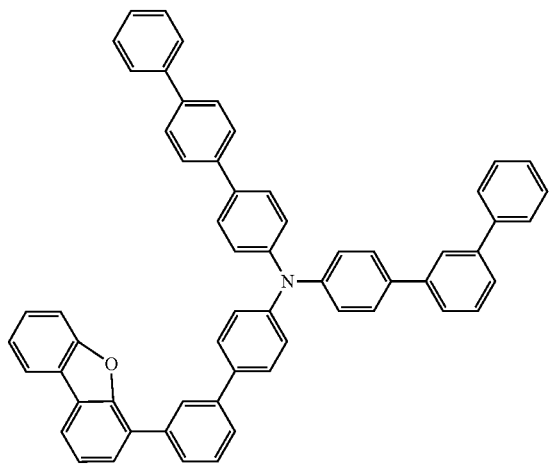
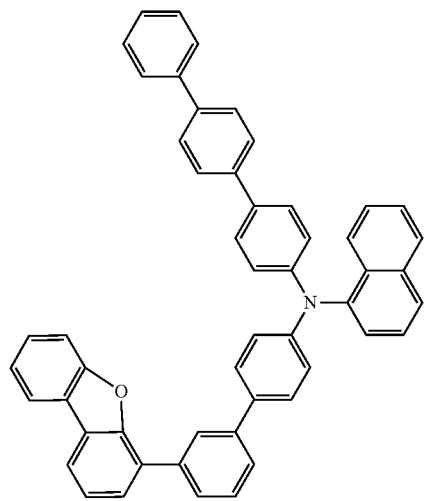
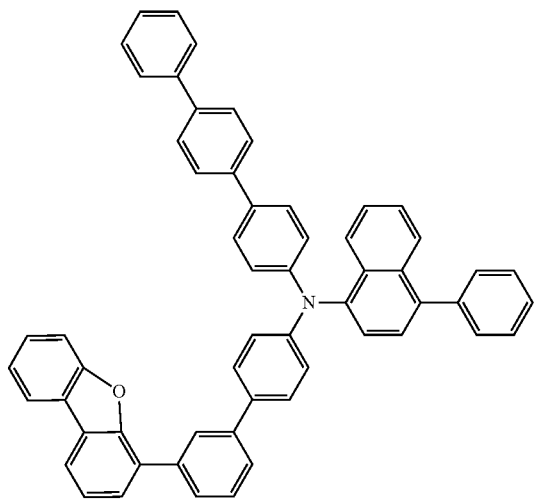
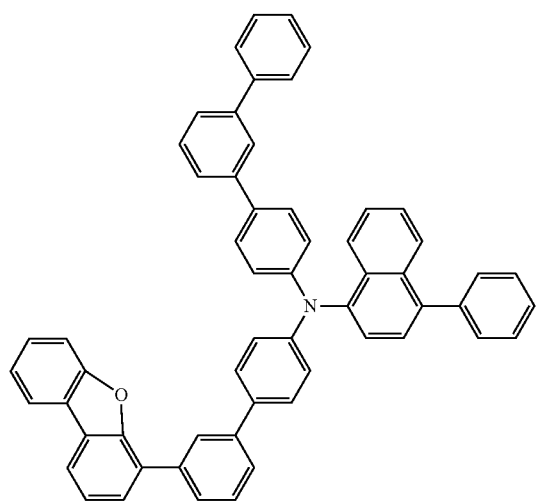

-continued
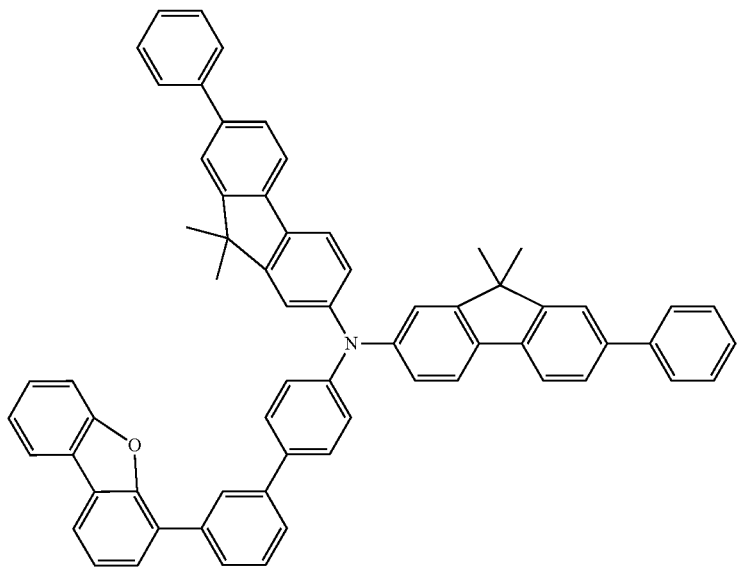
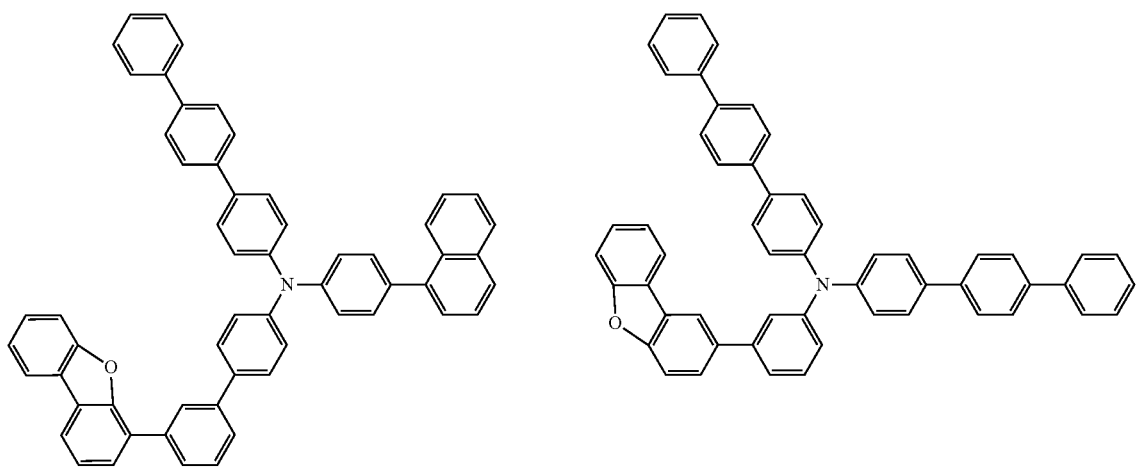
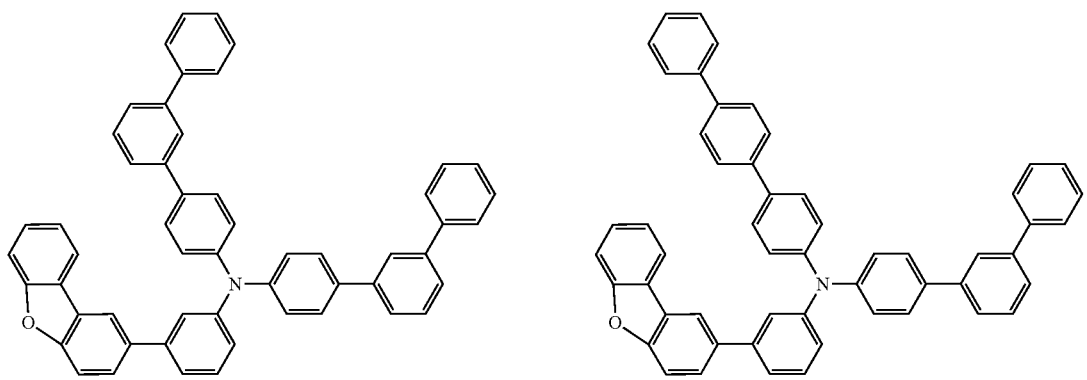

115 116
-continued
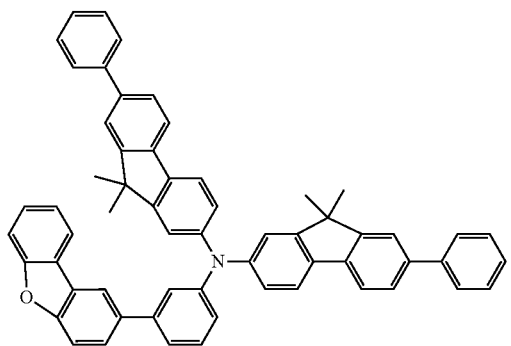
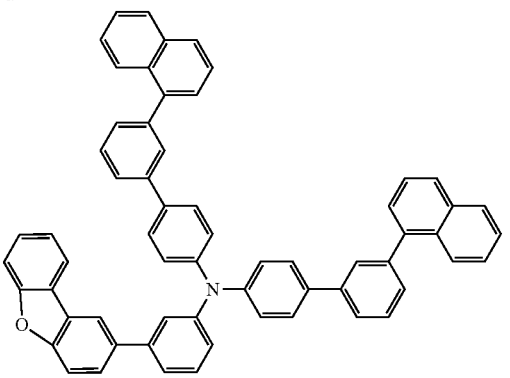
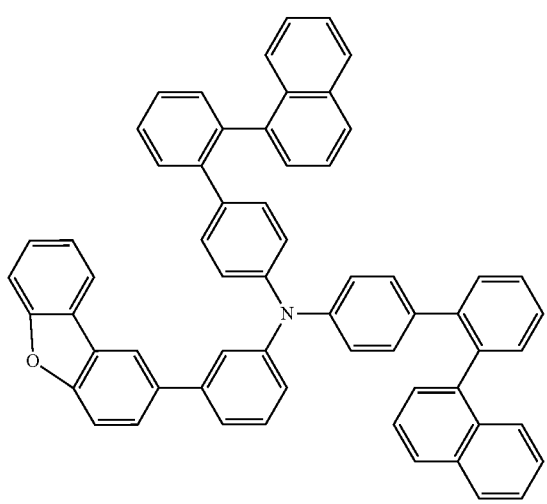
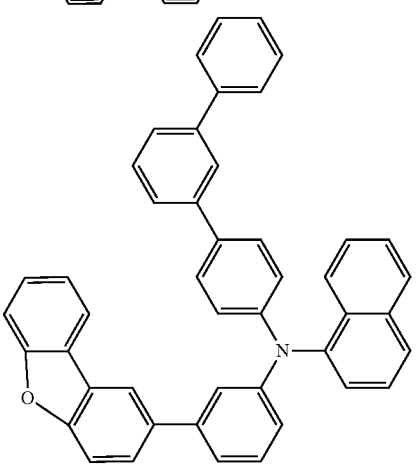
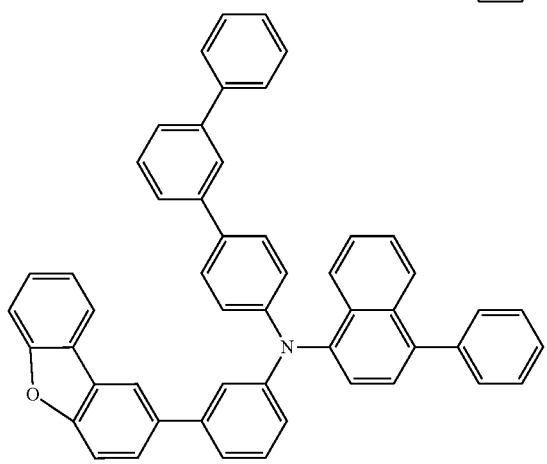
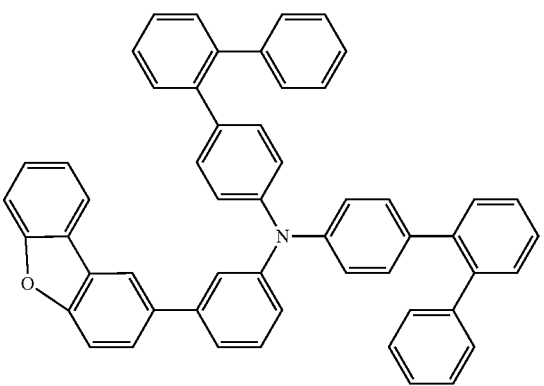
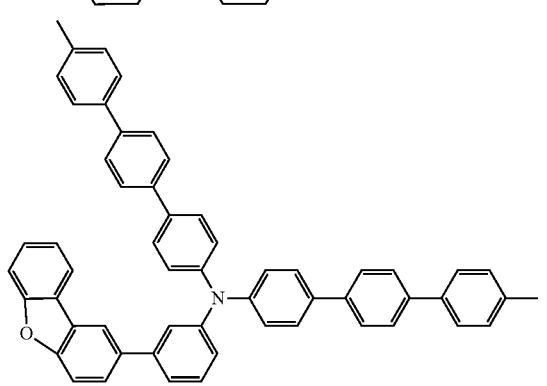
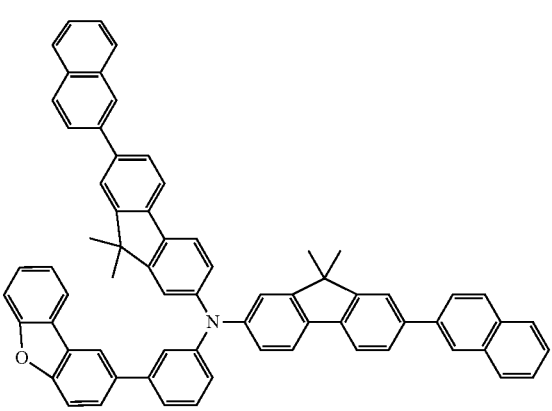

117
118
-continued
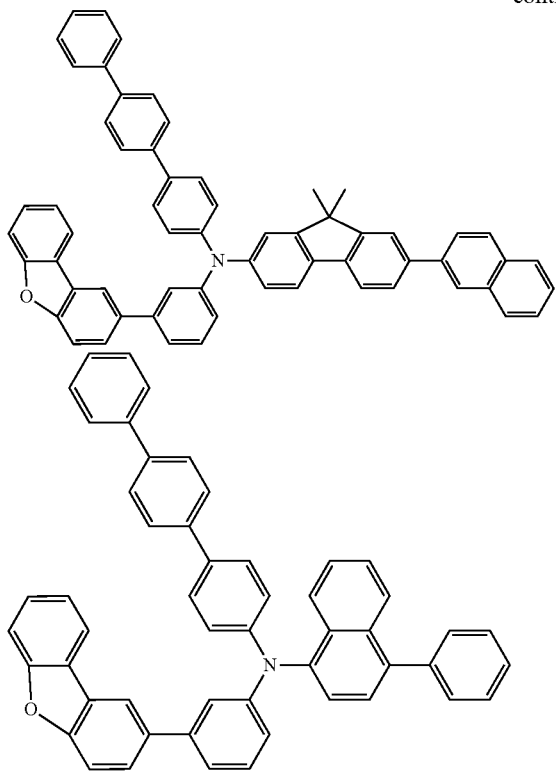
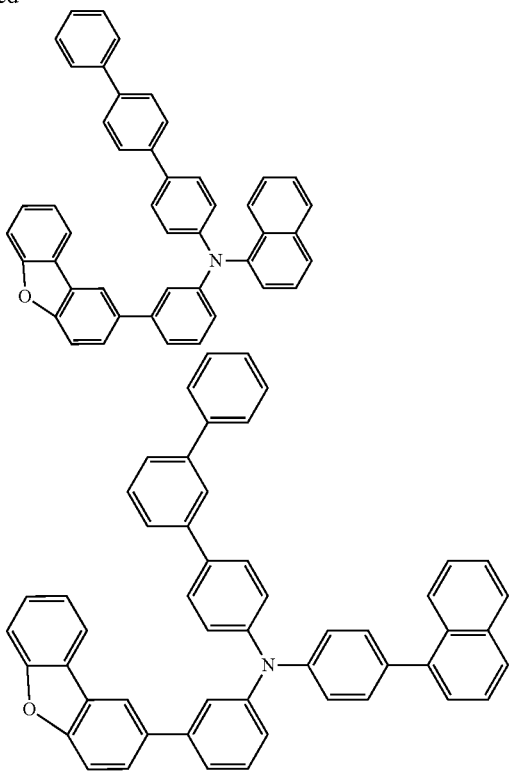
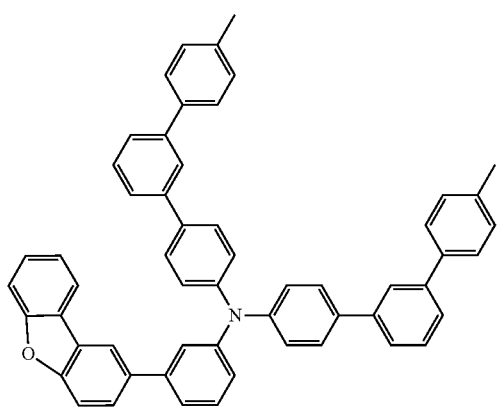
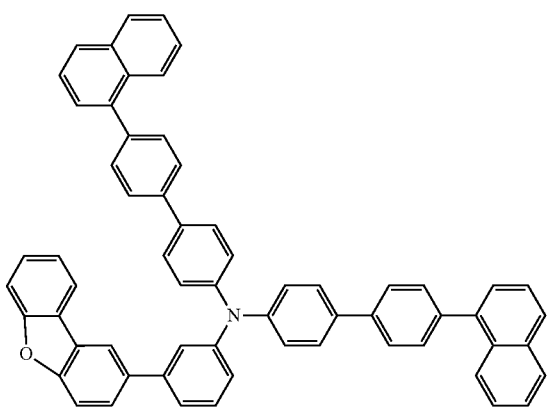
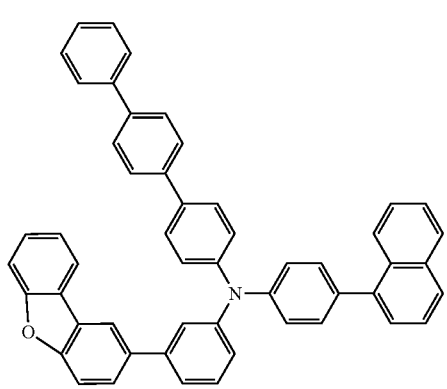
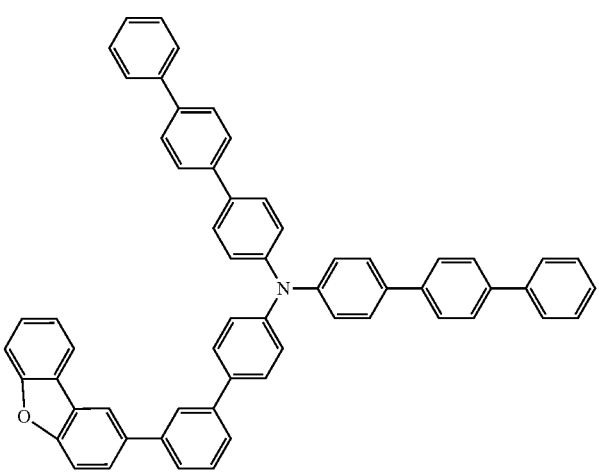

-continued
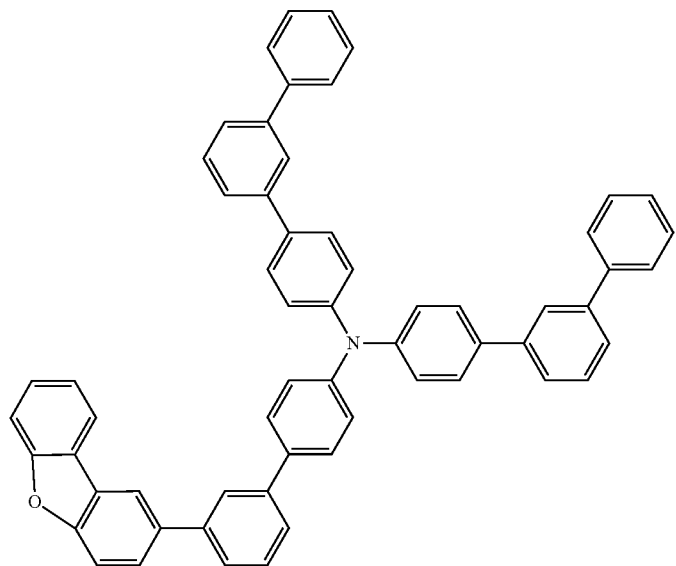
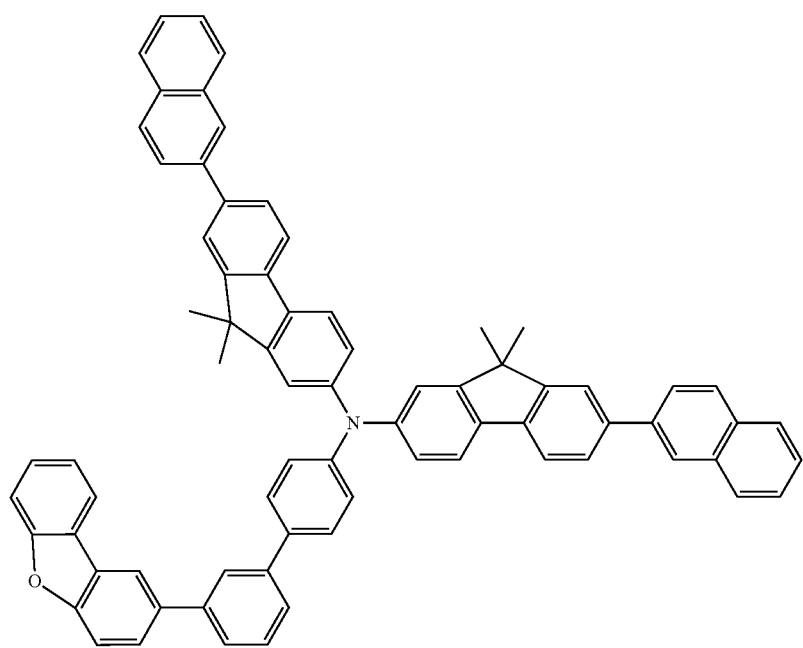

121
122
-continued
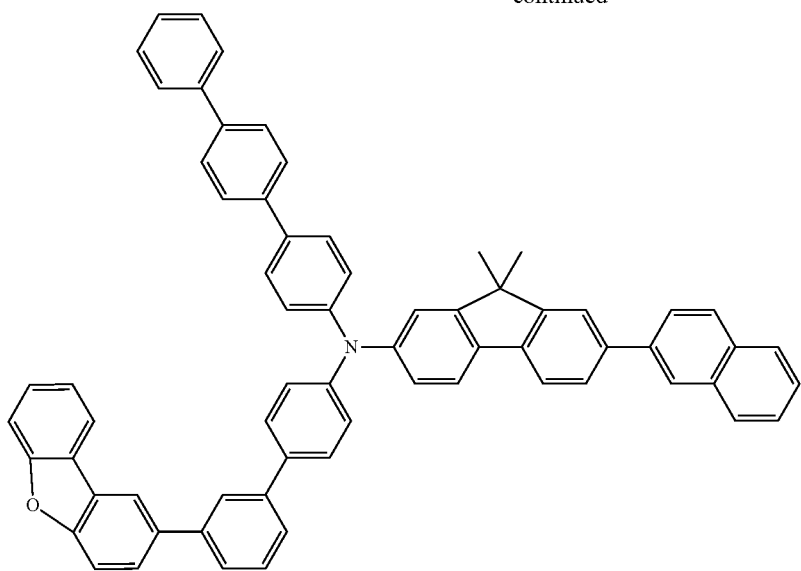
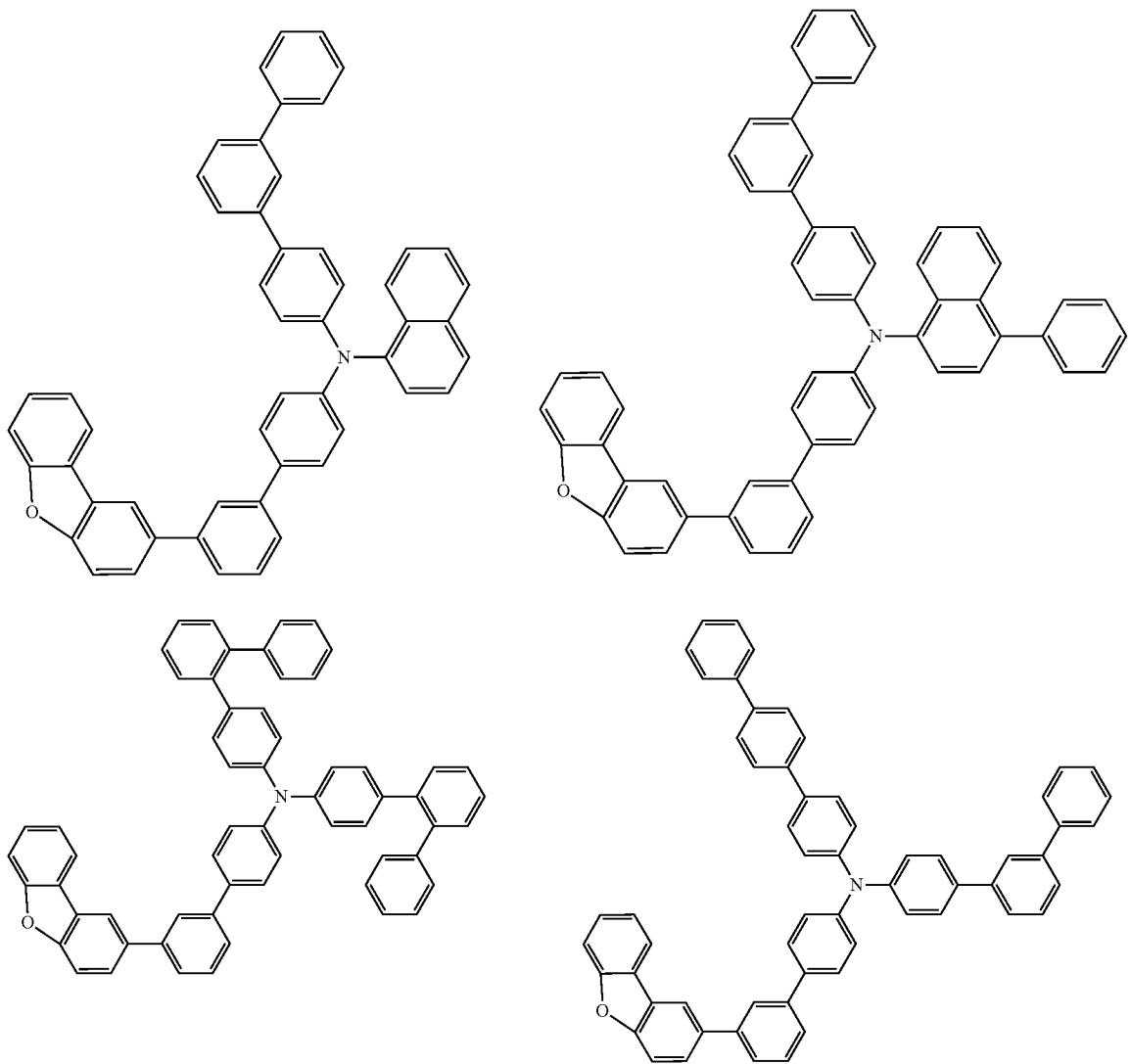

-continued
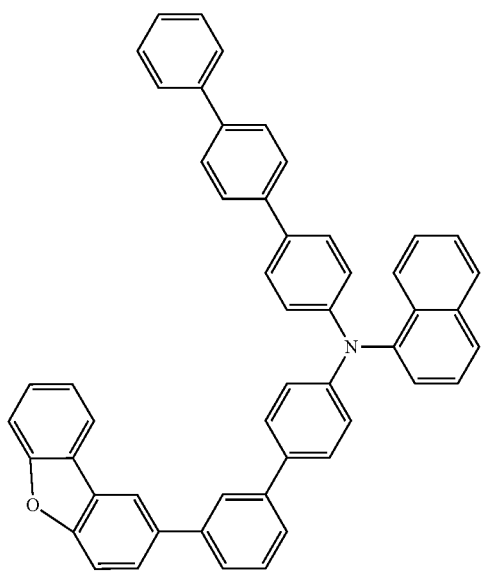
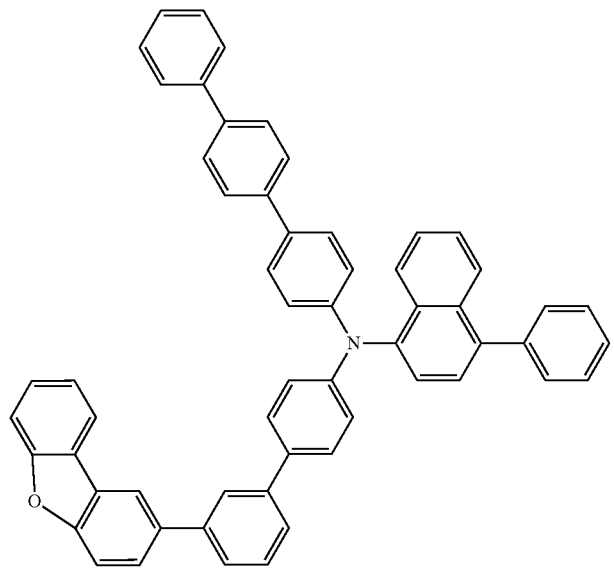
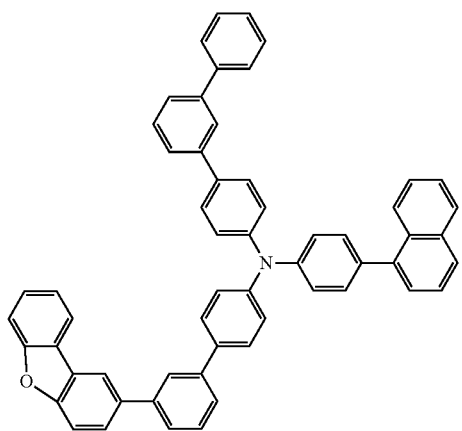
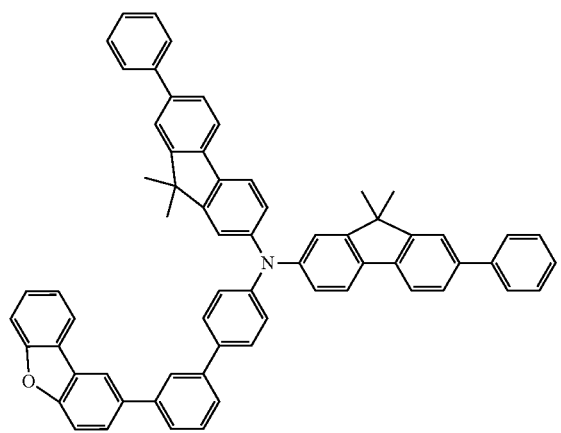
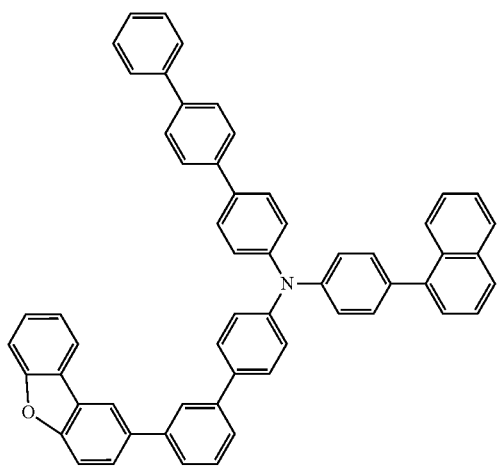
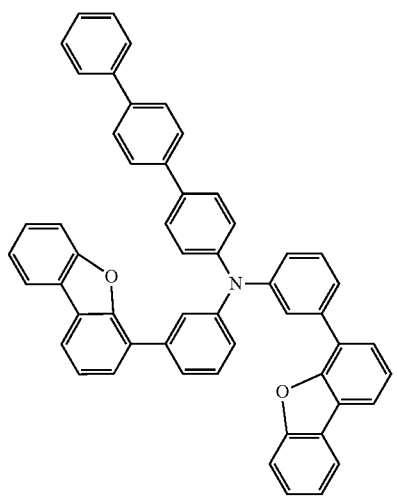

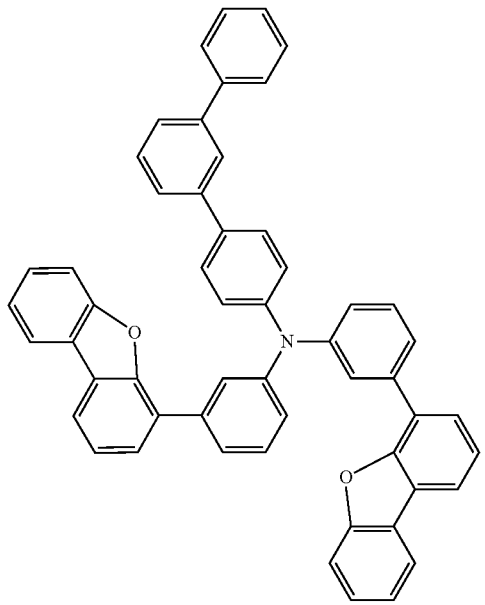
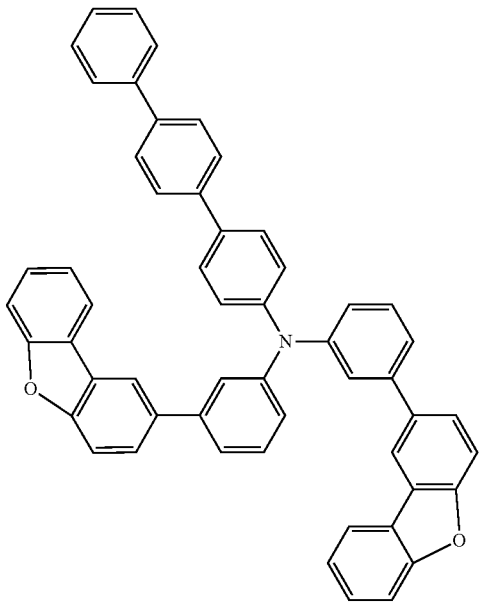
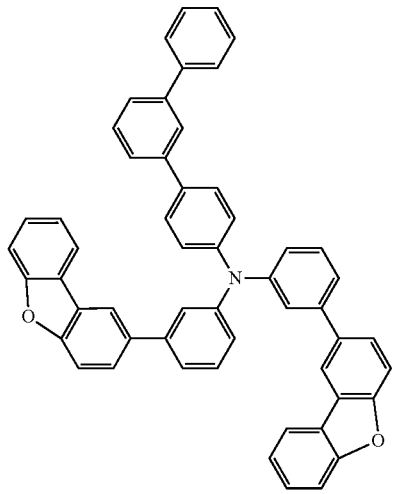
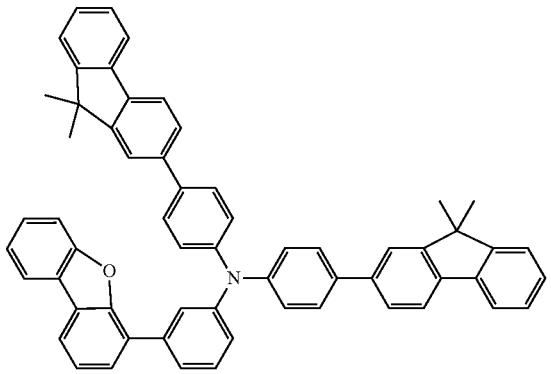
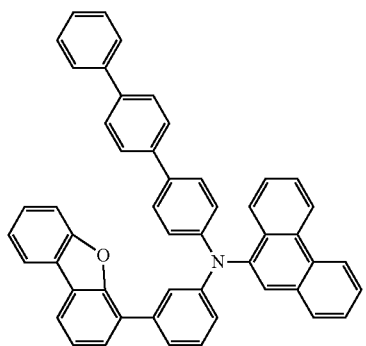
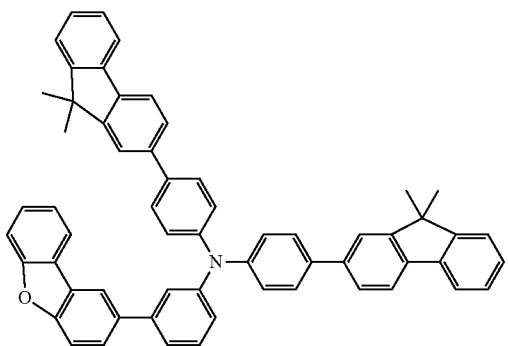

-continued
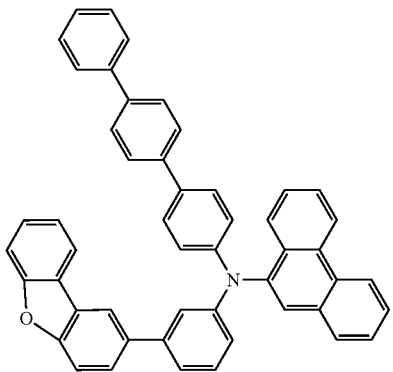
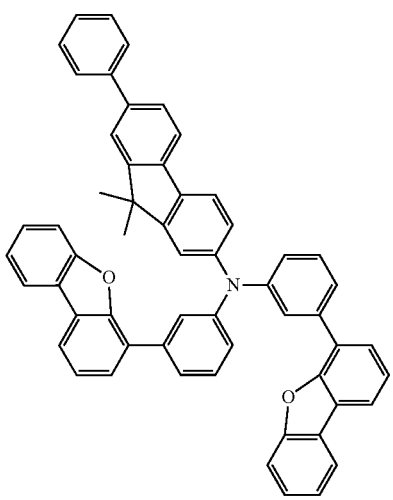
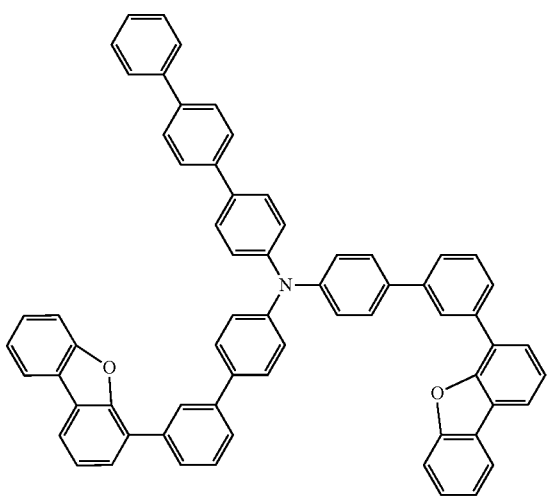
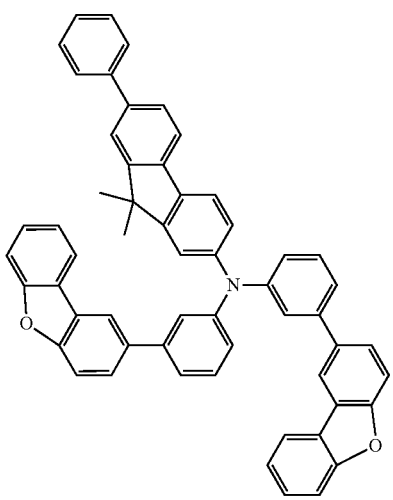
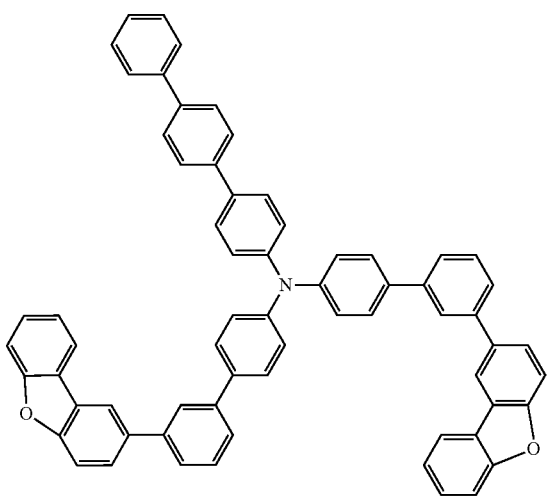

-continued
| 129 | 130 |
|---|---|
| 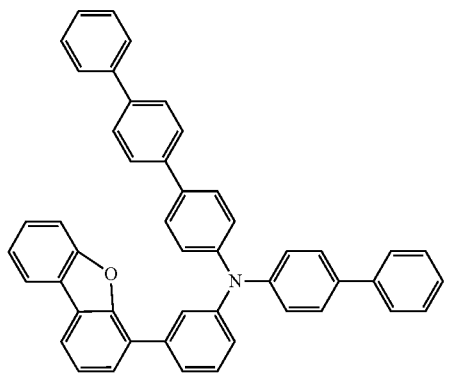 | 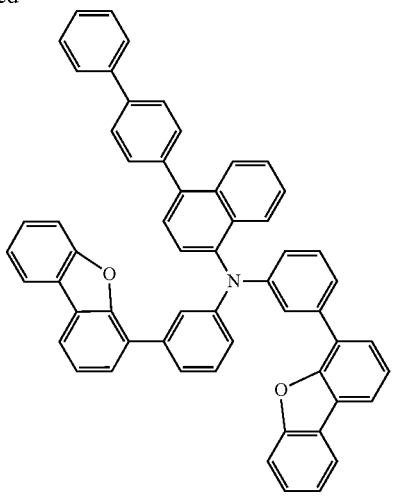 |
| 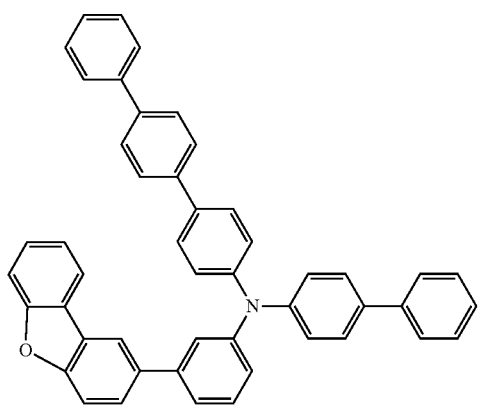 | 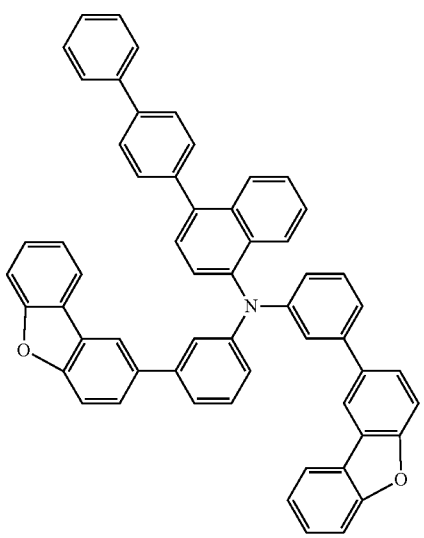 |
| 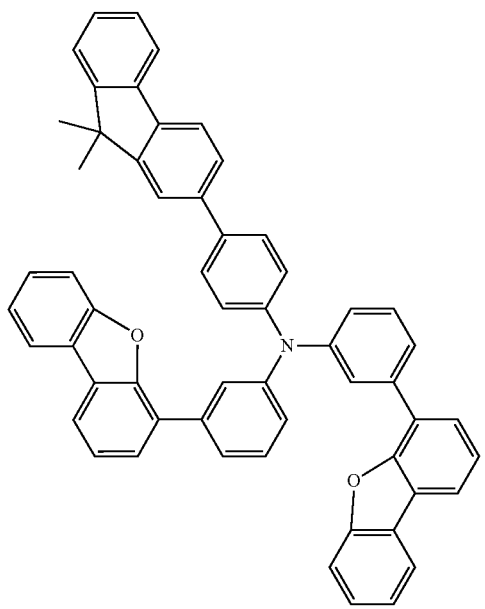 | 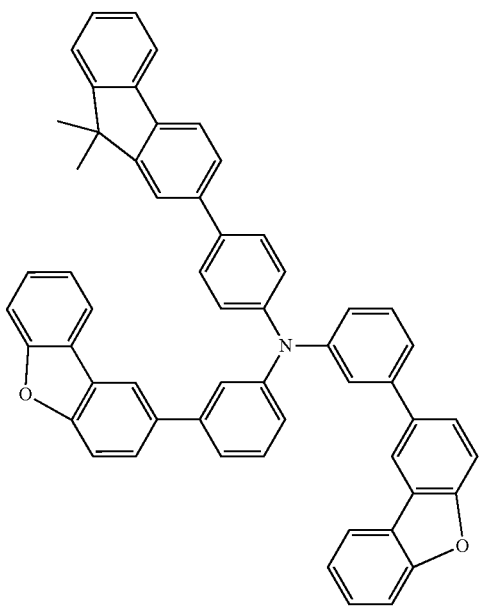 |

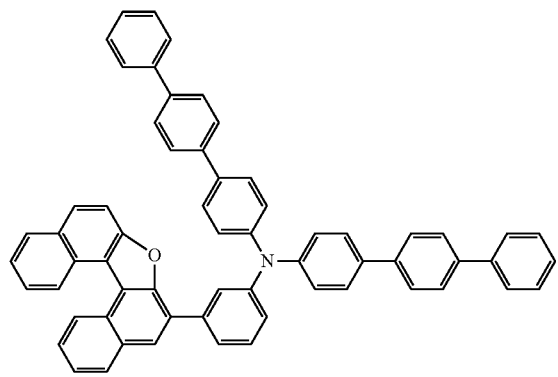
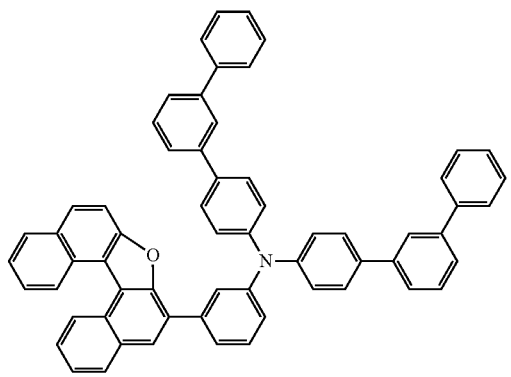
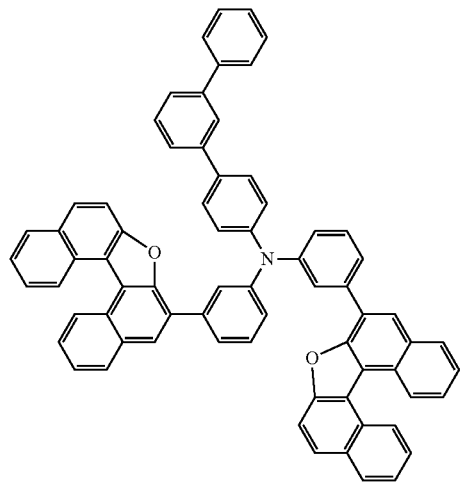
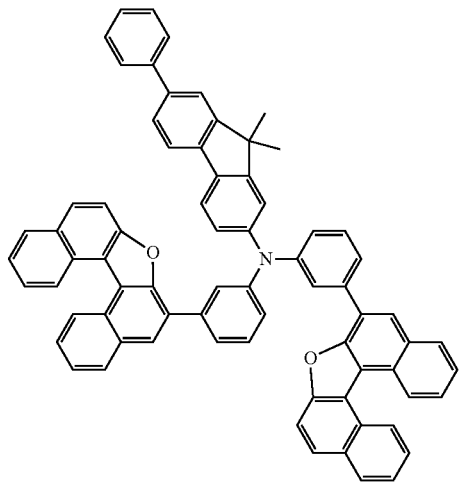
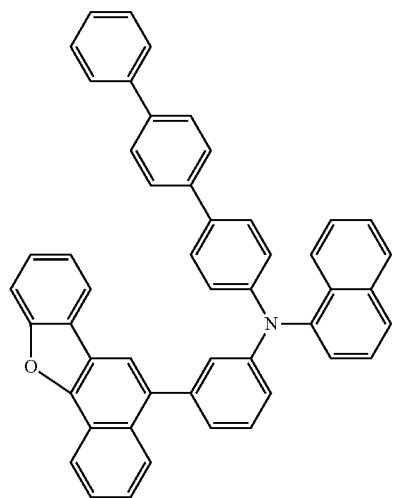
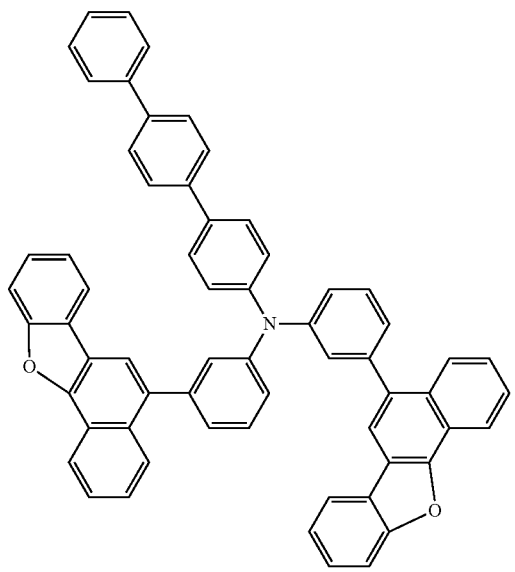

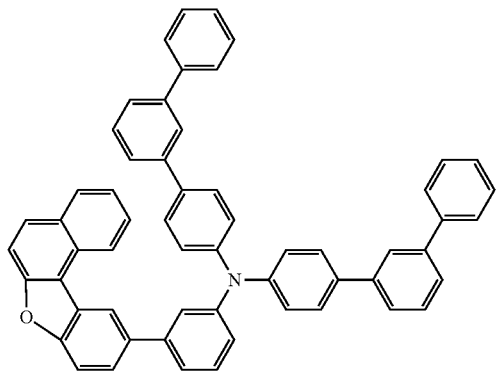
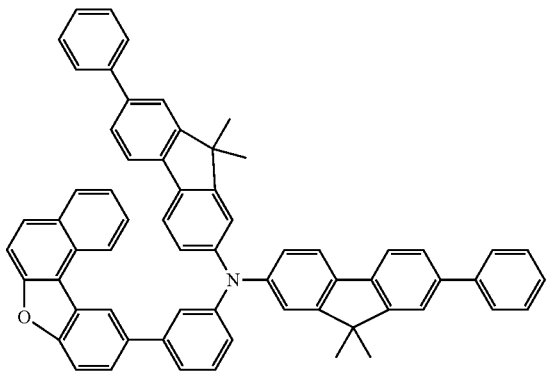
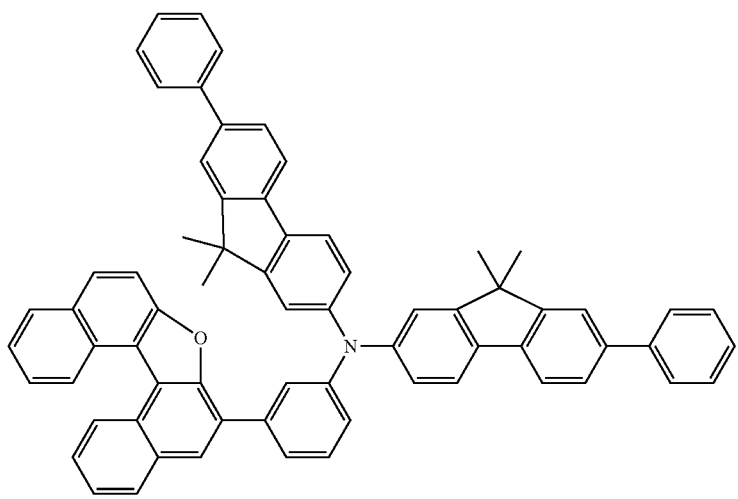
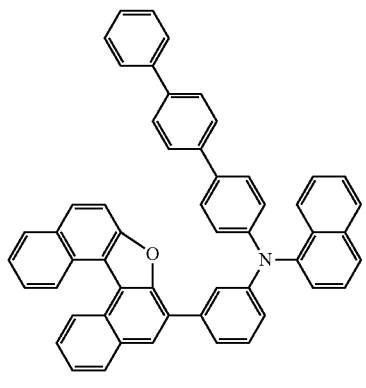
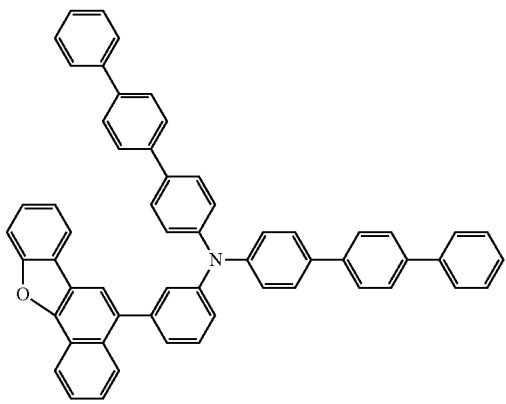

-continued
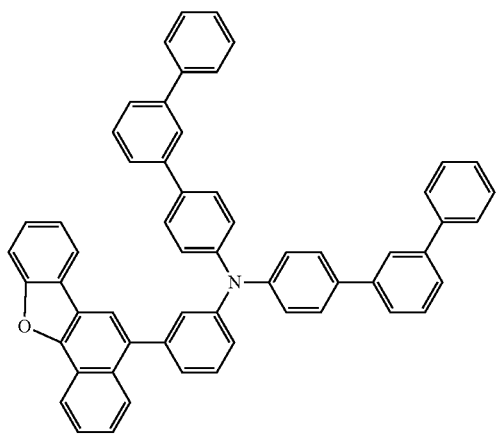
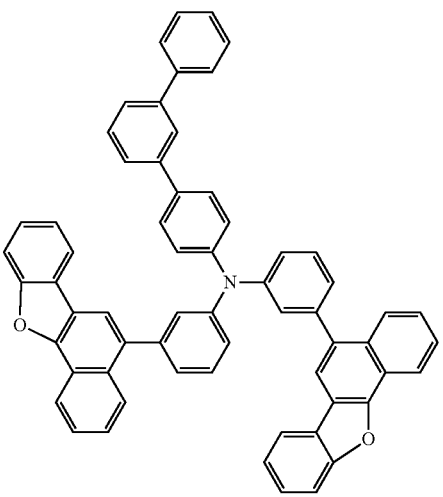
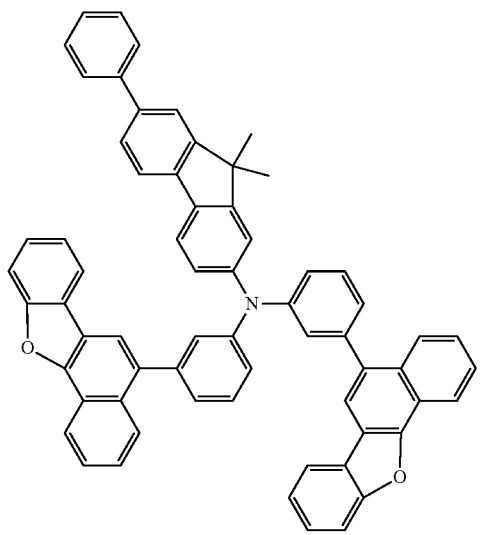
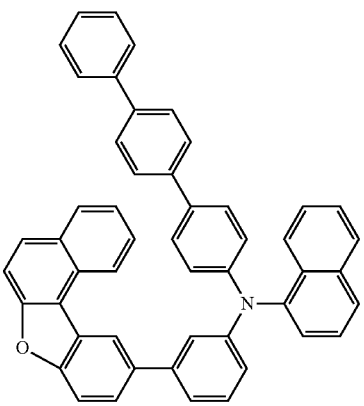
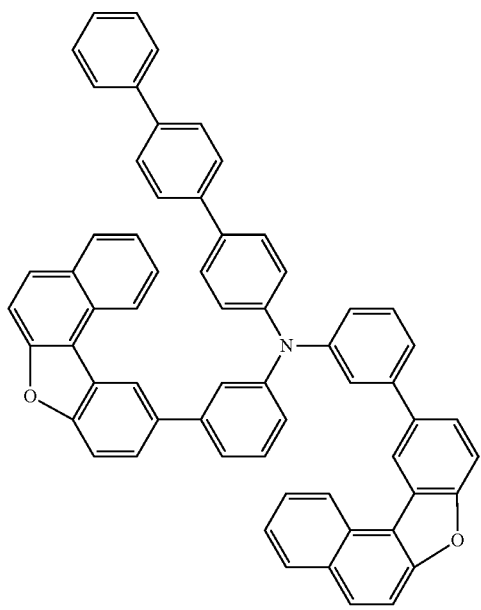

-continued
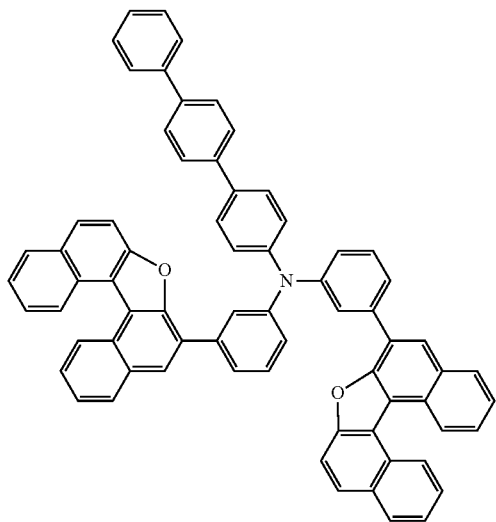
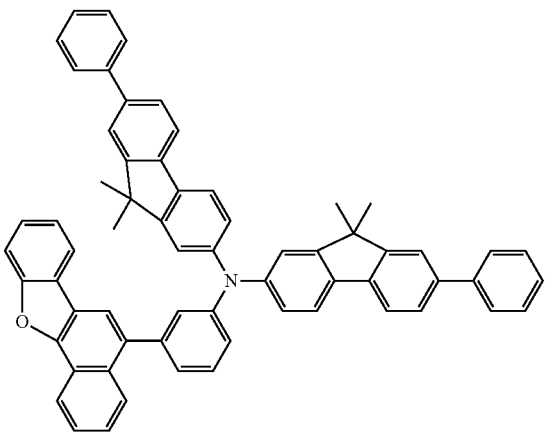
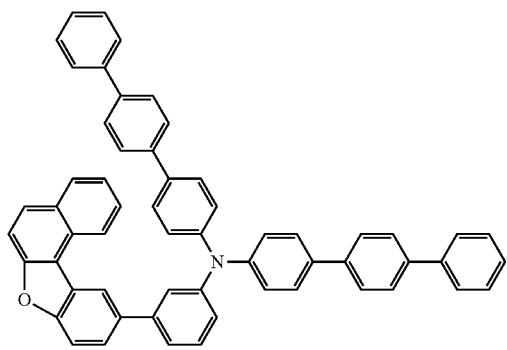
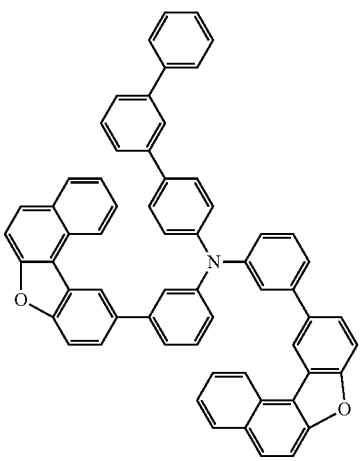
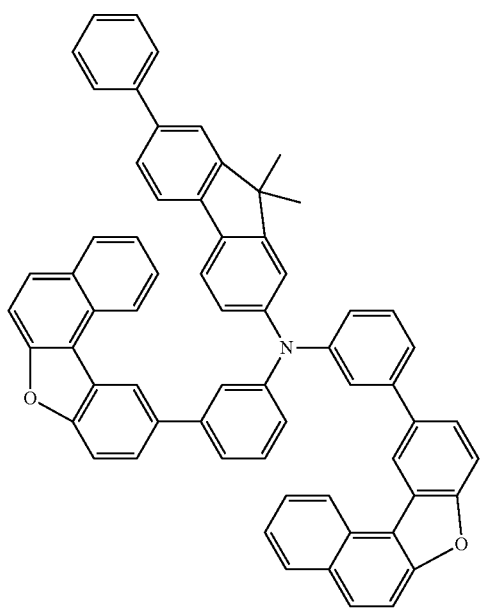

-continued
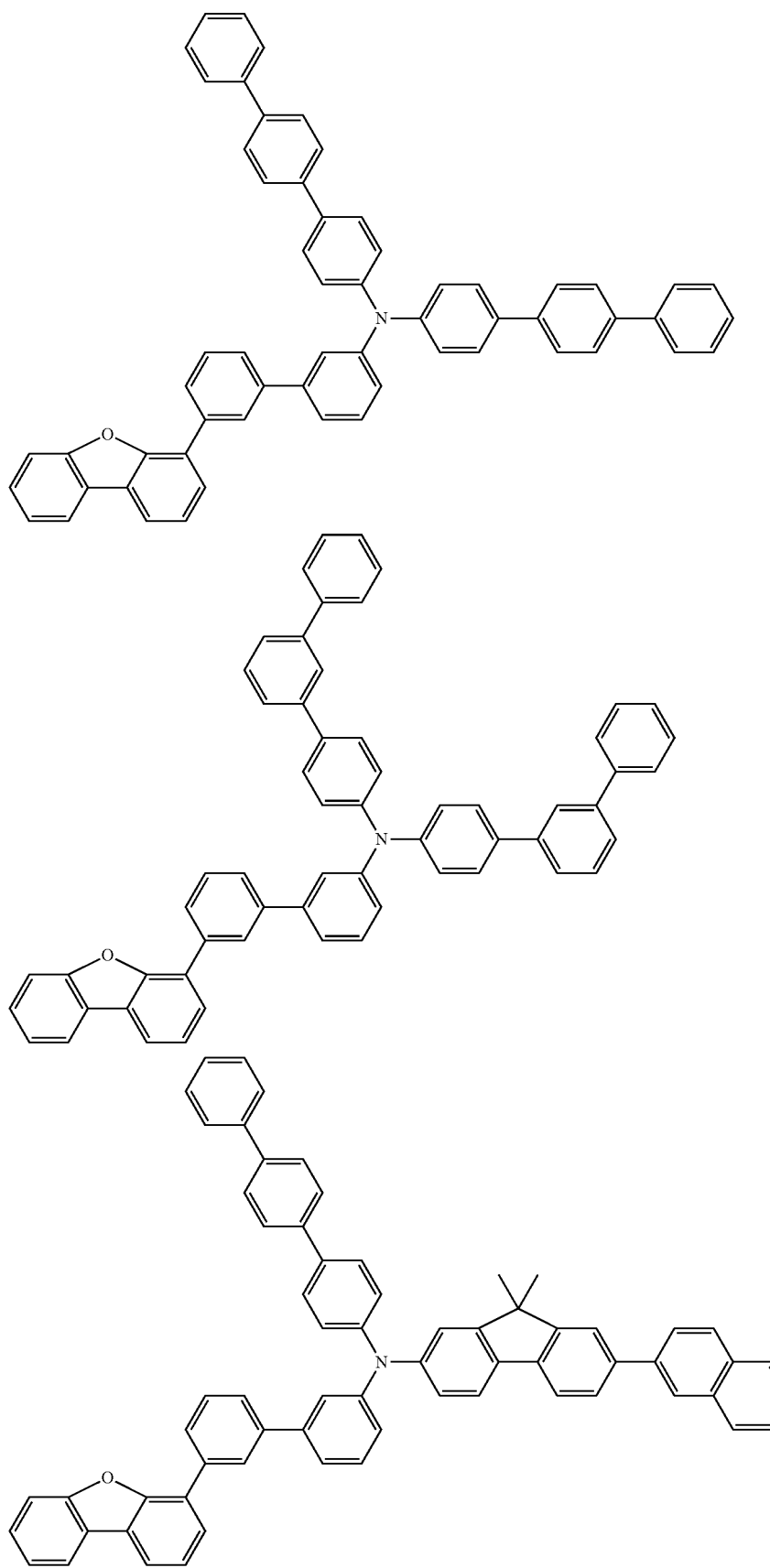

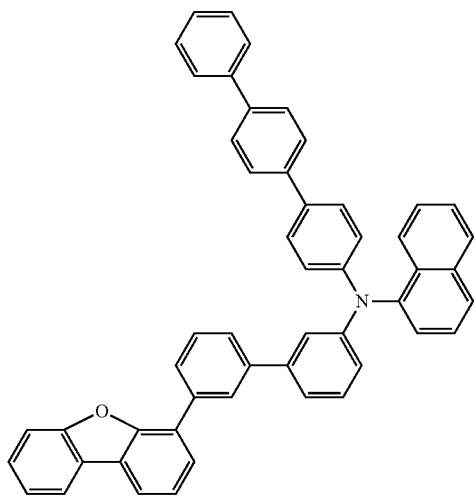
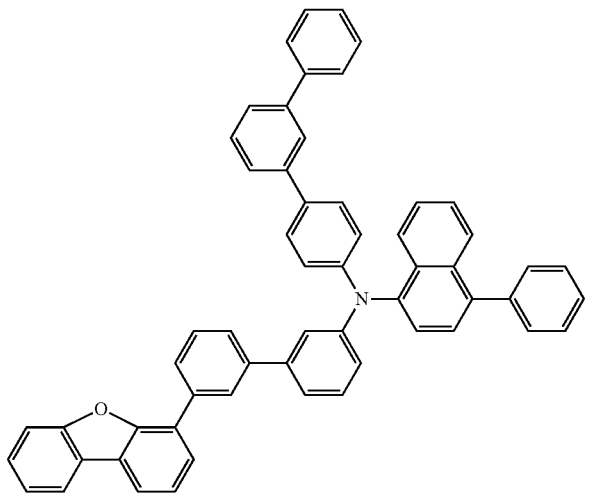
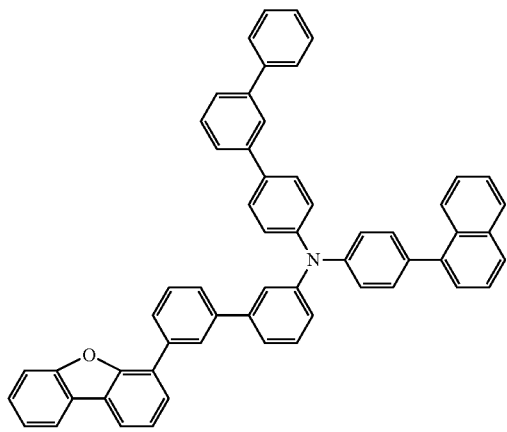
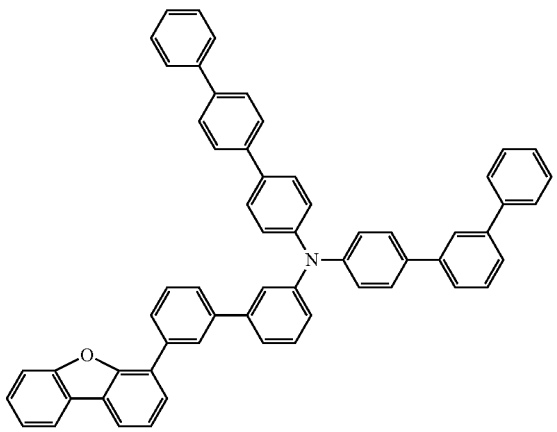
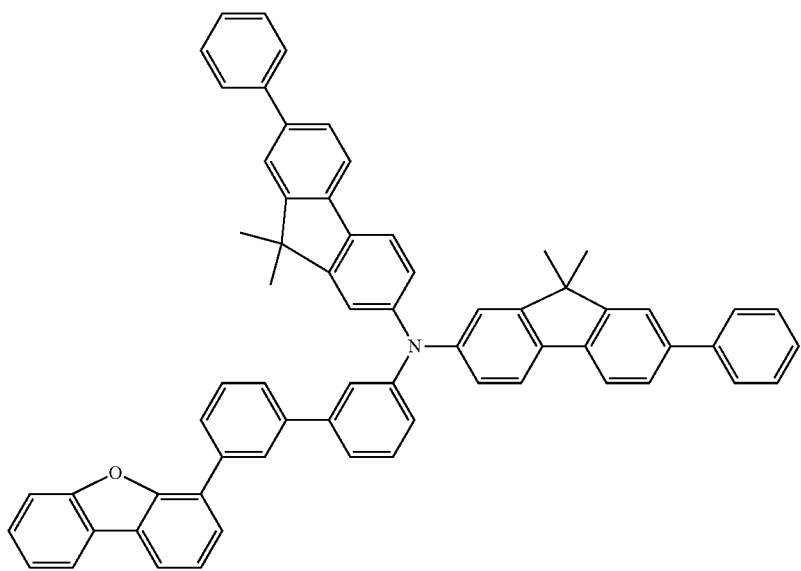

143 144
-continued
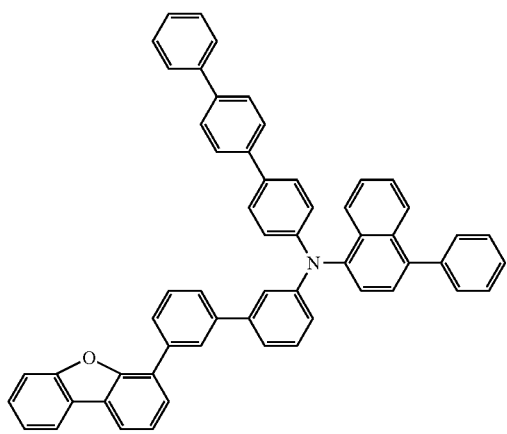
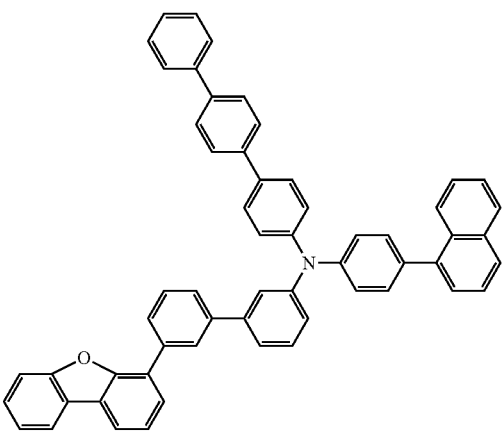
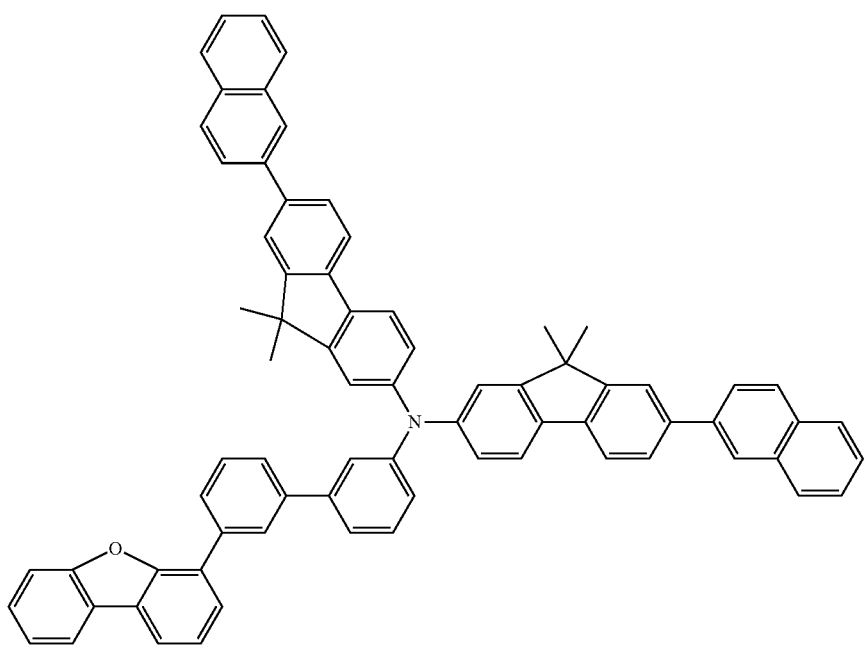
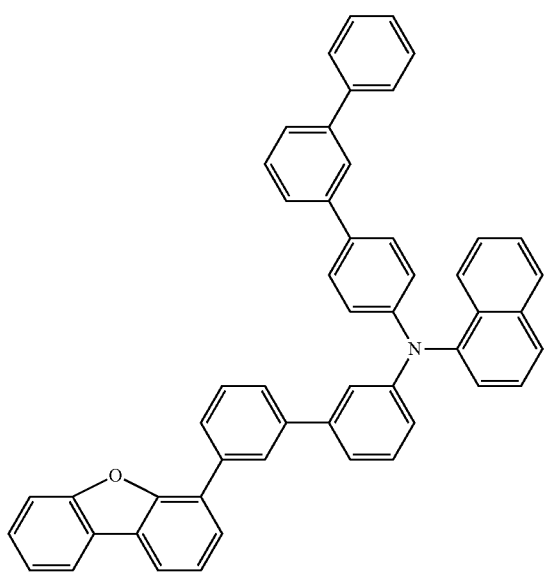

-continued
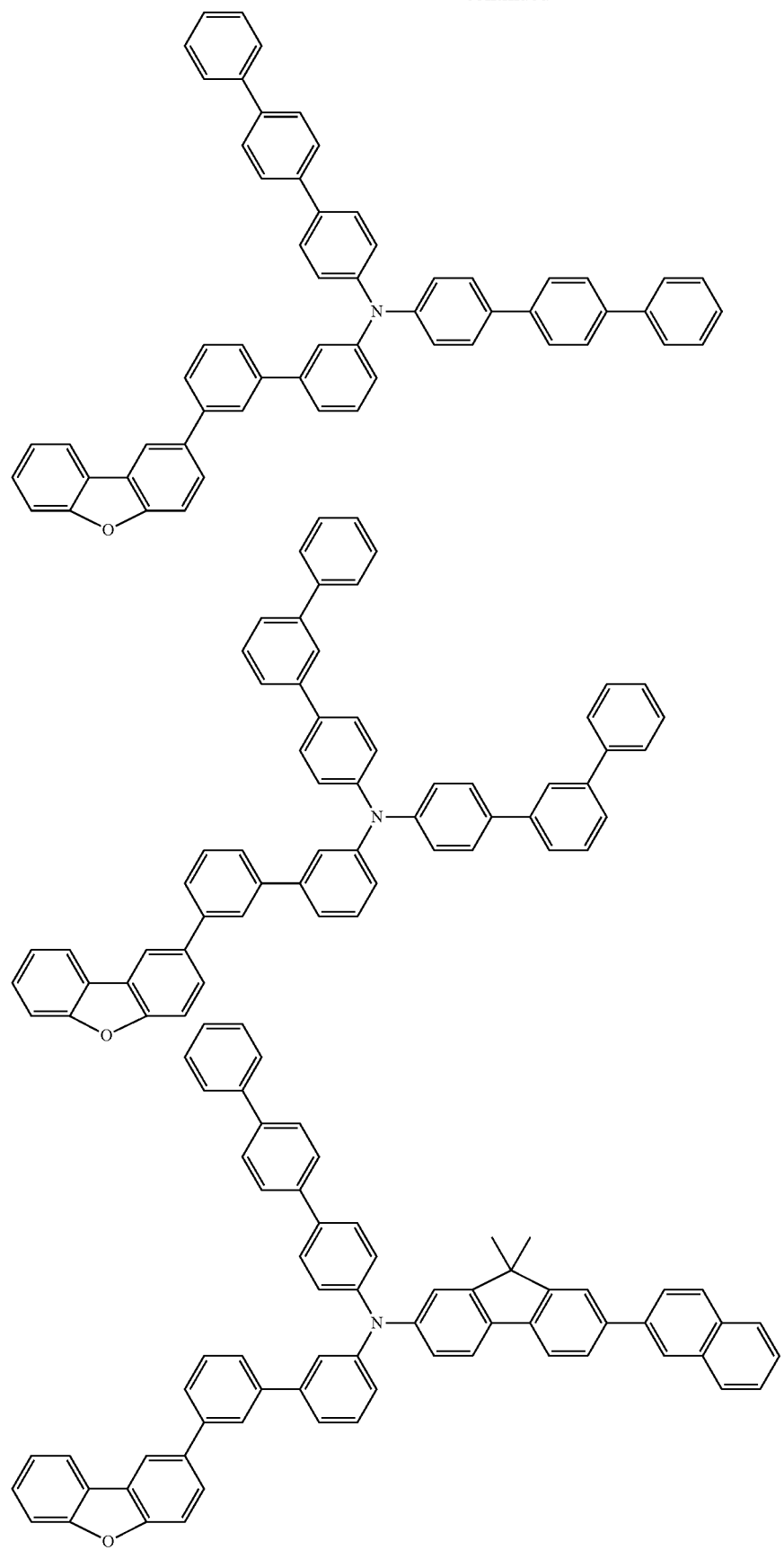

147
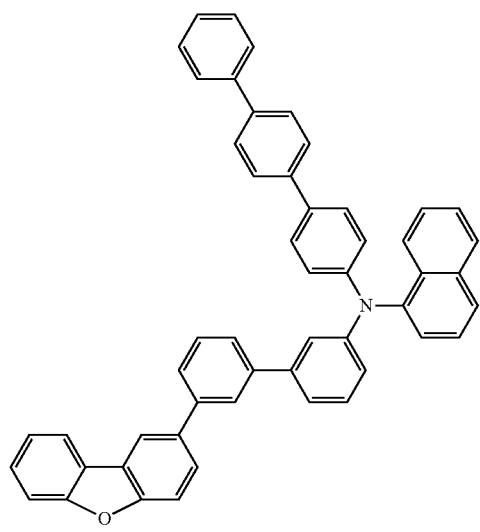
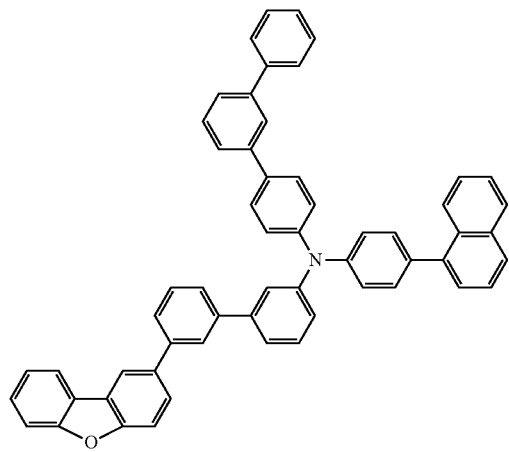
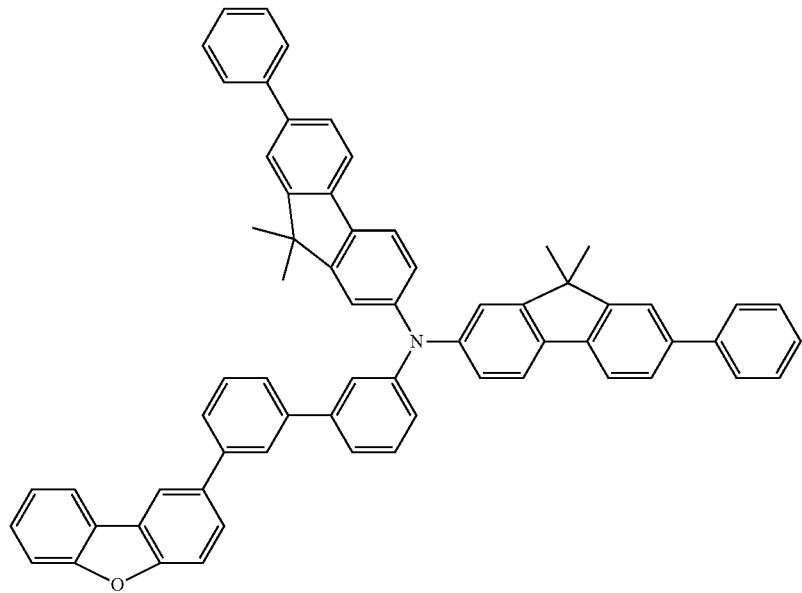
148
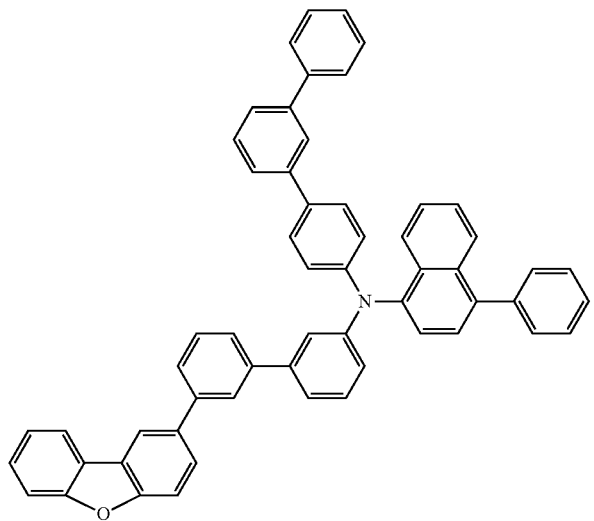
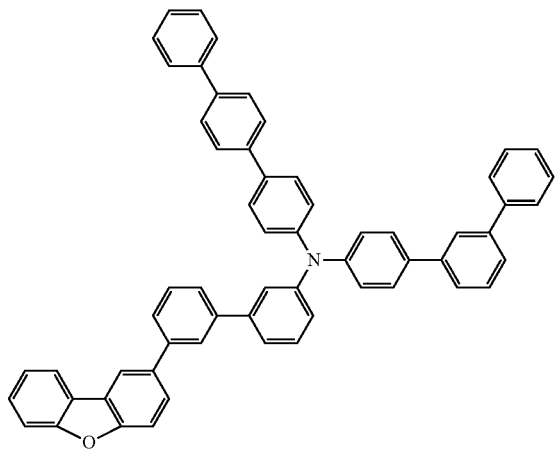

149
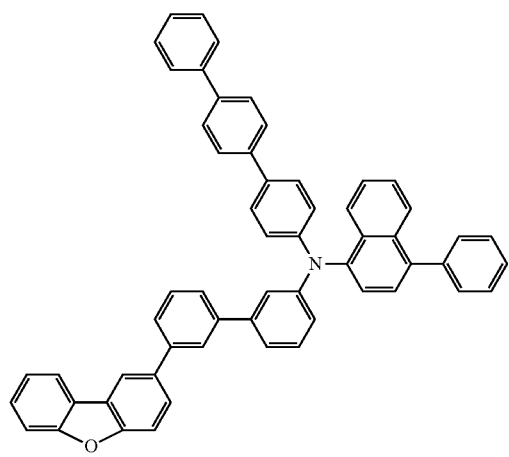
150
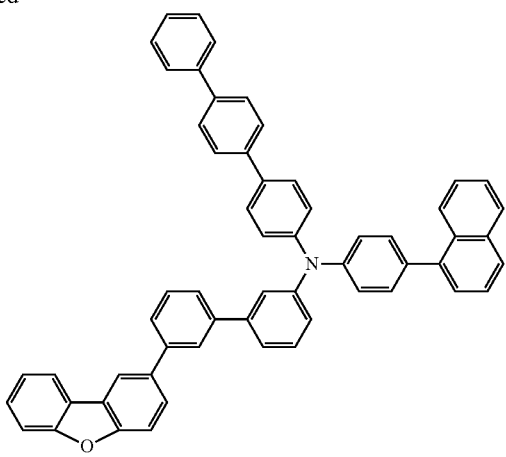
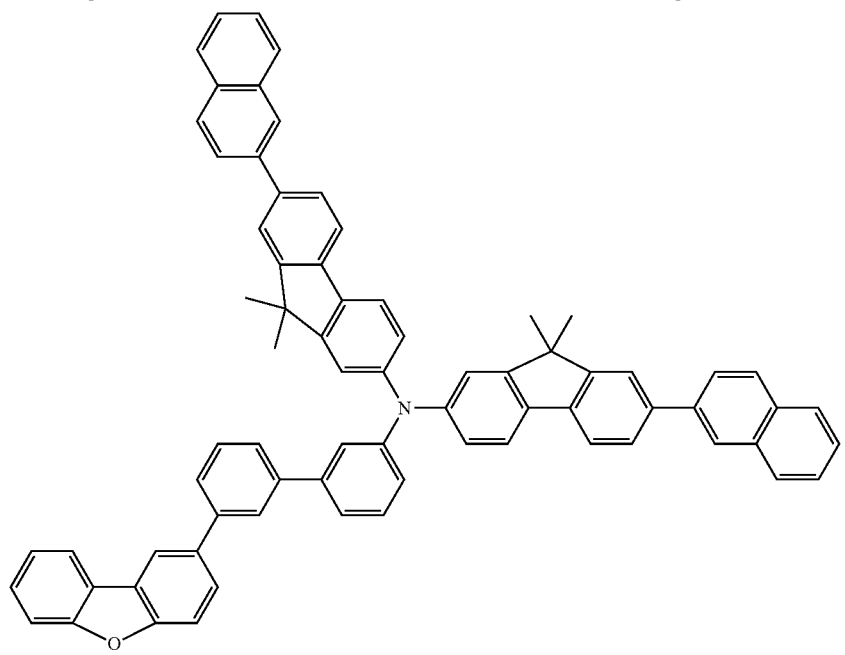
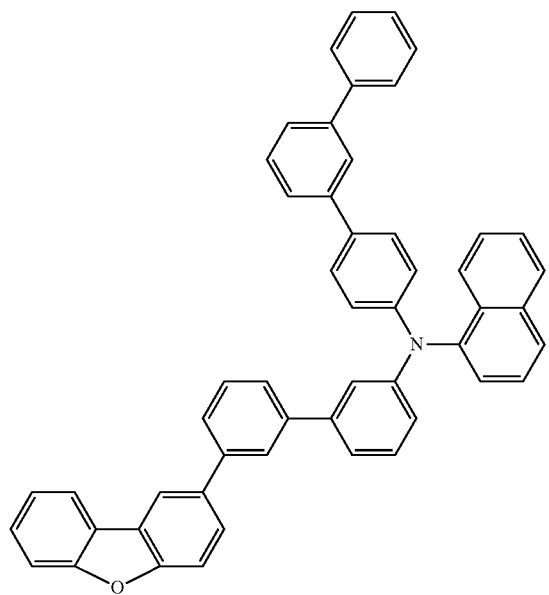

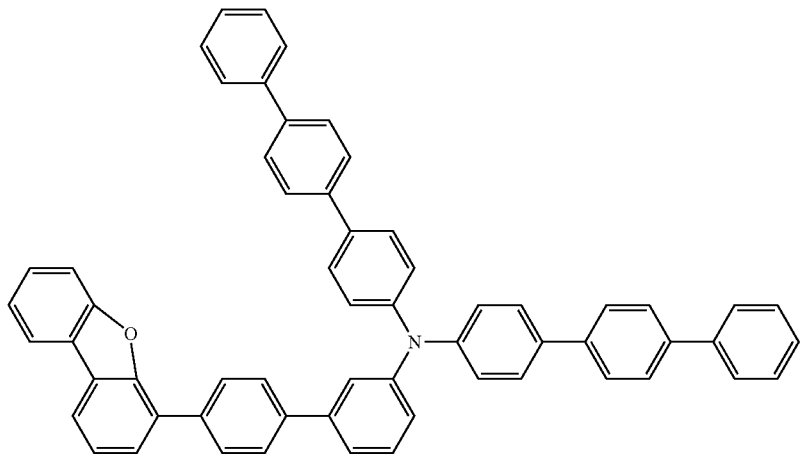
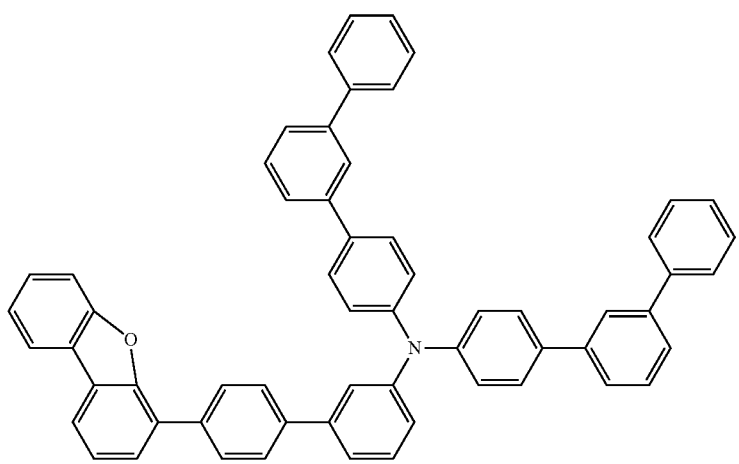
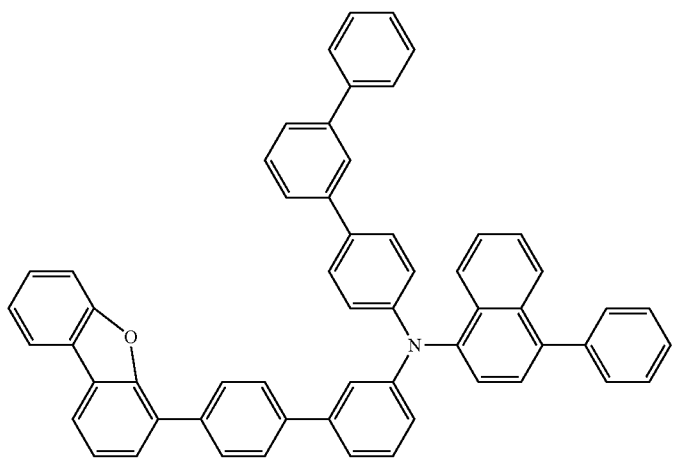

-continued
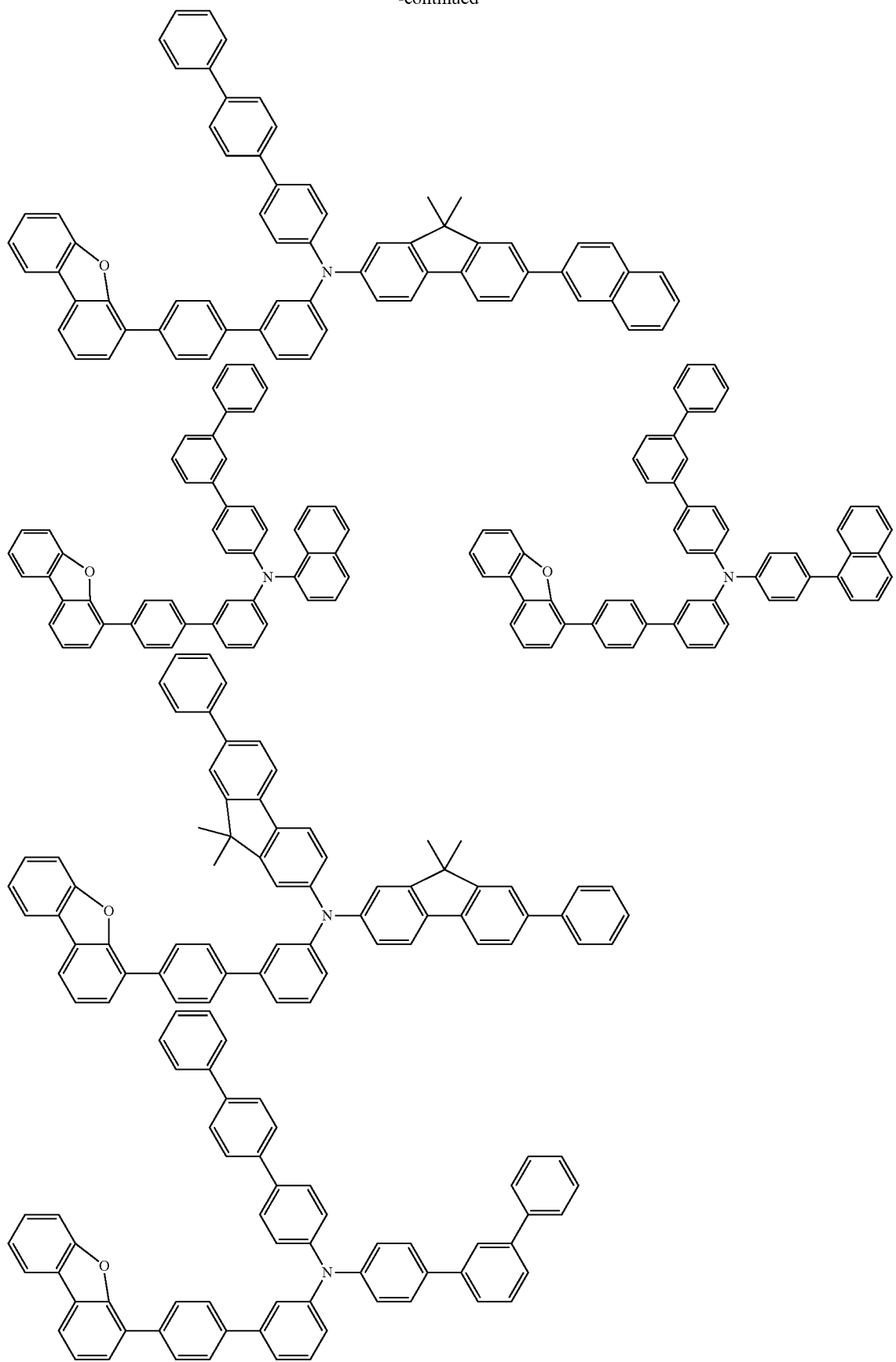

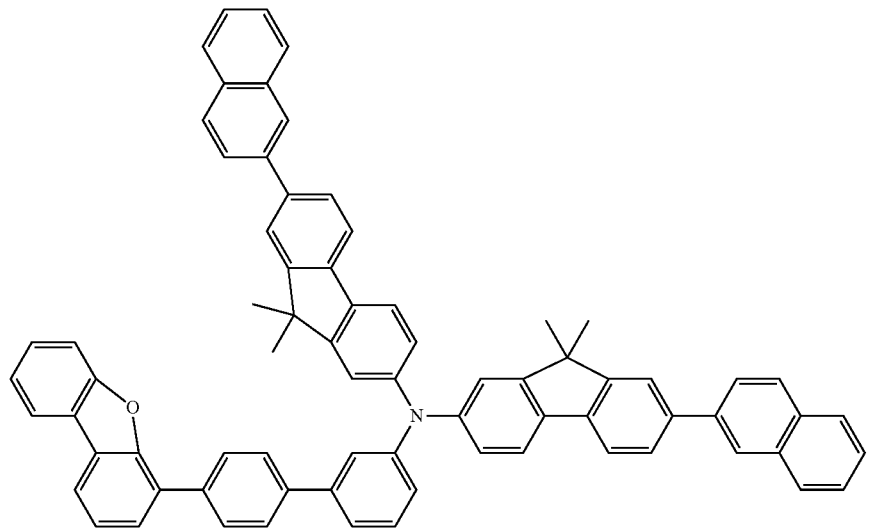
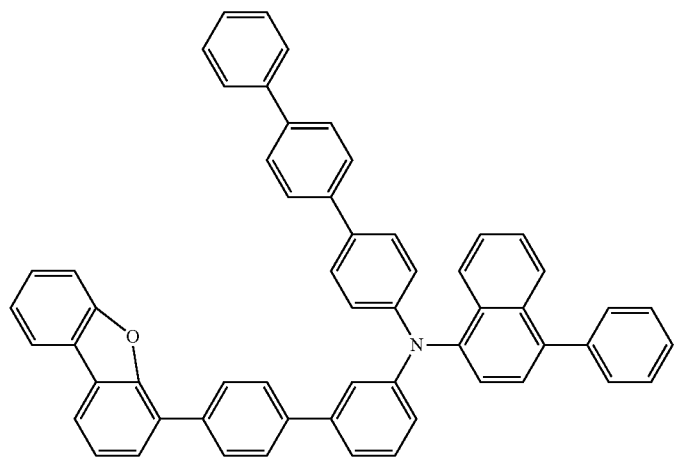
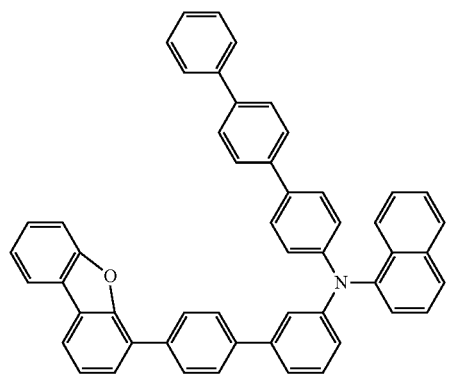
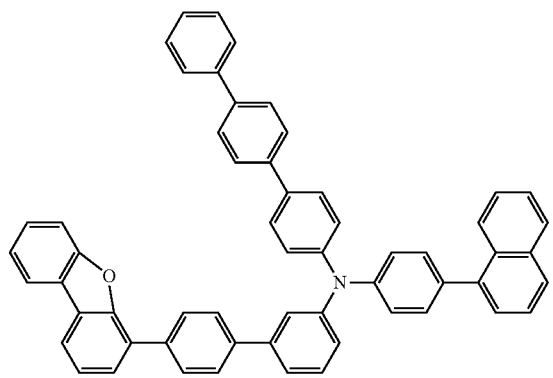

-continued
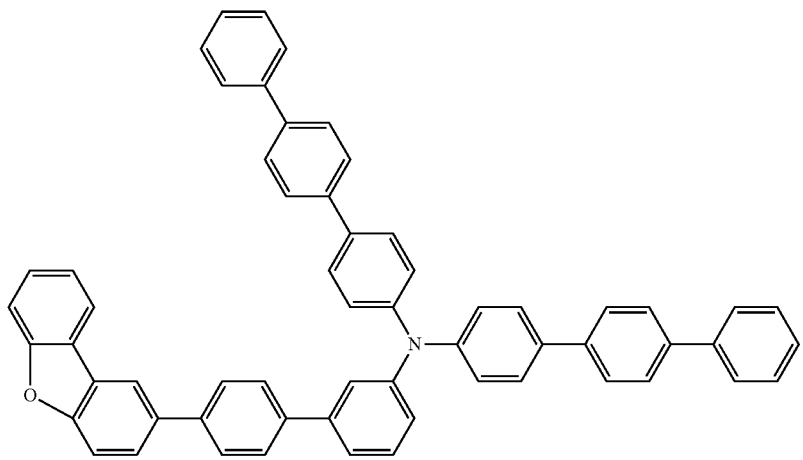
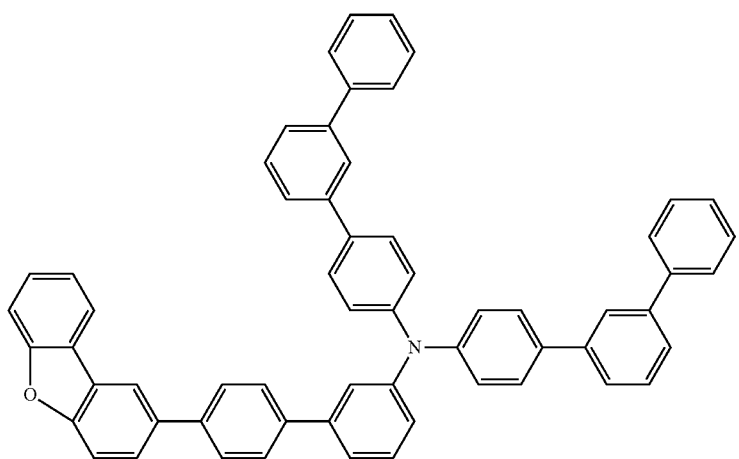
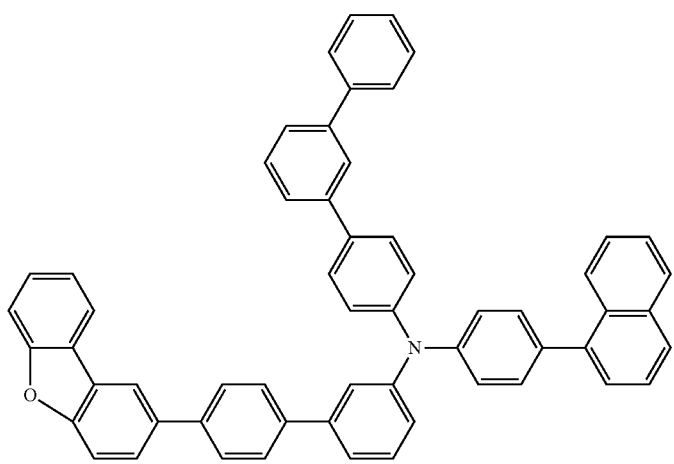

-continued
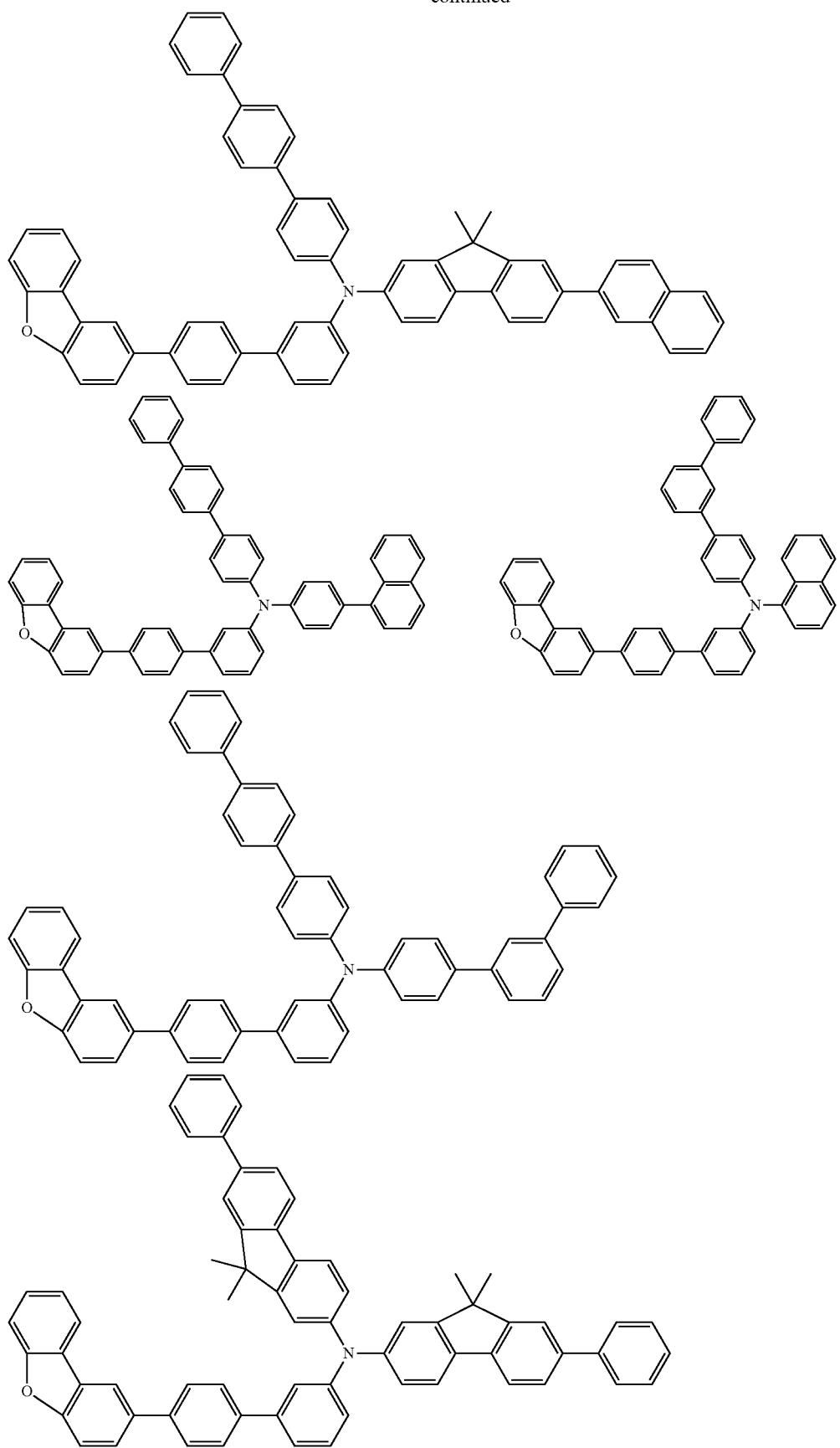

-continued
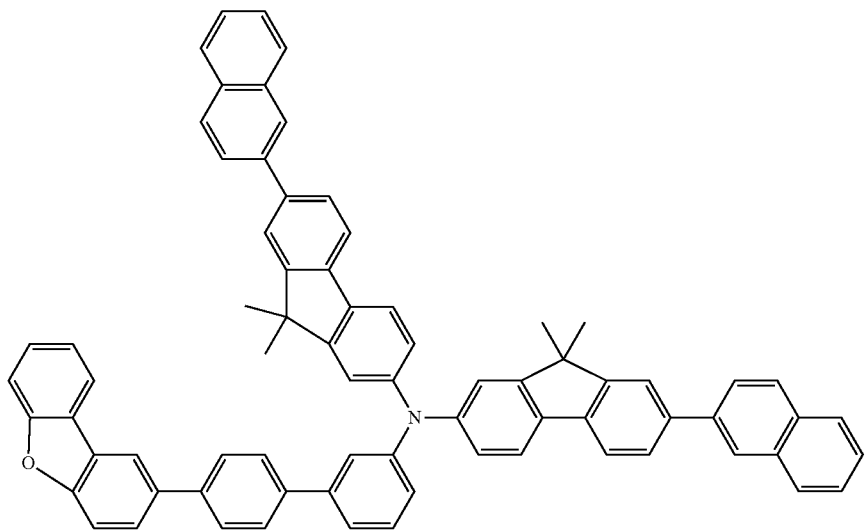
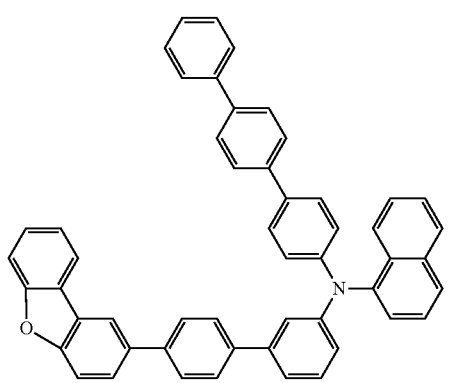
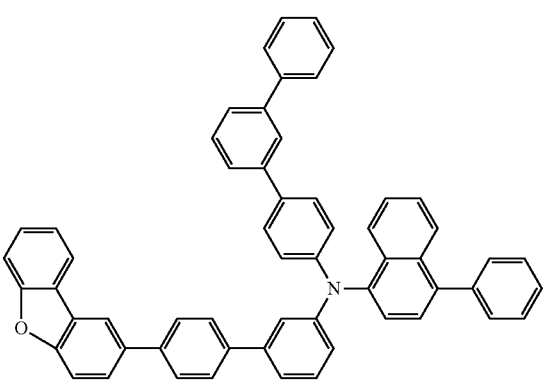
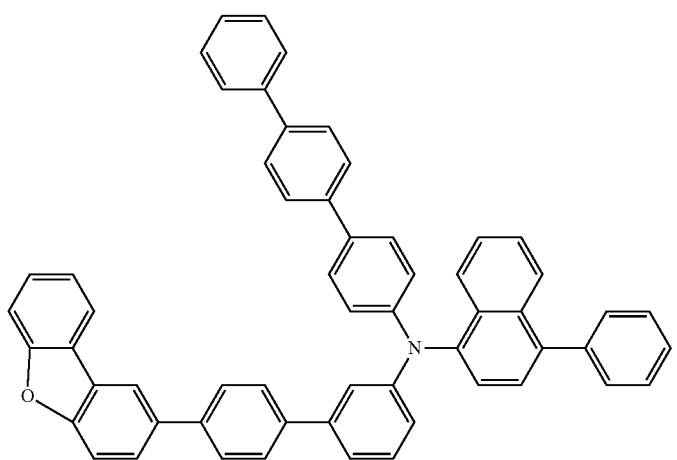

163
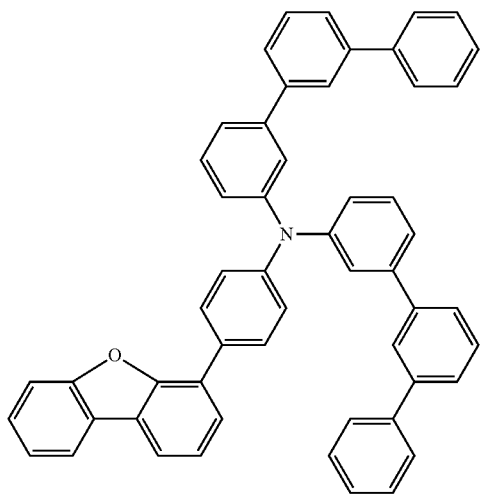
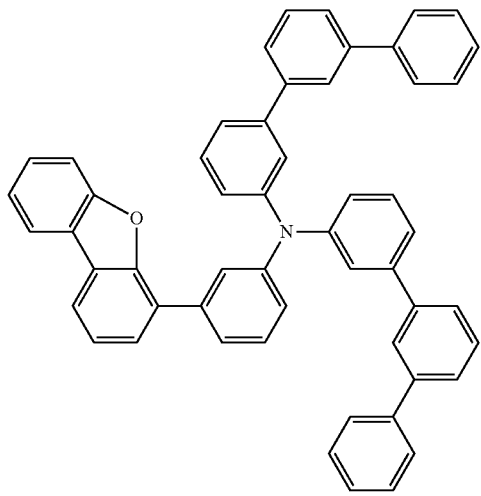
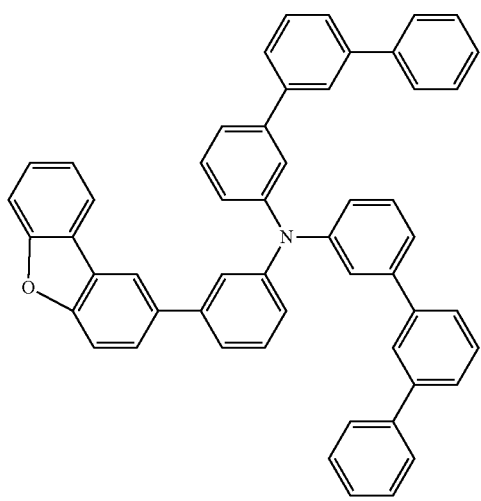
164
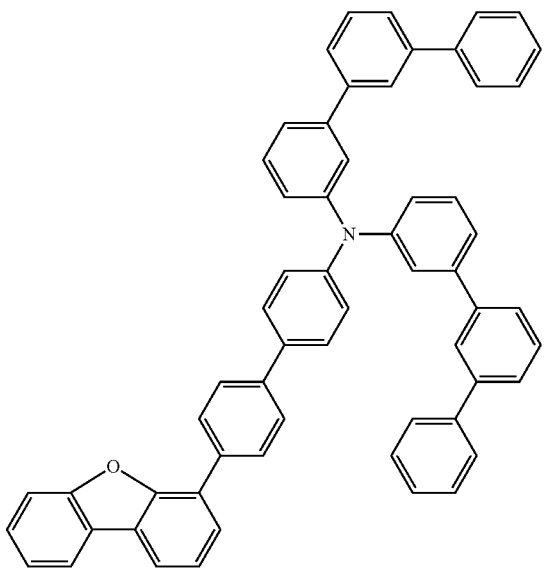
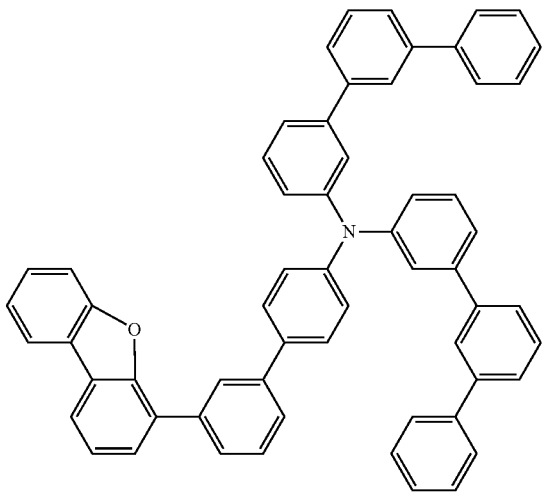
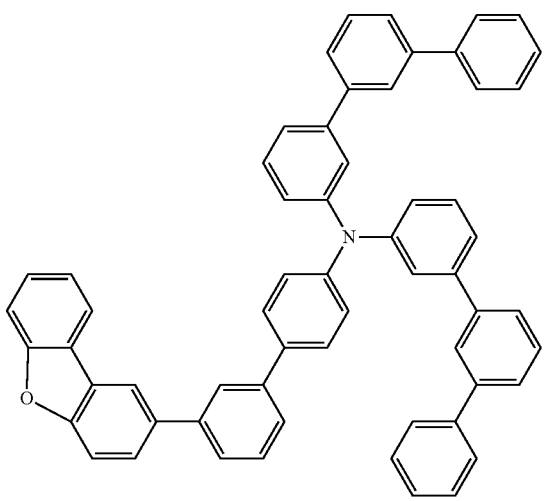

-continued
165
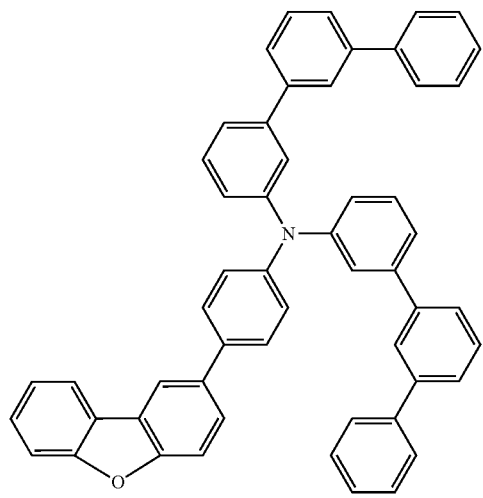
166
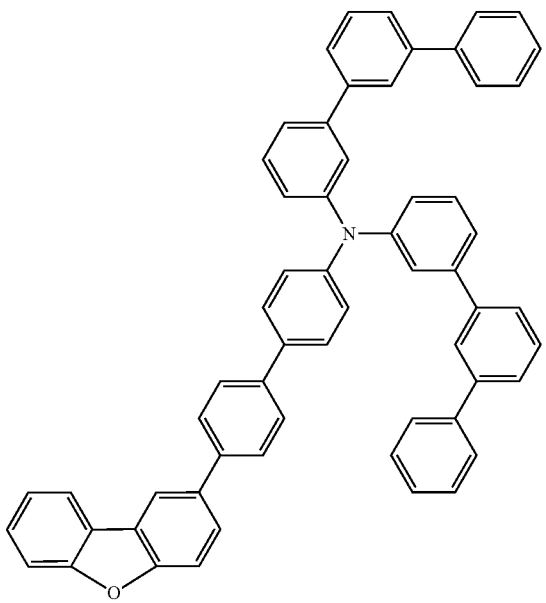
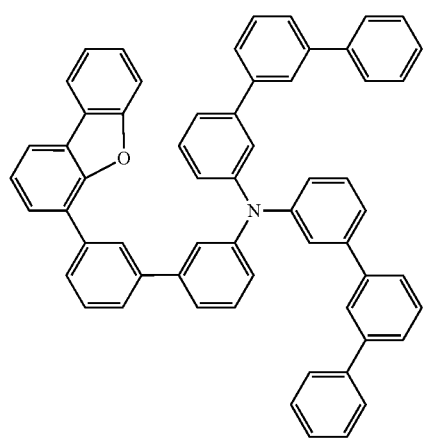
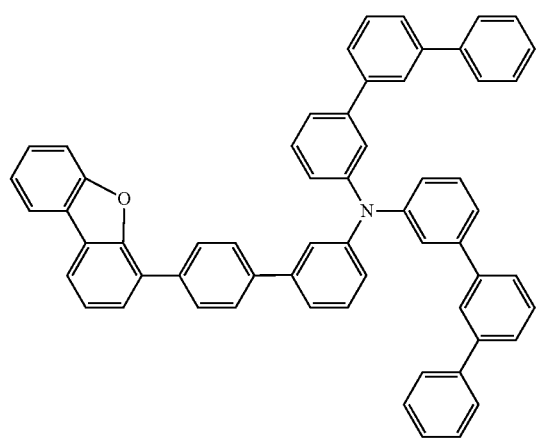
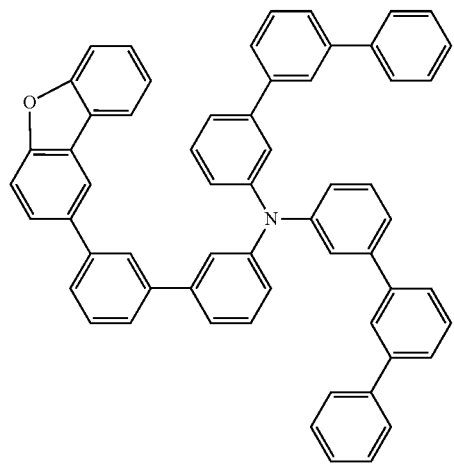
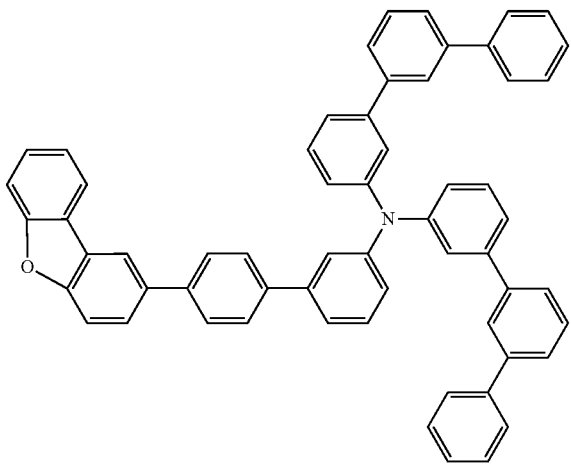

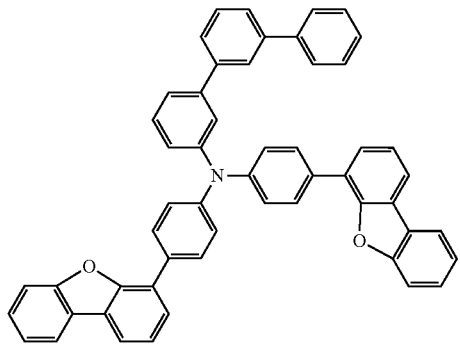
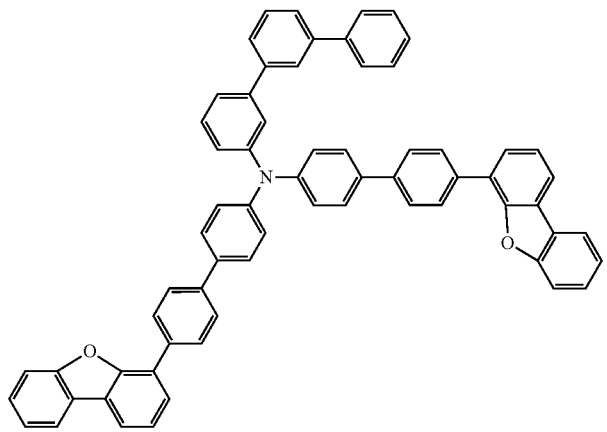
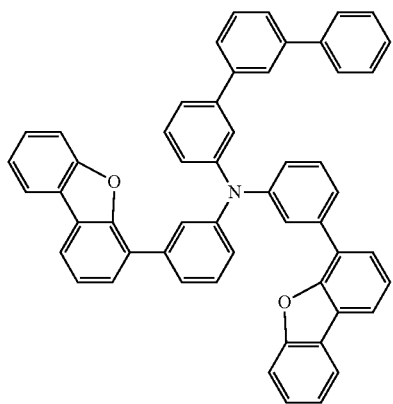
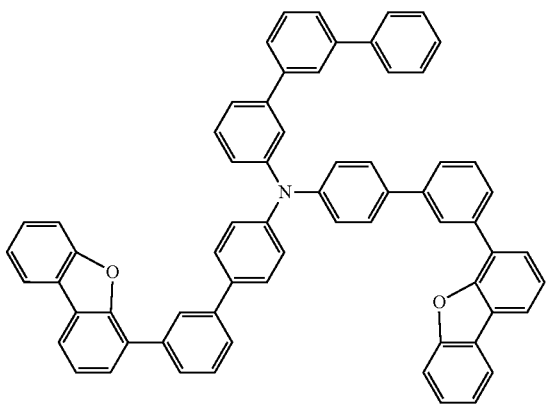
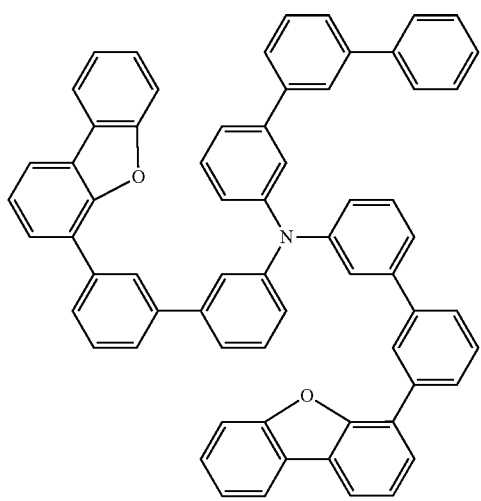

-continued
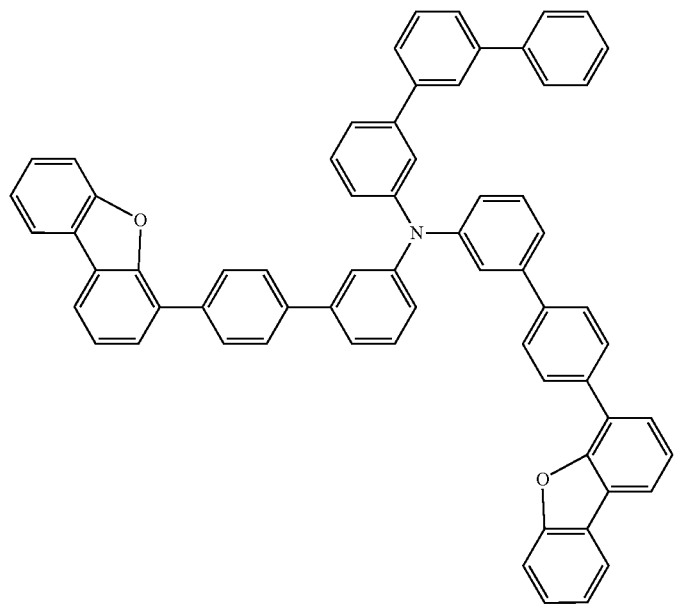
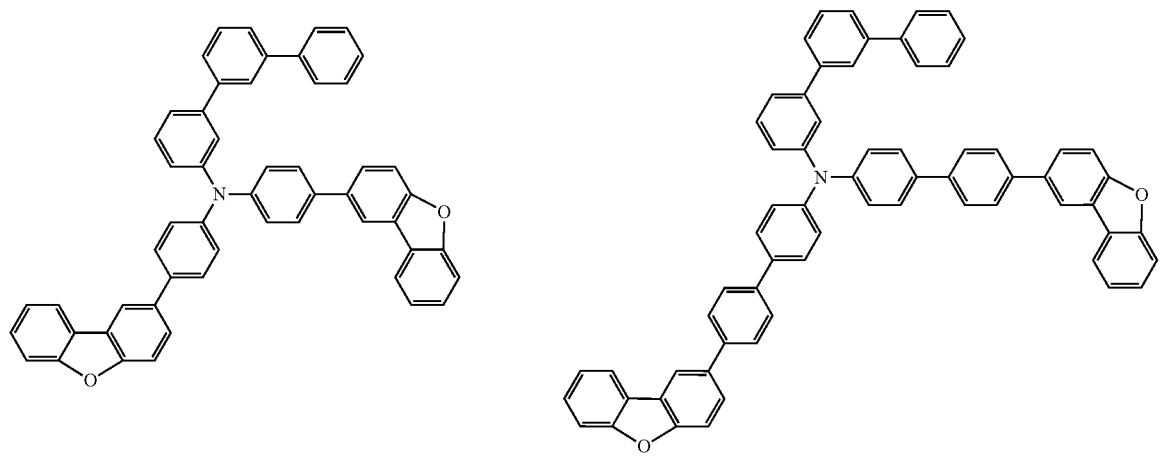
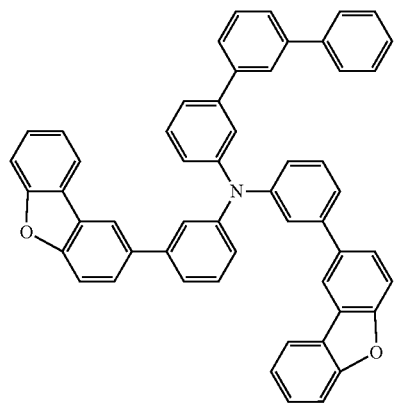
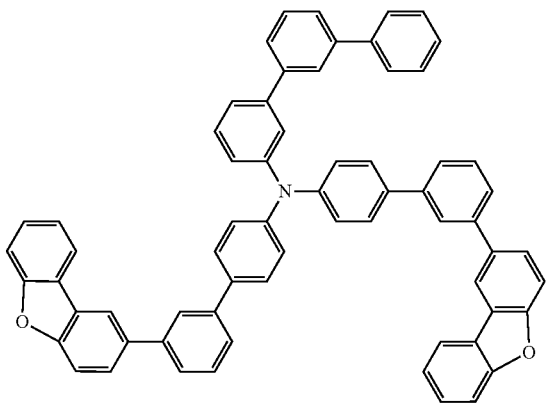

-continued
171
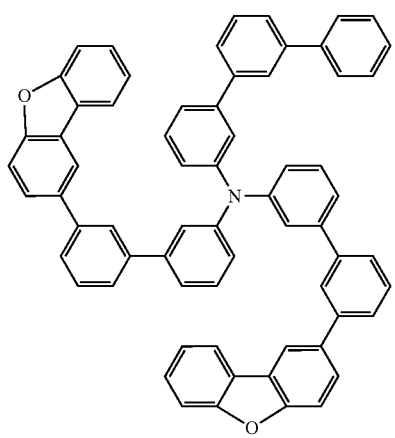
172
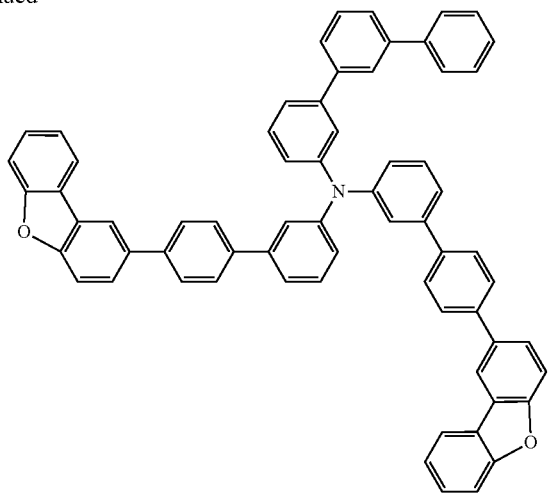
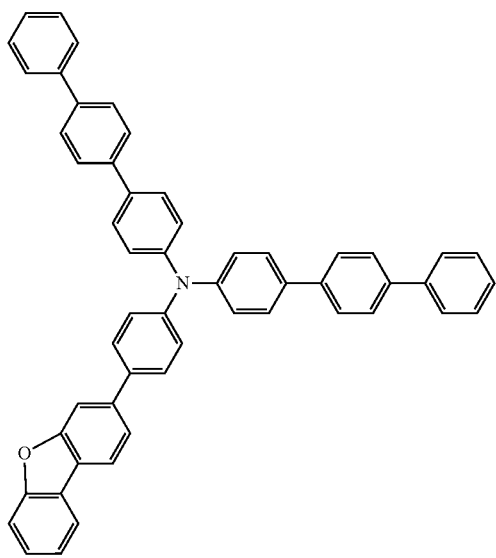
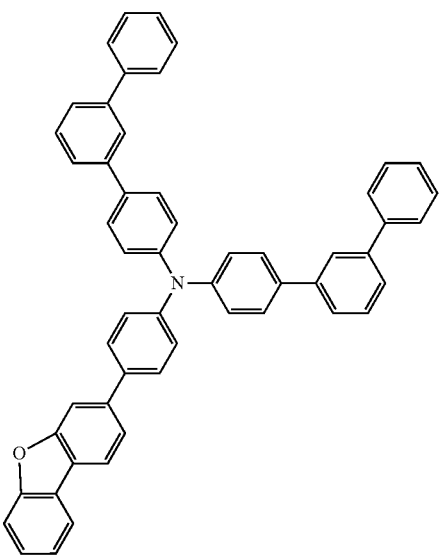
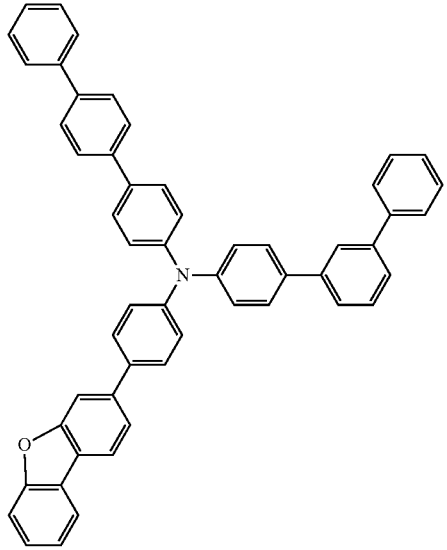
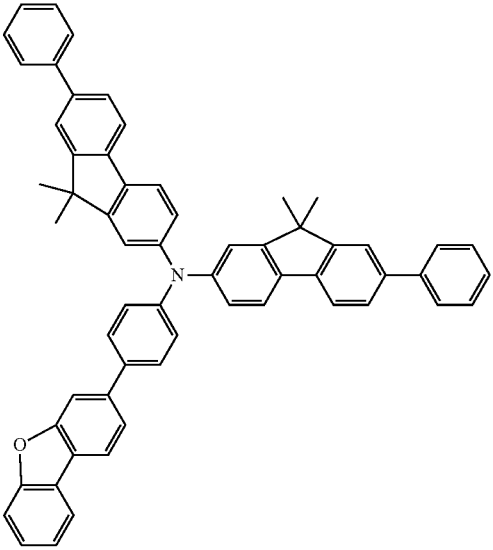

-continued
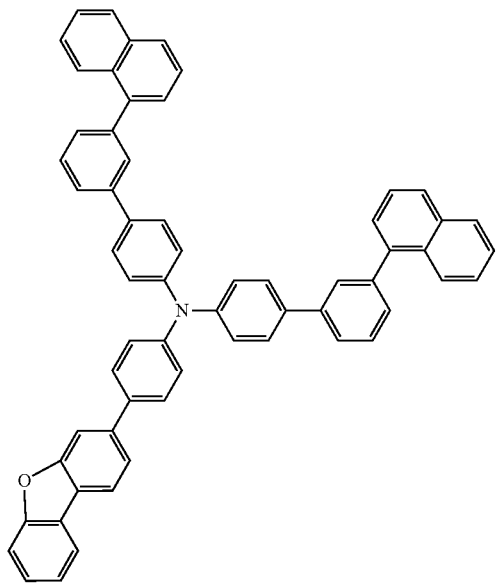
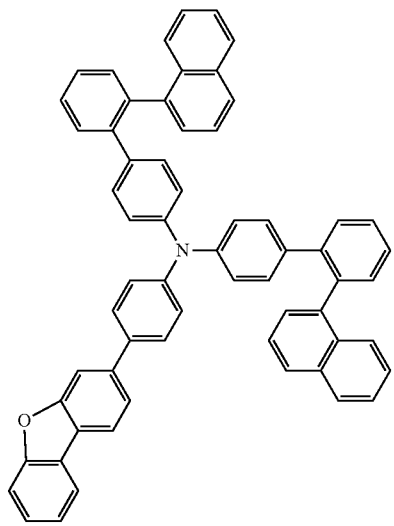
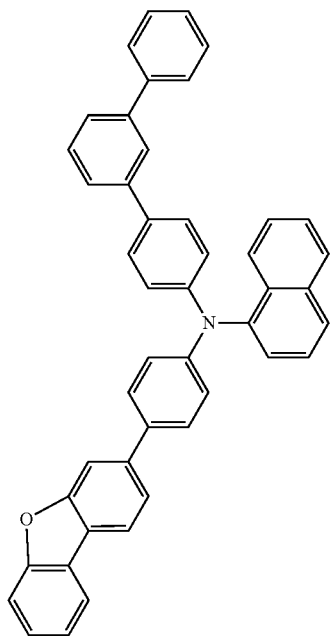
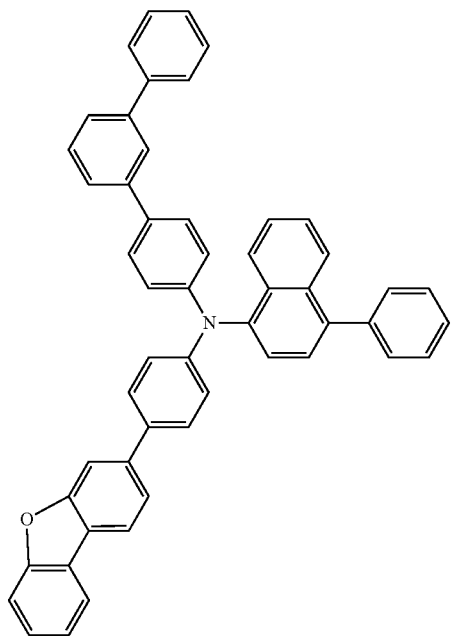

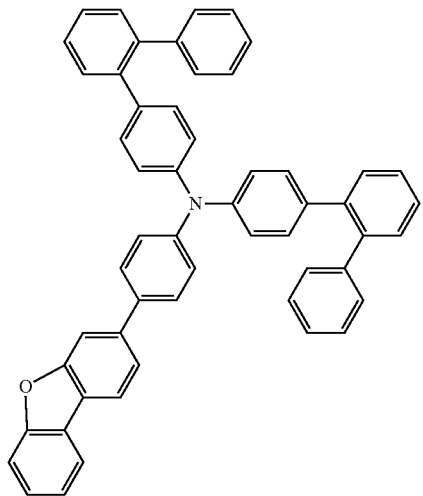
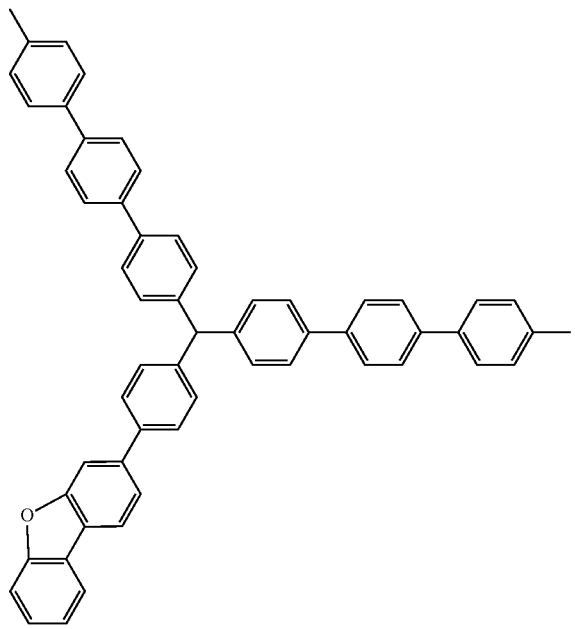
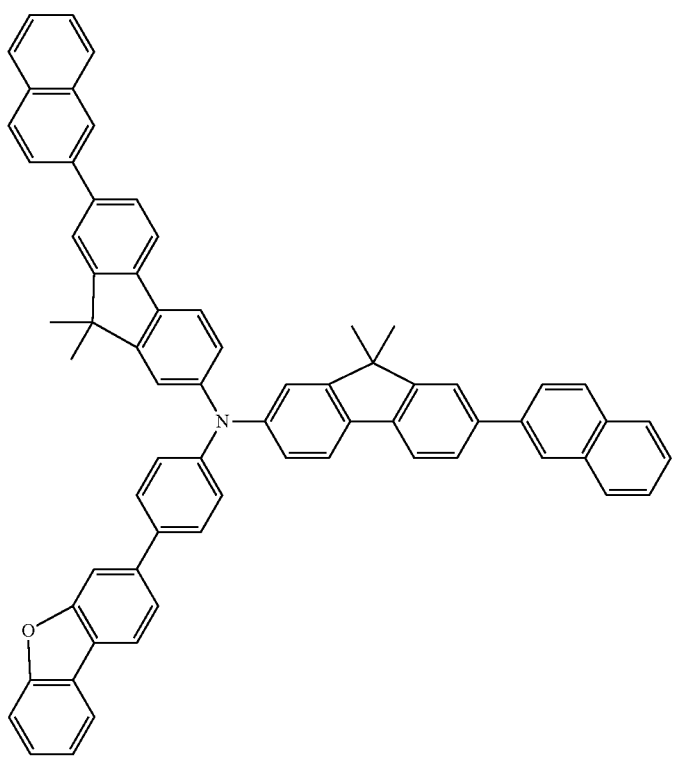

-continued
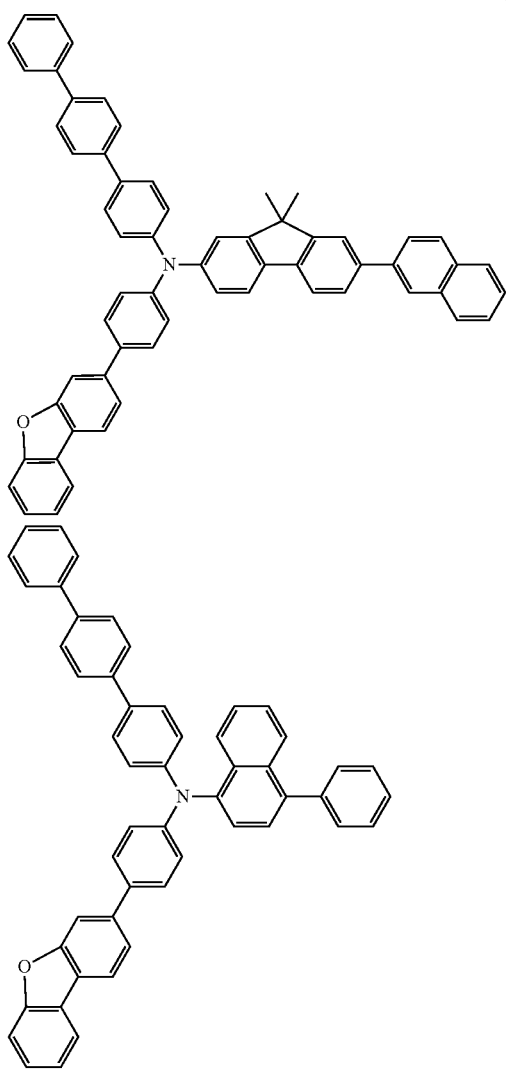
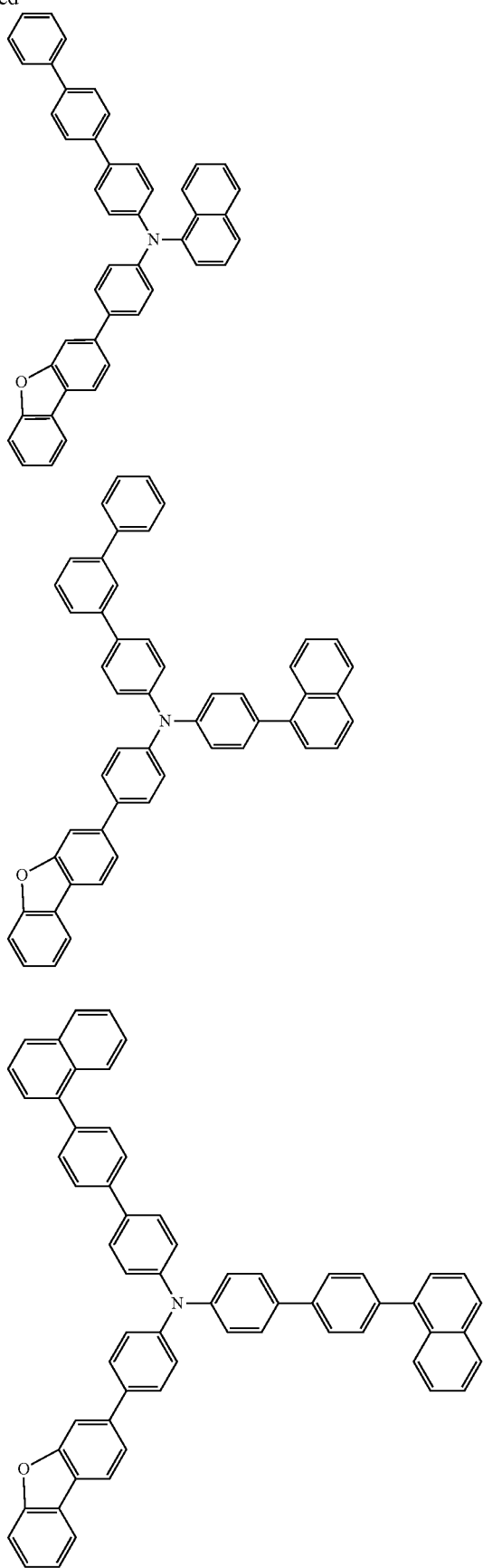

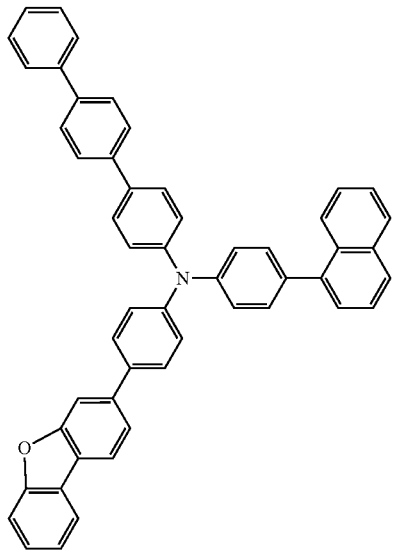
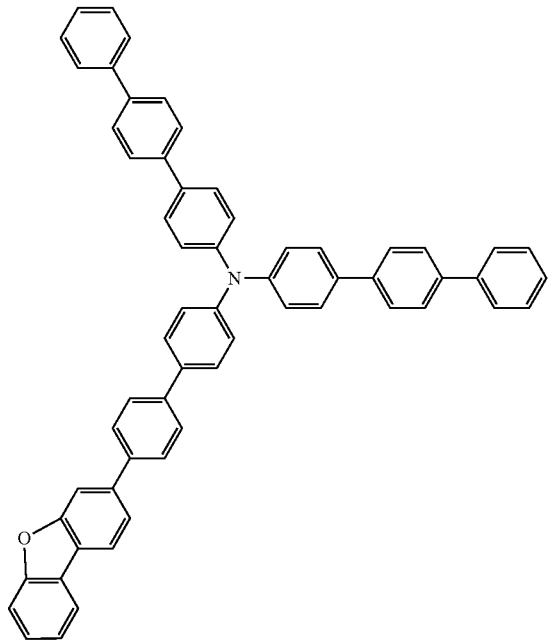
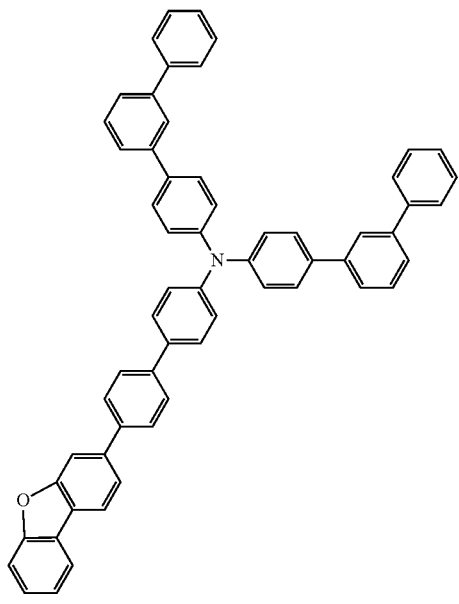
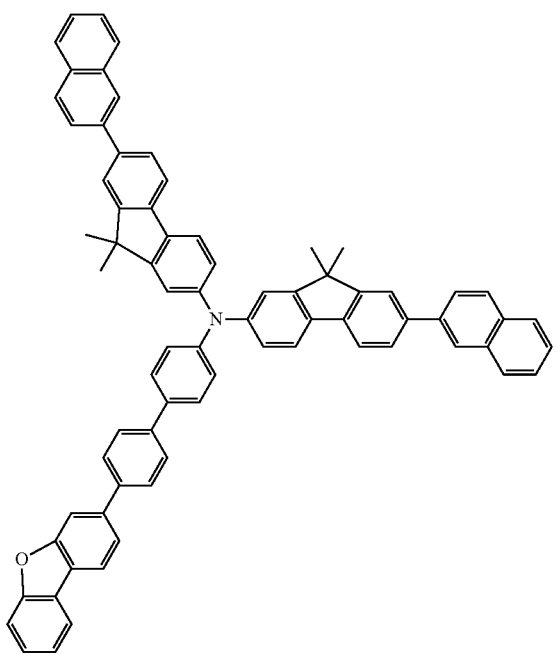

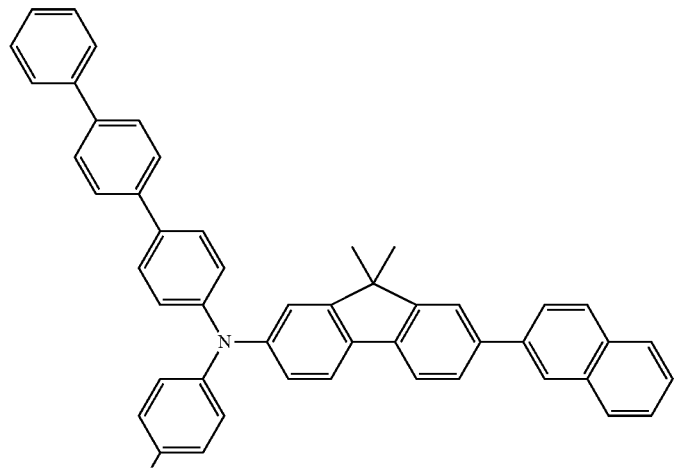
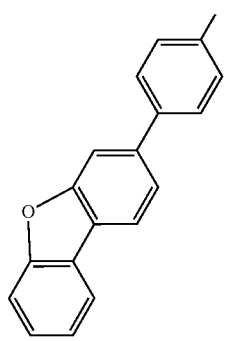
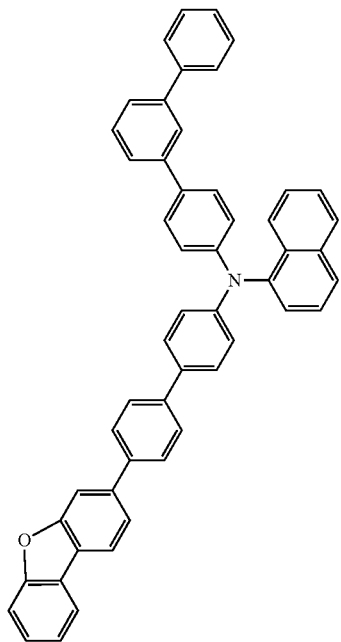
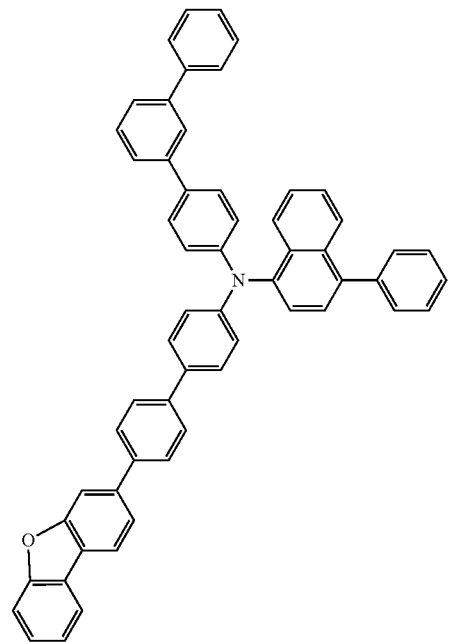

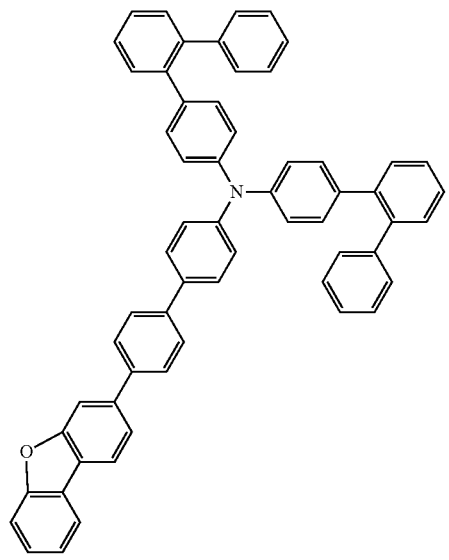
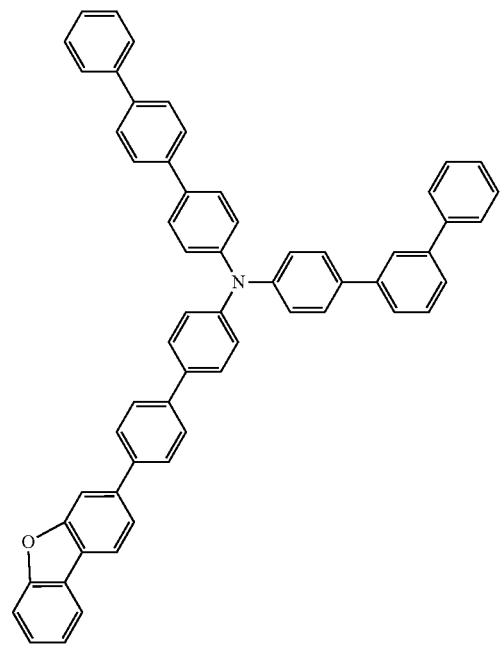
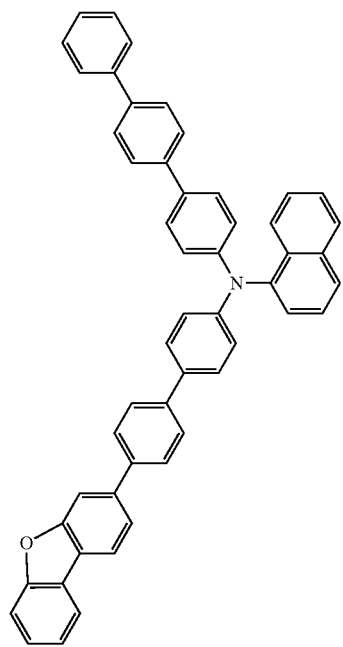
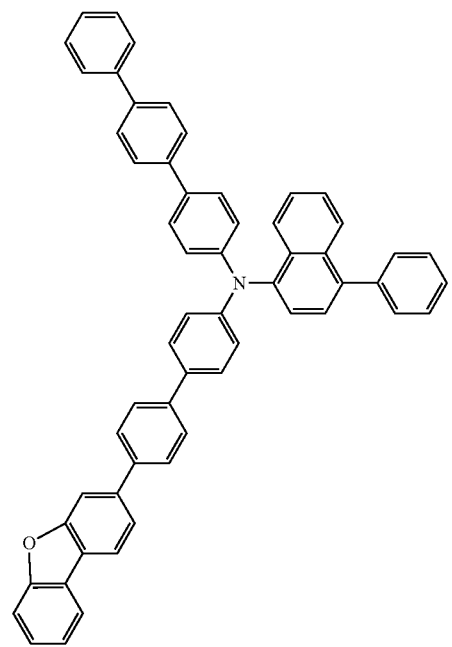

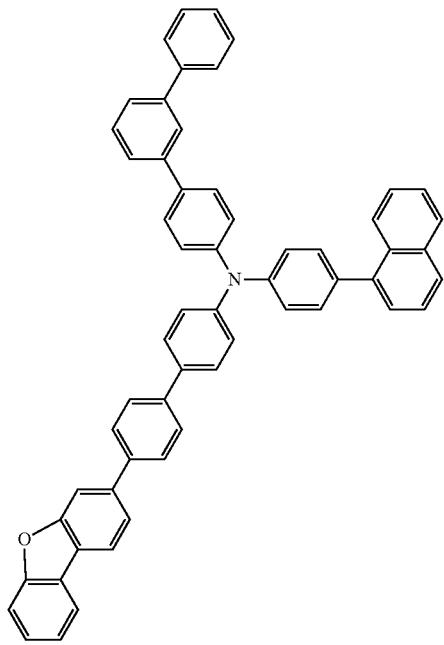
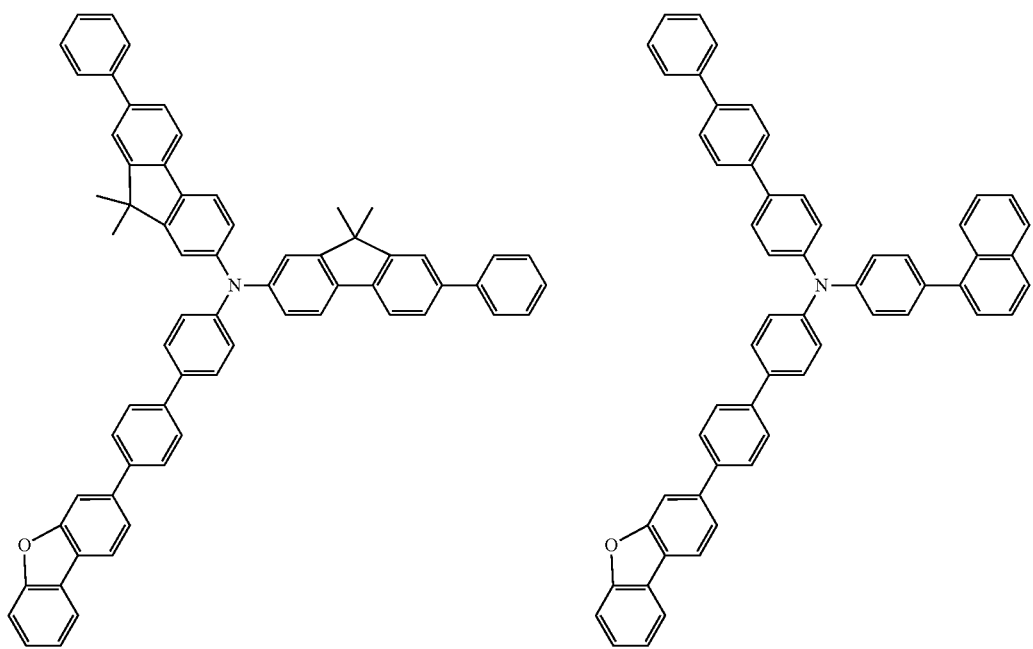

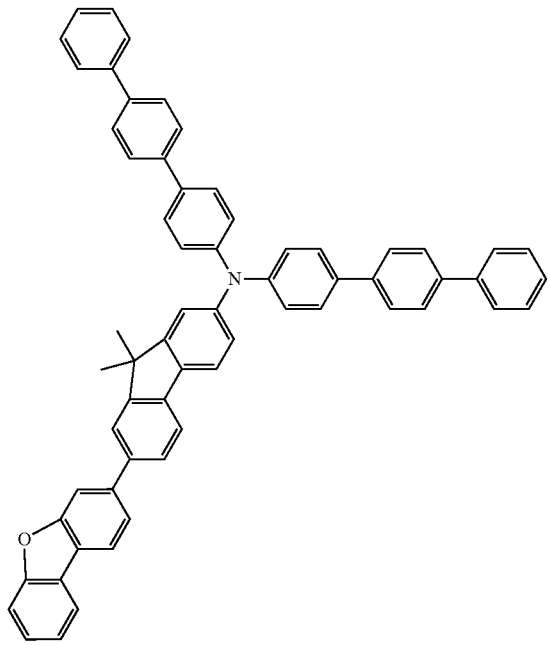
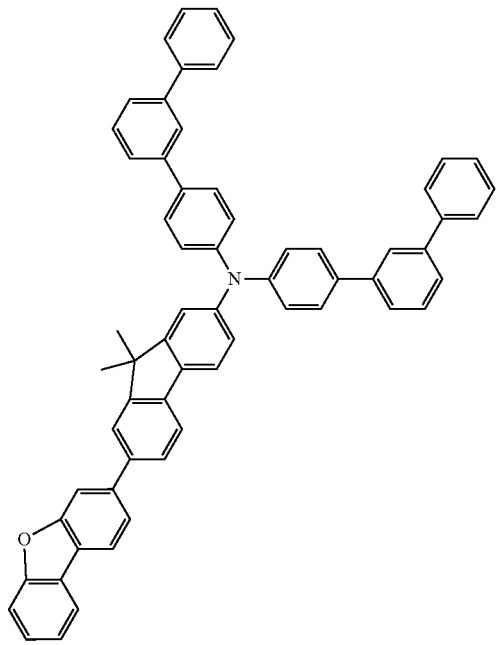
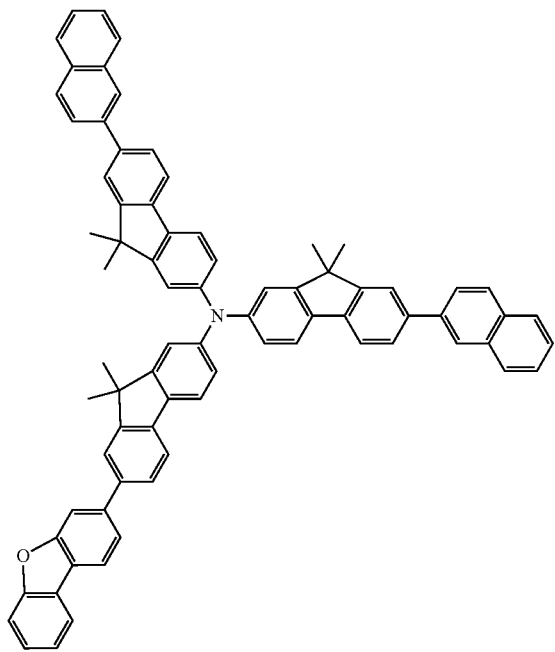
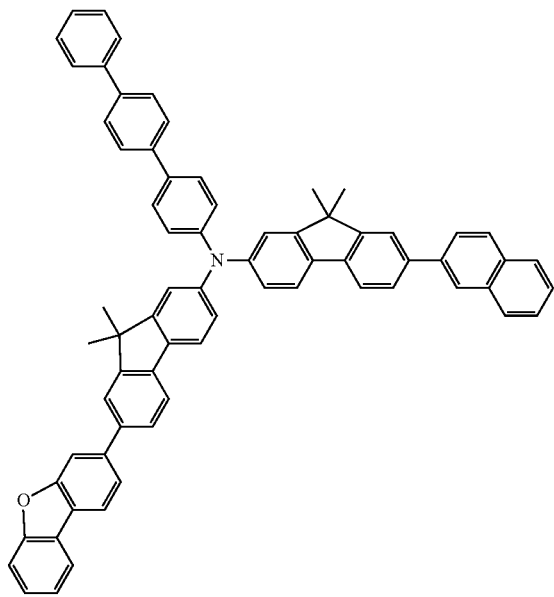

189
190
-continued
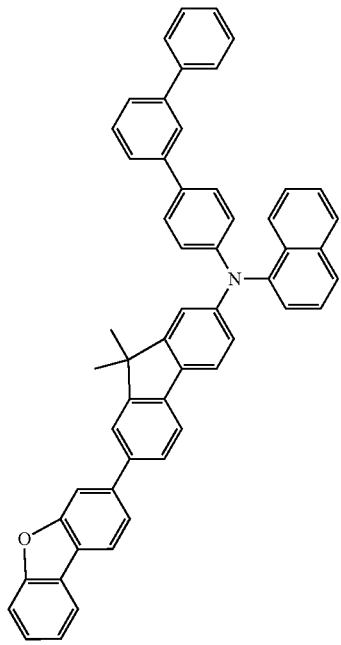
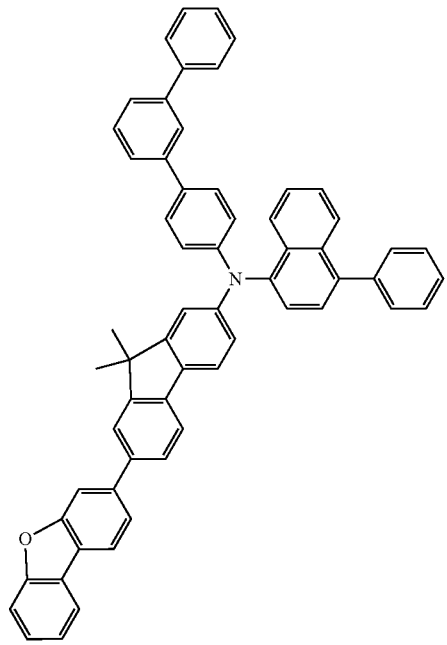
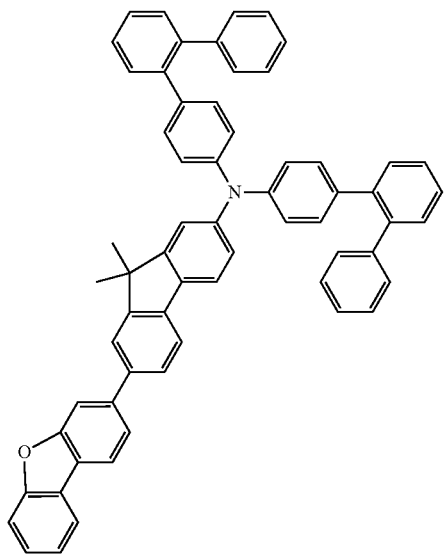
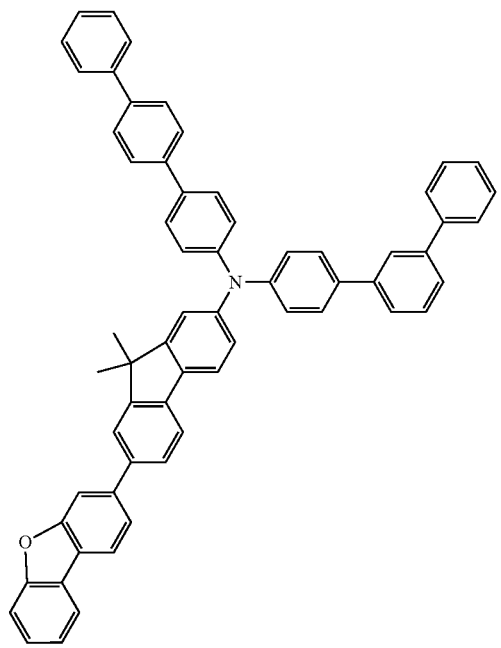

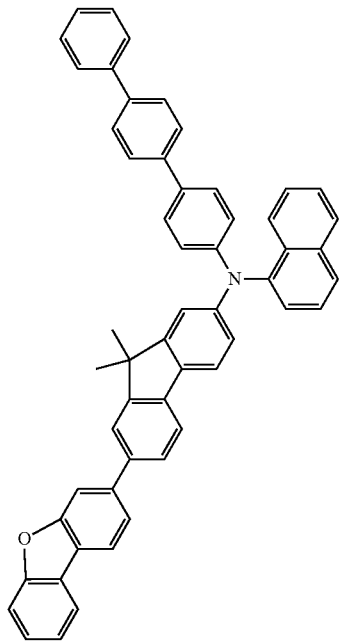
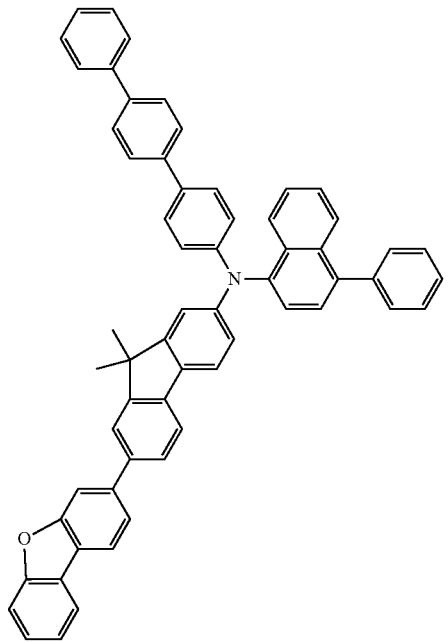
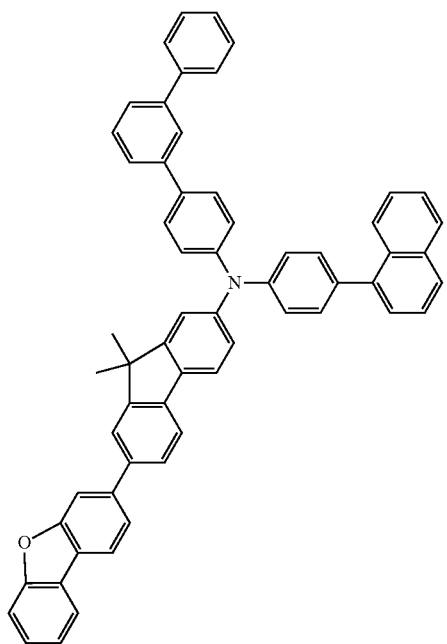
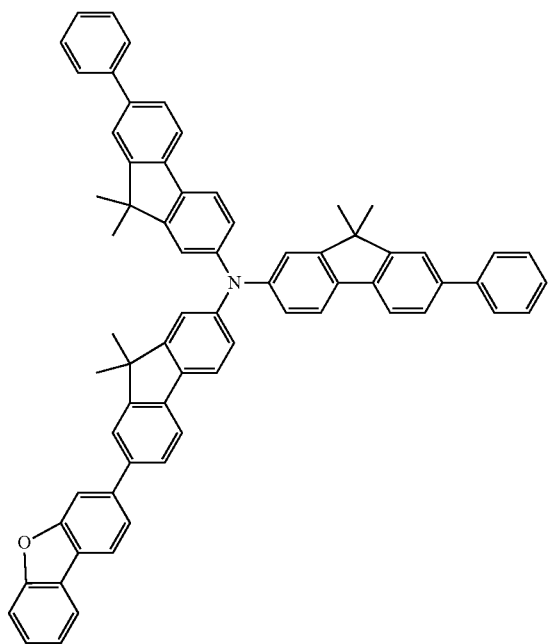

193 | 194
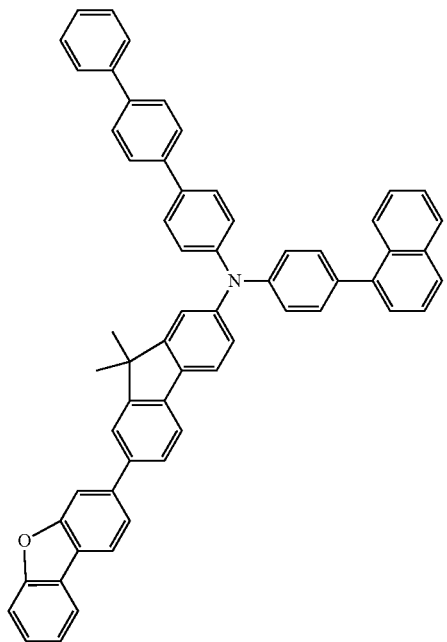 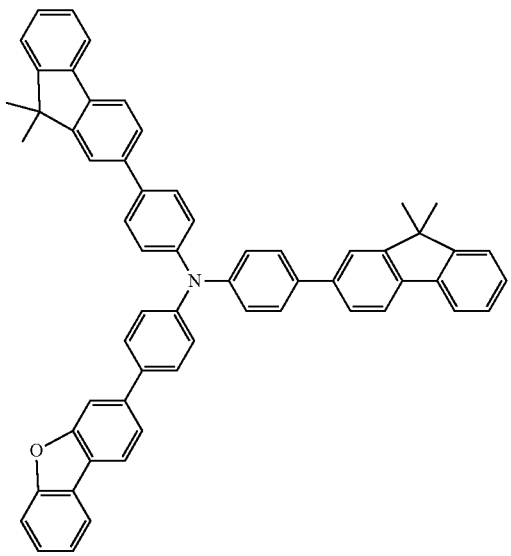
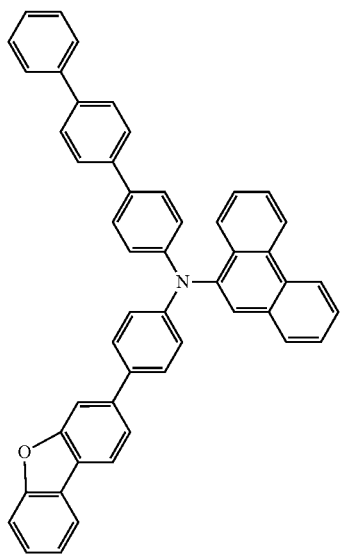 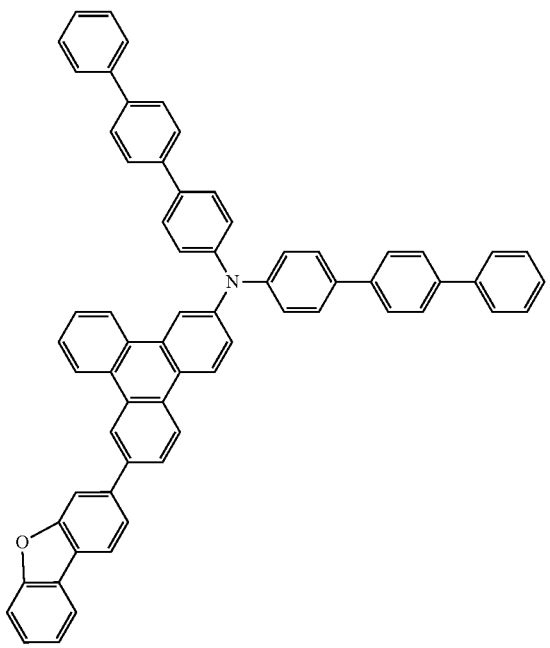

-continued
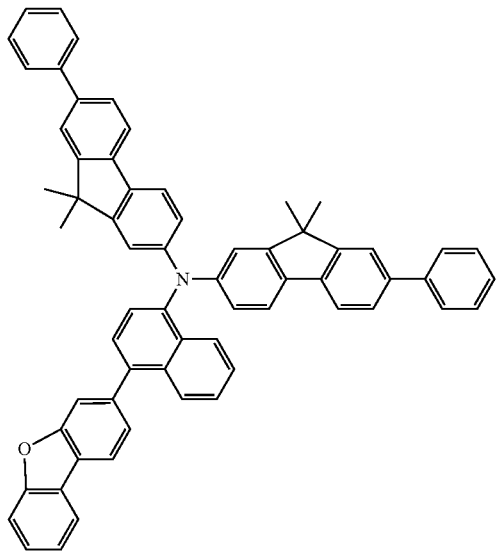 195
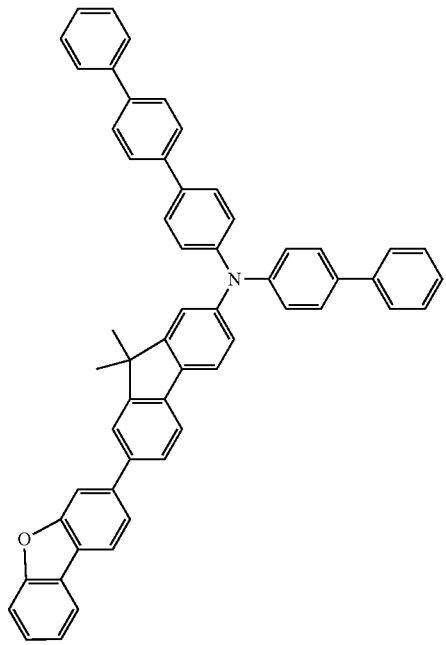 196
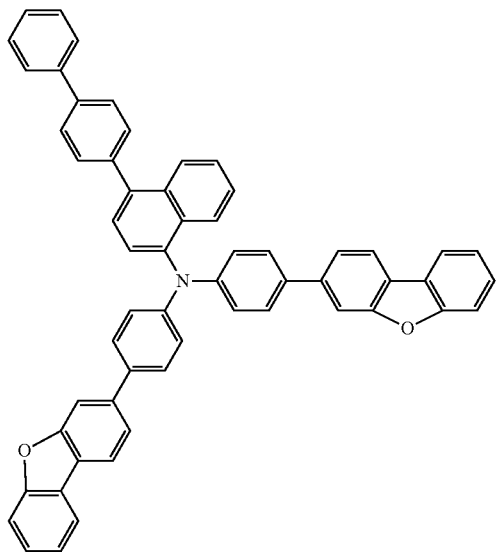
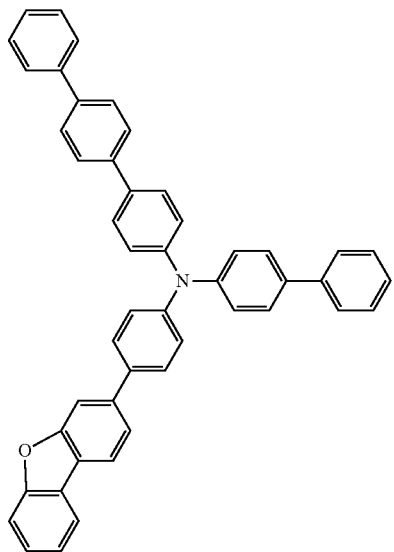

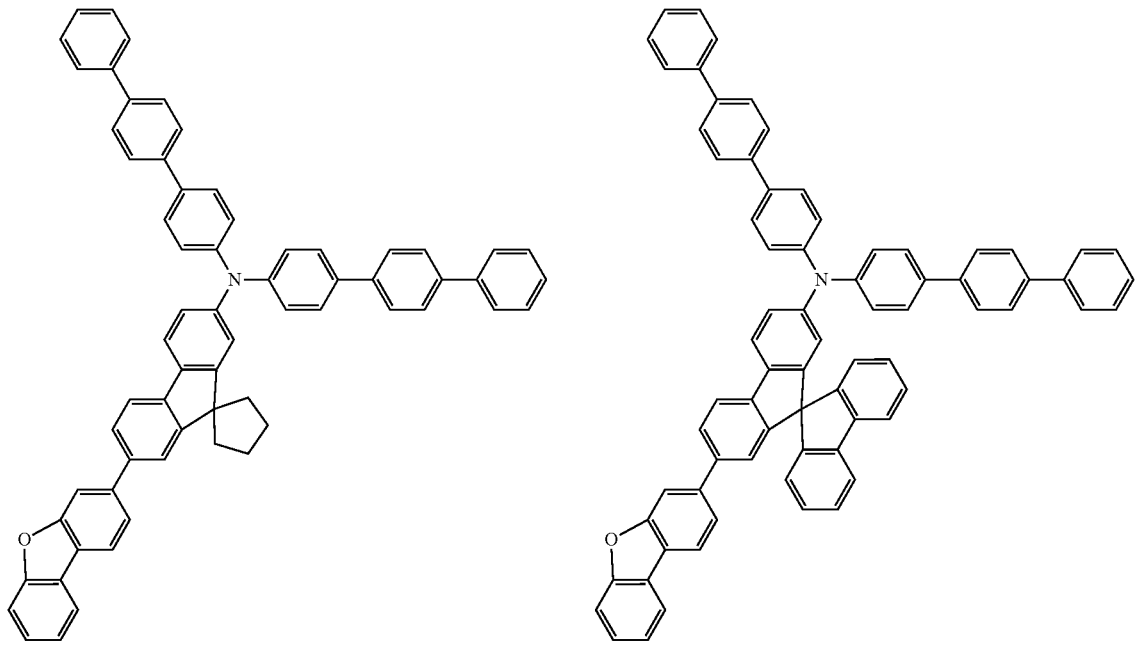
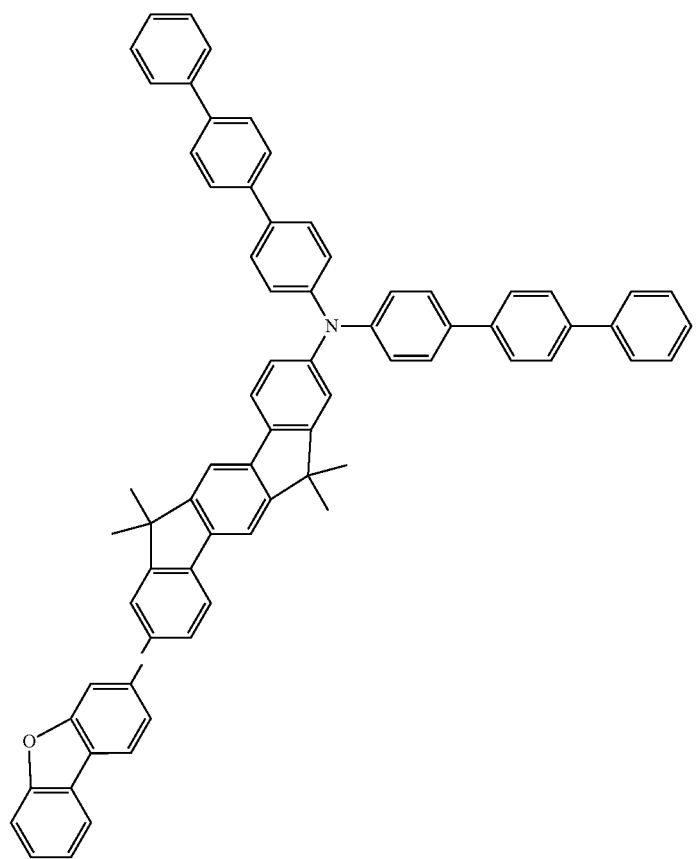

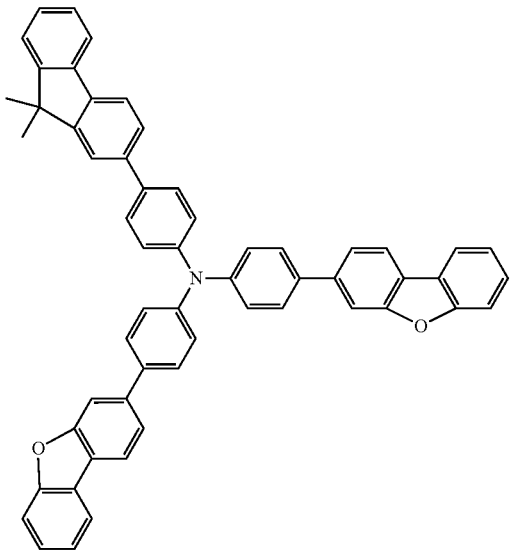
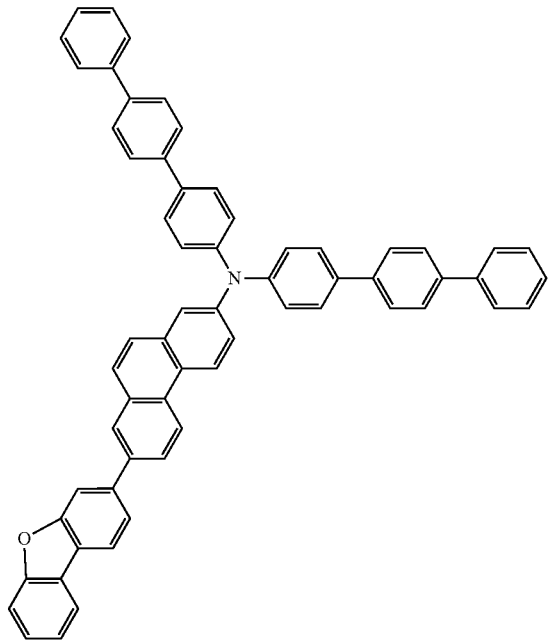
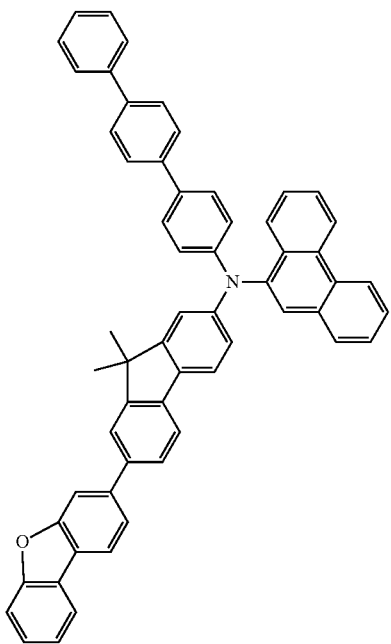
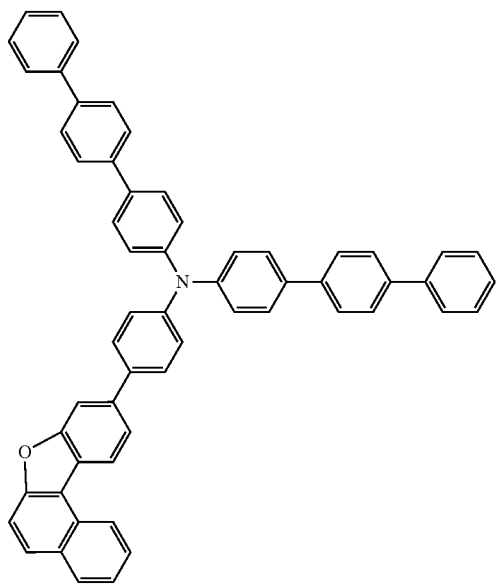

-continued
| 201 | 202 |
|---|---|
| 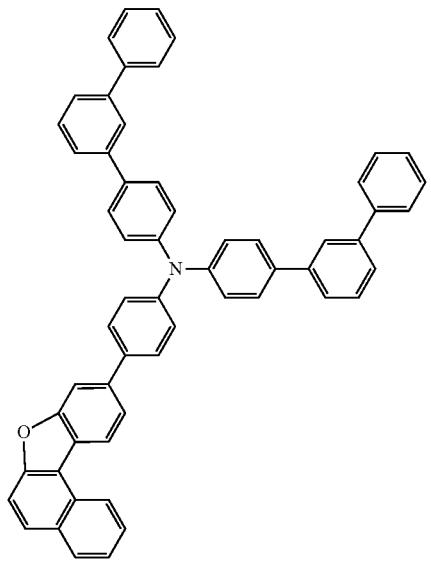 | 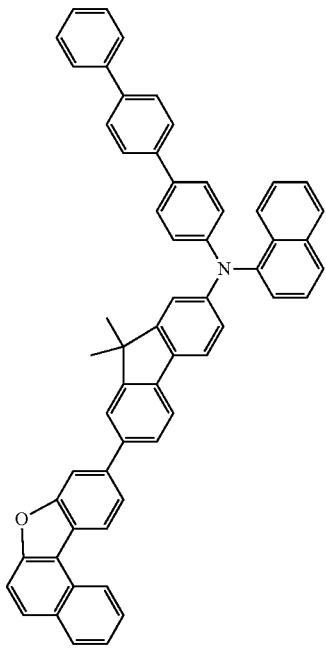 |
| 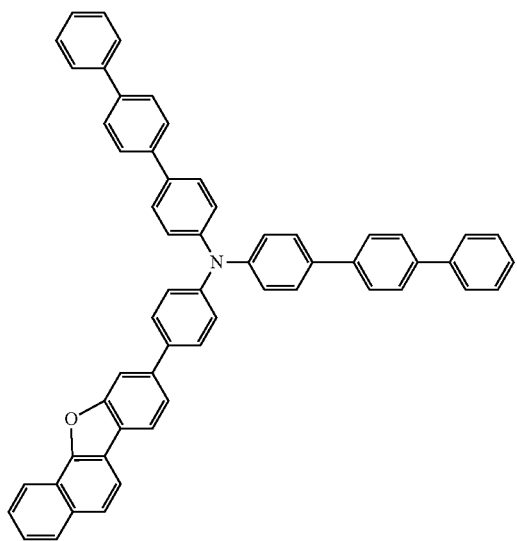 | 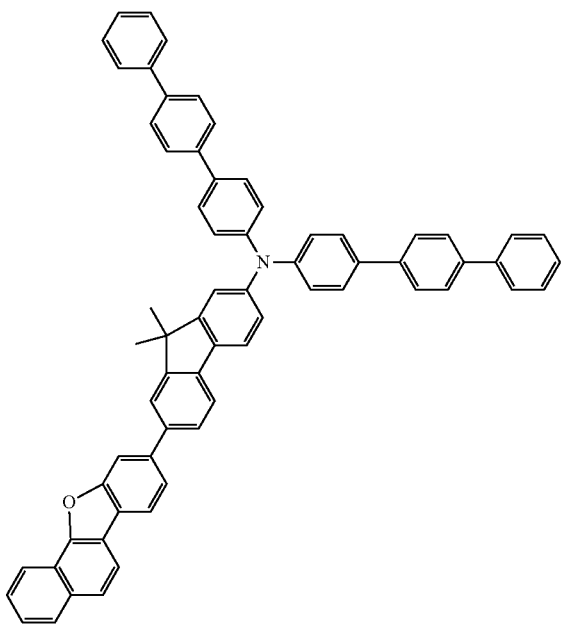 |

203
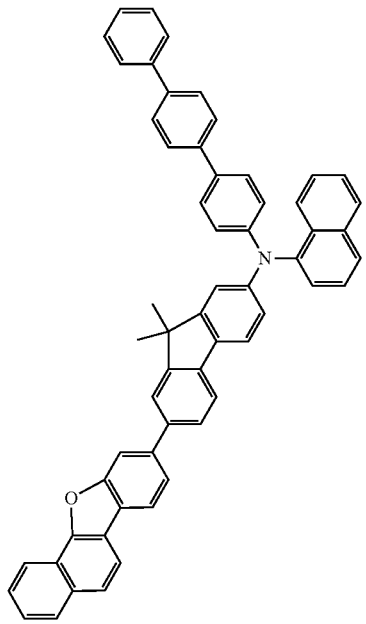
204
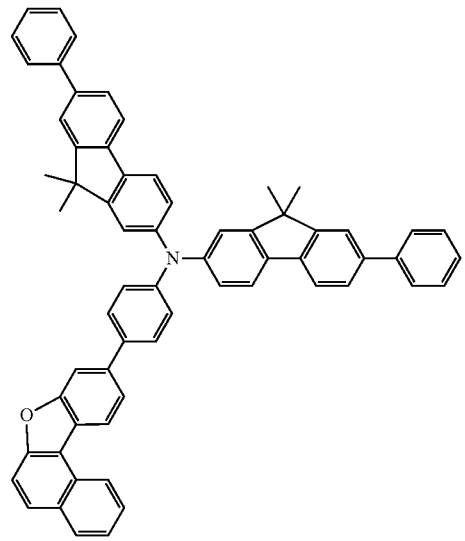
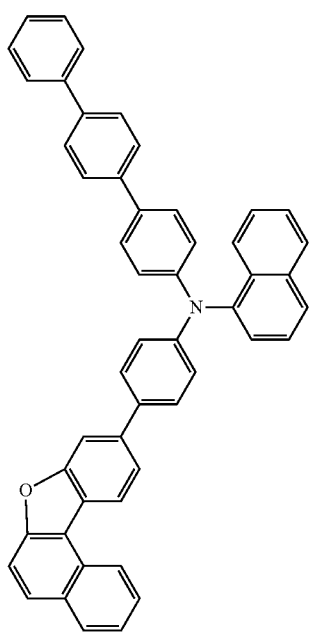
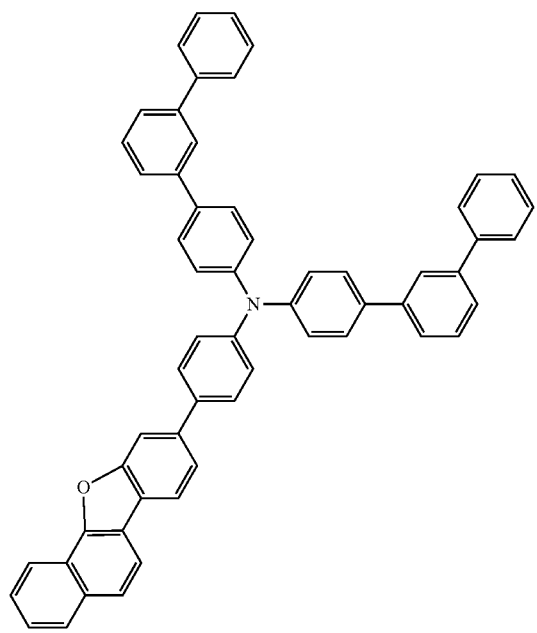

-continued
| 205 | 206 |
|---|---|
| 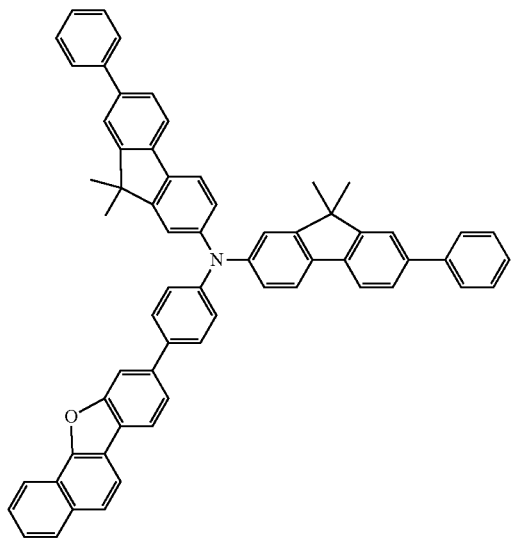 | 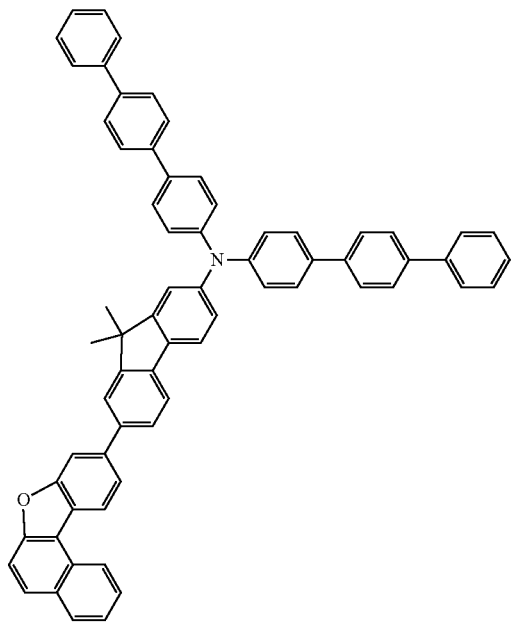 |
| 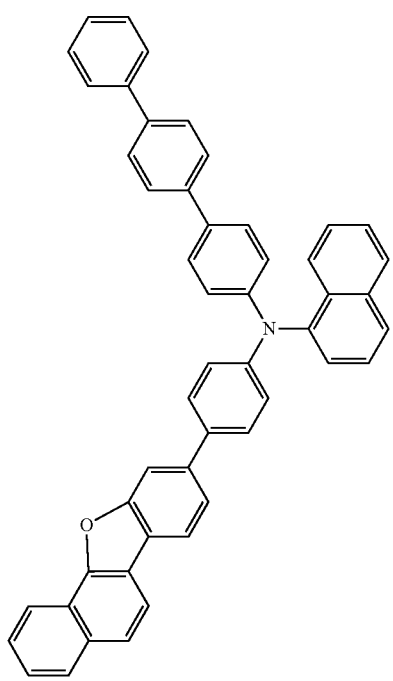 | 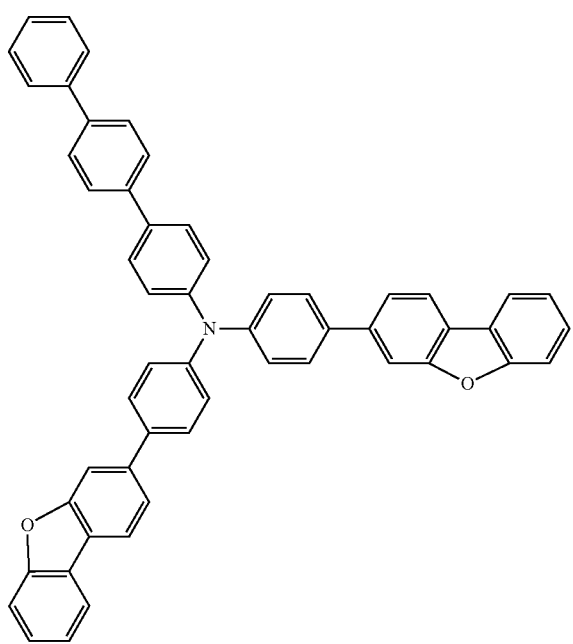 |

207 208
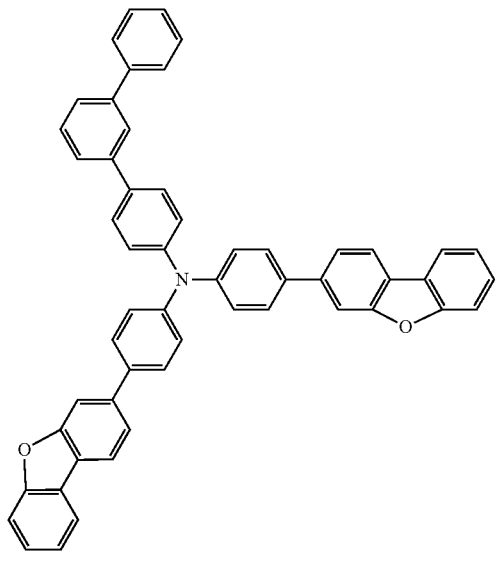
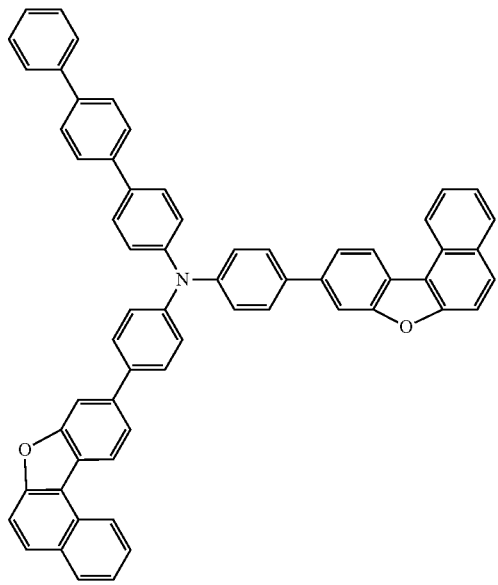
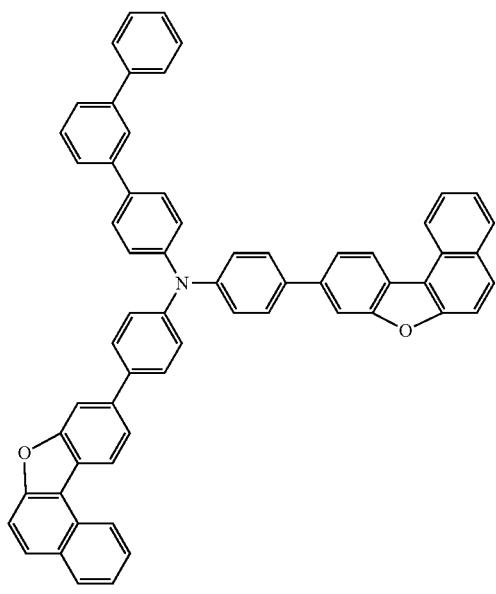
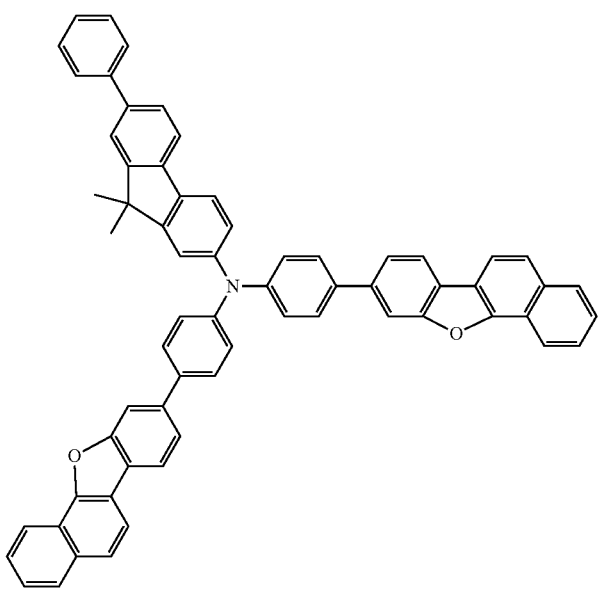

209 210
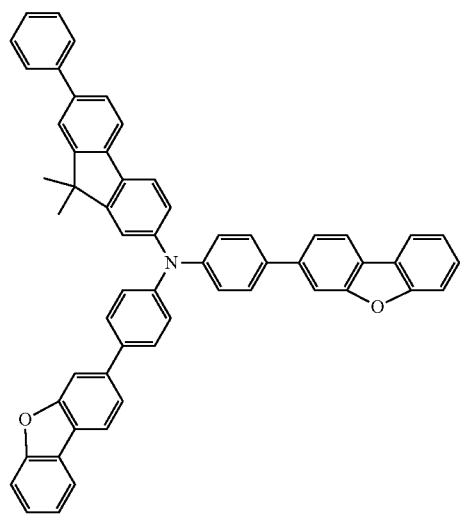
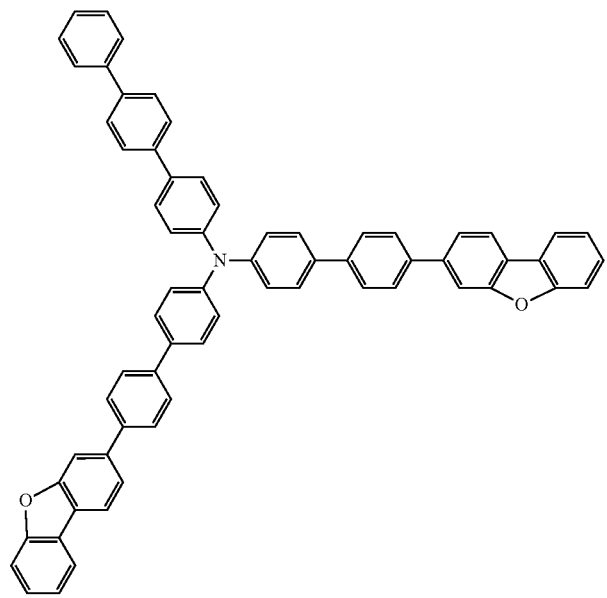
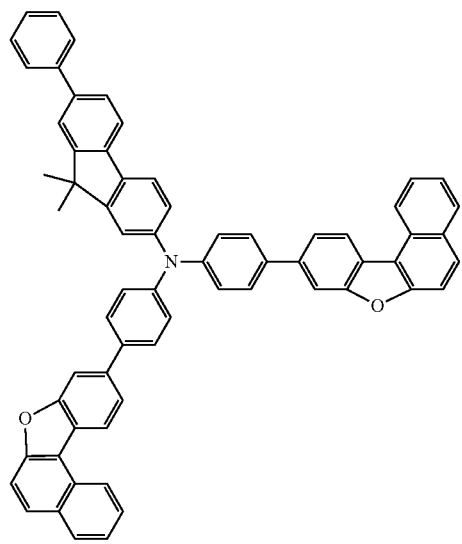
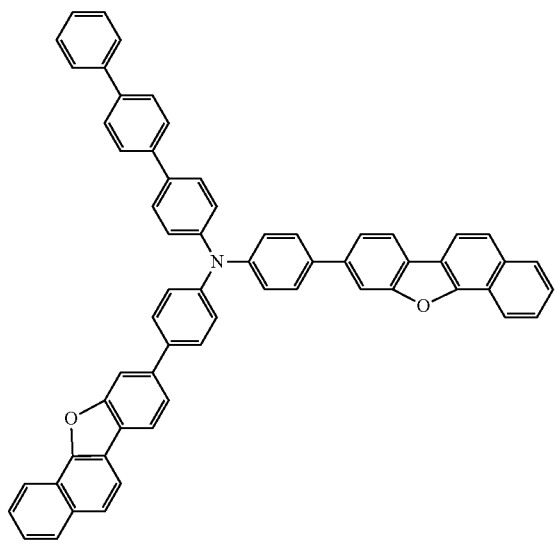

-continued

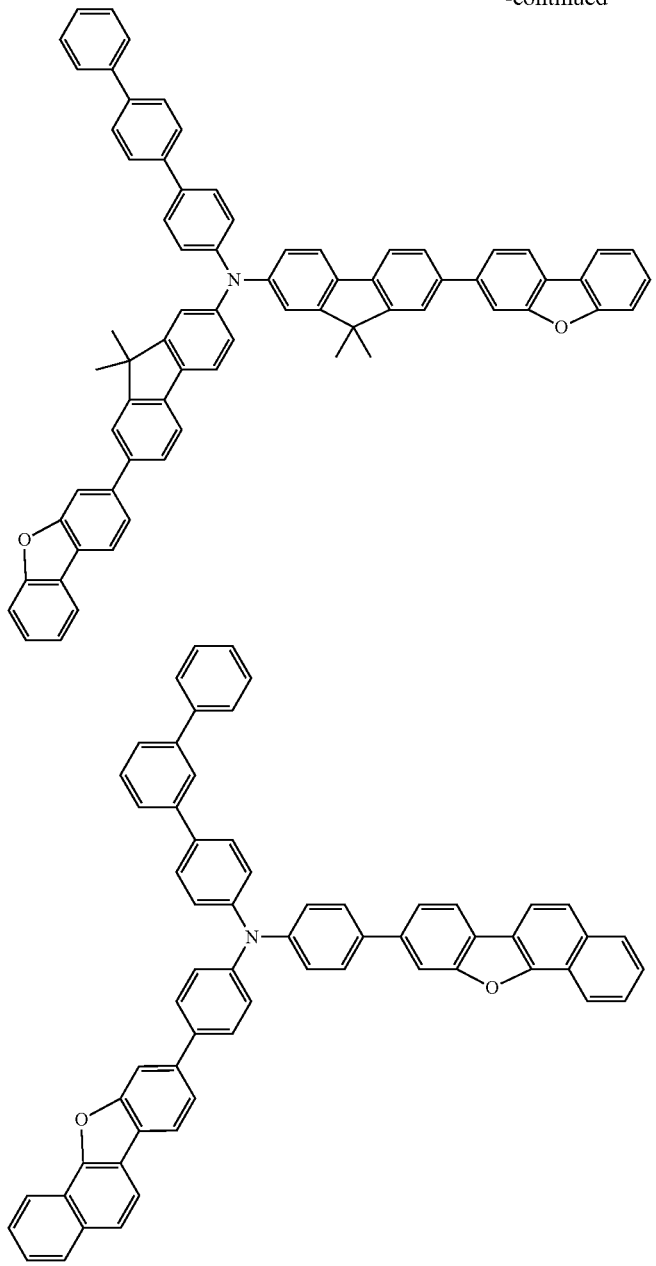

The aromatic amine derivative represented by the general formula (1) of the present invention is preferably used as a material for an organic EL device. Also, the aromatic amine derivative represented by the general formula (1) of the present invention is a light emitting material for an organic EL device.

The present invention provides an organic electroluminescence device which is composed of one or more organic thin film layers including at least one light emitting layer between a cathode and an anode, wherein at least one of the organic thin film layers contains any one of the aromatic amine derivative described hereinabove.

In the organic EL device of the present invention, the foregoing hole injecting layer or the hole transporting layer preferably contains the aromatic amine derivative represented by the above general formula (1).

Following is a description regarding a device structure about the organic EL device of the present invention.

Typical examples of the construction in the organic EL device of the present invention include the following:

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;

(8) An anode/a hole injecting layer/a hole transporting layer/a light emitting layer/an electron injecting layer/a cathode;

(9) An anode/an insulating layer/a light emitting layer/an insulating layer/a cathode;

(10) An anode/an inorganic semiconductor layer/an insulating layer/a light emitting layer/an insulating layer/a cathode;

(11) An anode/an organic semiconductor layer/an insulating layer/a light emitting layer/an insulating layer/a cathode;

(12) An anode/an insulating layer/a hole injecting layer/a hole transporting layer/a light emitting layer/an insulating layer/a cathode; and

(13) An anode/an insulating layer/a hole injecting layer/a hole transporting layer/a light emitting layer/an electron injecting layer/a cathode.

Among the above constructions, construction (8) is usually preferable though not limited thereto.

Although the material for the organic EL device of the present invention may be employed for any of the above organic thin layers in the organic EL devices, it is contained preferably in a light emitting zone, and particularly preferably in the hole injecting layer or the hole transporting layer. The amount to be contained in the device is selected from 30 to 100% by mole.

The aromatic amine derivative of the present invention is preferably used as a material for the hole injecting layer or the hole transporting layer.

The hole injecting layer and hole transporting layer are layers which help the injection of holes into the light emitting layer and transport the holes to the light emitting region. The layer exhibits a great mobility of holes and, in general, has an ionization energy as small as 5.5 eV or smaller. For the hole injecting and transporting layer, a material which transports holes to the light emitting layer at a small strength of the electric field is preferable. A material which exhibits, for example, a mobility of holes of at least $10^{-4}$ cm$^2$/V·s under application of an electric field of from $10^4$ to $10^6$ V/cm is preferable. The compound of the present invention has a small ionization energy, and a large hole mobility so that it is preferable as the hole transporting material. Further, because it contains a polar group in the molecule thereof, the adhesive property with the anode is excellent and it hardly suffers influences of cleaning condition about the substrate so that it is preferable as the hole injecting material. These factors conceivably prolong lifetime of the organic EL device utilizing the present invention.

To form the hole injecting layer and the hole transporting layer, a thin film may be formed from the aromatic amine derivative of the present invention in accordance with a well-known process such as the vacuum vapor deposition process, the spin coating process, the casting process and the LB process. Although the thickness of the hole injecting layer and the hole transporting layer is not particularly limited, the thickness is usually from 5 nm to 5 μm. The hole injecting layer or the hole transporting layer may be a single layer made of one or more kinds of materials mentioned above or may be laminated with another hole injecting layer or the hole transporting layer made of a different material, as long as the hole injecting layer or the hole transporting layer contains the aromatic amine derivative of the present invention in the hole transporting zone thereof.

An organic semiconductor layer is a layer which assists to inject the holes or to inject the electrons into the light emitting layer, and it is preferable for the organic semiconductor layer to have a conductance of $10^{-10}$ S/cm or greater. Examples of the materials for the organic semiconductor layer include electrically conductive oligomers such as an oligomer having thiophene and an oligomer having arylamine disclosed in JP 8-193191A; and electrically conductive dendrimers such as a dendrimer containing an aryl amine dendrimer.

The organic EL device of the present invention is prepared on a light-transmissive substrate. Here, the light-transmissive substrate is the substrate which supports the organic EL device. It is preferable that the light-transmissive substrate have a transmittance of light of 50% or higher in the visible region of 400 to 700 nm and be flat and smooth.

Preferred examples of the light-transmissive substrate include glass plates and polymer plates. Specific examples of the glass plate include soda ash glass, glass containing barium and strontium, lead glass, aluminosilicate glass, borosilicate glass, barium borosilicate glass and quartz. Specific examples of the synthetic resin plate include a plate made of polycarbonate resins, acrylic resins, polyethylene telephthalate resins, polyether sulfide resins and polysulfone resins.

The anode in the organic EL device of the present invention has a function of injecting holes into a hole transporting layer or a light emitting layer, and it is effective that the anode has a work function of 4.5 eV or greater. Specific examples of the material for the anode used in the present invention include indium tin oxide (ITO), mixture of indium oxide and zinc oxide (IZO$^R$), mixture of ITO and cerium oxide (ITCO), mixture of IZO$^R$ and cerium oxide (IZCO), mixture of indium oxide and cerium oxide (ICO), mixture of zinc oxide and aluminum oxide (AZO), tin oxide (NESA), gold, silver, platinum, and copper, etc.

The anode can be prepared by forming a thin film of the electrode materials in accordance with a process such as the vapor deposition process and the sputtering process.

When the light emitted from the light emitting layer is obtained through the anode, it is preferable that the anode has a transmittance of the emitted light greater than 10%. It is also preferable that the sheet resistivity of the anode is several hundreds Ω/□ or smaller. The thickness of the anode is, in general, selected in the range of 10 nm to 1 μm and preferably in the range of 10 to 200 nm although the preferable range may be different depending on the material to be used.

For the cathode, a material such as a metal, an alloy, an electrically conductive compound, or a mixture of the materials which has a small work function (4 eV or smaller) is used as an electrode material. Specific examples of the electrode substance include sodium, sodium-potassium alloy, magnesium, lithium, magnesium-silver alloy, aluminum/aluminum oxide, Al/Li$_2$O, Al/LiO, Al/LiF, aluminum-lithium alloy, indium, rare earth metal, etc.

The cathode can be prepared by forming a thin film of the electrode material described above in accordance with a process such as the vapor deposition process and the sputtering process.

When the light emitted from the light emitting layer is taken out of the cathode, it is preferable that the cathode has a transmittance of greater than 10% to the emitted light. It is also preferable that the sheet resistivity of the cathode is several hundreds Ω/□ or smaller and the thickness of the cathode is, usually selected from 10 nm to 1 μm and preferably from 50 to 200 nm.

In general, the organic EL device tends to form defects in pixels due to leak and short circuit since an electric field is applied to ultra-thin films. To prevent the defects, an insulating layer made of an electrically insulating thin film may be inserted between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be employed.

In the organic EL device of the present invention, the light emitting layer combines the following functions:
(i) The injecting function: the function of injecting holes from the anode or the hole injecting layer and injecting electrons from the cathode or the electron injecting layer when an electric field is applied;
(ii) The transporting function: the function of transporting the injected charges (electrons and holes) by the force of the electric field; and
(iii) The light emitting function: the function of providing the field for recombination of electrons and holes and promote the recombination to emit light.

As the process for forming the light emitting layer, a well-known process such as the vapor deposition process, the spin coating process and the LB process can be employed. It is particularly preferable for the light emitting layer to be a molecular deposit film. The molecular deposit film is a thin film formed by the deposition of a material compound in the gas phase or a thin film formed by the solidification of a material compound in a solution or liquid phase. In general, the molecular deposit film can be distinguished from the thin film formed in accordance with the LB process (the molecular accumulation film) based on the differences in the aggregation structure and higher order structures and functional differences caused by these structural differences.

In addition, as disclosed in JP 57-51781A, the light emitting layer can also be formed by dissolving a binder such as a resin and the material compounds into a solvent to prepare a solution, followed by forming a thin film from the prepared solution in accordance with the spin coating process or the like.

The thickness of the light emitting layer is preferably selected in the range of from 5 to 50 nm, more preferably in the range of from 7 to 50 nm and the most preferably in the range of from 10 to 50 nm. It is resulted in difficult to form the light emitting layer and to control chromaticity thereof when the thickness is thinner than 5 nm, and it may be resulted in possibility of elevating driving voltage when it exceeds 50 nm.

Examples of the material which can be used in the light emitting layer are not particularly limited and include polycyclic aromatic compound such as an anthracene compound, a phenanthrene compound, a fluoranthene compound, a tetracene compound, a triphenylene compound, a chrysene compound, a pyrene compound, a coronene compound, a perylene compound, a phthaloperylene compound, a naphthaloperylene compound, a naphthacene compound, and a pentacene compound; oxadiazole, bisbenzoxazoline, bis-styryl, cyclopentadiene, quinoline metal complexes, tris(8-hydroxyquinolinato) aluminum complexes, tris(4-methyl-8-quinolinato) aluminum complexes, tris(5-phenyl-8-quinolinato) aluminum complexes, aminoquinoline metal complexes, benzoquinoline metal complexes, tri-(p-terphenyl-4-yl)amine, 1-aryl-2,5-di(2-thienyl)pyrrole derivatives, pyran, quinacridone, rubrene, distyrylbenzene derivatives, distyrylarylene derivatives, porphyrin derivatives, stilbene derivatives, pyrazoline derivatives, coumarin based dyes, pyran based dyes, phthalocyanine based dyes, naphthalocyanine based dyes, croconium based dyes, sqarium based dyes, oxo benzanthracene based dyes, fluorescein based dyes, rhodamine based dyes, pyrylium based dyes, perylene based dyes, stilbene based dyes, polythiophene based dyes; or rare earth complex based fluorescent substances, rare earth-based phosphorescent light emitting complexes (e.g., Ir complexes) and polymer materials like electrically conductive polymers such as polyvinylcarbazole, polysilane, polyethylene dioxidethiophene (PEDOT). These may be used alone, or, alternatively, used as a mixture of two or more kinds thereof.

Preferable materials to be used for the light emitting layer of the present invention include compounds represented by the following general formulae (51) to (57).

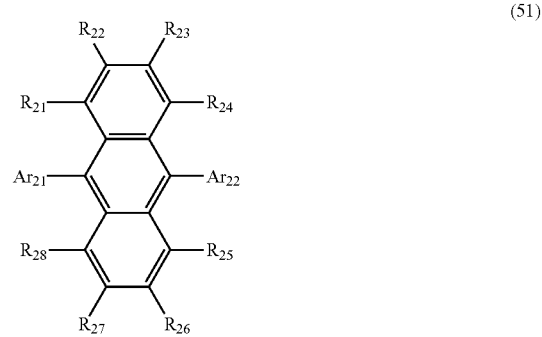

(51)

In the anthrathene derivative represented by the formula (51), $A_{21}$ and $A_{22}$ each independently represents a substituted or unsubstituted aromatic ring group having 6 to 60 carbon atoms. $R_{21}$ to $R_{28}$ each independently represents a hydrogen atom, a substituted or unsubstituted aromatic ring group having 6 to 50 carbon atoms, a substituted or unsubstituted aromatic heterocyclic group having 5 to 50 atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms, a substituted or unsubstituted alkoxycarbonyl group having 1 to 50 carbon atoms, a silyl group which is substituted by an alkyl group or an aryl group; or a fluorine atom. In particular, the following case is preferable: $R_{21}$ represents a hydrogen atom; $R_{22}$ represents a hydrogen atom, a phenyl group, a naphthyl group, a fluorenyl group, a dibenzofuranyl group or those combination; $R_{23}$ to $R_{28}$ each independently represents a hydrogen atom; $Ar_{21}$ and $Ar_{22}$ each independently represents a phenyl group, a naphthyl group, a fluorenyl group, a dibenzofuranyl group or those combination.

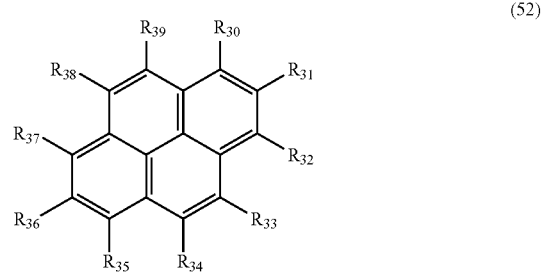

(52)

In the pyrene derivative represented by the formula (52), $R_{30}$ to $R_{39}$ each independently represents a hydrogen atom, a substituted or unsubstituted aromatic ring group having 6 to 50 carbon atoms, a substituted or unsubstituted aromatic heterocyclic group having 5 to 50 atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms, a substituted or unsubstituted arylthio group having 5 to 50 atoms, a substituted or unsubstituted alkoxycarbonyl group having 1 to 50 carbon atoms, a silyl group which is substituted by an alkyl group or an aryl group; or a fluorine atom. In particular, it is preferable that the substituent in $R_{30}$ to $R_{38}$ is a phenyl group, a naphthyl group, a fluorenyl group, a dibenzofuranyl group or those combinations.

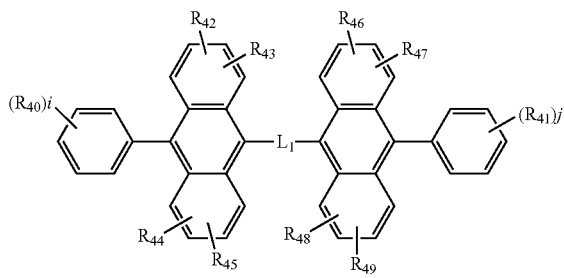

(53)

In the anthracene derivative represented by the formula (53), $R_{40}$ to $R_{49}$ each independently represents a hydrogen atom, an alkyl group, a cycloalkyl group, an aryl group which may be substituted, an alkoxyl group, an aryloxy group, an alkenyl group or a heterocyclic group which may be substituted; "I" and "j" each independently represents an integer of 1 to 5, and when "I" or "j" represents 2 or more, $R_{40}$'s or $R_{41}$'s may be identical to or different from each other. Further, $R_{40}$'s or $R_{41}$'s may be bonded to each other to form a ring; and any one couple of $R_{42}$ and $R_{43}$, $R_{44}$ and $R_{45}$, $R_{46}$ and $R_{47}$, or $R_{48}$ and $R_{49}$ may be bonded to each other to form a ring.

$L_1$ represents a single bond, —O—, —S—, —N(R)— (wherein R represents an alkyl group or an aryl group which may be substituted), an alkylene group or an arylene group.

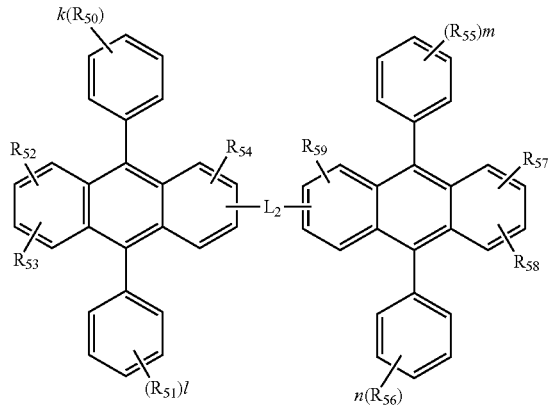

(54)

In the anthracene derivative represented by the formula (54), $R_{50}$ to $R_{59}$ each independently represents a hydrogen atom, an alkyl group, a cycloalkyl group, an aryl group which may be substituted, an alkoxyl group, an aryloxy group, or a heterocyclic group which may be substituted; "k", "l", "m" and "n" each independently represents an integer of 1 to 5, and when any one of "k", "l", "m" and "n" represents 2 or more, $R_{50}$'s, $R_{51}$'s, $R_{55}$'s or $R_{56}$'s may be identical to or different from each other. Further, $R_{52}$'s, $R_{53}$'s, $R_{54}$'s or $R_{55}$'s may be bonded to each other to form a ring; and any one couple of $R_{52}$ and $R_{53}$, or $R_{57}$ and $R_{58}$ may be bonded to each other to form a ring.

$L_2$ represents a single bond, —O—, —S—, —N(R)— (wherein R represents an alkyl group or an aryl group which may be substituted), an alkylene group or an arylene group.

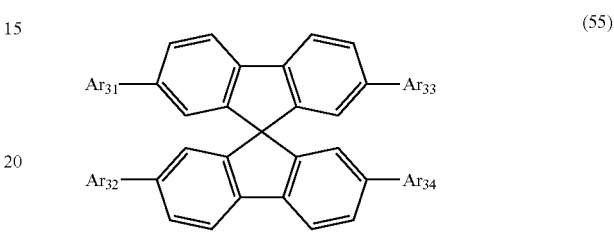

(55)

In the spirofluorene derivative represented by the formula (55), $Ar_{31}$ to $Ar_{34}$ each independently represents a substituted or unsubstituted biphenylyl group or a substituted or unsubstituted naphthyl group.

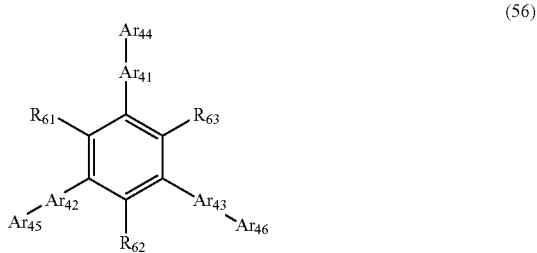

(56)

In the compound represented by the formula (56), $Ar_{41}$ to $Ar_{43}$ each independently represents a substituted or unsubstituted arylene group having 6 to 60 carbon atoms, and $Ar_{44}$ to $Ar_{46}$ each independently represents a hydrogen atom, or substituted or unsubstituted aryl group having 6 to 60 carbon atoms.

$R_{61}$ to $R_{63}$ each independently represents a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an ester group having 1 to 6 carbon atoms, or a fluorine atom.

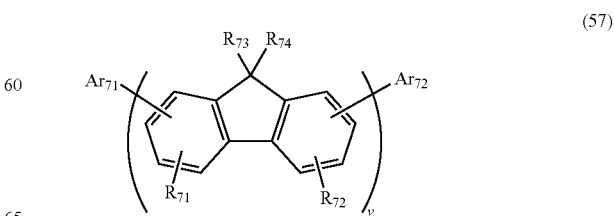

(57)

In the fluorene compound represented by the formula (57), $R_{73}$ and $R_{74}$ each independently represents a hydrogen atom, a substituted or unsubstituted alkyl group, a substituted or unsubstituted aralkyl group, a substituted or unsubstituted aryl group, a substituted or unsubstituted heterocyclic group, or a fluorine atom.

$R_{71}$'s and $R_{72}$'s bonded to respective fluorene groups may be identical to or different from each other, and $R_{71}$ and $R_{72}$ bonded to the same fluorene group may be identical to or different from each other.

$R_{73}$ and $R_{74}$ each independently represents a hydrogen atom, a substituted or unsubstituted alkyl group, a substituted or unsubstituted aralkyl group, a substituted or unsubstituted aryl group, or a substituted or unsubstituted heterocyclic group. $R_{73}$'s and $R_{74}$'s bonded to respective fluorene groups may be identical to or different from each other, and $R_{73}$ and $R_{74}$ bonded to the same fluorene group may be identical to or different from each other.

$Ar_{71}$ and $Ar_{72}$ each represents a substituted or unsubstituted fused polycyclic aromatic group having three or more benzene rings in total, or a substituted or unsubstituted fused polycyclic heterocyclic group that has three or more rings each of which is a benzene ring or a heterocyclic ring in total and that is bonded to a fluorene group by carbon. $Ar_{71}$ and $Ar_{72}$ may be identical to or different from each other; and "v" represents an integer of 1 to 10.

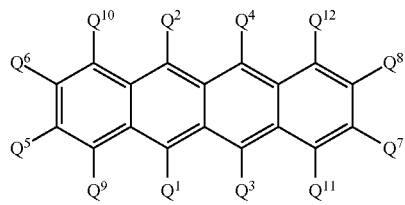

(xii)

In the pentacene compound represented by the formula (xii), $Q^1$ to $Q^{12}$ each independently represents a hydrogen atom, a substituted or unsubstituted alkyl group having 1 to 20 carbon atoms, a substituted or unsubstituted aryl group having 5 to 20 ring carbon atoms, an amino group, a substituted or unsubstituted alkoxy group having 1 to 20 carbon atoms, a substituted or unsubstituted alkylthio group having 1 to 20 carbon atoms, a substituted or unsubstituted aryloxy group having 5 to 20 ring carbon atoms, a substituted or unsubstituted arylthio group having 5 to 20 ring carbon atoms, a substituted or unsubstituted alkenyl group having 2 to 20 carbon atoms, a substituted or unsubstituted aralkyl group having 7 to 20 ring carbon atoms, or a substituted or unsubstituted heterocyclic group having 5 to 20 ring carbon atoms; which may be identical to or different from each other.

The naphthacene derivative represented by the above formula (xii) is more preferably the naphthacene derivative represented by the following formula (xiii).

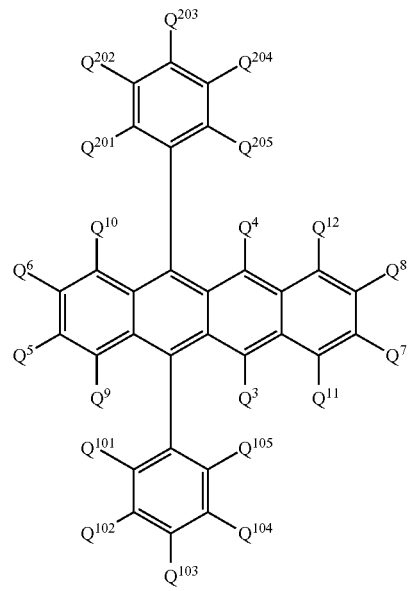

(xiii)

In the formula (xiii), $Q^3$ to $Q^{12}$, $Q^{101}$ to $Q^{105}$, and $Q^{201}$ to $Q^{205}$ each independently represents the same group as $Q^3$ to $Q^{12}$ in the above formula (xii), which may be identical to or different from each other, and adjacent 2 or more Qs among them may be bonded to each other to form a ring.

Among the above materials, the anthracene derivative (the monoanthracene derivative and the asymmetric anthracene is more preferable) and the pentacene derivative are preferable.

Regarding with the material which is suitable for phosphorescent light emission, a compound having a carbazole ring is preferably used. The compound has a function of causing a phosphorescent compound to emit light as a result of the occurrence of energy transfer from the excited state of the compound to the phosphorescent compound. The compound is not particularly limited as long as it is a compound capable of transferring exciton energy to a phosphorescent compound, and can be appropriately selected in accordance with a purpose. The compound may have, for example, an arbitrary heterocyclic ring in addition to a carbazole ring.

Specific examples of such the compound include carbazole derivatives, triazole derivatives, oxazole derivatives, oxadiazole derivatives, imidazole derivatives, polyarylalkane derivatives, pyrazoline derivatives, pyrazolone derivatives, phenylene diamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethane derivatives, anthrone derivatives, diphenylquinone derivatives, thiopyranedioxide derivatives, carbodiimide derivatives, fluorenilidene methane derivatives, distyryl pyrazine derivatives, heterocyclic tetracarboxylic anhydrides such as naphthaleneperylene, phthalocyanine derivatives, various metal complex polysilane-based compounds typified by a metal complex of an 8-quinolinol derivative or a metal complex having metal phthalocyanine, benzooxazole, or benzothiazole as a ligand, poly(N-vinylcarbazole) derivatives, aniline-based copolymers, electrically conductive high molecular weight oligomers such as a thiophene oligomer and polythiophene, polymer compounds such as polythiophene derivatives, polyphenylene derivatives, polyphenylene vinylene derivatives, and polyfluorene derivatives. One of the host compounds may be used alone, or two or more of them may be used in combination. Specific examples thereof include the compounds as described below.

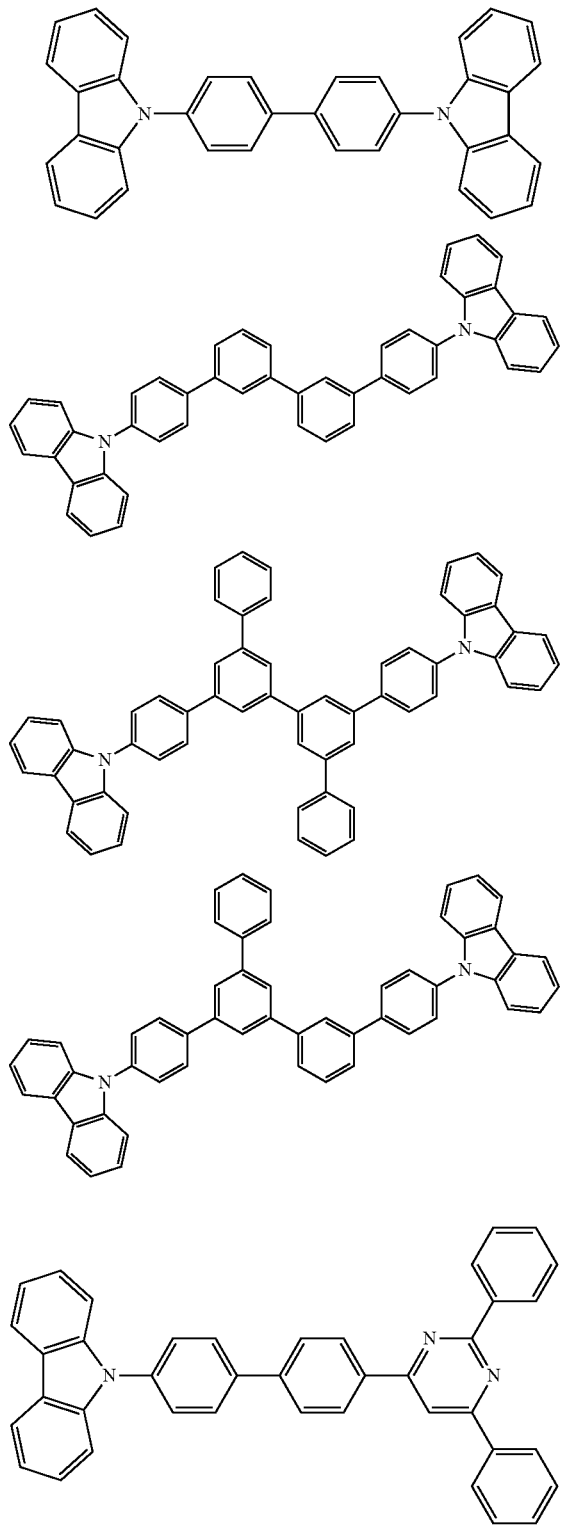

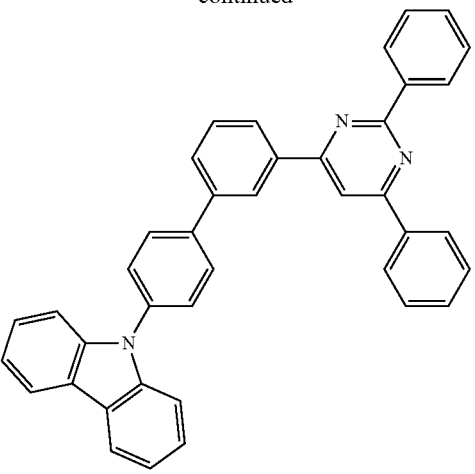

When the aromatic amine derivative of the present invention is used for the light emitting layer of the organic EL device, the following materials can be used as doping materials.

Examples of the doping materials to be used in the present invention include arylamine compounds, styryl amine compounds, anthracene derivatives, naphthalene derivatives, phenanthrene derivatives, pyrene derivatives, tetracene derivatives, coronene derivatives, chrysene derivatives, benzfluorescein derivatives, perylene derivatives, phthaloperylene derivatives, naphthaloperylene derivatives, perinone derivatives, phthaloperinone derivatives, naphthaloperinone derivatives, diphenyl butadiene derivatives, tetraphenyl butadiene derivatives, coumarin derivatives, oxadiazole derivatives, aldazine derivatives, bisbenzoxazoline derivatives, bis styryl derivatives, pyrazine derivatives, cyclopentadiene derivatives, quinoline metal complex derivatives, aminoquinoline metal complex derivatives, benzoquinoline metal complex derivatives, imine derivatives, diphenylethylene derivatives, vinyl anthracene derivatives, diamino carbazole derivatives, pyran derivatives, thiopyran derivatives, polymethine derivatives, merocyanine derivatives, imidazole chelated oxynoid derivatives, quinacridone derivatives, rubrene derivatives and fluorescent dye; like already described materials or other materials, though not limited thereto.

In the organic EL device of the present invention, the styrylamine compounds and/or arylamine compounds are preferably represented by the following general formula (50):

(50)

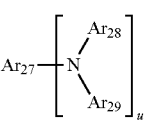

In the general formula (50), $Ar_{27}$ represents a substituted or unsubstituted monovalent or divalent aromatic group having the number of carbon atoms of 6 to 40 forming the aromatic ring, and $Ar_{28}$ to $Ar_{29}$ each independently represents a substituted or unsubstituted aromatic group having the number of carbon atoms of 6 to 40 forming the aromatic ring; "u" represents an integer of 1 to 4, and especially, "u" preferably represents an integer of 1 or 2. Any one of $Ar_{27}$ to $Ar_{29}$ may be an aromatic group having a styryl group. When the general formula (50) is a styryl amine compound, it is preferable that any one of the aromatic groups $Ar_{27}$ to $Ar_{29}$ has the styryl group, or alternatively, that at least one of $Ar_{28}$ and $Ar_{29}$ is preferably substituted by the styryl group.

Examples of the aromatic group having the number of carbon atoms of 6 to 40 forming the aromatic ring include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzthiophenyl group, an oxadiazolyl group, a diphenylanthranyl group, an indolyl group, a carbazolyl group, a pyridyl group, a benzquinolyl group, a fluoranthenyl group, an acenaphthofluoranthenyl group, a stilbene group, a perilenyl group, a crycenyl group, a picenyl group, a triphenylenyl group, a rubicenyl group, a benzanthracenyl group, a phenylanthranyl group, a bisanthracenyl group, or an arylene group represented by the following general formula (C) or (D). Among those, the naphthyl group, the anthranyl group, the crycenyl group, the pyrenyl group or the arylene group represented by the general formula (D) is preferable.

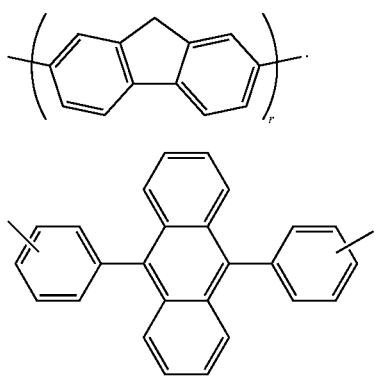

In the formula (C), "r" represents an integer of 1 to 3.

Examples of the polyvalent aromatic group having the number of carbon atoms of 6 to 40 forming the aromatic ring include those prepared by replacing the above examples of the monovalent aromatic group having 6 to 40 ring forming carbon atoms with a polyvalent aromatic group having 2 or more valence.

Additionally, the aromatic group having the number of carbon atoms of 6 to 40 forming the aromatic ring may be substituted. Preferable examples of the substituent include an alkyl group having 1 to 6 carbon atoms (an ethyl group, a methyl group, an i-propyl group, a n-propyl group, a sec-butyl group, a tert-butyl group, a pentyl group, a hexyl group, a cyclopentyl group, a cyclohexyl group, etc.); an alkoxy group having 1 to 6 carbon atoms (an ethoxy group, a methoxy group, an i-propoxy group, an n-propoxy group, an s-butoxy group, a t-butoxy group, a pentoxy group, a hexyloxy group, a cyclopentoxy group, a cyclohexyloxy group, etc.); an aryl group having 5 to 40 carbon atoms; an ester group which has an aryl group having 5 to 40 carbon atoms; an ester group which has an alkyl group having 1 to 6 carbon atoms; a fluorine atom, a trialkylsilyl group, a triarylsilyl group, etc.

A phosphorescent dopant is a compound capable of emitting light from a triplet exciton. The phosphorescent dopant is not restricted as long as light from the triplet exciton is emitted, and is preferably a metal complex containing at least one metal selected from the group consisting of Ir, Ru, Pd, Pt, Os and Re, more preferably a porphyrin metal complex or an ortho-metallated metal complex. A porphyrin platinum complex is preferable as the porphyrin metal complex. One kind of a phosphorescent compound may be used alone, or two or more kinds of phosphorescent compounds may be used in combination.

There are various ligands to form the ortho-metallated metal complex, and preferred are 2-phenylpyridine derivatives, 7,8-benzoquinoline derivatives, 2-(2-thienyl)pyridine derivatives, 2-(1-naphthyl)pyridine derivatives, and 2-phenylquinoline derivatives. The derivatives may have a substituent as occasion demands. A fluoride of any one of those derivatives, or one obtained by introducing a trifluoromethyl group into any one of those derivatives is a particularly preferable blue-based dopant. The metal complex may further include a ligand other than the above-mentioned ligands such as acetylacetonato or picric acid as an auxiliary ligand.

The content of the phosphorescent dopant in the light emitting layer may be appropriately selected without particular limitation and, for example, it may be from 0.1 to 70% by mass, preferably from 1 to 30% by mass. When the content of the phosphorescent compound is less than 0.1% by mass, the intensity of emitted light is weak, and an effect of the incorporation of the compound is not sufficiently exerted. When the content exceeds 70% by mass, a phenomenon referred to as concentration quenching becomes remarkable, and device performance reduces.

Subsequently, the electron injecting and transporting layer is a layer which helps injection of electrons into the light emitting layer, transports the holes to the light emitting region, and exhibits a great mobility of electrons. The adhesion improving layer is an electron injecting layer including a material exhibiting particularly improved adhesion with the cathode.

In addition, it is known that, in an organic EL device, emitted light is reflected by an electrode (cathode in this case), so emitted light directly extracted from an anode and emitted light extracted via the reflection by the electrode interfere with each other. The thickness of an electron transporting layer is appropriately selected from the range of several nanometers to several micrometers in order that the interference effect may be effectively utilized. When the thickness is particularly large, an electron mobility is preferably at least $10^{-5}$ cm$^2$/Vs or more upon application of an electric field of $10^4$ to $10^6$ V/cm in order to avoid an increase in voltage.

A metal complex of 8-hydroxyquinoline or of a derivative of 8-hydroxyquinoline, or an oxadiazole derivative is suitable as a material to be used in the electron injecting layer. Specific examples of the metal complex of 8-hydroxyquinoline or of the derivative of 8-hydroxyquinoline that can be used as an electron injecting material include metal chelate oxynoid compounds each containing a chelate of oxine (generally 8-quinolinol or 8-hydroxyquinoline), such as tris(8-quinolinol)aluminum.

On the other hand, examples of the oxadiazole derivatives include electron transfer compounds represented by the following general formulae:

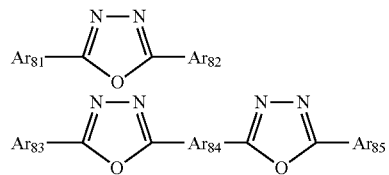

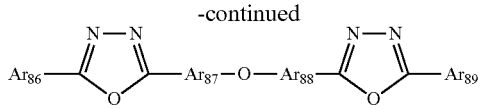
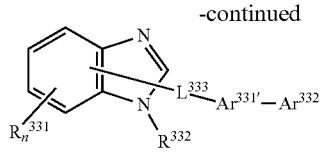

wherein $Ar_{81}$, $Ar_{82}$, $Ar_{83}$, $Ar_{85}$, $Ar_{86}$ and $Ar_{89}$ each represent a substituted or unsubstituted aryl group and may represent the same group or different groups; and $Ar_{84}$, $Ar_{87}$ and $Ar_{88}$ each represent a substituted or unsubstituted arylene group and may represent the same group or different groups.

Examples of the aryl group include a phenyl group, a biphenyl group, an anthryl group, a perilenyl group and a pyrenyl group. Examples of the arylene group include a phenylene group, a naphthylene group, a biphenylene group, an anthranylene group, a perilenylene group, a pyrenylene group, etc. Examples of the substituent include an alkyl group having 1 to 10 carbon atoms, an alkoxy group having 1 to 10 carbon atoms and a cyano group. As the electron transfer compound, compounds which can form thin films are preferable.

Examples of the electron transfer compounds described above include the following.

wherein $A^{331}$ to $A^{333}$ each independently represents a nitrogen atom or a carbon atom; $R^{331}$ and $R^{332}$ each independently represents a substituted or unsubstituted aryl group having 6 to 60 ring atoms, a substituted or unsubstituted heteroaryl group having 3 to 60 ring atoms, an alkyl group having 1 to 20 carbon atoms, a haloalkyl group having 1 to 20 carbon atoms, or an alkoxy group having 1 to 20 carbon atoms; "n" represents an integer of 0 to 5, and when "n" is an integer of 2 or more, a plurality of $R^{331}$'s may be identical to or different from each other. Further, the plurality of $R^{331}$ groups adjacent to each other may be bonded to each other to form a substituted or unsubstituted carbocyclic aliphatic ring or a substituted or unsubstituted carbocyclic aromatic ring.

$Ar^{331}$ represents a substituted or unsubstituted aryl group having 6 to 60 ring atoms or a substituted or unsubstituted heteroaryl group having 3 to 60 ring atoms.

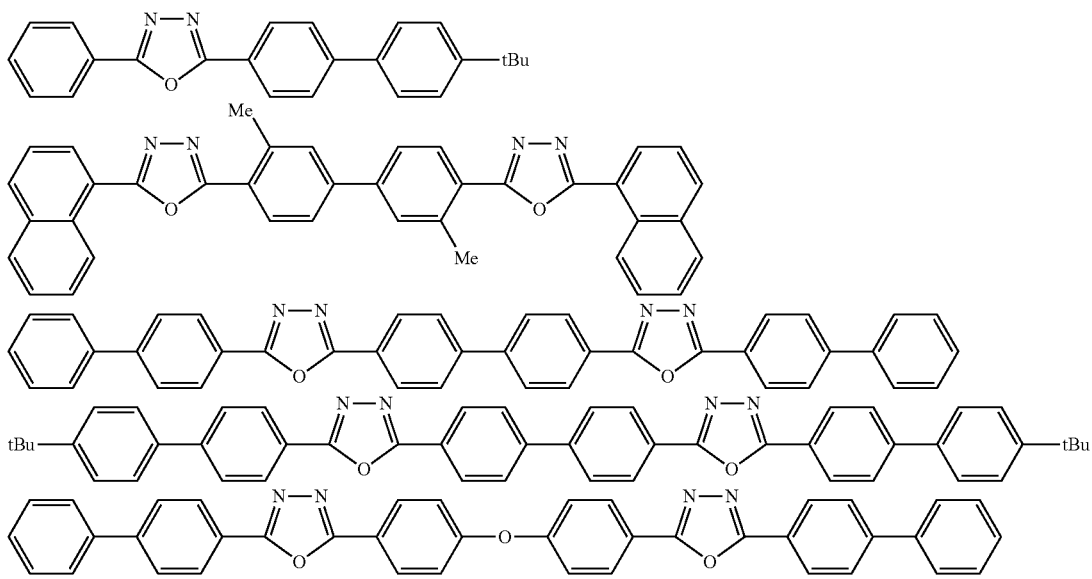

Further, nitrogen-containing heterocyclic ring derivatives represented by the following general formula are preferably used in the electron injecting layer and the electron transporting layer (particularly in the electron transporting layer). As compared with other electron transporting materials (e.g., Alq), the following nitrogen-containing heterocyclic ring derivatives can enhance the effects of elevating the efficiencies and reducing the driving voltages by using together with the aromatic amine derivatives of the present invention.

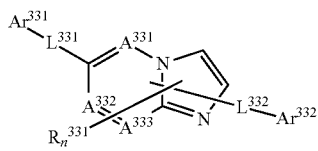

$Ar^{331'}$ represents a substituted or unsubstituted arylene group having 6 to 60 ring atoms or a substituted or unsubstituted heteroarylene group having 3 to 60 ring atoms.

$Ar^{332}$ represents a hydrogen atom, an alkyl group having 1 to 20 carbon atoms, a haloalkyl group having 1 to 20 carbon atoms, an alkoxy group having 1 to 20 carbon atoms, a substituted or unsubstituted aryl group having 6 to 60 ring atoms, or a substituted or unsubstituted heteroaryl group having 3 to 60 ring atoms.

However, at least one of $Ar^{331}$ and $Ar^{332}$ represents a substituted or unsubstituted fused ring group having 10 to 60 ring atoms, or a substituted or unsubstituted hetero fused ring group having 3 to 60 ring atoms.

$L^{331}$, $L^{332}$ and $L^{333}$ each independently represents a single bond, a substituted or unsubstituted arylene group having 6 to 60 ring atoms, a substituted or unsubstituted divalent hetero fused ring group having 3 to 60 ring atoms or a substituted or unsubstituted fluorenylene group.

The compound represented by the following formula can be used as a compound to be used as other electron transporting materials.

HAr-L-Ar$^{1a}$—Ar$^{2a}$     (C)

wherein HAr represents a nitrogen-containing heterocyclic ring which has 3 to 40 carbon atoms and may have a substituent; "L" represents a single bond, an arylene group which has 6 to 60 carbon atoms and may have a substituent, a heteroarylene group which has 3 to 60 carbon atoms and may have a substituent, or a fluorenylene group which may have a substituent; Ar$^{1a}$ represents a divalent aromatic hydrocarbon group which has 6 to 60 carbon atoms and may have a substituent; and Ar$^{2a}$ represents an aryl group which has 6 to 60 carbon atoms and may have a substituent, or a heteroaryl group which has 3 to 60 carbon atoms and may have a substituent.

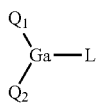     (F)

wherein $Q_1$ and $Q_2$ each independently represents a ligand represented by the following general formula (G), and L represents a halogen atom, a substituted or unsubstituted alkyl group, a substituted or unsubstituted cycloalkyl group, a substituted or unsubstituted aryl group, a substituted or unsubstituted heterocyclic group, —OR$^1$ (R$^1$ represents a hydrogen atom, a substituted or unsubstituted alkyl group, a substituted or unsubstituted cycloalkyl group, a substituted or unsubstituted aryl group, a substituted or unsubstituted heterocyclic group), or a ligand represented by —O—Ga-Q$^3$ (Q$^4$) wherein Q$^3$ and Q$^4$ are identical to $Q_1$ and $Q_2$.

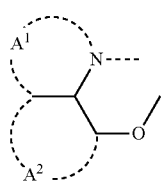     (G)

wherein rings A$^1$ and A$^2$ are six-membered aryl ring structures which are fused with each other and each of which may be substituted.

This metal complex behaves strongly as an n-type semiconductor, and has a large electron injecting ability. Further, generation energy upon formation of the complex is low. As a result, the metal and the ligand of the formed metal complex are bonded to each other so strongly that the fluorescent quantum efficiency of the complex as a light emitting material improves.

Specific examples of a substituent in the rings A$^1$ and A$^2$ which each form a ligand of the general formula (G) include: a halogen atom such as chlorine, bromine, iodine, or fluorine; a substituted or unsubstituted alkyl group such as a methyl group, an ethyl group, a propyl group, a butyl group, a sec-butyl group, a tert-butyl group, a pentyl group, a hexyl group, a heptyl group, an octyl group, a stearyl group, or trichloromethyl group; a substituted or unsubstituted aryl group such as a phenyl group, a naphthyl group, a 3-methylphenyl group, 3-methoxyphenyl group, 3-fluorophenyl group, 3-trichloromethylphenyl group, 3-trifluoromethylphenyl group, or a 3-nitrophenyl group; a substituted or unsubstituted alkoxy group such as a methoxy group, an n-butoxy group, a t-butoxy group, a trichloromethoxy group, a trifluoroethoxy group, a pentafluoropropoxy group, 2,2,3,3-tetrafluoropropoxy group, 1,1,1,3,3,3-hexafluoro-2-propoxy group, or 6-(perfluoroethyl)hexyloxy group; a substituted or unsubstituted aryloxy group such as a phenoxy group, a p-nitrophenoxy group, a p-tert-butylphenoxy group, a 3-fluorophenoxy group, a pentafluorophenyl group, or a 3-trifluoromethylphenoxy group; a substituted or unsubstituted alkylthio group such as a methylthio group, an ethylthio group, a tert-butylthio group, a hexylthio group, an octylthio group, or a trifluoromethylthio group; a substituted or unsubstituted arylthio group such as a phenylthio group, a p-nitrophenylthio group, a p-tert-butylphenylthio group, 3-fluorophenylthio group, a pentafluorophenylthio group, or 3-trifluoromethylphenylthio group; a mono-substituted or di-substituted amino group such as a cyano group, a nitro group, an amino group, a methylamino group, a diethylamino group, an ethylamino group, a diethylamino group, a dipropylamino group, a dibutylamino group, or a diphenylamino group; an acylamino group such as a bis(acetoxymethyl) amino group, a bis(acetoxyethyl)amino group, a bis(acetoxypropyl)amino group, or a bis(acetoxybutyl)amino group; a carbamoyl group such as a hydroxyl group, a siloxy group, an acyl group, a methylcarbamoyl group, a dimethylcarbamoyl group, an ethylcarbamoyl group, a diethylcarbamoyl group, a propylcarbamoyl group, a butylcarbamoyl group, or a phenylcarbamoyl group; a cycloalkyl group such as a carboxylic acid group, a sulfonic acid group, an imide group, a cyclopentane group, or a cyclohexyl group; an aryl group such as a phenyl group, a naphthyl group, a biphenylyl group, an anthryl group, a phenanthryl group, a fluorenyl group, or a pyrenyl group; and a heterocyclic group such as a pyridinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a triathinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzoimidazolyl group, or a puranyl group. In addition, the above-mentioned substituents may be bound to each other to further form a six-membered aryl ring or a heterocycle.

Besides, the nitrogen-containing heterocyclic ring derivative represented by the following formula can be also used.

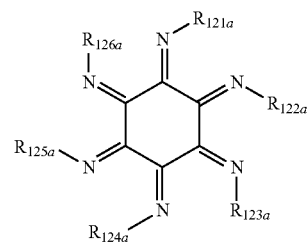

wherein $R_{121a}$ to $R_{126a}$ each independently represents any one of a substituted or unsubstituted alkyl group, a substituted or unsubstituted aryl group, a substituted or unsubstituted aralkyl group or a substituted or unsubstituted heterocyclic ring group. However, $R_{121a}$ to $R_{126a}$ may be identical to or different from each other. Further, $R_{121a}$ and $R_{122a}$, $R_{123a}$ and $R_{124a}$, $R_{125a}$ and $R_{126a}$, $R_{121a}$ and $R_{126a}$, $R_{122a}$ and $R_{123a}$, $R_{124a}$ and $R_{125a}$ may form a fused ring.

Further, compounds represented by the formula below may be employable.

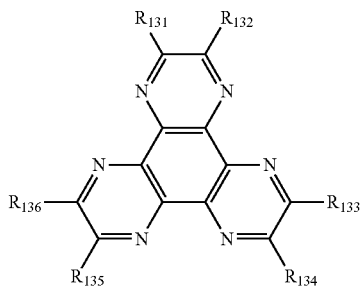

wherein $R_{131}$ to $R_{136}$ are substituents, and preferably, they each independently represents an electron withdrawing group such as a cyano group, a nitro group, a sulfonyl group, a carbonyl group, a trifluoromethyl group, a halogen atom, etc.

Typically exemplified as those materials, a material having an acceptor property is also employable as a hole injecting material. Specific examples of those are the same as described hereinabove.

In addition to the above-mentioned aromatic dimethylidene compound described hereinabove as a material for the light emitting layer, inorganic compound such as p-type Si and p-type SiC may be used as the material for the hole injecting layer and the hole transporting layer.

A preferable embodiment for the organic EL device of the present invention includes an element containing a reducing dopant in the region of an electron transport or in the interfacial region of the cathode and the organic layer. The reducing dopant is defined as a substance which can reduce a compound having the electron transporting property. Various substances can be used as the reducing dopant as long as the substances have a uniform reductive property. For example, at least one substance selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, organic complexes of alkali metals, organic complexes of alkaline earth metals, and organic complexes of rare earth metals can be preferably used.

Examples of the preferable reductive dopant include at least one alkali metal selected from a group consisting of Li (the work function: 2.9 eV), Na (the work function: 2.36 eV), K (the work function: 2.28 eV), Rb (the work function: 2.16 eV) and Cs (the work function: 1.95 eV) or at least one alkaline earth metals selected from a group consisting of Ca (the work function: 2.9 eV), Sr (the work function: 2.0 to 2.5 eV) and Ba (the work function: 2.52 eV). Reductive dopants having a work function of 2.9 eV or smaller are particularly preferable. Among those, more preferable reductive dopants include at least one alkali metal selected from the group consisting of K, Rb and Cs, more preferably Rb or Cs and most preferably Cs. Since those alkali metals have a particularly high reducing capability, the luminance is improved and the lifetime is prolonged by the addition thereof into an electron injection region in a relatively small amount. A combination of two or more alkali metals is also preferably used as the reductive dopant having a work function of 2.9 eV or smaller. A combination containing Cs such as Cs and Na, Cs and K, Cs and Rb and Cs, Na and K is particularly preferred. By containing Cs in combination, the reducing capability is effectively performed, and the luminance is enhanced and the lifetime is prolonged in the organic EL device by the addition into the electron injection region.

The present invention may further include an electron injecting layer which is composed of an insulating material or a semiconductor and disposed between the cathode and the organic layer. At this time, the electron injecting property can be improved by preventing a leak of electric current effectively. As the insulating material, at least one metal compound selected from the group consisting of alkali metal chalcogenides, alkaline earth metal chalcogenides, alkali metal halides, and alkaline earth metal halides is preferable. It is preferable that the electron injecting layer be composed of the above-mentioned substance such as the alkali metal chalcogenide since the electron injecting property can be further improved. To be specific, preferable examples of the alkali metal chalcogenide include $Li_2O$, $K_2O$, $Na_2S$, $Na_2Se$, and $Na_2O$. Preferable examples of the alkaline earth metal chalcogenide include CaO, BaO, SrO, BeO, BaS, and CaSe. Preferable examples of the alkali metal halide include LiF, NaF, KF, LiCl, KCl, and NaCl. Preferable examples of the alkaline earth metal halide include fluorides such as $CaF_2$, $BaF_2$, $SrF_2$, $MgF_2$, and $BeF_2$ and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound for constituting the electron transporting layer is in the form of a crystallite or amorphous insulating thin film. When the electron transporting layer is constituted with the above insulating thin film, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

The hole injecting and transporting layer is a layer which helps the injection of holes into the light emitting layer and transports the holes to the light emitting region. The layer exhibits a great mobility of holes and, in general, has an ionization energy as small as 5.6 eV or smaller. For the hole injecting and transporting layer, a material which transports holes to the light emitting layer at a small strength of the electric field is preferable. A material which exhibits, for example, a mobility of holes of at least $10^{-4}$ $cm^2/V \cdot s$ under an electric field of from $10^4$ to $10^6$ V/cm is preferable.

When the aromatic amine derivative of the present invention is employed in the hole transporting region, the hole injecting and transporting layer may be composed of the aromatic amine derivative of the present invention alone or in combination with another material.

With regard to the material which may be employed for forming the hole injecting and transporting layer in combination with the aromatic amine derivative of the present invention, any material having the foregoing preferable properties is employed without particularly restricted, which is selected from compounds commonly used as a hole transporting material of photoconductive materials and compounds used for forming the hole injecting and transporting layer of EL devices. In the present invention, a material capable of transporting holes and being employable in a transporting region is defined as a hole transporting material.

Regarding with the aromatic amine derivative to be used for the hole injecting and transporting layer, compounds represented by the following general formulae are employable.

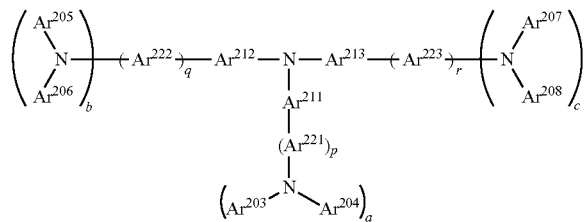

wherein $Ar^{211}$ to $Ar^{213}$, $Ar^{221}$ to $Ar^{223}$ and $Ar^{203}$ to $Ar^{208}$ each independently represents a substituted or unsubstituted aromatic hydrocarbon group having 6 to 50 ring carbon atoms, a substituted or unsubstituted aromatic heterocyclic group having 5 to 50 ring atoms; a, b, c, p, q and r each independently represents an integer of 0 to 3; $Ar^{203}$ and $Ar^{204}$, $Ar^{205}$ and $Ar^{206}$, $Ar^{207}$ and $Ar^{208}$ may be bonded to each other to form a saturated or unsaturated ring.

Examples of the substituted or unsubstituted aromatic hydrocarbon group having 6 to 50 ring carbon atoms include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-tert-butylphenyl group, p-(2-phenylpropyl)phenyl group, 3-methyl-2-naphthyl group, 4-methyl-1-naphthyl group, 4-methyl-1-anthryl group, 4'-methylbiphenyl-yl group, 4''-tert-butyl-p-terphenyl-4-yl group.

Specific examples of the substituted or unsubstituted aromatic heterocyclic group having 5 to 50 ring atoms include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-tert-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-tert-butyl-1-indolyl group, 4-tert-butyl-1-indolyl group, 2-tert-butyl-3-indolyl group, 4-tert-butyl-3-indolyl group.

Further, the compound represented by the following formula can be used for the hole injecting layer and the hole transporting layer.

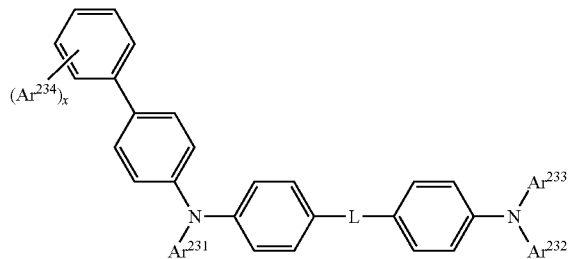

wherein $Ar^{231}$ to $Ar^{234}$ each independently represents a substituted or unsubstituted aromatic hydrocarbon group having 6 to 50 ring carbon atoms, or a substituted or unsubstituted aromatic heterocyclic group having 5 to 50 ring atoms. L represents a bonding group, which is a single bond, a substituted or unsubstituted aromatic hydrocarbon group having 6 to 50 ring carbon atoms, or a substituted or unsubstituted aromatic heterocyclic ring group having 5 to 50 ring atoms; and x represents an integer of 0 to 5. Also, $Ar^{232}$ and $Ar^{233}$ may be bonded to each other to form a saturated or unsaturated ring. Specific examples of the substituted or unsubstituted aromatic hydrocarbon group having 6 to 50 ring carbon atoms and the substituted or unsubstituted aromatic heterocyclic group having 5 to 50 ring atoms include the same as those above mentioned description.

Furthermore, specific examples of the materials for the hole injecting layer and hole transporting layer include triazole derivatives, oxadiazole derivatives, imidazole derivatives, polyarylalkane derivatives, pyrazoline derivatives and pyrazolone derivatives, phenylenediamine derivatives, arylamine derivatives, amino substituted chalcone derivatives, oxazole derivatives, styryl anthracene derivatives, fluorenone derivatives, hydrazone derivatives, stilbene derivatives, silazane derivatives, aniline based copolymers, electrically conductive polymer oligomers (in particular, thiophene oligomers), etc.

Specific examples include triazole derivatives (see, for example, U.S. Pat. No. 3,112,197), oxadiazole derivatives (see, for example, U.S. Pat. No. 3,189,447), imidazole derivatives (see, for example, JP-B 37-16096, etc.), polyarylalkane derivatives (see, for example, U.S. Pat. Nos. 3,615,402; 3,820,989; 3,542,544, JP-B 45-555, JP-B 51-10983, JP 51-93224A, JP 55-17105A, JP 56-4148A, JP 55-108667A, JP 55-156953A, JP 56-36656A, etc.), pyrazoline derivatives and pyrazolone derivatives (see, for example, U.S. Pat. Nos. 3,180,729; 4,278,746; JP 55-88064A, JP 55-88065A, JP 49-105537A, JP 55-51086A, JP 56-80051A, JP 56-88141A, JP 57-45545A, JP 54-112637A and JP 55-74546A), phenylenediamine derivatives (see, for example, U.S. Pat. No. 3,615,404; JP-B 51-10105, JP-B 46-3712, JP-B 47-25336, JP 54-53435A, JP 54-110536A and JP 54-119925A), arylamine derivatives (see, for example, U.S. Pat. Nos. 3,567,450; 3,180,703; 3,240,597; 3,658,520; 4,232,103; 4,175,961; 4,012,376; JP-B 49-35702, JP 39-27577B, JP 55-144250A, JP 56-119132A, JP 56-22437A and German Patent No. 1,110,518), amino-substituted chalcone derivatives (see, for example, U.S. Pat. No. 3,526,501), oxazole derivatives (disclosed in U.S. Pat. No. 3,257,203, etc.), styrylanthracene derivatives (see, for example, JP 56-46234A), fluorenone derivatives (see, for example, JP 54-110837A), hydrazone derivatives (see, for example, U.S. Pat. No. 3,717,462, JP 54-59143A, JP 55-52063A, JP 55-52064A, JP 55-46760A, JP 55-85495A, JP 57-11350A, JP 57-148749A and JP 2-311591A), stilbene derivatives (see, for example, JP 61-210363A, JP 61-228451A, JP 61-14642A, JP 61-72255A, JP 62-47646A, JP 62-36674A, JP 62-10652A, JP 62-30255A, JP 60-93455A, JP 60-94462A, JP 60-174749A, JP 60-175052A, etc.), silazane derivatives (U.S. Pat. No. 4,950,950), polysilane-based polymer (JP 2-204996A), aniline based copolymer (JP 2-282263A), etc.

With regard to the material for the hole injecting and transporting layer, the above materials are also employable, and porphyrin compounds (disclosed in, for example, JP 63-295665A), aromatic tertiary amine compounds and styryl amine compounds (see, for example, U.S. Pat. No. 4,127,412, JP 53-27033A, JP 54-58445A, JP 55-79450A, JP 55-144250A, JP 56-119132A, JP 61-295558A, JP 61-98353A and JP 63-295695A) are preferable and the aromatic tertiary amine compounds are particularly preferable.

Further examples include, 4,4'-bis(N-(1-naphthyl)-N-phenylamino)biphenyl (NPD) which has 2 fused aromatic rings in the molecule thereof described in U.S. Pat. No. 5,061,569 and 4,4',4''-tris(N-(3-methylphenyl)-N-phenylamino)triphenylamine (MTDATA) described in JP 4-308688A which includes three triphenylamine units connected in a star burst configuration.

Besides, a nitrogen-containing compound with heterocyclic ring derivative represented by the following general formula disclosed in Japanese Registered Patent No. 03571977 is also employable.

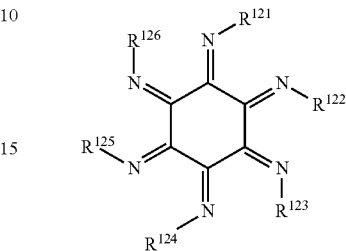

wherein $R^{121}$ to $R^{126}$ each independently represents any one of a substituted or unsubstituted alkyl group, a substituted or unsubstituted aryl group, a substituted or unsubstituted aralkyl group or a substituted or unsubstituted heterocyclic group. However, $R^{121}$ to $R^{126}$ may be the same with or different from each other. Further, $R^{121}$ and $R^{122}$, $R^{123}$ and $R^{124}$, $R^{125}$ and $R^{126}$, $R^{121}$ and $R^{126}$, $R^{122}$ and $R^{123}$, $R^{124}$ and $R^{125}$ may form a fused ring.

Still further, a compound represented by the following formula disclosed in US Patent Application Publication No. 2004/0113547 is also employable.

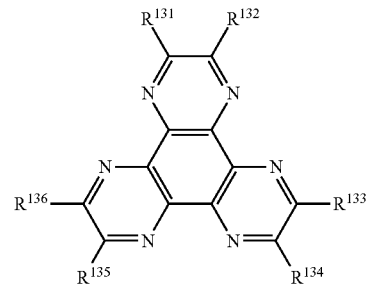

wherein $R^{131}$ to $R^{136}$ are substituents, and preferably, they each independently represents an electron withdrawing group such as a cyano group, a nitro group, a sulfonyl group, a carbonyl group, a trifluoromethyl group, a halogen atom, etc.

Typically exemplified as those materials, a material having an acceptor property is also employable as a hole injecting material. Specific examples of those are the same as described above.

In addition to the above-mentioned aromatic dimethylidene compound described as a material for the light emitting layer, inorganic compound such as p-type Si and p-type SiC may be used as the material for the hole injecting and transporting layer.

To form the hole injecting and transporting layer, a thin film may be formed from the aromatic amine derivative of the present invention in accordance with a well-known process such as the vacuum vapor deposition process, the spin coating process, the casting process and the LB process. Although the thickness of the hole injecting and transporting layer is not particularly limited, the thickness is usually from 5 nm to 5 μm. The hole injecting and transporting layer may be a single layer made of one or more kinds of materials mentioned above or may be laminated with another hole injecting and transporting layer made of a different material, as long as the hole injecting and transporting layer contains the aromatic amine derivative of the present invention in the hole transporting region thereof.

An organic semiconductor layer which preferably has an electric conductance of $10^{-10}$ S/cm or greater may be provided to assist the injection of holes into the light emitting layer. Examples of the materials for the organic semiconductor layer include electrically conductive oligomers such as an oligomer having thiophene and an oligomer having arylamine disclosed in JP 8-193191A; and electrically conductive dendrimers such as a dendrimer having an arylamine dendrimer.

The materials which are usually used in the organic EL devices can be used for forming the hole injecting layer or the hole transporting layer. Specific examples of include triazole derivatives, oxadiazole derivatives, imidazole derivatives, poly arylalkane derivatives, pyrazoline derivatives and pyrazolone derivatives, phenylenediamine derivatives, arylamine derivatives, amino substituted chalcone derivatives, oxazole derivatives, styryl anthracene derivatives, fluorenone derivatives, hydrazone derivatives, stilbene derivatives, silazane derivatives, polysilane based and aniline based copolymers, electrically conductive polymer oligomers, etc. The materials which are usually used in the organic EL devices can be used for forming the electron transporting layer. As the material for the electron transporting layer, 8-hydroxyquinoline, metal complexes of derivatives thereof and oxadiazole derivatives are preferable. Specific examples of the metal complex of 8-hydroxyquinoline or of the derivative of 8-hydroxyquinoline include metal chelate oxynoid compounds each containing a chelate of oxine (generally 8-quinolinol or 8-hydroxyquinoline), such as tris(8-quinolinol)aluminum. Regarding with the thickness and the method for formation of these layers, those usually used for the organic EL device may be appropriately adopted.

The electron injecting material is preferably made of compounds which have a good electron transportability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the compound include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the compound is not limited thereto. Further, an electron accepting substance and an electron donating substance may be added to the hole injecting material and the electron injecting material, respectively, for enhancing sensitization thereof.

In order to prepare the organic EL device of the present invention, for example, the anode, the light emitting layer, the hole injecting layer and the electron injecting layer are formed in accordance with the illustrated process using the illustrated materials, and the cathode is formed in the last step. Alternatively, each layer may be formed in a reverse order from the cathode to the anode.

Hereinafter, an embodiment of the process for preparing an organic EL device having a construction in which the anode, the hole injecting layer, the light emitting layer, the electron injecting layer, and the cathode are disposed successively on a light transmissive substrate will be described.

First, on a suitable light transmissive substrate, a thin film of an anode substance is formed so as to have a film thickness of 1 μm or thinner, preferably from 10 nm to 200 nm in accordance with a vapor deposition process, a sputtering process, etc. Then, a hole injecting layer is formed on the anode. The hole injecting layer can be formed in accordance with the vacuum vapor deposition process, the spin coating process, the casting process or the LB process, as described above. The vacuum vapor deposition process is preferable because a uniform film can be easily obtained and pinhole is little formed. When the hole injecting layer is formed in accordance with the vacuum vapor deposition process, the conditions are preferably selected from the following ranges: temperature of deposition source: 50 to 450° C.; degree of vacuum: $10^{-7}$ to $10^{-3}$ Torr; vapor deposition rate: 0.01 to 50 nm/s; temperature of the substrate: 50 to 300° C.; and film thickness: 5 nm to 5 μm; although depending on the employed compound (material for the hole injecting layer), the crystal structure and the recombination structure.

Subsequently, the light emitting layer is formed on the hole injecting layer by depositing a thin film of the organic light emitting material in accordance with the vacuum vapor deposition process, the sputtering process, the spin coating process or the casting process. The vacuum vapor deposition process is preferable because a uniform film can be easily obtained and pinhole is little formed. When the light emitting layer is formed in accordance with the vacuum vapor deposition process, the conditions of the vacuum vapor deposition can be selected in the same ranges as in the deposition of the hole injecting layer, although depending on the compound to be used. With regard to the film thickness, it is preferable to be within the range of from 10 to 40 nm.

Subsequently, the electron injecting layer is formed on the light emitting layer. Similarly to the formation of the hole injecting layer and light emitting layer, the electron injecting layer is preferably formed in accordance with the vacuum vapor deposition process, because a uniform film is required. The conditions of the vacuum vapor deposition can be selected from the same ranges as in the formation of the hole injecting layer and the light emitting layer.

Finally, the cathode is formed on the electron injecting layer, to obtain an organic EL device. The cathode is made of a metal and can be formed in accordance with the vacuum vapor deposition process or the sputtering process. However, the vacuum vapor deposition process is preferably employed in order to prevent the underlying organic layers from being damaged during the formation of the film.

In the above fabrication of the organic EL device, the layers from the anode to the cathode are successively formed preferably in a single evacuation operation.

The process for forming the layers in the organic EL device of the present invention is not particularly limited. A conventional process such as the vacuum vapor deposition process and the spin coating process or so can be employed. The organic thin film layer containing the compound of the formula (1) included in the organic EL device of the present invention can be formed in accordance with the vacuum vapor deposition process, the molecular beam epitaxy process (the MBE process) or a known method of coating a solution of the compound such as the dipping process, the spin coating process, the casting process, the bar coating process and the roller coating process. Although the thickness of each layer in the organic thin film layer in the organic EL device of the present invention is not particularly limited, a thickness in the range of several nanometers to 1 μm is preferable usually in order to avoid defects such as pin holes, and to improve the efficiency.

The organic EL device emits light when a direct voltage of 5 to 40 V is applied with the anode being +terminal and the cathode being −terminal. In the reverse polarity, no electric current flows and no light is emitted upon the application of voltage. When an alternating voltage is applied, the uniform light emission is observed only in the polarity where the anode is + and the cathode is −. When an alternating voltage is applied to the organic EL device, any type of wave shape can be used.

EXAMPLES

This invention will be described in further detail with reference to Examples, which does not limit the scope of this invention.

The structural formulae of Intermediates 1 to 17 and 18 to 27 to be produced in Synthesis Examples 1 to 17 and 18 to 27 are as shown below.

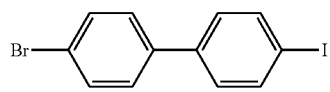

Intermediate 1

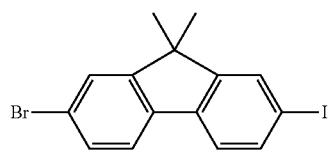

Intermediate 2

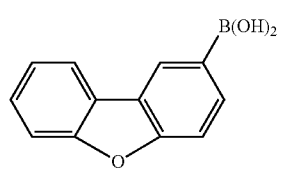

Intermediate 3

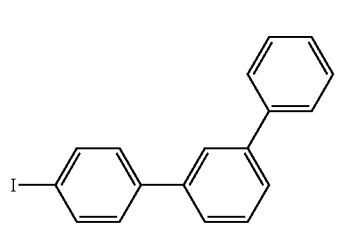

Intermediate 4

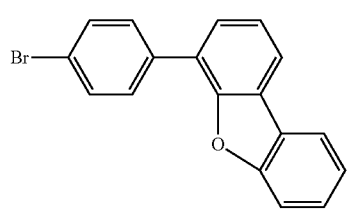

Intermediate 5

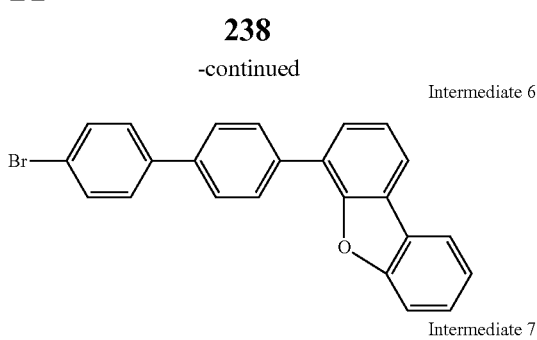

Intermediate 6

Intermediate 7

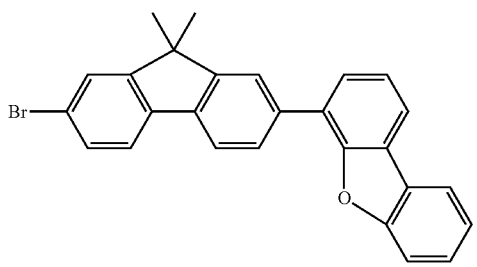

Intermediate 10

Intermediate 9

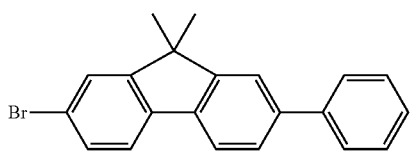

Intermediate 9

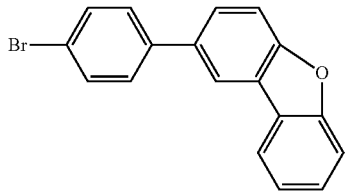

Intermediate 8

Intermediate 11

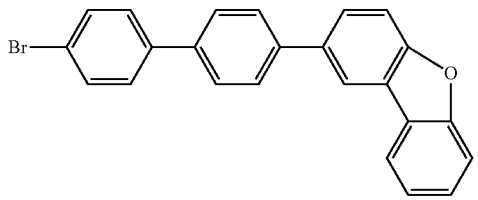

Intermediate 12
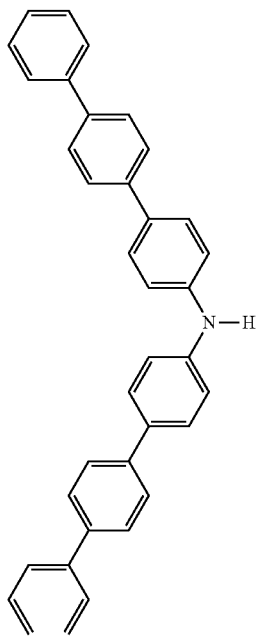
Intermediate 13
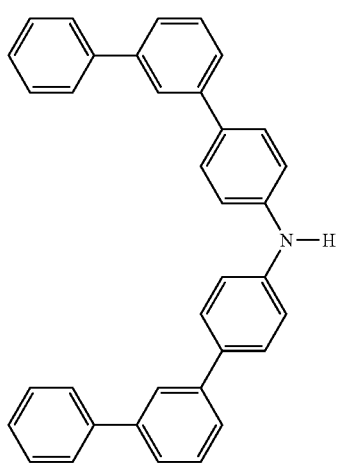
Intermediate 14
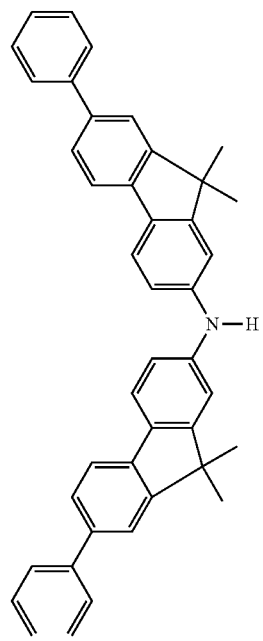
Intermediate 15
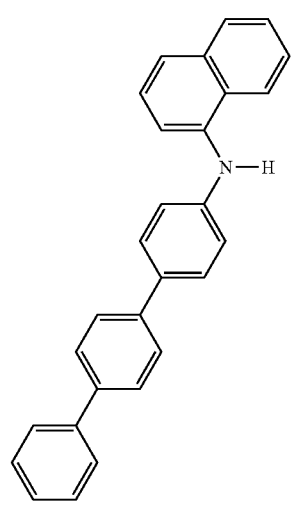
Intermediate 16
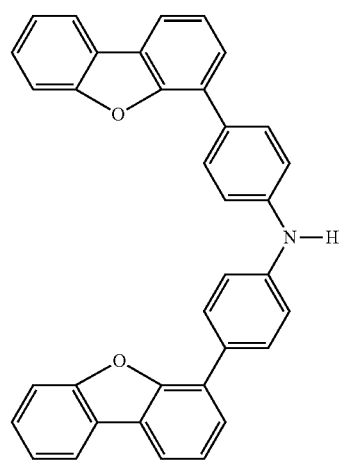

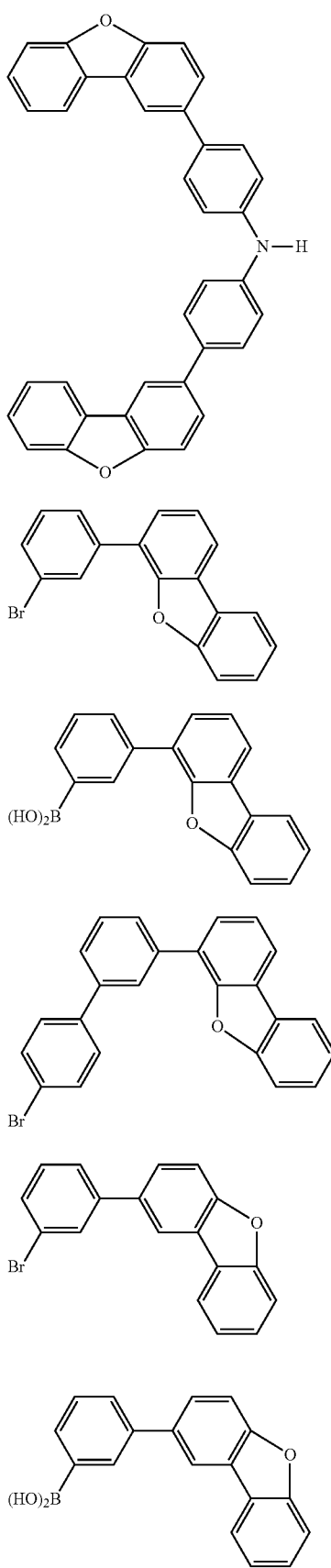

-continued

Intermediate 27

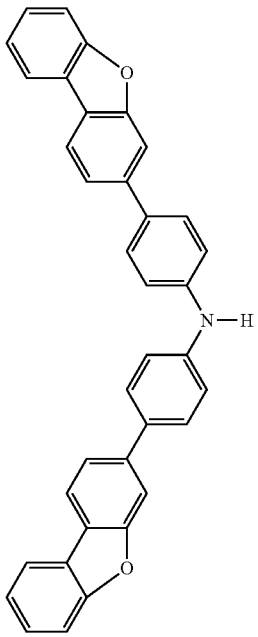

Synthesis Example 1

Synthesis of Intermediate 1

Under an argon gas flow, 47 g of 4-bromobiphenyl, 23 g of iodine, 9.4 g of periodic acid dihydrate, 42 ml of water, 360 ml of acetic acid and 11 ml of sulfuric acid were placed into a 1000-ml three-necked flask. After stirring the resultant solution at 65° C. for 30 minutes, the reaction was allowed to proceed at 90° C. for 6 hours. The resultant mixture was poured into iced water, and then filtered. After having been washed with water, the resultant was washed with methanol to obtain 67 g of a white powder. The white powder was identified as Intermediate 1 from the analysis in accordance with Field Desorption Mass Spectrum (hereinafter, FD-MS) because the main peaks of m/z=358 and 360 were shown for $C_{12}H_8BrI=359$.

Synthesis Example 2

Synthesis of Intermediate 2

Performing a reaction in the same manner as in Synthesis Example 1 except that 2-bromo-9,9-dimethylfluorene was used instead of 4-bromobiphenyl, 61 g of a white powder was obtained. The white powder was identified as Intermediate 2 from the analysis in accordance with the FD-MS because the main peaks of m/z=398 and 400 were shown for $C_{15}H_{12}BrI=399$.

Synthesis Example 3

Synthesis of Intermediate 3

Providing 150 g (892 mmol) of dibenzofuran and 1 liter of acetic acid into a flask, the inside of the flask was replaced with the nitrogen gas and the resultant mixture was heated and dissolved. After dropping 188 g (1.18 mol) of bromine while sometimes cooling with water, the mixture was stirred under air-cooling for 20 hours. The precipitated crystal was separated by filtration, washed with acetic acid and water sequentially, and was dried under reduced pressure. After refining the resultant crystal with reduced-pressure distillation, it was subjected to re-crystallization with methanol repeatedly several times to obtain 66.8 g (yield: 31%) of 2-bromodibenzofuran.

Under the atmosphere of argon gas, 400 ml of anhydrous THF was added to 24.7 g (100 mmol) of 2-bromodibenzofuran, and while stirring at −40° C., a hexane solution of n-butyllithium with 1.6 M concentration in an amount of 63 ml (100 mmol) was further added. The reacted solution was stirred for 1 hour while warming up to a temperature of 0° C. Cooling the reacted solution down to −78° C. again, 50 ml solution of dried THF of trimethyl borate in an amount of 26.0 g (250 mmol) was dropped. The reacted solution was stirred at a room temperature for 5 hours. Adding 100 ml of 1N hydrochloric acid and after stirring the resultant solution for 1 hour, a water layer was removed. After drying an organic layer over magnesium sulfate, the solvent was distillated away under a reduced pressure. The resultant solid was washed with toluene to obtain 15.2 g (yield: 72%) of dibenzofuran-2-boronic acid. The resultant was identified as Intermediate 3 from the analysis in accordance with the FD-MS because the main peak of m/z=212 was shown for $C_{12}H_9BO_3=212$.

Synthesis Example 4

Synthesis of Intermediate 4

Into a three-necked flask, 250 g of m-terphenyl (manufactured by SIGMA-ALDRICH Corp.), 50 g of hydroiodic acid-dihydrate, 75 g of iodine, 750 ml of acetic acid and 25 ml of sulfuric acid were placed; and they were allowed to react each other at 70° C. for 3 hours. After the reaction, 5 l of methanol was entered into the resultant, followed by stirring for 1 hour. The mixture was taken by filtration, and the resultant crystal was subjected to column chromatography purification, followed by re-crystallization with acetonitrile to obtain 64 g of a white powder. The resultant white powder was identified as Intermediate 4 from the result in accordance with the FD-MS analysis.

Synthesis Example 5

Synthesis of Intermediate 5

Under the atmosphere of argon gas, 300 ml of toluene and 150 ml of 2 M concentration sodium carbonate aqueous solution was added to 28.3 g (100 mmol) of 4-iodobromobenzene, 22.3 g (105 mmol) of dibenzofuran-4-boronic acid and 2.31 g (2.00 mmol) of tetrakis(triphenylphosphine)palladium (0), and the resultant mixture solution was heated while refluxing for 10 hours.

After the reaction was completed, filtration was carried out immediately and a water layer was removed. After drying the organic layer over sodium sulfate, the resultant was concentrated. The residue was subjected to a chromatography purification using a silica gel column to obtain 26.2 g of 4-(4-bromophenyl)dibenzofuran in the state of a white crystal (yield: 81%). The resultant white crystal was identified as Intermediate 5 from the result in accordance with the FD-MS analysis.

Synthesis Example 6

Synthesis of Intermediate 6

Performing a reaction in the same manner as in Synthesis Example 5 except that 36 g of Intermediate 1 was used instead of 4-iodobromobenzene, 28.1 g of a white powder was obtained. The resultant white powder was identified as Intermediate 6 from the result in accordance with the FD-MS analysis.

Synthesis Example 7

Synthesis of Intermediate 7

Performing a reaction in the same manner as in Synthesis Example 5 except that 40 g of Intermediate 2 was used instead of 4-iodobromobenzene, 30.2 g of a white powder was obtained. The resultant white powder was identified as Intermediate 7 from the result in accordance with the FD-MS analysis.

Synthesis Example 8

Synthesis of Intermediate 8

Performing a reaction in the same manner as in Synthesis Example 7 except that 12.8 g of phenylboronic acid was used instead of dibenzofuran-4-boronic acid, 19.7 g of a white powder was obtained. The resultant white powder was identified as Intermediate 8 from the result in accordance with the FD-MS analysis.

Synthesis Example 9

Synthesis of Intermediate 9

Performing a reaction in the same manner as in Synthesis Example 5 except that 22.3 g of Intermediate 3 was used instead of dibenzofuran-4-boronic acid, 23.1 g of a white powder was obtained. The resultant white powder was identified as Intermediate 9 from the result in accordance with the FD-MS analysis.

Synthesis Example 10

Synthesis of Intermediate 10

Performing a reaction in the same manner as in Synthesis Example 6 except that 22.3 g of Intermediate 3 was used instead of dibenzofuran-4-boronic acid, 25.8 g of a white powder was obtained. The resultant white powder was identified as Intermediate 10 from the result in accordance with the FD-MS analysis.

Synthesis Example 11

Synthesis of Intermediate 11

Performing a reaction in the same manner as in Synthesis Example 7 except that 22.3 g of Intermediate 3 was used instead of dibenzofuran-4-boronic acid, 27.8 g of a white powder was obtained. The resultant white powder was identified as Intermediate 11 from the result in accordance with the FD-MS analysis.

Synthesis Example 12

Synthesis of Intermediate 12

Under an argon gas flow, 5.7 g of benzamide (manufactured by TOKYO Chemical Industries, Co., Ltd.), 32.3 g of 4-bromo-p-terphenyl (manufactured by Tokyo Chemical Industries, Co., Ltd.), 1.64 g of copper (I) iodide (manufactured by Wako Pure Chemical Industries, Ltd.), 1.52 g of N,N'-dimethylethylenediamine (manufactured by SIGMA-ALDRICH Corp.), 23.2 g of potassium carbonate (manufactured by Wako Pure Chemical Industries, Ltd.), and 120 ml of xylene were placed into a 200-ml three-necked flask, and the reaction was allowed to proceed at 130° C. for 36 hours.

The resultant solution was cooled down, filtered and washed with toluene. Further, after washing with water and methanol, the solution was dried to obtain 23 g of a pale yellow powder.

Into a 300 ml three-necked flask, 23.0 g of the above white powder, 24.8 g of potassium hydroxide (manufactured by Wako Pure Chemical Industries, Ltd.), 21 ml of ion-exchange water, 28 ml of xylene (manufactured by Wako Pure Chemical Industries, Ltd.) and 15 ml of ethanol (manufactured by Wako Pure Chemical Industries, Ltd.) were entered, and the resultant mixture solution was heated while being refluxed for 36 hours. After the reaction was completed, extraction with toluene was carried out and the extract was dried over magnesium sulfate. The dried substance was condensed under reduced pressure and the coarse product was subjected to column purification. The purified substance was re-crystallized with a use of toluene and after the resultant crystal was taken by filtration, the crystal was dried and as a result, 11.2 g of Intermediate Compound 12 in the state of a white powder was obtained.

Synthesis Example 13

Synthesis of Intermediate 13

Performing a reaction in the same manner as in Synthesis Example 12 except that Intermediate 4 was used instead of 4-bromo-p-terphenyl, 8.2 g of a white powder was obtained. The resultant white powder was identified as Intermediate 13 from the result in accordance with the FD-MS analysis.

Synthesis Example 14

Synthesis of Intermediate 14

Performing a reaction in the same manner as in Synthesis Example 12 except that Intermediate 8 was used instead of 4-bromo-p-terphenyl, 9.1 g of a white powder was obtained. The resultant white powder was identified as Intermediate 14 from the result in accordance with the FD-MS analysis.

Synthesis Example 15

Synthesis of Intermediate 15

Performing a reaction in the same manner as in Synthesis Example 12 except that 16.2 g of 4-bromo-p-terphenyl was used, and 8.8 g of 1-acetamide naphthalene was used instead of benzamide, 6.2 g of a white powder was obtained. The resultant white powder was identified as Intermediate 15 from the result in accordance with the FD-MS analysis.

Synthesis Example 16

Synthesis of Intermediate 16

Performing a reaction in the same manner as in Synthesis Example 12 except that Intermediate 5 was used instead of 4-bromo-p-terphenyl, 7.3 g of a white powder was obtained. The resultant white powder was identified as Intermediate 16 from the result in accordance with the FD-MS analysis.

Synthesis Example 17

Synthesis of Intermediate 17

Performing a reaction in the same manner as in Synthesis Example 12 except that Intermediate 5 was used instead of 4-bromo-p-terphenyl, 8.1 g of a white powder was obtained. The resultant white powder was identified as Intermediate 17 from the result in accordance with the FD-MS analysis.

Synthesis Example 18

Synthesis of Intermediate 18

Performing a reaction in the same manner as in Synthesis Example 5 except that 28.3 g of 3-iodobromobenzene was used instead of 4-iodobromobenzene, 21.5 g of a white powder was obtained. The resultant white powder was identified as Intermediate 18 from the result in accordance with the FD-MS analysis.

Synthesis Example 19

Synthesis of Intermediate 19

Performing a reaction in the same manner as in Synthesis Example 3 except that 32.3 g of Intermediate 18 was used instead 2-bromodibenzofuran; 20.2 g of a white powder was obtained. The resultant white powder was identified as Intermediate 19 from the result in accordance with the FD-MS analysis.

Synthesis Example 20

Synthesis of Intermediate 20

Performing a reaction in the same manner as in Synthesis Example 5 except that 30.3 g of Intermediate 19 was used instead of dibenzofuran-4-boronic acid, 31.9 g of a white powder was obtained. The resultant white powder was identified as Intermediate 20 from the result in accordance with the FD-MS analysis.

Synthesis Example 21

Synthesis of Intermediate 21

Performing a reaction in the same manner as in Synthesis Example 18 except that 22.3 g of Intermediate 3 was used instead of dibenzofuran-4-boronic acid, 25.9 g of a white powder was obtained. The resultant white powder was identified as Intermediate 21 from the result in accordance with the FD-MS analysis.

Synthesis Example 22

Synthesis of Intermediate 22

Performing a reaction in the same manner as in Synthesis Example 3 except that 32.3 g of Intermediate 21 was used instead of 2-bromodibenzofuran, 21.6 g of a white powder was obtained. The resultant white powder was identified as Intermediate 22 from the result in accordance with the FD-MS analysis.

Synthesis Example 23

Synthesis of Intermediate 23

Performing a reaction in the same manner as in Synthesis Example 5 except that 30.3 g of Intermediate 22 was used instead of dibenzofuran-4-boronic acid, 30.6 g of a white powder was obtained. The resultant white powder was identified as Intermediate 23 from the result in accordance with the FD-MS analysis.

Synthesis Example 24

Synthesis of Intermediate 24

Performing a reaction in the same manner as in Synthesis Example 12 except that Intermediate 18 was used instead of 4-bromo-p-terphenyl, 9.8 g of a white powder was obtained. The resultant white powder was identified as Intermediate 24 from the result in accordance with the FD-MS analysis.

Synthesis Example 25

Synthesis of Intermediate 25

Performing a reaction in the same manner as in Synthesis Example 12 except that Intermediate 21 was used instead of 4-bromo-p-terphenyl, 10.2 g of a white powder was obtained. The resultant white powder was identified as Intermediate 25 from the result in accordance with the FD-MS analysis.

Synthesis Example 26

Synthesis of Intermediate 26

Under the atmosphere of argon gas, 1000 ml of toluene and 500 ml of 2 M concentration sodium carbonate aqueous solution was added to 120.0 g (399 mmol) of 1-bromo-3-fluoro-4-iodobromobenzene, 72.7 g (479 mmol) of 2-methoxyphenyl boronic acid and 9.2 g (7.96 mmol) of tetrakis(triphenylphosphine) palladium (0), and the resultant mixture solution was heated while being refluxed for 10 hours.

After the reaction was completed, extraction with toluene was carried out immediately and a water layer was removed. After drying the organic layer over sodium sulfate, the resultant was condensed. The residue was subjected to a chromatography purification using a silica gel column to obtain 89.6 g of 4-bromo-2-fluoro-2'-methoxybiphenyl in the state of white crystal (yield: 80%).

Under the atmosphere of argon gas, 900 ml of dichloromethane was added to 89.6 g (319 mmol) of 4-bromo-2-fluoro-2'-methoxybiphenyl, and the resultant mixture solution was stirred while cooling with ice. After adding 95.9 g (382 mmol) of boron tribromide by dropping, the solution was stirred at a room temperature for 12 hours.

After completion of the reaction, 200 ml of water was added, and the resultant mixture solution was stirred for 1 hour, followed by removing a water layer. After drying the organic layer over magnesium sulfate, the resultant was condensed. The residue was subjected to a chromatography purification using a silica gel column to obtain 68.1 g of 4-bromo-2-fluoro-2'-hydroxybiphenyl in the state of white crystal (yield: 70%).

Onto 68.1 g (255 mmol) of 4-bromo-2-fluoro-2'-hydroxybiphenyl and 70.4 g (510 mmol) of potassium carbonate, 1500 ml of N-methylpyrrolidone was added and the resultant solution was stirred at 180° C. for 3 hours.

After completion of the reaction, water was added and extraction by toluene was conducted. After drying an organic layer over sodium sulfate, the resultant was condensed. The resultant residue was re-crystallized through toluene and 44.2 g of 3-bromodibenzofuran in the state of white crystal was obtained (yield: 60%).

Under the atmosphere of argon gas, 350 ml of toluene and 170 ml of 2 M concentration sodium carbonate aqueous solution was added to 34.2 g (138 mmol) of 3-bromobenzofram, 26.0 g (166 mmol) of 4-chlorophenyl boronic acid and 3.2 g (2.77 mmol) of tetrakis(triphenylphosphine)palladium (0), and the resultant mixture solution was heated while being refluxed for 12 hours.

After the reaction was completed, filtration was carried out immediately and a water layer was removed. After drying the organic layer over sodium sulfate, the resultant was concentrated. The residue was subjected to a chromatography purification using a silica gel column to obtain 23.1 g of white crystal (yield: 60%). The resultant white crystal was identified as Intermediate 26 from the result in accordance with the FD-MS analysis.

Synthesis Example 27

Synthesis of Intermediate 27

Performing a reaction in the same manner as in Synthesis Example 12 except that Intermediate 26 was used instead of 4-bromo-p-terphenyl, 8.5 g of a white powder was obtained. The resultant white powder was identified as Intermediate 27 from the result in accordance with the FD-MS analysis.

The structural formulae of Compounds H1 to H14 to be produced in Examples-of-Synthesis 1 to 14 each serving as the aromatic amine derivative of the present invention and Comparative Compounds 1 to 4 used in Comparative Examples 1 to 4 are as shown below.

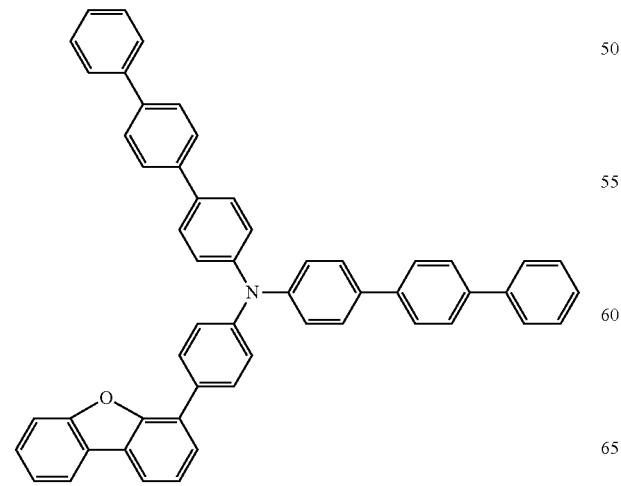

H1

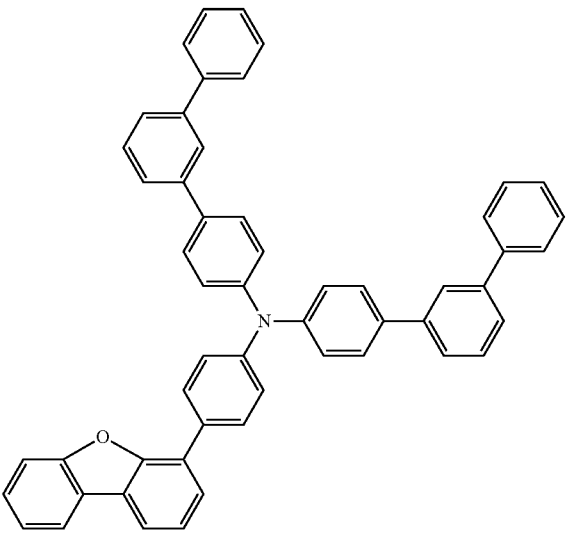

H2

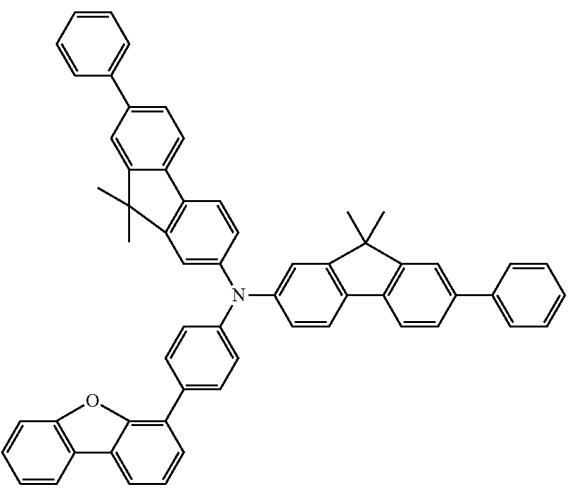

H3

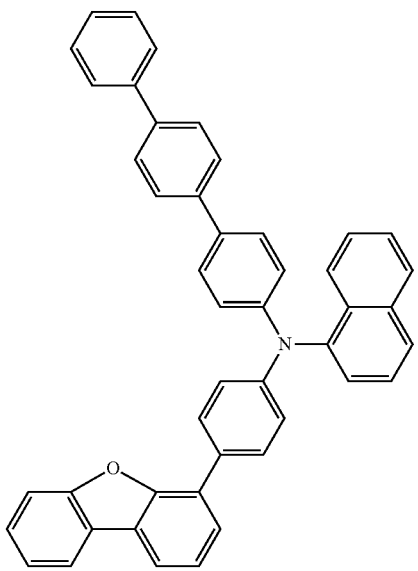

H4

251
-continued
H5
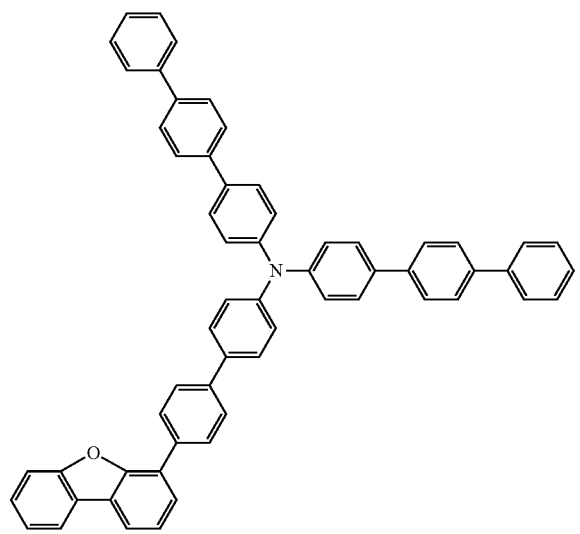
H6
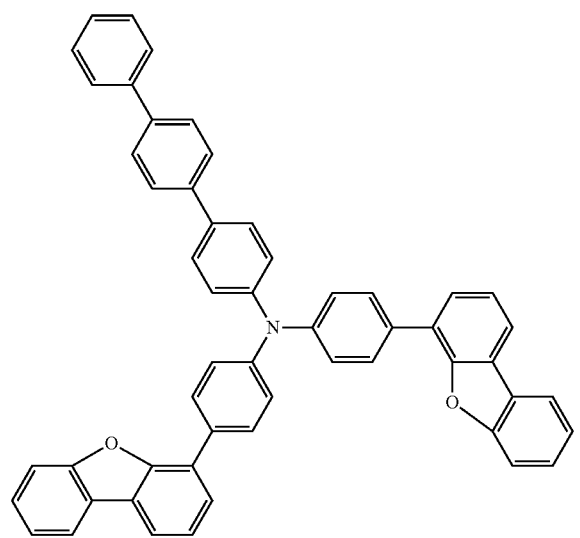
H7
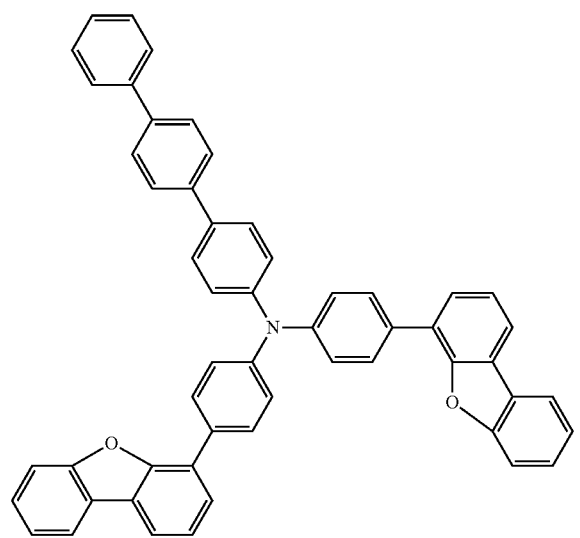
252
-continued
H8
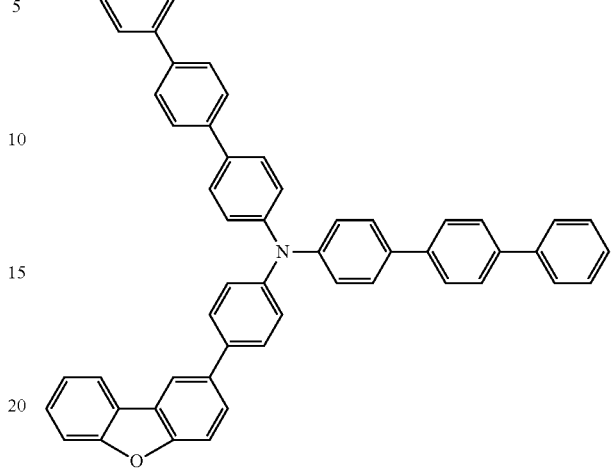
H9
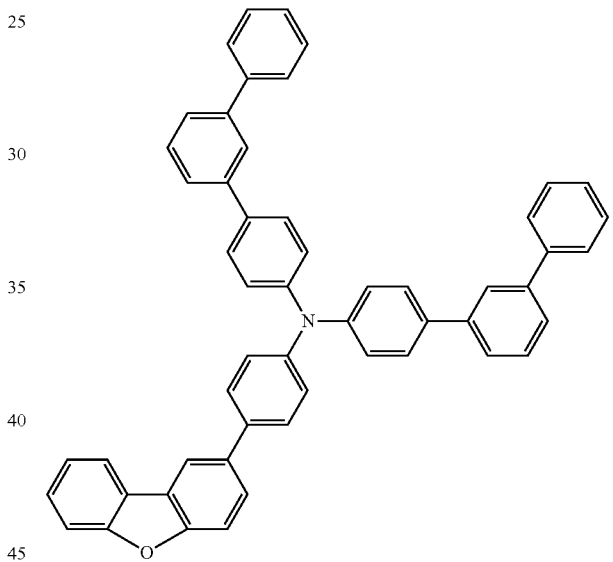
H10
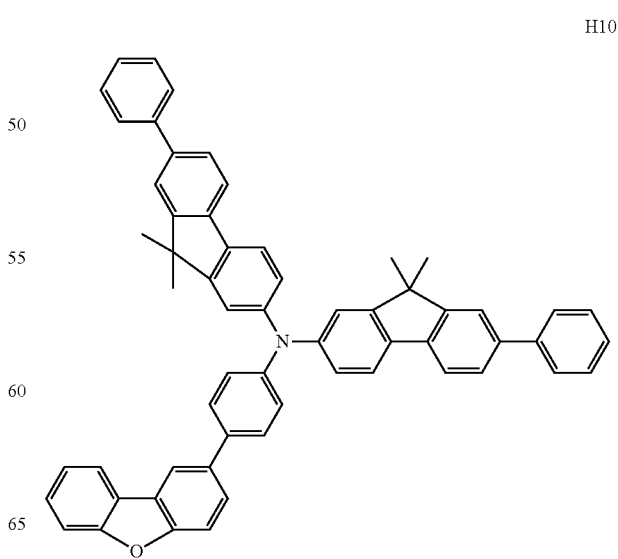

H11
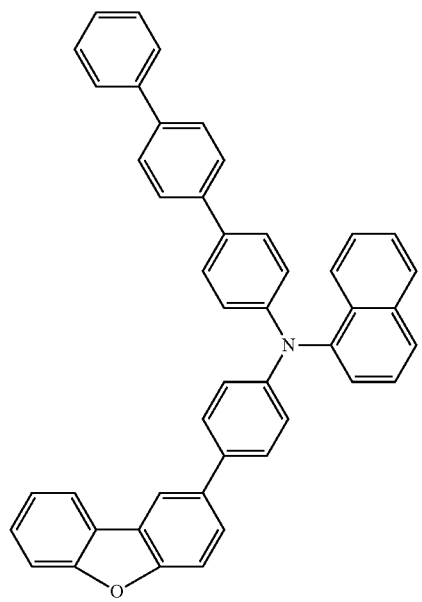
H12
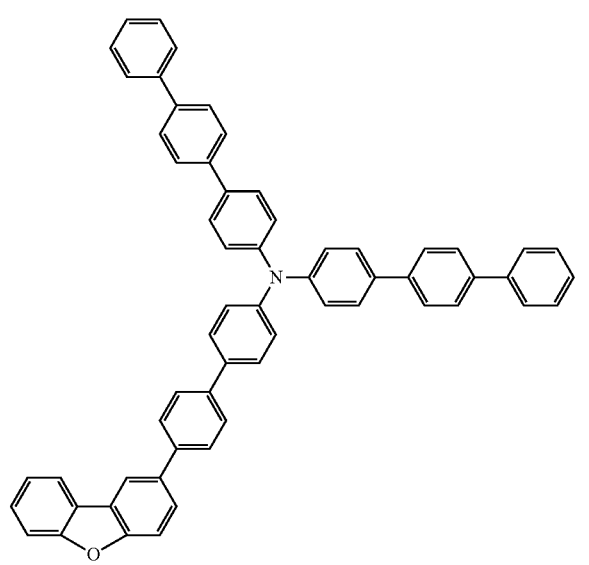
H13
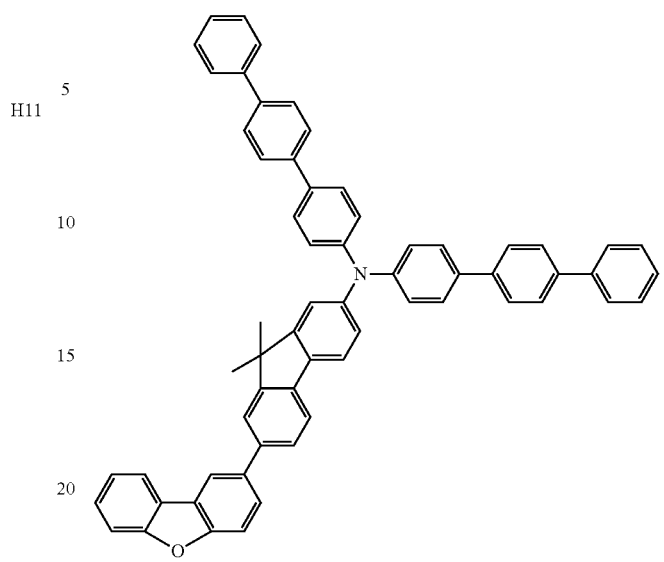
H14
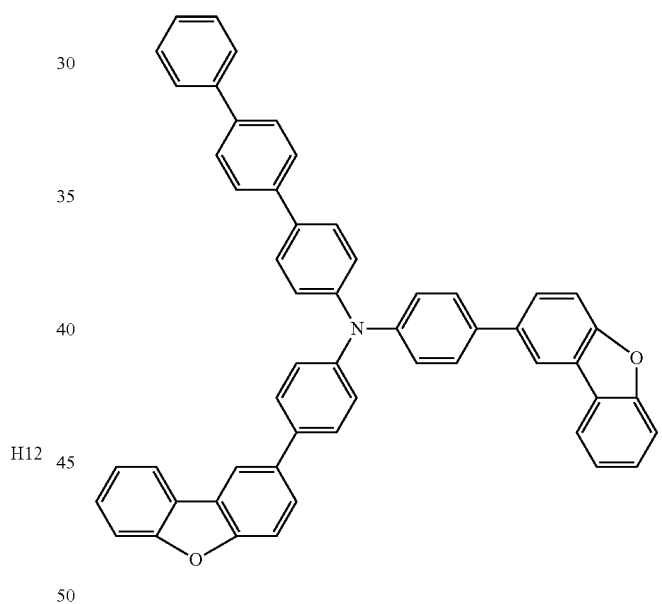
Comparative Compound 1
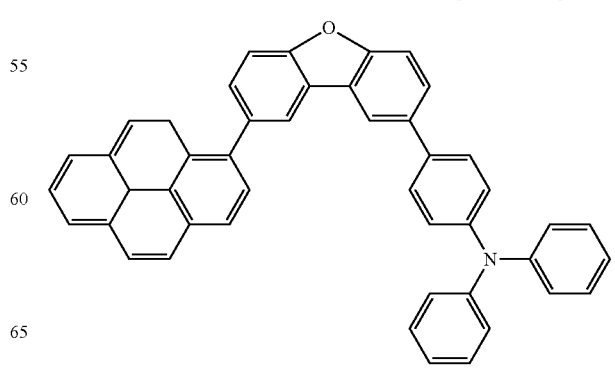

Comparative Compound 2

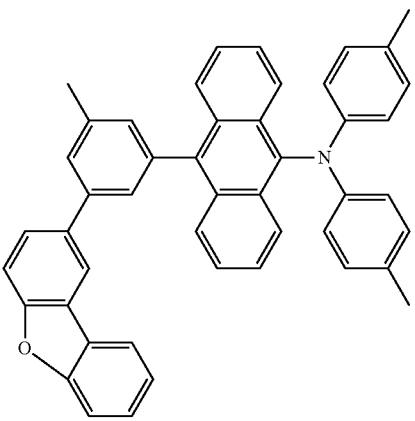

Comparative Compound 3

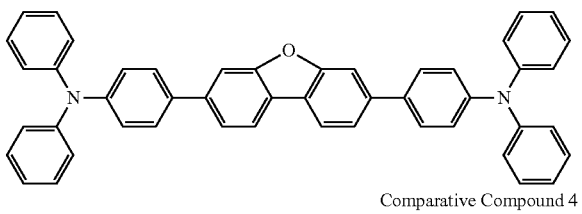

Comparative Compound 4

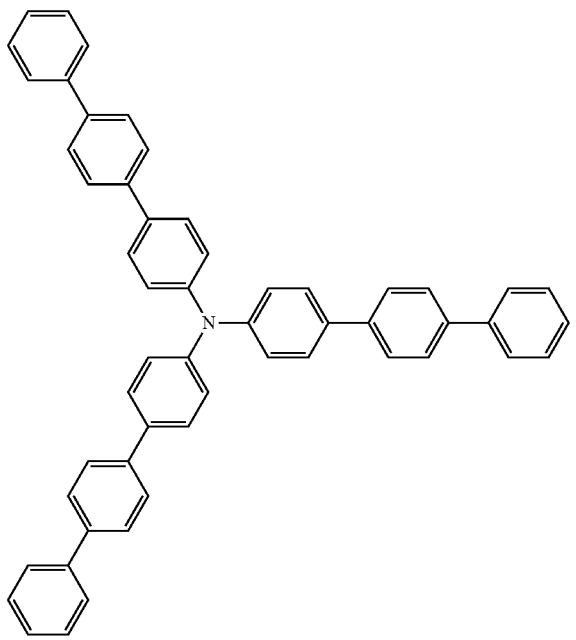

Example-of-Synthesis 1

Synthesis of Compound H1

Under an argon gas flow, 6.5 g of Intermediate 5, 9.5 g of Intermediate 12, 2.6 g of t-butoxy sodium (manufactured by Hiroshima Wako Co., Ltd.), 92 mg of tris(dibenzylideneacetone) dipalladium(0) (manufactured by SIGMA-ALDRICH Corp.), 42 mg of tri-tert-butylphosphine and 100 ml of dehydrated toluene were placed and the reaction was allowed to proceed at 80° C. for 8 hours.

The resultant solution was cooled down, added with 500 ml of water and filtered through sellite. The resultant filtrate was extracted with toluene, and the extract was dried over dehydrated magnesium sulfate. The dried substance was condensed under reduced pressure and the coarse product was subjected to column purification. The purified substance was re-crystallized with a use of toluene and after the resultant crystal was taken by filtration, the crystal was dried and as a result, 8.1 g of a pale yellow powder was obtained. The pale yellow powder was identified as Compound H1 from the result in accordance with the FD-MS analysis.

Example-of-Synthesis 2

Synthesis of Compound 112

Performing a reaction in the same manner as in Example-of-Synthesis 1 except that Intermediate 13 was used instead of Intermediate 12; 7.6 g of a pale yellow powder was obtained. The pale yellow powder was identified as Compound H2 from the result in accordance with the FD-MS analysis.

Example-of-Synthesis 3

Synthesis of Compound H3

Performing a reaction in the same manner as in Example-of-Synthesis 1 except that Intermediate 14 was used instead of Intermediate 12; 8.4 g of a pale yellow powder was obtained. The pale yellow powder was identified as Compound H3 from the result in accordance with the FD-MS analysis.

Example-of-Synthesis 4

Synthesis of Compound H4

Performing a reaction in the same manner as in Example-of-Synthesis 1 except that Intermediate 15 was used instead of Intermediate 12; 4.6 g of a pale yellow powder was obtained. The pale yellow powder was identified as Compound H4 from the result in accordance with the FD-MS analysis.

Example-of-Synthesis 5

Synthesis of Compound H5

Performing a reaction in the same manner as in Example-of-Synthesis 1 except that Intermediate 6 was used instead of Intermediate 5; 8.3 g of a pale yellow powder was obtained. The pale yellow powder was identified as Compound H5 from the result in accordance with the FD-MS analysis.

Example-of-Synthesis 6

Synthesis of Compound H6

Performing a reaction in the same manner as in Example-of-Synthesis 1 except that Intermediate 7 was used instead of Intermediate 5; 7.3 g of a pale yellow powder was obtained. The pale yellow powder was identified as Compound H6 from the result in accordance with the FD-MS analysis.

Example-of-Synthesis 7

Synthesis of Compound H7

Performing a reaction in the same manner as in Example-of-Synthesis 1 except that 4-bromo-p-terphenyl was used instead of Intermediate 5, and that Intermediate 16 was used instead of Intermediate 12; 6.5 g of a pale yellow powder was obtained. The pale yellow powder was identified as Compound H7 from the result in accordance with the FD-MS analysis.

Example-of-Synthesis 8

Synthesis of Compound H8

Performing a reaction in the same manner as in Example-of-Synthesis 1 except that Intermediate 9 was used instead of Intermediate 5; 7.9 g of a pale yellow powder was obtained. The pale yellow powder was identified as Compound H8 from the result in accordance with the FD-MS analysis.

Example-of-Synthesis 9

Synthesis of Compound H9

Performing a reaction in the same manner as in Example-of-Synthesis 8 except that Intermediate 13 was used instead of Intermediate 12; 7.1 g of a pale yellow powder was obtained. The pale yellow powder was identified as Compound H9 from the result in accordance with the FD-MS analysis.

Example-of-Synthesis 10

Synthesis of Compound H10

Performing a reaction in the same manner as in Example-of-Synthesis 8 except that Intermediate 14 was used instead of Intermediate 12; 7.6 g of a pale yellow powder was obtained. The pale yellow powder was identified as Compound H10 from the result in accordance with the FD-MS analysis.

Example-of-Synthesis 11

Synthesis of Compound H11

Performing a reaction in the same manner as in Example-of-Synthesis 8 except that Intermediate 15 was used instead of Intermediate 12; 4.9 g of a pale yellow powder was obtained. The pale yellow powder was identified as Compound H11 from the result in accordance with the FD-MS analysis.

Example-of-Synthesis 12

Synthesis of Compound H12

Performing a reaction in the same manner as in Example-of-Synthesis 8 except that Intermediate 10 was used instead of Intermediate 9; 5.9 g of a pale yellow powder was obtained. The pale yellow powder was identified as Compound H12 from the result in accordance with the FD-MS analysis.

Example-of-Synthesis 13

Synthesis of Compound H13

Performing a reaction in the same manner as in Example-of-Synthesis 8 except that Intermediate 11 was used instead of Intermediate 9; 7.9 g of a pale yellow powder was obtained. The pale yellow powder was identified as Compound H13 from the result in accordance with the FD-MS analysis.

Example-of-Synthesis 14

Synthesis of Compound H14

Performing a reaction in the same manner as in Example-of-Synthesis 8 except that 4-bromo-p-terphenyl was used instead of Intermediate 9, and that Intermediate 17 was used instead of Intermediate 12; 6.1 g of a pale yellow powder was obtained. The pale yellow powder was identified as Compound H14 from the result in accordance with the FD-MS analysis.

Example-of-Synthesis 15

Synthesis of Compound H15

Performing a reaction in the same manner as in Example-of-Synthesis 1 except that Intermediate 18 was used instead of Intermediate 5; 6.9 g of a pale yellow powder was obtained. The pale yellow powder was identified as Compound H15 from the result in accordance with the FD-MS analysis.

Example-of-Synthesis 16

Synthesis of Compound H16

Performing a reaction in the same manner as in Example-of-Synthesis 1 except that Intermediate 20 was used instead of Intermediate 5; 7.1 g of a pale yellow powder was obtained. The pale yellow powder was identified as Compound H16 from the result in accordance with the FD-MS analysis.

Example-of-Synthesis 17

Synthesis of Compound H17

Performing a reaction in the same manner as in Example-of-Synthesis 1 except that 4-bromo-p-terphenyl was used instead of Intermediate 5, and that Intermediate 24 was used instead of Intermediate 12; 4.6 g of a pale yellow powder was obtained. The pale yellow powder was identified as Compound H17 from the result in accordance with the FD-MS analysis.

Example-of-Synthesis 18

Synthesis of Compound H18

Performing a reaction in the same manner as in Example-of-Synthesis 1 except that Intermediate 21 was used instead of Intermediate 5; 6.6 g of a pale yellow powder was obtained. The pale yellow powder was identified as Compound H18 from the result in accordance with the FD-MS analysis.

Example-of-Synthesis 19

Synthesis of Compound H19

Performing a reaction in the same manner as in Example-of-Synthesis 1 except that Intermediate 23 was used instead of Intermediate 5; 5.1 g of a pale yellow powder was obtained. The pale yellow powder was identified as Compound H19 from the result in accordance with the FD-MS analysis.

Example-of-Synthesis 20

Synthesis of Compound H20

Performing a reaction in the same manner as in Example-of-Synthesis 1 except that 4-bromo-p-terphenyl was used instead of Intermediate 5, and that Intermediate 25 was used instead of Intermediate 12; 4.7 g of a pale yellow powder was obtained. The pale yellow powder was identified as Compound H20 from the result in accordance with the FD-MS analysis.

Example-of-Synthesis 21

Synthesis of Compound H21

Performing a reaction in the same manner as in Example-of-Synthesis 1 except that Intermediate 26 was used instead of Intermediate 5; 5.3 g of a pale yellow powder was obtained. The pale yellow powder was identified as Compound H21 from the result in accordance with the FD-MS analysis.

Example-of-Synthesis 22

Synthesis of Compound H22

Performing a reaction in the same manner as in Example-of-Synthesis 1 except that 4-bromo-p-terphenyl was used instead of Intermediate 5, and that Intermediate 27 was used instead of Intermediate 12; 4.2 g of a pale yellow powder was obtained. The pale yellow powder was identified as Compound H22 from the result in accordance with the FD-MS analysis.

Constitutional formulae of Compounds H15 to H22 are shown as the following:

H15

H16

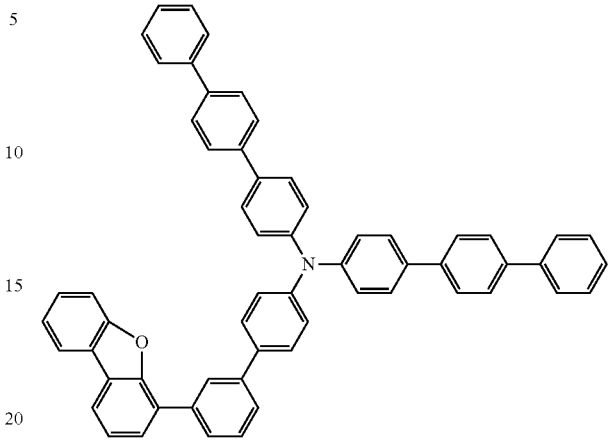

H17

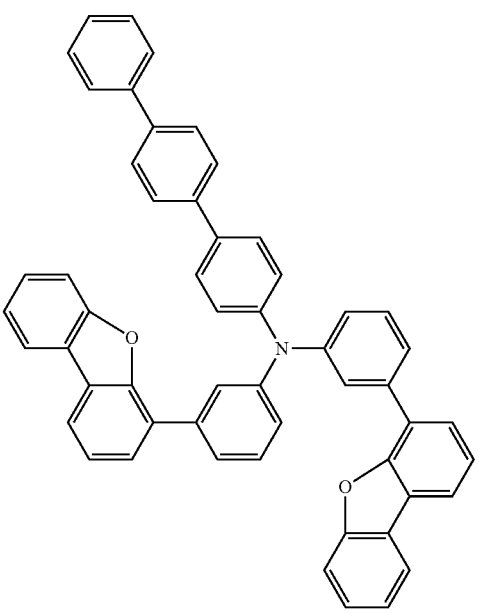

H18

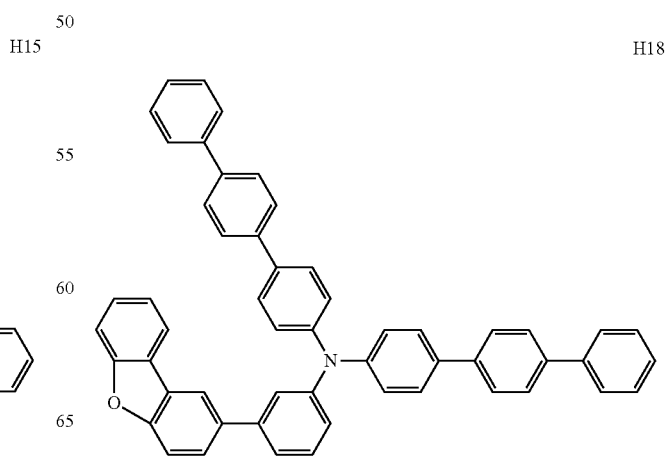

-continued

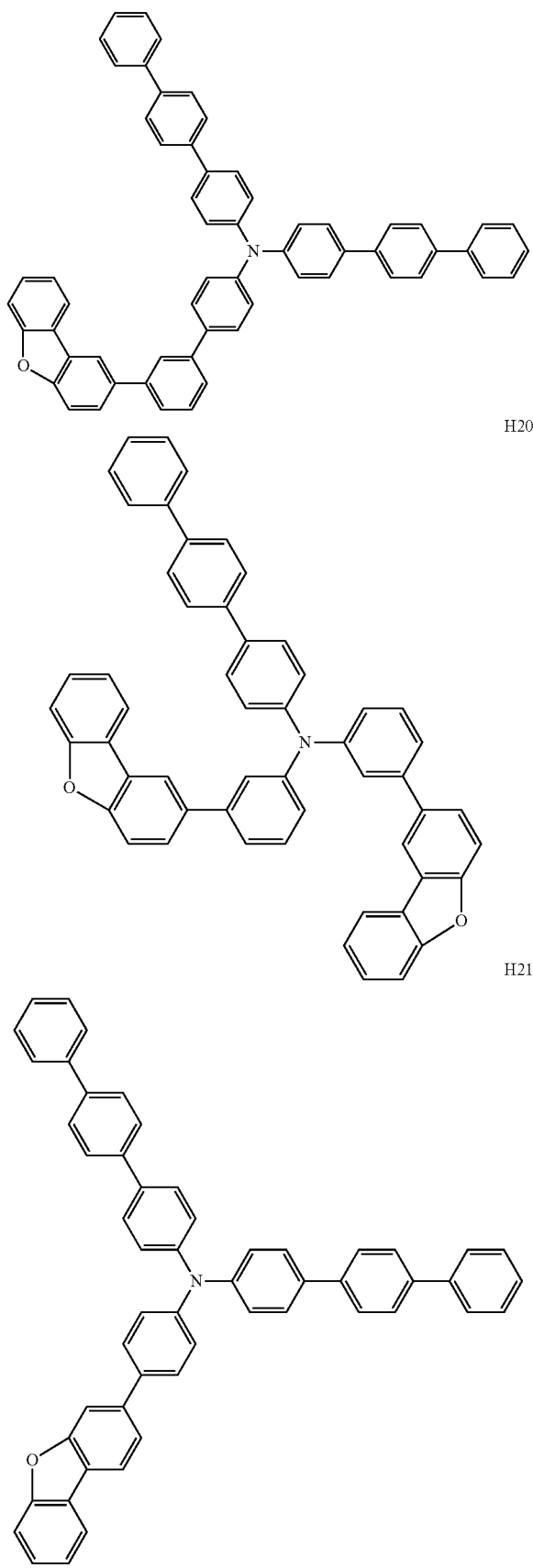

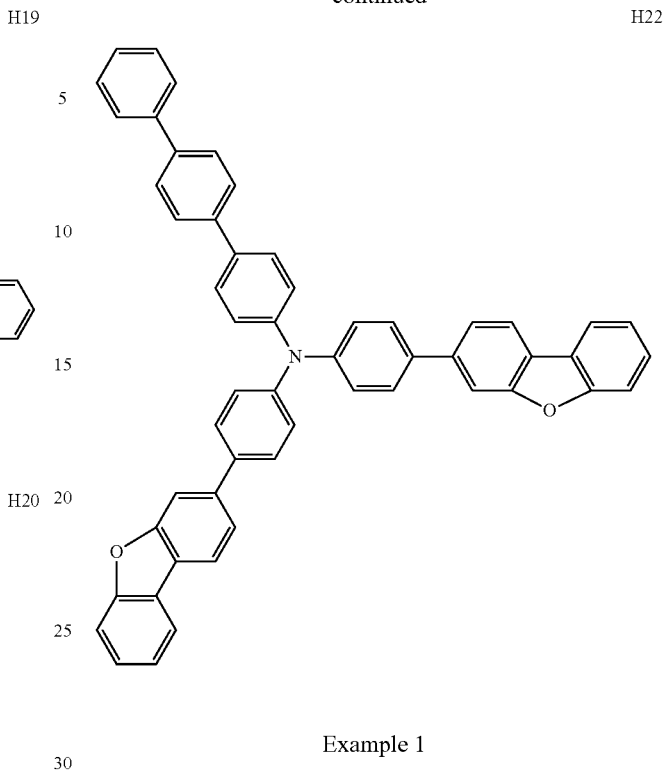

Example 1

Production Of Organic EL Device

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes.

The cleaned glass substrate having the transparent electrode lines was attached to a substrate holder of a vacuum vapor deposition apparatus. On the surface of the cleaned substrate at the side having the transparent electrode, a layer of Compound H1 having a thickness of 80 nm was formed so as to cover the transparent electrode. The formed film worked as a hole injecting and hole transporting layer. Further, Compound EM1 below was vapor deposited thereby forming a film having a thickness of 40 nm. At the same time, the following amine compound D1 having styryl group below as a light emitting molecule was deposited with a weight ratio of EM1:D1=40:2. The formed film worked as a light emitting layer.

On the film formed above, a film of Alq having a thickness of 10 nm was formed. The formed film worked as an electron injecting layer. Thereafter, $L_1$ (the source of lithium: manufactured by SAES GETTERS Company) as a reductive dopant and Alq were binary vapor deposited and an Alq:Li film (film thickness: 10 nm) was formed as the electron injecting layer (or a cathode). On the Alq:Li film, aluminum was vapor deposited to form a metal cathode and an organic EL device was fabricated.

The resultant organic EL device was measured for the emission efficiency and observed for the luminescent color. The emission efficiency at 10 mA/cm² was calculated as current efficiency from the luminance measured by CS1000 produced by MINOLTA. The half lifetime of emission when driven by constant DC current at an initial luminance of 5000 cd/m² and room temperature was measured. The results are shown in Table 1.

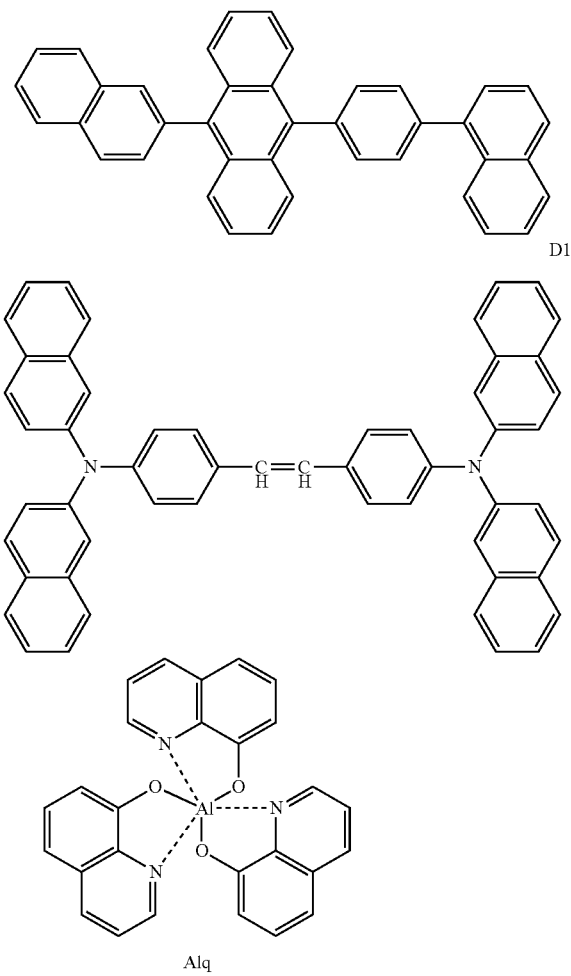

Examples 2 to 14

Production of Organic EL Device

Organic EL devices were fabricated in the same manner as in Example 1 except that compounds described in Table 1 were used as the hole transporting material instead of Compound H1.

The organic EL devices were measured for the emission efficiency and observed from the luminescent color. The half lifetime of emission when driven by constant DC current at an initial luminance of 5000 cd/m² and room temperature was measured. The results are shown in Table 1.

Comparative Example 1 to 4

Organic EL devices were fabricated in the same manner as in Example 1 except that Comparative Compounds 1 (Comparative Example 1) to 4 (Comparative Example 4) were used as the hole transporting material instead of Compound H1.

The organic EL devices were measured for the emission efficiency and observed from the luminescent color. The half lifetime of emission when driven by constant DC current at an initial luminance of 5000 cd/m² and room temperature was measured. The results are shown in Table 1.

Example 15

Production of Organic EL Device

An organic EL device was fabricated in the same manner as in Example 1 except that the following arylamine compound D2 was used instead of the amine compound D1 having styryl group. Me in the Compound D2 is a methyl group.

The organic EL device was measured for the emission efficiency and observed from the luminescent color. The half lifetime of emission when driven by constant DC current at an initial luminance of 5000 cd/m² and room temperature was measured. The results are shown in Table 1.

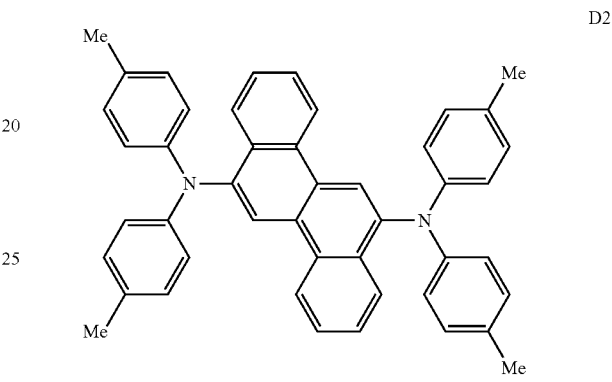

Comparative Example 5

An organic EL device was fabricated in the same manner as in Example 15 except that the Comparative Compound 1 was used as the hole transporting material instead of Compound H1.

The organic EL device was measured for the emission efficiency and observed from the luminescent color. The half lifetime of emission when driven by constant DC current at an initial luminance of 5000 cd/m² and room temperature was measured. The results are shown in Table 1.

| Examples/ Comparative Examples | Hole-Transporting Material | Luminescent Color | Half Lifetime (Hour) |
| --- | --- | --- | --- |
| Example 1 | H1 | Blue | 460 |
| Example 2 | H2 | Blue | 450 |
| Example 3 | H3 | Blue | 390 |
| Example 4 | H4 | Blue | 400 |
| Example 5 | H5 | Blue | 420 |
| Example 6 | H6 | Blue | 450 |
| Example 7 | H7 | Blue | 430 |
| Example 8 | H8 | Blue | 450 |
| Example 9 | H9 | Blue | 430 |
| Example 10 | H10 | Blue | 400 |
| Example 11 | H11 | Blue | 390 |
| Example 12 | H12 | Blue | 410 |
| Example 13 | H13 | Blue | 430 |
| Example 14 | H14 | Blue | 440 |
| Example 15 | H15 | Blue | 410 |
| Example 16 | H16 | Blue | 390 |
| Example 17 | H19 | Blue | 400 |
| Example 18 | H1 | Blue | 450 |
| Comparative Example 1 | Comparative Compound 1 | Blue | 130 |
| Comparative Example 2 | Comparative Compound 2 | Blue | 160 |

-continued

| Examples/Comparative Examples | Hole-Transporting Material | Luminescent Color | Half Lifetime (Hour) |
|---|---|---|---|
| Comparative Example 3 | Comparative Compound 3 | Blue | 90 |
| Comparative Example 4 | Comparative Compound 4 | Blue | 260 |
| Comparative Example 5 | Comparative Compound 1 | Blue | 120 |

INDUSTRIAL APPLICABILITY

As described above in detail, molecules in the aromatic amine derivative of the present invention hardly crystallize; furthermore, an organic EL device having a long lifetime can be produced in improved yield by incorporating the derivative into the organic thin film layer of the device.

The invention claimed is:

1. An organic electroluminescence device which comprises one or more organic thin film layers including at least one light emitting layer sandwiched between a cathode and an anode,
wherein at least one of the organic thin film layers is a hole transporting layer which comprises at least one aromatic amine compound represented by formula (1):

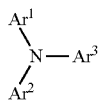
(1)

wherein
Ar$^1$ is represented by formula (2):

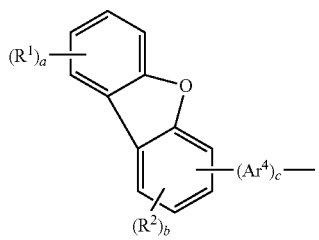
(2)

wherein
R$^1$ and R$^2$ each independently represents a substituted or unsubstituted aryl group having the number of carbon atoms of 6 to 50 forming the aromatic ring, or a substituted or unsubstituted alkyl group having 1 to 50 carbon atoms respectively;
a represents an integer of 0 to 4;
b represents an integer of 0 to 3;
c represents an integer of 1 to 3;
plural R$^1$'s or R$^2$'s together may be bonded to each other to form a saturated or unsaturated, five- or six-membered ring structure which may be substituted;
Ar$^4$ represents a substituted or unsubstituted arylene group having the number of carbon atoms of 6 to 50 forming the aromatic ring, or a substituted or unsubstituted fluorenylene group;

Ar$^2$ is represented by formula (3):

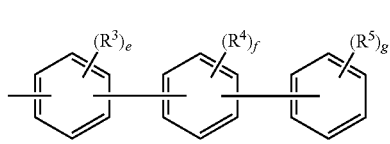
(3)

wherein
R$^3$ to R$^5$ are each independently a substituted or unsubstituted aryl group having the number of carbon atoms of 6 to 50 forming the aromatic ring, or a substituted or unsubstituted alkyl group having 1 to 50 carbon atoms;
e and f each independently represents an integer of 0 to 4;
g represents an integer of 0 to 5; and
two R$^3$'s, two R$^4$'s, two R$^5$'s, R$^3$ and R$^4$, or R$^4$ and R$^5$ may be bonded to each other to form a saturated or unsaturated, five- or six-membered ring structure which may be substituted; and
Ar$^3$ is a group represented by formula (2), a group represented by formula (3), or a substituted or unsubstituted aryl group having the number of carbon atoms of 6 to 50 forming the aromatic ring wherein the substituent is an aryl group having the number of carbon atoms of 6 to 50 forming the aromatic ring or an alkyl group having 1 to 50 carbon atoms, with the proviso that it does not include the structure of formula (3).

2. The organic electroluminescence device according to claim 1, wherein Ar$^4$ is represented by any one of the following general formula (4), (5) or (6):

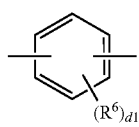
(4)

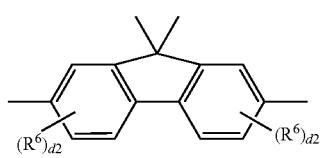
(5)

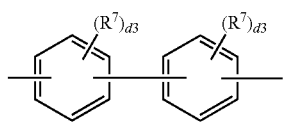
(6)

wherein
R$^6$'s each independently represents a substituted or unsubstituted aryl group having the number of carbon atoms of 6 to 50 forming the aromatic ring, or a substituted or unsubstituted alkyl group having 1 to 50 carbon atoms respectively;
d1 represents an integer of 0 to 4;
d2 represents an integer of 0 to 3;
plural R$^6$'s on the same benzene rings or R$^6$'s on 2 neighboring benzene rings together may be bonded to each other to form a saturated or unsaturated, five- or six-membered ring structure which may be substituted;

R$^7$'s each independently represents a substituted or unsubstituted aryl group having the number of carbon atoms of 6 to 50 forming the aromatic ring, or a substituted or unsubstituted alkyl group having 1 to 50 carbon atoms respectively, and d3 represents an integer of 0 to 4.

3. The electroluminescence device according to claim 1, wherein the general formula (3) is represented by any one of the following general formula (7), (8) or (9):

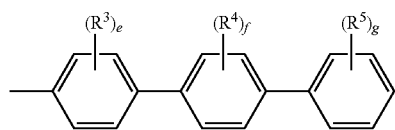
(7)

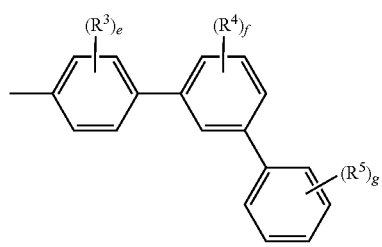
(8)

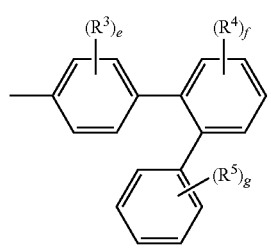
(9)

wherein
R$^3$ to R$^5$ are each independently a substituted or unsubstituted aryl group having the number of carbon atoms of 6 to 50 forming the aromatic ring, or a substituted or unsubstituted alkyl group having 1 to 50 carbon atoms;

e and f each independently represents an integer of 0 to 4;

g represents an integer of 0 to 5; and two R$^3$'s, two R$^4$'s, two R$^5$'s, R$^3$ and R$^4$, or R$^4$ and R$^5$ may be bonded to each other to form a saturated or unsaturated, five- or six-membered ring structure which may be substituted.

4. The electroluminescence device according to claim 1, wherein
Ar$^1$ is represented by the general formula (2); and
Ar$^2$ and Ar$^3$ are represented by the general formula (3).

5. The electroluminescence device according to claim 1, wherein
Ar$^1$ and Ar$^3$ are represented by the general formula (2); and
Ar$^2$ is represented by the general formula (3).

6. The electroluminescence device according to claim 2, wherein
Ar$^1$ is represented by the general formula (2);
Ar$^4$ is represented by the general formula (4), (5) or (6):

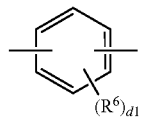
(4)

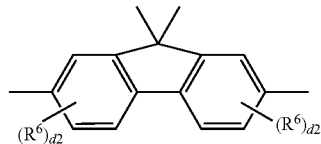
(5)

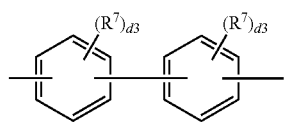
(6)

wherein
R$^6$'s each independently represents a substituted or unsubstituted aryl group having the number of carbon atoms of 6 to 50 forming the aromatic ring, or a substituted or unsubstituted alkyl group having 1 to 50 carbon atoms respectively;

d1 represents an integer of 0 to 4;

d2 represents an integer of 0 to 3;

plural R$^6$'s on the same benzene rings or R$^6$'s on 2 neighboring benzene rings together may be bonded to each other to form a saturated or unsaturated, five- or six-membered ring structure which may be substituted;

R$^7$'s each independently represents a substituted or unsubstituted aryl group having the number of carbon atoms of 6 to 50 forming the aromatic ring, or a substituted or unsubstituted alkyl group having 1 to 50 carbon atoms respectively;

d3 represents an integer of 0 to 4;

Ar$^2$ and Ar$^3$ are each represented by any one of the general formula (7) or (8) respectively:

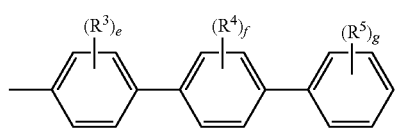
(7)

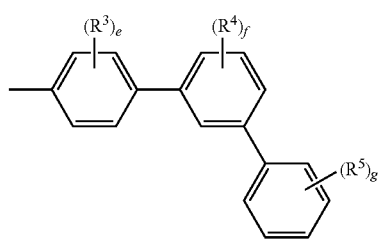
(8)

wherein
R$^3$ to R$^5$ are each independently a substituted or unsubstituted aryl group having the number of carbon atoms of 6 to 50 forming the aromatic ring, or a substituted or unsubstituted alkyl group having 1 to 50 carbon atoms;
e and f each independently represents an integer of 0 to 4;
g represents an integer of 0 to 5; and
two R$^3$'s, two R$^4$'s, two R$^5$'s, R$^3$ and R$^4$, or R$^4$ and R$^5$ may be bonded to each other to form a saturated or unsaturated, five- or six-membered ring structure which may be substituted.

7. The electroluminescence device according to claim 2, wherein
Ar$^1$ and Ar$^3$ are represented by the general formula (2);
Ar$^4$ is represented by the general formula (4), (5) or (6):

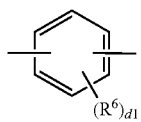

(4)

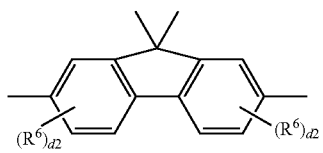

(5)

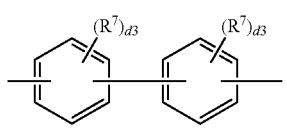

(6)

wherein
R$^6$'s each independently represents a substituted or unsubstituted aryl group having the number of carbon atoms of 6 to 50 forming the aromatic ring, or a substituted or unsubstituted alkyl group having 1 to 50 carbon atoms respectively;
d1 represents an integer of 0 to 4;
d2 represents an integer of 0 to 3;
plural R$^6$'s on the same benzene rings or R$^6$'s on 2 neighboring benzene rings together may be bonded to each other to form a saturated or unsaturated, five- or six-membered ring structure which may be substituted;
R$^7$'s each independently represents a substituted or unsubstituted aryl group having the number of carbon atoms of 6 to 50 forming the aromatic ring, or a substituted or unsubstituted alkyl group having 1 to 50 carbon atoms respectively;
d3 represents an integer of 0 to 4;
Ar$^2$ is represented by the general formula (7) or (8):

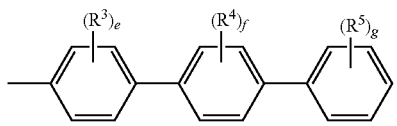

(7)

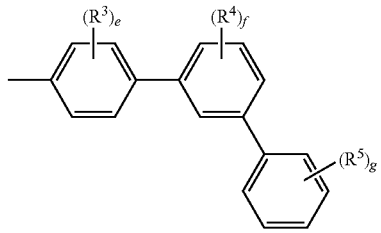

(8)

wherein
R$^3$ to R$^5$ are each independently a substituted or unsubstituted aryl group having the number of carbon atoms of 6 to 50 forming the aromatic ring, or a substituted or unsubstituted alkyl group having 1 to 50 carbon atoms;
e and f each independently represents an integer of 0 to 4;
g represents an integer of 0 to 5; and
two R$^3$'s, two R$^4$'s, two R$^5$'s, R$^3$ and R$^4$, or R$^4$ and R$^5$ may be bonded to each other to form a saturated or unsaturated, five- or six-membered ring structure which may be substituted.

8. The electroluminescence device according to claim 1, wherein the general formula (2) has a structure represented by the following general formula (10):

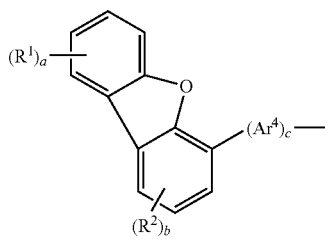

(10)

wherein
R$^1$ and R$^2$ each independently represents a substituted or unsubstituted aryl group having the number of carbon atoms of 6 to 50 forming the aromatic ring, or a substituted or unsubstituted alkyl group having 1 to 50 carbon atoms respectively;
a represents an integer of 0 to 4;
b represents an integer of 0 to 3;
c represents an integer of 1 to 3;
plural R$^1$'s or R$^2$'s together may be bonded to each other to form a saturated or unsaturated, five- or six-membered ring structure which may be substituted; and
Ar$^4$ represents a substituted or unsubstituted arylene group having the number of carbon atoms of 6 to 50 forming the aromatic ring, or a substituted or unsubstituted fluorenylene group.

9. The electroluminescence device according to claim 3, wherein
Ar$^1$ is represented by the general formula (2); and
Ar$^2$ and Ar$^3$ are each represented by any one of the general formula (7) or (8) respectively:

(7)

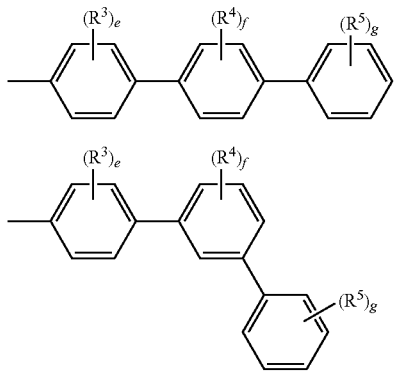

(8)

wherein
R³ to R⁵ are each independently a substituted or unsubstituted aryl group having the number of carbon atoms of 6 to 50 forming the aromatic ring, or a substituted or unsubstituted alkyl group having 1 to 50 carbon atoms;
e and f each independently represents an integer of 0 to 4;
g represents an integer of 0 to 5; and
two R³'s, two R⁴'s, two R⁵'s, R³ and R⁴, or R⁴ and R⁵ may be bonded to each other to form a saturated or unsaturated, five- or six-membered ring structure which may be substituted.

10. The electroluminescence device according to claim 3, wherein
Ar¹ and Ar³ are represented by the general formula (2); and Ar² is represented by the general formula (7) or (8):

(7)

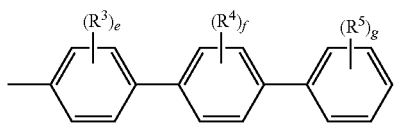

(8)

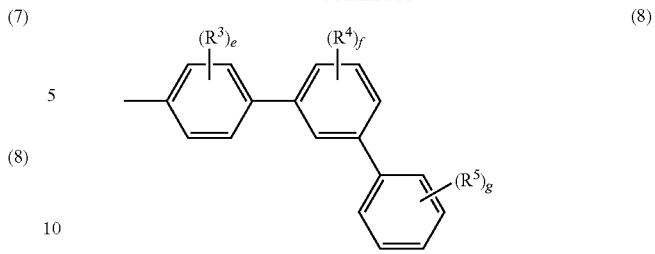

wherein
R³ to R⁵ are each independently a substituted or unsubstituted aryl group having the number of carbon atoms of 6 to 50 forming the aromatic ring, or a substituted or unsubstituted alkyl group having 1 to 50 carbon atoms;
e and f each independently represents an integer of 0 to 4;
g represents an integer of 0 to 5; and
two R³'s, two R⁴'s, two R⁵'s, R³ and R⁴, or R⁴ and R⁵ may be bonded to each other to form a saturated or unsaturated, five- or six-membered ring structure which may be substituted.

11. The organic electroluminescence device according to claim 1, further comprising at least one of styrylamine and an arylamine in the light emitting layer.

12. The organic electroluminescence device according to claim 1, which emits blue light.

13. The organic electroluminescence device according to claim 1, wherein the organic thin film layer comprises a hole transporting layer comprising at least one aromatic amine derivative represented by formula (1) and another hole transporting layer which is laminated with the hole transporting layer.

14. The organic electroluminescence device according to claim 1, which has a half lifetime of 390 to 460 hours.

* * * * *